US012773317B2

(12) United States Patent
Brauon et al.

(10) Patent No.: US 12,773,317 B2
(45) **Date of Patent: *Oct. 27, 2026**

(54) FASTENER AND TECHNIQUES THEREFOR

(71) Applicant: Edwards Lifesciences Innovation (Israel) Ltd., Caesarea (IL)

(72) Inventors: Haim Brauon, Beit Dagan (IL); Tal Sheps, Givat Shmuel (IL); Aviv Galon, Tel Aviv (IL); Rafael Pintor, Mission Viejo, CA (US)

(73) Assignee: Edwards Lifesciences Innovation (Israel) Ltd., Caesarea (IL)

( * ) Notice: Subject to any disclaimer, the term of this patent is extended or adjusted under 35 U.S.C. 154(b) by 341 days.

This patent is subject to a terminal disclaimer.

(21) Appl. No.: 18/392,388

(22) Filed: Dec. 21, 2023

(65) Prior Publication Data

US 2024/0122708 A1 Apr. 18, 2024

Related U.S. Application Data

(63) Continuation of application No. 17/478,800, filed on Sep. 17, 2021, now Pat. No. 11,890,191, which is a (Continued)

(51) Int. Cl.
*A61F 2/24* (2006.01)
*A61B 17/00* (2006.01)

(52) U.S. Cl.
CPC .......... *A61F 2/2445* (2013.01); *A61F 2/2412* (2013.01); *A61F 2/2466* (2013.01); (Continued)

(58) Field of Classification Search
CPC . A61B 2017/00243; A61B 2017/00783; A61F 2/2466; A61F 2/2445
See application file for complete search history.

(56) References Cited

U.S. PATENT DOCUMENTS

| | | | |
|---|---|---|---|
| 3,604,488 | A | 9/1971 | Wishart et al. |
| 3,656,185 | A | 4/1972 | Carpentier |

(Continued)

FOREIGN PATENT DOCUMENTS

| | | | |
|---|---|---|---|
| CN | 113331995 | A | 9/2021 |
| EP | 1034753 | A1 | 9/2000 |

(Continued)

OTHER PUBLICATIONS

Agarwal et al. International Cardiology Perspective Functional Tricuspid Regurgitation, Circ Cardiovasc Interv 2009;2;2;565-573 (2009).

(Continued)

*Primary Examiner* — Dinah Baria
(74) *Attorney, Agent, or Firm* — Anya Adams

(57) ABSTRACT

An annuloplasty structure includes a contracting member. A fastener is configured to receive the contracting member therethrough, the fastener including a housing and a clamping structure disposed therein. The fastener has an open state in which the contracting member can pass through the fastener, and is biased toward assuming a closed state in which the clamping structure clamps onto the contracting member disposed through the fastener. A stop is coupled to the fastener in a manner that maintains the fastener in the open state. A tool includes static and dynamic cutting elements, and is configured to (a) apply tension to the contracting member by pulling the contracting member proximally through the fastener, (b) lock the tension in the contracting member by pulling the stop proximally out from the fastener, and (c) sever the contracting member by moving the dynamic cutting element. Other embodiments are also described.

20 Claims, 40 Drawing Sheets

Related U.S. Application Data continuation of application No. 16/534,875, filed on Aug. 7, 2019, now Pat. No. 11,123,191, which is a continuation of application No. PCT/IL2019/050777, filed on Jul. 11, 2019.

(60) Provisional application No. 62/811,693, filed on Feb. 28, 2019, provisional application No. 62/697,186, filed on Jul. 12, 2018.

(52) U.S. Cl.
CPC ............... *A61B 2017/00243* (2013.01); *A61B 2017/00783* (2013.01); *A61F 2/2463* (2013.01); *A61F 2220/0016* (2013.01); *A61F 2230/0013* (2013.01)

(56) References Cited

U.S. PATENT DOCUMENTS 3,840,018 A 10/1974 Heifetz
3,881,366 A 5/1975 Bradley et al.
3,898,701 A 8/1975 La Russa
4,042,979 A 8/1977 Angell
4,118,805 A 10/1978 Reimels
4,214,349 A 7/1980 Munch
4,261,342 A 4/1981 Aranguren Duo
4,290,151 A 9/1981 Massana
4,434,828 A 3/1984 Trincia
4,473,928 A 10/1984 Johnson
4,602,911 A 7/1986 Ahmadi et al.
4,625,727 A 12/1986 Leiboff
4,712,549 A 12/1987 Peters et al.
4,778,468 A 10/1988 Hunt et al.
4,917,698 A 4/1990 Carpentier et al.
4,935,027 A 6/1990 Yoon
4,961,738 A 10/1990 Mackin
5,042,707 A 8/1991 Taheri
5,061,277 A 10/1991 Carpentier et al.
5,064,431 A 11/1991 Gilbertson et al.
5,104,407 A 4/1992 Lam et al.
5,108,420 A 4/1992 Marks
5,201,880 A 4/1993 Wright et al.
5,258,008 A 11/1993 Wilk
5,300,034 A 4/1994 Behnke et al.
5,325,845 A 7/1994 Adair
5,346,498 A 9/1994 Greelis et al.
5,383,852 A 1/1995 Stevens-Wright
5,449,368 A 9/1995 Kuzmak
5,450,860 A 9/1995 O'Connor
5,464,404 A 11/1995 Abela et al.
5,474,518 A 12/1995 Farrer Velazquez
5,477,856 A 12/1995 Lundquist
5,593,424 A 1/1997 Northrup, III
5,601,572 A 2/1997 Middleman et al.
5,626,609 A 5/1997 Zvenyatsky et al.
5,643,317 A 7/1997 Pavcnik et al.
5,669,919 A 9/1997 Sanders et al.
5,676,653 A 10/1997 Taylor et al.
5,683,402 A 11/1997 Cosgrove et al.
5,702,397 A 12/1997 Goble et al.
5,702,398 A 12/1997 Tarabishy
5,709,695 A 1/1998 Northrup, III
5,716,370 A 2/1998 Williamson, IV et al.
5,716,397 A 2/1998 Myers
5,728,116 A 3/1998 Rosenman
5,730,150 A 3/1998 Peppel et al.
5,749,371 A 5/1998 Zadini et al.
5,752,963 A 5/1998 Allard et al.
5,782,844 A 7/1998 Yoon et al.
5,810,882 A 9/1998 Bolduc et al.
5,824,066 A 10/1998 Gross
5,830,221 A 11/1998 Stein et al.
5,843,120 A 12/1998 Israel et al.
5,855,614 A 1/1999 Stevens et al.
5,876,373 A 3/1999 Giba et al.
5,935,098 A 8/1999 Blaisdell et al.
5,957,953 A 9/1999 DiPoto et al.
5,961,440 A 10/1999 Schweich, Jr. et al.
5,961,539 A 10/1999 Northrup, III et al.
5,984,959 A 11/1999 Robertson et al.
5,993,459 A 11/1999 Larsen et al.
6,042,554 A 3/2000 Rosenman et al.
6,045,497 A 4/2000 Schweich, Jr. et al.
6,050,936 A 4/2000 Schweich, Jr. et al.
6,059,715 A 5/2000 Schweich, Jr. et al.
6,074,341 A 6/2000 Anderson et al.
6,074,401 A 6/2000 Gardiner et al.
6,074,417 A 6/2000 Peredo
6,086,582 A 7/2000 Altman et al.
6,102,945 A 8/2000 Campbell
6,106,550 A 8/2000 Magovern et al.
6,110,200 A 8/2000 Hinnenkamp
6,132,390 A 10/2000 Cookston et al.
6,143,024 A 11/2000 Campbell et al.
6,159,240 A 12/2000 Sparer et al.
6,165,119 A 12/2000 Schweich, Jr. et al.
6,174,332 B1 1/2001 Loch et al.
6,183,411 B1 2/2001 Mortier et al.
6,187,040 B1 2/2001 Wright
6,210,347 B1 4/2001 Forsell
6,217,610 B1 4/2001 Carpentier et al.
6,228,032 B1 5/2001 Eaton et al.
6,231,602 B1 5/2001 Carpentier et al.
6,251,092 B1 6/2001 Qin et al.
6,296,656 B1 10/2001 Bolduc et al.
6,315,784 B1 11/2001 Djurovic
6,319,281 B1 11/2001 Patel
6,328,746 B1 12/2001 Gambale
6,332,893 B1 12/2001 Mortier et al.
6,355,030 B1 3/2002 Aldrich et al.
6,361,559 B1 3/2002 Houser et al.
6,368,348 B1 4/2002 Gabbay
6,402,780 B2 6/2002 Williamson, IV et al.
6,406,420 B1 6/2002 McCarthy et al.
6,406,493 B1 6/2002 Tu et al.
6,419,696 B1 7/2002 Ortiz et al.
6,451,054 B1 9/2002 Stevens
6,458,076 B1 10/2002 Pruitt
6,461,336 B1 10/2002 Larre
6,461,366 B1 10/2002 Seguin
6,470,892 B1 10/2002 Forsell
6,503,274 B1 1/2003 Howanec, Jr. et al.
6,524,338 B1 2/2003 Gundry
6,527,780 B1 3/2003 Wallace et al.
6,530,952 B2 3/2003 Vesely
6,533,772 B1 3/2003 Sherts et al.
6,537,314 B2 3/2003 Langberg et al.
6,547,801 B1 4/2003 Dargent et al.
6,554,845 B1 4/2003 Fleenor et al.
6,564,805 B2 5/2003 Garrison et al.
6,565,603 B2 5/2003 Cox
6,569,198 B1 5/2003 Wilson et al.
6,579,297 B2 6/2003 Bicek et al.
6,589,160 B2 7/2003 Schweich, Jr. et al.
6,592,593 B1 7/2003 Parodi et al.
6,602,288 B1 8/2003 Cosgrove et al.
6,602,289 B1 8/2003 Colvin et al.
6,613,078 B1 9/2003 Barone
6,613,079 B1 9/2003 Wolinsky et al.
6,619,291 B2 9/2003 Hlavka et al.
6,626,899 B2 9/2003 Houser et al.
6,626,917 B1 9/2003 Craig
6,626,930 B1 9/2003 Allen et al.
6,629,534 B1 10/2003 St. Goar et al.
6,629,921 B1 10/2003 Schweich, Jr. et al.
6,651,671 B1 11/2003 Donlon et al.
6,652,556 B1 11/2003 VanTassel et al.
6,682,558 B2 1/2004 Tu et al.
6,689,125 B1 2/2004 Keith et al.
6,689,164 B1 2/2004 Seguin
6,695,866 B1 2/2004 Kuehn et al.
6,702,826 B2 3/2004 Liddicoat et al.
6,702,846 B2 3/2004 Mikus et al.

(56) References Cited

U.S. PATENT DOCUMENTS 6,706,065 B2 3/2004 Langberg et al.
6,709,385 B2 3/2004 Forsell
6,709,456 B2 3/2004 Langberg et al.
6,711,444 B2 3/2004 Koblish
6,719,786 B2 4/2004 Ryan et al.
6,723,038 B1 4/2004 Schroeder et al.
6,726,716 B2 4/2004 Marquez
6,726,717 B2 4/2004 Alfieri et al.
6,730,121 B2 5/2004 Ortiz et al.
6,733,509 B2 5/2004 Nobles et al.
6,749,630 B2 6/2004 McCarthy et al.
6,752,813 B2 6/2004 Goldfarb et al.
6,764,310 B1 7/2004 Ichihashi et al.
6,764,510 B2 7/2004 Vidlund et al.
6,764,810 B2 7/2004 Ma et al.
6,770,083 B2 8/2004 Seguin
6,786,924 B2 9/2004 Ryan et al.
6,786,925 B1 9/2004 Schoon et al.
6,790,231 B2 9/2004 Liddicoat et al.
6,797,001 B2 9/2004 Mathis et al.
6,797,002 B2 9/2004 Spence et al.
6,802,319 B2 10/2004 Stevens et al.
6,805,710 B2 10/2004 Bolling et al.
6,805,711 B2 10/2004 Quijano et al.
6,855,126 B2 2/2005 Flinchbaugh
6,858,039 B2 2/2005 McCarthy
6,884,250 B2 4/2005 Monassevitch et al.
6,893,459 B1 5/2005 Macoviak
6,908,478 B2 6/2005 Alferness et al.
6,908,482 B2 6/2005 McCarthy et al.
6,918,917 B1 7/2005 Nguyen et al.
6,926,730 B1 8/2005 Nguyen et al.
6,960,217 B2 11/2005 Bolduc
6,964,684 B2 11/2005 Ortiz et al.
6,964,686 B2 11/2005 Gordon
6,976,995 B2 12/2005 Mathis et al.
6,986,775 B2 1/2006 Morales et al.
6,989,028 B2 1/2006 Lashinski et al.
6,997,951 B2 2/2006 Solem et al.
7,004,176 B2 2/2006 Lau
7,007,798 B2 3/2006 Happonen et al.
7,011,669 B2 3/2006 Kimblad
7,011,682 B2 3/2006 Lashinski et al.
7,018,406 B2 3/2006 Seguin et al.
7,037,334 B1 5/2006 Hlavka et al.
7,077,850 B2 7/2006 Kortenbach
7,077,862 B2 7/2006 Vidlund et al.
7,087,064 B1 8/2006 Hyde
7,101,395 B2 9/2006 Tremulis et al.
7,101,396 B2 9/2006 Artof et al.
7,112,207 B2 9/2006 Allen et al.
7,118,595 B2 10/2006 Ryan et al.
7,125,421 B2 10/2006 Tremulis et al.
7,150,737 B2 12/2006 Purdy et al.
7,159,593 B2 1/2007 McCarthy et al.
7,166,127 B2 1/2007 Spence et al.
7,169,187 B2 1/2007 Datta et al.
7,172,625 B2 2/2007 Shu et al.
7,175,660 B2 2/2007 Cartledge et al.
7,186,262 B2 3/2007 Saadat
7,186,264 B2 3/2007 Liddicoat et al.
7,189,199 B2 3/2007 McCarthy et al.
7,192,443 B2 3/2007 Solem et al.
7,220,277 B2 5/2007 Arru et al.
7,226,467 B2 6/2007 Lucatero et al.
7,226,477 B2 6/2007 Cox
7,226,647 B2 6/2007 Kasperchik et al.
7,229,452 B2 6/2007 Kayan
7,238,191 B2 7/2007 Bachmann
7,288,097 B2 10/2007 Seguin
7,294,148 B2 11/2007 McCarthy
7,311,728 B2 12/2007 Solem et al.
7,311,729 B2 12/2007 Mathis et al.
7,314,485 B2 1/2008 Mathis
7,316,710 B1 1/2008 Cheng et al.
7,329,279 B2 2/2008 Haug et al.
7,329,280 B2 2/2008 Bolling et al.
7,335,213 B1 2/2008 Hyde et al.
7,361,190 B2 4/2008 Shaoulian et al.
7,364,588 B2 4/2008 Mathis et al.
7,377,941 B2 5/2008 Rhee et al.
7,390,329 B2 6/2008 Westra et al.
7,404,824 B1 7/2008 Webler et al.
7,431,692 B2 10/2008 Zollinger et al.
7,442,207 B2 10/2008 Rafiee
7,452,376 B2 11/2008 Lim et al.
7,455,690 B2 11/2008 Cartledge et al.
7,485,142 B2 2/2009 Milo
7,485,143 B2 2/2009 Webler et al.
7,500,989 B2 3/2009 Solem et al.
7,507,252 B2 3/2009 Lashinski et al.
7,510,575 B2 3/2009 Spenser et al.
7,510,577 B2 3/2009 Moaddeb et al.
7,527,647 B2 5/2009 Spence
7,530,995 B2 5/2009 Quijano et al.
7,549,983 B2 6/2009 Roue et al.
7,559,936 B2 7/2009 Levine
7,562,660 B2 7/2009 Saadat
7,563,267 B2 7/2009 Goldfarb et al.
7,563,273 B2 7/2009 Goldfarb et al.
7,569,062 B1 8/2009 Kuehn et al.
7,585,321 B2 9/2009 Cribier
7,588,582 B2 9/2009 Starksen et al.
7,591,826 B2 9/2009 Alferness et al.
7,604,646 B2 10/2009 Goldfarb et al.
7,608,091 B2 10/2009 Goldfarb et al.
7,608,103 B2 10/2009 McCarthy
7,618,449 B2 11/2009 Tremulis et al.
7,625,403 B2 12/2009 Krivoruchko
7,632,303 B1 12/2009 Stalker et al.
7,635,329 B2 12/2009 Goldfarb et al.
7,635,386 B1 12/2009 Gammie
7,655,015 B2 2/2010 Goldfarb et al.
7,666,204 B2 2/2010 Thornton et al.
7,682,319 B2 3/2010 Martin et al.
7,682,369 B2 3/2010 Seguin
7,686,822 B2 3/2010 Shayani
7,699,892 B2 4/2010 Rafiee et al.
7,704,269 B2 4/2010 St. Goar et al.
7,704,277 B2 4/2010 Zakay et al.
7,722,666 B2 5/2010 Lafontaine
7,736,388 B2 6/2010 Goldfarb et al.
7,748,389 B2 7/2010 Salahieh et al.
7,753,924 B2 7/2010 Starksen et al.
7,758,632 B2 7/2010 Hojeibane et al.
7,780,726 B2 8/2010 Seguin
7,871,368 B2 1/2011 Zollinger et al.
7,871,433 B2 1/2011 Lattouf
7,883,475 B2 2/2011 Dupont et al.
7,883,538 B2 2/2011 To et al.
7,892,281 B2 2/2011 Seguin et al.
7,927,370 B2 4/2011 Webler et al.
7,927,371 B2 4/2011 Navia et al.
7,942,927 B2 5/2011 Kaye et al.
7,947,056 B2 5/2011 Griego et al.
7,955,315 B2 6/2011 Feinberg et al.
7,955,377 B2 6/2011 Melsheimer
7,981,152 B1 7/2011 Webler et al.
7,992,567 B2 8/2011 Hirotsuka et al.
7,993,368 B2 8/2011 Gambale et al.
7,993,397 B2 8/2011 Lashinski et al.
8,012,201 B2 9/2011 Lashinski et al.
8,034,103 B2 10/2011 Burriesci et al.
8,052,592 B2 11/2011 Goldfarb et al.
8,057,493 B2 11/2011 Goldfarb et al.
8,062,355 B2 11/2011 Figulla et al.
8,070,804 B2 12/2011 Hyde et al.
8,070,805 B2 12/2011 Vidlund et al.
8,075,616 B2 12/2011 Solem et al.
8,100,964 B2 1/2012 Spence
8,123,801 B2 2/2012 Milo
8,142,493 B2 3/2012 Spence et al.
8,142,495 B2 3/2012 Hasenkam et al.
8,142,496 B2 3/2012 Berreklouw

(56) References Cited

U.S. PATENT DOCUMENTS 8,147,542 B2 4/2012 Maisano et al.
8,152,844 B2 4/2012 Rao et al.
8,163,013 B2 4/2012 Machold et al.
8,187,299 B2 5/2012 Goldfarb et al.
8,187,324 B2 5/2012 Webler et al.
8,202,315 B2 6/2012 Hlavka et al.
8,206,439 B2 6/2012 Gomez Duran
8,216,302 B2 7/2012 Wilson et al.
8,231,671 B2 7/2012 Kim
8,262,725 B2 9/2012 Subramanian
8,265,758 B2 9/2012 Policker et al.
8,277,502 B2 10/2012 Miller et al.
8,287,584 B2 10/2012 Salahieh et al.
8,287,591 B2 10/2012 Keidar et al.
8,292,884 B2 10/2012 Levine et al.
8,303,608 B2 11/2012 Goldfarb et al.
8,323,334 B2 12/2012 Deem et al.
8,328,868 B2 12/2012 Paul et al.
8,333,777 B2 12/2012 Schaller et al.
8,343,173 B2 1/2013 Starksen et al.
8,343,174 B2 1/2013 Goldfarb et al.
8,343,213 B2 1/2013 Salahieh et al.
8,349,002 B2 1/2013 Milo
8,353,956 B2 1/2013 Miller et al.
8,357,195 B2 1/2013 Kuehn
8,382,829 B1 2/2013 Call et al.
8,388,680 B2 3/2013 Starksen et al.
8,393,517 B2 3/2013 Milo
8,419,825 B2 4/2013 Burgler et al.
8,430,926 B2 4/2013 Kirson
8,449,573 B2 5/2013 Chu
8,449,599 B2 5/2013 Chau et al.
8,454,686 B2 6/2013 Alkhatib
8,460,370 B2 6/2013 Zakay
8,460,371 B2 6/2013 Hlavka et al.
8,475,491 B2 7/2013 Milo
8,475,525 B2 7/2013 Maisano et al.
8,480,732 B2 7/2013 Subramanian
8,518,107 B2 8/2013 Tsukashima et al.
8,523,940 B2 9/2013 Richardson et al.
8,551,161 B2 10/2013 Dolan
8,585,755 B2 11/2013 Chau et al.
8,591,576 B2 11/2013 Hasenkam et al.
8,608,797 B2 12/2013 Gross et al.
8,628,569 B2 1/2014 Benichou et al.
8,628,571 B1 1/2014 Hacohen et al.
8,641,727 B2 2/2014 Starksen et al.
8,652,202 B2 2/2014 Alon et al.
8,652,203 B2 2/2014 Quadri et al.
8,679,174 B2 3/2014 Ottma et al.
8,685,086 B2 4/2014 Navia et al.
8,728,097 B1 5/2014 Sugimoto et al.
8,728,155 B2 5/2014 Montorfano et al.
8,734,467 B2 5/2014 Miller et al.
8,734,699 B2 5/2014 Heideman et al.
8,740,920 B2 6/2014 Goldfarb et al.
8,747,463 B2 6/2014 Fogarty et al.
8,778,021 B2 7/2014 Cartledge
8,784,481 B2 7/2014 Alkhatib et al.
8,790,367 B2 7/2014 Nguyen et al.
8,790,394 B2 7/2014 Miller et al.
8,795,298 B2 8/2014 Hernlund et al.
8,795,355 B2 8/2014 Alkhatib
8,795,356 B2 8/2014 Quadri et al.
8,795,357 B2 8/2014 Yohanan et al.
8,808,366 B2 8/2014 Braido et al.
8,808,368 B2 8/2014 Maisano et al.
8,845,717 B2 9/2014 Khairkhahan et al.
8,845,723 B2 9/2014 Spence et al.
8,852,261 B2 10/2014 White
8,852,272 B2 10/2014 Gross et al.
8,858,623 B2 10/2014 Miller et al.
8,864,822 B2 10/2014 Spence et al.
8,870,948 B1 10/2014 Erzberger et al.
8,870,949 B2 10/2014 Rowe
8,888,843 B2 11/2014 Khairkhahan et al.
8,889,861 B2 11/2014 Skead et al.
8,894,702 B2 11/2014 Quadri et al.
8,911,461 B2 12/2014 Traynor et al.
8,911,494 B2 12/2014 Hammer et al.
8,926,696 B2 1/2015 Cabiri et al.
8,926,697 B2 1/2015 Gross et al.
8,932,343 B2 1/2015 Alkhatib et al.
8,932,348 B2 1/2015 Solem et al.
8,940,044 B2 1/2015 Hammer et al.
8,945,211 B2 2/2015 Sugimoto
8,951,285 B2 2/2015 Sugimoto et al.
8,951,286 B2 2/2015 Sugimoto et al.
8,961,594 B2 2/2015 Maisano et al.
8,961,595 B2 2/2015 Alkhatib
8,961,602 B2 2/2015 Kovach et al.
8,979,922 B2 3/2015 Jayasinghe et al.
8,992,604 B2 3/2015 Gross et al.
9,005,273 B2 4/2015 Salahieh et al.
9,011,520 B2 4/2015 Miller et al.
9,011,530 B2 4/2015 Reich et al.
9,023,100 B2 5/2015 Quadri et al.
9,072,603 B2 7/2015 Tuval et al.
9,107,749 B2 8/2015 Bobo et al.
9,119,719 B2 9/2015 Zipory et al.
9,125,632 B2 9/2015 Loulmet et al.
9,125,742 B2 9/2015 Yoganathan et al.
9,138,316 B2 9/2015 Bielefeld
9,173,646 B2 11/2015 Fabro
9,173,711 B2 11/2015 Butler et al.
9,180,005 B1 11/2015 Lashinski et al.
9,180,007 B2 11/2015 Reich et al.
9,192,472 B2 11/2015 Gross et al.
9,198,756 B2 12/2015 Aklog et al.
9,226,825 B2 1/2016 Starksen et al.
9,265,608 B2 2/2016 Miller et al.
9,326,857 B2 5/2016 Cartledge et al.
9,414,921 B2 8/2016 Miller et al.
9,427,316 B2 8/2016 Schweich, Jr. et al.
9,474,606 B2 10/2016 Zipory et al.
9,526,613 B2 12/2016 Gross et al.
9,561,104 B2 2/2017 Miller et al.
9,579,090 B1 2/2017 Simms et al.
9,693,865 B2 7/2017 Gilmore et al.
9,730,793 B2 8/2017 Reich et al.
9,788,941 B2 10/2017 Hacohen
9,801,720 B2 10/2017 Gilmore et al.
9,907,547 B2 3/2018 Gilmore et al.
10,368,852 B2 8/2019 Gerhardt et al.
2001/0021874 A1 9/2001 Carpentier et al.
2002/0022862 A1 2/2002 Grafton et al.
2002/0082525 A1 6/2002 Oslund et al.
2002/0087048 A1 7/2002 Brock et al.
2002/0103532 A1 8/2002 Langberg et al.
2002/0120292 A1 8/2002 Morgan
2002/0151916 A1 10/2002 Muramatsu et al.
2002/0151970 A1 10/2002 Garrison et al.
2002/0169358 A1 11/2002 Mortier et al.
2002/0177904 A1 11/2002 Huxel et al.
2002/0188301 A1 12/2002 Dallara et al.
2002/0188350 A1 12/2002 Arru et al.
2002/0198586 A1 12/2002 Inoue
2003/0050693 A1 3/2003 Quijano et al.
2003/0078465 A1 4/2003 Pai et al.
2003/0078653 A1 4/2003 Vesely et al.
2003/0083538 A1 5/2003 Adams et al.
2003/0093148 A1 5/2003 Bolling et al.
2003/0105519 A1 6/2003 Fasol et al.
2003/0114901 A1 6/2003 Loeb et al.
2003/0120340 A1 6/2003 Liska et al.
2003/0144657 A1 7/2003 Bowe et al.
2003/0167062 A1 9/2003 Gambale et al.
2003/0171760 A1 9/2003 Gambale
2003/0199974 A1 10/2003 Lee et al.
2003/0204193 A1 10/2003 Gabriel et al.
2003/0204195 A1 10/2003 Keane et al.
2003/0229350 A1 12/2003 Kay
2003/0229395 A1 12/2003 Cox
2004/0002735 A1 1/2004 Lizardi et al.

(56) References Cited

U.S. PATENT DOCUMENTS

| | | | |
|---|---|---|---|
| 2004/0010287 | A1 | 1/2004 | Bonutti |
| 2004/0019359 | A1 | 1/2004 | Worley et al. |
| 2004/0019377 | A1 | 1/2004 | Taylor et al. |
| 2004/0024451 | A1 | 2/2004 | Johnson et al. |
| 2004/0039442 | A1 | 2/2004 | St. Goar et al. |
| 2004/0044350 | A1 | 3/2004 | Martin et al. |
| 2004/0049211 | A1 | 3/2004 | Tremulis et al. |
| 2004/0059413 | A1 | 3/2004 | Argento |
| 2004/0068273 | A1 | 4/2004 | Fariss et al. |
| 2004/0106950 | A1 | 6/2004 | Grafton et al. |
| 2004/0111095 | A1 | 6/2004 | Gordon et al. |
| 2004/0122514 | A1 | 6/2004 | Fogarty et al. |
| 2004/0127982 | A1 | 7/2004 | Machold et al. |
| 2004/0133274 | A1 | 7/2004 | Webler et al. |
| 2004/0133374 | A1 | 7/2004 | Kattan |
| 2004/0138744 | A1 | 7/2004 | Lashinski et al. |
| 2004/0138745 | A1 | 7/2004 | Macoviak et al. |
| 2004/0148019 | A1 | 7/2004 | Vidlund et al. |
| 2004/0148020 | A1 | 7/2004 | Vidlund et al. |
| 2004/0148021 | A1 | 7/2004 | Cartledge et al. |
| 2004/0176788 | A1 | 9/2004 | Opolski |
| 2004/0181287 | A1 | 9/2004 | Gellman |
| 2004/0186566 | A1 | 9/2004 | Hindrichs et al. |
| 2004/0193191 | A1 | 9/2004 | Starksen et al. |
| 2004/0243227 | A1 | 12/2004 | Starksen et al. |
| 2004/0260317 | A1 | 12/2004 | Bloom et al. |
| 2004/0260344 | A1 | 12/2004 | Lyons et al. |
| 2004/0260393 | A1 | 12/2004 | Rahdert et al. |
| 2004/0260394 | A1 | 12/2004 | Douk et al. |
| 2004/0267358 | A1 | 12/2004 | Reitan |
| 2005/0004668 | A1 | 1/2005 | Aklog et al. |
| 2005/0010287 | A1 | 1/2005 | Macoviak et al. |
| 2005/0010787 | A1 | 1/2005 | Tarbouriech |
| 2005/0016560 | A1 | 1/2005 | Voughlohn |
| 2005/0049692 | A1 | 3/2005 | Numamoto et al. |
| 2005/0055038 | A1 | 3/2005 | Kelleher et al. |
| 2005/0055087 | A1 | 3/2005 | Starksen |
| 2005/0060030 | A1 | 3/2005 | Lashinski et al. |
| 2005/0065601 | A1 | 3/2005 | Lee et al. |
| 2005/0070999 | A1 | 3/2005 | Spence |
| 2005/0075654 | A1 | 4/2005 | Kelleher |
| 2005/0075727 | A1 | 4/2005 | Wheatley |
| 2005/0090827 | A1 | 4/2005 | Gedebou |
| 2005/0090834 | A1 | 4/2005 | Chiang et al. |
| 2005/0096740 | A1 | 5/2005 | Langberg et al. |
| 2005/0107871 | A1 | 5/2005 | Realyvasquez et al. |
| 2005/0119734 | A1 | 6/2005 | Spence et al. |
| 2005/0125002 | A1 | 6/2005 | Baran et al. |
| 2005/0125011 | A1 | 6/2005 | Spence et al. |
| 2005/0131533 | A1 | 6/2005 | Alfieri et al. |
| 2005/0137686 | A1 | 6/2005 | Salahieh et al. |
| 2005/0137688 | A1 | 6/2005 | Salahieh et al. |
| 2005/0137695 | A1 | 6/2005 | Salahieh et al. |
| 2005/0159728 | A1 | 7/2005 | Armour et al. |
| 2005/0159810 | A1 | 7/2005 | Filsoufi |
| 2005/0171601 | A1 | 8/2005 | Cosgrove et al. |
| 2005/0177180 | A1 | 8/2005 | Kaganov et al. |
| 2005/0177228 | A1 | 8/2005 | Solem et al. |
| 2005/0187568 | A1 | 8/2005 | Klenk et al. |
| 2005/0192596 | A1 | 9/2005 | Jugenheimer et al. |
| 2005/0203549 | A1 | 9/2005 | Realyvasquez |
| 2005/0203606 | A1 | 9/2005 | VanCamp |
| 2005/0216039 | A1 | 9/2005 | Lederman |
| 2005/0216079 | A1 | 9/2005 | MaCoviak |
| 2005/0222665 | A1 | 10/2005 | Aranyi |
| 2005/0234481 | A1 | 10/2005 | Waller |
| 2005/0240199 | A1 | 10/2005 | Martinek et al. |
| 2005/0251177 | A1 | 11/2005 | Saadat et al. |
| 2005/0256532 | A1 | 11/2005 | Nayak et al. |
| 2005/0267478 | A1 | 12/2005 | Corradi et al. |
| 2005/0273138 | A1 | 12/2005 | To et al. |
| 2005/0288778 | A1 | 12/2005 | Shaoulian et al. |
| 2006/0004442 | A1 | 1/2006 | Spenser et al. |
| 2006/0004443 | A1 | 1/2006 | Liddicoat et al. |
| 2006/0020326 | A9 | 1/2006 | Bolduc et al. |
| 2006/0020327 | A1 | 1/2006 | Lashinski et al. |
| 2006/0020333 | A1 | 1/2006 | Lashinski et al. |
| 2006/0020336 | A1 | 1/2006 | Liddicoat |
| 2006/0025787 | A1 | 2/2006 | Morales et al. |
| 2006/0025858 | A1 | 2/2006 | Alameddine |
| 2006/0030885 | A1 | 2/2006 | Hyde |
| 2006/0041319 | A1 | 2/2006 | Taylor et al. |
| 2006/0069429 | A1 | 3/2006 | Spence et al. |
| 2006/0074486 | A1 | 4/2006 | Liddicoat et al. |
| 2006/0085012 | A1 | 4/2006 | Dolan |
| 2006/0095009 | A1 | 5/2006 | Lampropoulos et al. |
| 2006/0106423 | A1 | 5/2006 | Weisel et al. |
| 2006/0116757 | A1 | 6/2006 | Lashinski et al. |
| 2006/0122633 | A1 | 6/2006 | To et al. |
| 2006/0129166 | A1 | 6/2006 | Lavelle |
| 2006/0142694 | A1 | 6/2006 | Bednarek et al. |
| 2006/0149280 | A1 | 7/2006 | Harvie et al. |
| 2006/0149368 | A1 | 7/2006 | Spence |
| 2006/0161265 | A1 | 7/2006 | Levine et al. |
| 2006/0173251 | A1 | 8/2006 | Govari et al. |
| 2006/0184240 | A1 | 8/2006 | Jimenez et al. |
| 2006/0184242 | A1 | 8/2006 | Lichtenstein |
| 2006/0195134 | A1 | 8/2006 | Crittenden |
| 2006/0206203 | A1 | 9/2006 | Yang et al. |
| 2006/0212048 | A1 | 9/2006 | Crainich |
| 2006/0241622 | A1 | 10/2006 | Zergiebel |
| 2006/0241656 | A1 | 10/2006 | Starksen et al. |
| 2006/0241748 | A1 | 10/2006 | Lee et al. |
| 2006/0247763 | A1 | 11/2006 | Slater |
| 2006/0259135 | A1 | 11/2006 | Navia et al. |
| 2006/0271175 | A1 | 11/2006 | Woolfson et al. |
| 2006/0276871 | A1 | 12/2006 | Lamson et al. |
| 2006/0282161 | A1 | 12/2006 | Huynh et al. |
| 2006/0287661 | A1 | 12/2006 | Bolduc et al. |
| 2006/0287716 | A1 | 12/2006 | Banbury et al. |
| 2007/0001627 | A1 | 1/2007 | Lin et al. |
| 2007/0010800 | A1 | 1/2007 | Weitzner et al. |
| 2007/0016287 | A1 | 1/2007 | Cartledge et al. |
| 2007/0016288 | A1 | 1/2007 | Gurskis et al. |
| 2007/0021781 | A1 | 1/2007 | Jervis et al. |
| 2007/0027533 | A1 | 2/2007 | Douk |
| 2007/0027536 | A1 | 2/2007 | Mihaljevic et al. |
| 2007/0032823 | A1 | 2/2007 | Tegg |
| 2007/0038221 | A1 | 2/2007 | Fine et al. |
| 2007/0038293 | A1 | 2/2007 | St.Goar et al. |
| 2007/0038296 | A1 | 2/2007 | Navia et al. |
| 2007/0039425 | A1 | 2/2007 | Wang |
| 2007/0049942 | A1 | 3/2007 | Hindrichs et al. |
| 2007/0049970 | A1 | 3/2007 | Belef et al. |
| 2007/0051377 | A1 | 3/2007 | Douk et al. |
| 2007/0055206 | A1 | 3/2007 | To et al. |
| 2007/0060922 | A1 | 3/2007 | Dreyfuss |
| 2007/0061010 | A1 | 3/2007 | Hauser et al. |
| 2007/0066863 | A1 | 3/2007 | Rafiee et al. |
| 2007/0078297 | A1 | 4/2007 | Rafiee et al. |
| 2007/0080188 | A1 | 4/2007 | Spence et al. |
| 2007/0083168 | A1 | 4/2007 | Whiting et al. |
| 2007/0083235 | A1 | 4/2007 | Jervis et al. |
| 2007/0100427 | A1 | 5/2007 | Perouse |
| 2007/0106328 | A1 | 5/2007 | Wardle et al. |
| 2007/0112359 | A1 | 5/2007 | Kimura et al. |
| 2007/0112422 | A1 | 5/2007 | Dehdashtian |
| 2007/0112425 | A1 | 5/2007 | Schaller et al. |
| 2007/0118151 | A1 | 5/2007 | Davidson |
| 2007/0118154 | A1 | 5/2007 | Crabtree |
| 2007/0118213 | A1 | 5/2007 | Loulmet |
| 2007/0118215 | A1 | 5/2007 | Moaddeb |
| 2007/0142907 | A1 | 6/2007 | Moaddeb et al. |
| 2007/0162111 | A1 | 7/2007 | Fukamachi et al. |
| 2007/0173931 | A1 | 7/2007 | Tremulis et al. |
| 2007/0198082 | A1 | 8/2007 | Kapadia et al. |
| 2007/0219558 | A1 | 9/2007 | Deutsch |
| 2007/0239208 | A1 | 10/2007 | Crawford |
| 2007/0244554 | A1 | 10/2007 | Rafiee et al. |
| 2007/0244556 | A1 | 10/2007 | Rafiee et al. |
| 2007/0255397 | A1 | 11/2007 | Ryan et al. |
| 2007/0255400 | A1 | 11/2007 | Parravicini et al. |
| 2007/0270755 | A1 | 11/2007 | Von Oepen et al. |
| 2007/0276437 | A1 | 11/2007 | Call et al. |

(56) References Cited

U.S. PATENT DOCUMENTS

2007/0282375 A1 12/2007 Hindrichs et al.
2007/0282429 A1 12/2007 Hauser et al.
2007/0295172 A1 12/2007 Swartz
2007/0299424 A1 12/2007 Cumming et al.
2008/0004697 A1 1/2008 Lichtenstein et al.
2008/0027483 A1 1/2008 Cartledge et al.
2008/0027555 A1 1/2008 Hawkins
2008/0033460 A1 2/2008 Ziniti et al.
2008/0035160 A1 2/2008 Woodson et al.
2008/0039935 A1 2/2008 Buch et al.
2008/0051703 A1 2/2008 Thornton et al.
2008/0058595 A1 3/2008 Snoke et al.
2008/0065011 A1 3/2008 Marchand et al.
2008/0065204 A1 3/2008 Macoviak et al.
2008/0066764 A1 3/2008 Paraschac et al.
2008/0071366 A1 3/2008 Tuval et al.
2008/0086138 A1 4/2008 Stone et al.
2008/0086203 A1 4/2008 Roberts
2008/0091169 A1 4/2008 Heideman et al.
2008/0091257 A1 4/2008 Andreas et al.
2008/0097483 A1 4/2008 Ortiz et al.
2008/0097523 A1 4/2008 Bolduc et al.
2008/0103572 A1 5/2008 Gerber
2008/0140116 A1 6/2008 Bonutti
2008/0167713 A1 7/2008 Bolling
2008/0167714 A1 7/2008 St. Goar et al.
2008/0177380 A1 7/2008 Starksen et al.
2008/0195126 A1 8/2008 Solem
2008/0195200 A1 8/2008 Vidlund et al.
2008/0208265 A1 8/2008 Frazier et al.
2008/0221672 A1 9/2008 Lamphere et al.
2008/0228030 A1 9/2008 Godin
2008/0228223 A1 9/2008 Alkhatib
2008/0234729 A1 9/2008 Page et al.
2008/0262480 A1 10/2008 Stahler et al.
2008/0262609 A1 10/2008 Gross et al.
2008/0275300 A1 11/2008 Rothe et al.
2008/0275469 A1 11/2008 Fanton et al.
2008/0275551 A1 11/2008 Alfieri
2008/0281353 A1 11/2008 Aranyi et al.
2008/0281411 A1 11/2008 Berreklouw
2008/0287862 A1 11/2008 Weitzner et al.
2008/0288044 A1 11/2008 Osborne
2008/0288062 A1 11/2008 Andrieu et al.
2008/0294251 A1 11/2008 Annest et al.
2008/0300537 A1 12/2008 Bowman
2008/0300629 A1 12/2008 Surti
2008/0312506 A1 12/2008 Spivey et al.
2009/0024110 A1 1/2009 Heideman et al.
2009/0028670 A1 1/2009 Garcia et al.
2009/0043381 A1 2/2009 Macoviak et al.
2009/0054723 A1 2/2009 Khairkhahan et al.
2009/0054969 A1 2/2009 Salahieh et al.
2009/0062866 A1 3/2009 Jackson
2009/0076586 A1 3/2009 Hauser et al.
2009/0076600 A1 3/2009 Quinn
2009/0082797 A1 3/2009 Fung et al.
2009/0088837 A1 4/2009 Gillinov et al.
2009/0093877 A1 4/2009 Keidar et al.
2009/0099650 A1 4/2009 Bolduc et al.
2009/0105816 A1 4/2009 Olsen et al.
2009/0125102 A1 5/2009 Cartledge et al.
2009/0166913 A1 7/2009 Guo et al.
2009/0171439 A1 7/2009 Nissl
2009/0177266 A1 7/2009 Powell et al.
2009/0177274 A1 7/2009 Scorsin et al.
2009/0248148 A1 10/2009 Shaolian et al.
2009/0254103 A1 10/2009 Deutsch
2009/0264994 A1 10/2009 Saadat
2009/0287231 A1 11/2009 Brooks et al.
2009/0287304 A1 11/2009 Dahlgren et al.
2009/0299409 A1 12/2009 Coe et al.
2009/0326648 A1 12/2009 Machold et al.
2010/0001038 A1 1/2010 Levin et al.
2010/0010538 A1 1/2010 Juravic et al.
2010/0023118 A1 1/2010 Medlock et al.
2010/0030014 A1 2/2010 Ferrazzi
2010/0030328 A1 2/2010 Seguin et al.
2010/0042147 A1 2/2010 Janovsky et al.
2010/0049213 A1 2/2010 Serina et al.
2010/0063542 A1 3/2010 van der Burg et al.
2010/0063550 A1 3/2010 Felix et al.
2010/0076499 A1 3/2010 McNamara et al.
2010/0094248 A1 4/2010 Nguyen et al.
2010/0094314 A1 4/2010 Hernlund et al.
2010/0106141 A1 4/2010 Osypka et al.
2010/0114180 A1 5/2010 Rock et al.
2010/0121349 A1 5/2010 Meier et al.
2010/0121435 A1 5/2010 Subramanian et al.
2010/0121437 A1 5/2010 Subramanian et al.
2010/0130989 A1 5/2010 Bourque et al.
2010/0130992 A1 5/2010 Machold et al.
2010/0152845 A1 6/2010 Bloom et al.
2010/0161043 A1 6/2010 Maisano et al.
2010/0161047 A1 6/2010 Cabiri
2010/0168845 A1 7/2010 Wright
2010/0174358 A1 7/2010 Rabkin et al.
2010/0179574 A1 7/2010 Longoria et al.
2010/0217184 A1 8/2010 Koblish et al.
2010/0217382 A1 8/2010 Chau et al.
2010/0234935 A1 9/2010 Bashiri et al.
2010/0249497 A1 9/2010 Peine et al.
2010/0249908 A1 9/2010 Chau et al.
2010/0249915 A1 9/2010 Zhang
2010/0249920 A1 9/2010 Bolling et al.
2010/0262232 A1 10/2010 Annest
2010/0262233 A1 10/2010 He
2010/0286628 A1 11/2010 Gross
2010/0298929 A1 11/2010 Thornton et al.
2010/0305475 A1 12/2010 Hinchliffe et al.
2010/0324598 A1 12/2010 Anderson
2011/0004210 A1 1/2011 Johnson et al.
2011/0004298 A1 1/2011 Lee et al.
2011/0009956 A1 1/2011 Cartledge et al.
2011/0011917 A1 1/2011 Loulmet
2011/0026208 A1 2/2011 Utsuro et al.
2011/0029066 A1 2/2011 Gilad et al.
2011/0035000 A1 2/2011 Nieminen et al.
2011/0066231 A1 3/2011 Cartledge et al.
2011/0067770 A1 3/2011 Pederson et al.
2011/0071626 A1 3/2011 Wright et al.
2011/0082538 A1 4/2011 Dahlgren et al.
2011/0087146 A1 4/2011 Ryan et al.
2011/0093002 A1 4/2011 Rucker et al.
2011/0118832 A1 5/2011 Punjabi
2011/0137410 A1 6/2011 Hacohen
2011/0144576 A1 6/2011 Rothe et al.
2011/0144703 A1 6/2011 Krause et al.
2011/0202130 A1 8/2011 Cartledge et al.
2011/0208283 A1 8/2011 Rust
2011/0230941 A1 9/2011 Markus
2011/0230961 A1 9/2011 Langer et al.
2011/0238088 A1 9/2011 Bolduc et al.
2011/0257433 A1 10/2011 Walker
2011/0257633 A1 10/2011 Cartledge et al.
2011/0264208 A1 10/2011 Duffy et al.
2011/0276062 A1 11/2011 Bolduc
2011/0288435 A1 11/2011 Christy et al.
2011/0301498 A1 12/2011 Maenhout et al.
2012/0053628 A1 3/2012 Sojka et al.
2012/0053642 A1 3/2012 Lozier et al.
2012/0065464 A1 3/2012 Ellis et al.
2012/0078355 A1 3/2012 Zipory et al.
2012/0078359 A1 3/2012 Li et al.
2012/0089022 A1 4/2012 House et al.
2012/0089125 A1 4/2012 Scheibe et al.
2012/0095552 A1 4/2012 Spence et al.
2012/0101571 A1 4/2012 Thambar et al.
2012/0109155 A1 5/2012 Robinson et al.
2012/0143226 A1 6/2012 Belson et al.
2012/0150290 A1 6/2012 Gabbay
2012/0158021 A1 6/2012 Morrill
2012/0158023 A1 6/2012 Mitelberg et al.
2012/0179086 A1 7/2012 Shank et al.

(56) References Cited

U.S. PATENT DOCUMENTS

2012/0191182 A1 7/2012 Hauser et al.
2012/0226349 A1 9/2012 Tuval et al.
2012/0239142 A1 9/2012 Liu et al.
2012/0245604 A1 9/2012 Tegzes
2012/0271198 A1 10/2012 Whittaker et al.
2012/0296349 A1 11/2012 Smith et al.
2012/0296417 A1 11/2012 Hill et al.
2012/0310330 A1 12/2012 Buchbinder et al.
2012/0323313 A1 12/2012 Seguin
2013/0030522 A1 1/2013 Rowe et al.
2013/0046373 A1 2/2013 Cartledge et al.
2013/0053884 A1 2/2013 Roorda
2013/0079873 A1 3/2013 Migliazza et al.
2013/0085529 A1 4/2013 Housman
2013/0090724 A1 4/2013 Subramanian et al.
2013/0096673 A1 4/2013 Hill et al.
2013/0116776 A1 5/2013 Gross et al.
2013/0116780 A1 5/2013 Miller et al.
2013/0123910 A1 5/2013 Cartledge et al.
2013/0131791 A1 5/2013 Hlavka et al.
2013/0166017 A1 6/2013 Cartledge et al.
2013/0190863 A1 7/2013 Call et al.
2013/0204361 A1 8/2013 Adams et al.
2013/0218206 A1 8/2013 Gadlage
2013/0226289 A1 8/2013 Shaolian et al.
2013/0226290 A1 8/2013 Yellin et al.
2013/0231701 A1 9/2013 Voss et al.
2013/0233324 A1 9/2013 Witt et al.
2013/0268069 A1 10/2013 Zakai et al.
2013/0282059 A1 10/2013 Ketai et al.
2013/0289718 A1 10/2013 Tsukashima et al.
2013/0297013 A1 11/2013 Klima et al.
2013/0304093 A1 11/2013 Serina et al.
2013/0331930 A1 12/2013 Rowe et al.
2014/0067054 A1 3/2014 Chau et al.
2014/0081394 A1 3/2014 Keranen et al.
2014/0088368 A1 3/2014 Park
2014/0088646 A1 3/2014 Wales et al.
2014/0094826 A1 4/2014 Sutherland et al.
2014/0094903 A1 4/2014 Miller et al.
2014/0094906 A1 4/2014 Spence et al.
2014/0114390 A1 4/2014 Tobis et al.
2014/0135799 A1 5/2014 Henderson
2014/0142619 A1 5/2014 Serina et al.
2014/0142695 A1 5/2014 Gross et al.
2014/0148849 A1 5/2014 Serina et al.
2014/0155783 A1 6/2014 Starksen et al.
2014/0163615 A1 6/2014 Gadlage et al.
2014/0163670 A1 6/2014 Alon et al.
2014/0163690 A1 6/2014 White
2014/0188108 A1 7/2014 Goodine et al.
2014/0188140 A1 7/2014 Meier et al.
2014/0188215 A1 7/2014 Hlavka et al.
2014/0194976 A1 7/2014 Starksen et al.
2014/0207231 A1 7/2014 Hacohen et al.
2014/0243859 A1 8/2014 Robinson
2014/0243894 A1 8/2014 Groothuis et al.
2014/0243963 A1 8/2014 Sheps et al.
2014/0251042 A1 9/2014 Asselin et al.
2014/0275757 A1 9/2014 Goodwin et al.
2014/0276648 A1 9/2014 Hammer et al.
2014/0296962 A1 10/2014 Cartledge et al.
2014/0303649 A1 10/2014 Nguyen et al.
2014/0303720 A1 10/2014 Sugimoto et al.
2014/0309661 A1 10/2014 Sheps et al.
2014/0309730 A1 10/2014 Alon et al.
2014/0343668 A1 11/2014 Zipory et al.
2014/0350660 A1 11/2014 Cocks et al.
2014/0379006 A1 12/2014 Sutherland et al.
2015/0018940 A1 1/2015 Quill et al.
2015/0051697 A1 2/2015 Spence et al.
2015/0066139 A1 3/2015 Van Bladel et al.
2015/0081014 A1 3/2015 Gross et al.
2015/0094800 A1 4/2015 Chawla
2015/0100116 A1 4/2015 Mohl et al.
2015/0112432 A1 4/2015 Reich et al.
2015/0127097 A1 5/2015 Neumann et al.
2015/0133997 A1 5/2015 Deitch et al.
2015/0182336 A1 7/2015 Zipory et al.
2015/0230919 A1 8/2015 Chau et al.
2015/0272586 A1 10/2015 Herman et al.
2015/0272734 A1 10/2015 Sheps et al.
2015/0282931 A1 10/2015 Brunnett et al.
2015/0351910 A1 12/2015 Gilmore et al.
2016/0008132 A1 1/2016 Cabiri et al.
2016/0029920 A1 2/2016 Kronstrom et al.
2016/0030034 A1 2/2016 Graul et al.
2016/0058557 A1 3/2016 Reich et al.
2016/0113767 A1 4/2016 Miller et al.
2016/0120642 A1 5/2016 Shaolian et al.
2016/0120645 A1 5/2016 Alon
2016/0158008 A1 6/2016 Miller et al.
2016/0242762 A1 8/2016 Gilmore et al.
2016/0256149 A1 9/2016 Sampson et al.
2016/0256274 A1 9/2016 Hayoz et al.
2016/0262755 A1 9/2016 Zipory et al.
2016/0302917 A1 10/2016 Schewel
2016/0317302 A1 11/2016 Madjarov et al.
2016/0346084 A1 12/2016 Taylor et al.
2016/0361058 A1 12/2016 Bolduc et al.
2016/0361168 A1 12/2016 Gross et al.
2016/0361169 A1 12/2016 Gross et al.
2017/0000609 A1 1/2017 Gross et al.
2017/0042670 A1 2/2017 Shaolian et al.
2017/0049435 A1 2/2017 Sauer et al.
2017/0086975 A1 3/2017 Gilmore et al.
2017/0100119 A1 4/2017 Baird et al.
2017/0224489 A1 8/2017 Starksen et al.
2017/0245993 A1 8/2017 Gross et al.
2018/0008409 A1 1/2018 Kutzik et al.
2018/0049875 A1 2/2018 Iflah et al.
2018/0140420 A1 5/2018 Hayoz et al.
2018/0168803 A1 6/2018 Pesce et al.
2018/0177503 A1 6/2018 Miraki
2018/0228608 A1 8/2018 Sheps et al.
2018/0256334 A1 9/2018 Sheps et al.
2018/0280019 A1 10/2018 Azar et al.
2018/0289480 A1 10/2018 D'ambra et al.
2018/0318080 A1 11/2018 Quill et al.
2018/0318083 A1 11/2018 Bolling et al.
2019/0000625 A1 1/2019 O'Carroll et al.
2019/0029498 A1 1/2019 Mankowski et al.
2019/0038411 A1 2/2019 Alon
2019/0091445 A1 3/2019 House
2019/0111239 A1 4/2019 Bolduc et al.
2019/0117400 A1 4/2019 Medema et al.
2019/0125325 A1 5/2019 Sheps et al.
2019/0151093 A1 5/2019 Keidar et al.
2019/0159898 A1 5/2019 Kutzik et al.
2019/0175344 A1 6/2019 Khairkhahan
2019/0175345 A1 6/2019 Schaffner et al.
2019/0175346 A1 6/2019 Schaffner et al.
2019/0183648 A1 6/2019 Trapp et al.
2019/0240023 A1 8/2019 Spence et al.
2019/0290260 A1 9/2019 Caffes et al.
2019/0290431 A1 9/2019 Genovese et al.
2019/0321049 A1 10/2019 Herman et al.
2019/0343633 A1 11/2019 Garvin et al.
2020/0015810 A1 1/2020 Piccirillo
2020/0015971 A1 1/2020 Brauon et al.
2020/0178956 A1 6/2020 Mitelberg et al.
2020/0289267 A1 9/2020 Peleg et al.
2020/0337840 A1 10/2020 Reich
2020/0390551 A1 12/2020 McCarthy
2021/0015475 A1 1/2021 Lau
2021/0052387 A1 2/2021 Greenan et al.
2021/0059820 A1 3/2021 Clark et al.
2021/0085461 A1 3/2021 Neumark et al.
2021/0093453 A1 4/2021 Peleg et al.
2021/0145584 A1 5/2021 Kasher et al.
2022/0071620 A1 3/2022 Brauon et al.
2022/0096232 A1 3/2022 Skaro et al.
2022/0110656 A1 4/2022 Azar et al.
2022/0142779 A1 5/2022 Sharon

(56) References Cited

U.S. PATENT DOCUMENTS

| | | | |
|---|---|---|---|
| 2022/0176076 | A1 | 6/2022 | Keidar |
| 2022/0233316 | A1 | 7/2022 | Sheps et al. |
| 2022/0273436 | A1 | 9/2022 | Aviv et al. |
| 2022/0313438 | A1 | 10/2022 | Chappel-Ram |
| 2022/0323221 | A1 | 10/2022 | Sharon et al. |
| 2023/0016867 | A1 | 1/2023 | Tennenbaum |
| 2023/0218291 | A1 | 7/2023 | Zarbatany et al. |
| 2023/0320856 | A1 | 10/2023 | Zarbatany et al. |
| 2024/0008985 | A1 | 1/2024 | Yuan et al. |
| 2024/0099736 | A1 | 3/2024 | Elsheikh et al. |

FOREIGN PATENT DOCUMENTS

| | | | |
|---|---|---|---|
| EP | 3531975 | A1 | 9/2019 |
| JP | H09248307 | A | 9/1997 |
| JP | H09510382 | A | 10/1997 |
| WO | 9205093 | A1 | 4/1992 |
| WO | 9846149 | A1 | 10/1998 |
| WO | WO-2002085250 | A2 | 10/2002 |
| WO | 02085250 | A3 | 2/2003 |
| WO | 03047467 | A1 | 6/2003 |
| WO | WO-2006105084 | A2 | 10/2006 |
| WO | 2007098512 | A1 | 9/2007 |
| WO | 2010000454 | A1 | 1/2010 |
| WO | WO-2012176195 | A2 | 12/2012 |
| WO | 2012176195 | A3 | 3/2013 |
| WO | WO-2013069019 | A2 | 5/2013 |
| WO | 2014064964 | A1 | 5/2014 |
| WO | 2016174669 | A1 | 11/2016 |
| WO | WO-2017109151 | A1 | 6/2017 |
| WO | 2017204848 | A1 | 11/2017 |
| WO | 2018148324 | A1 | 8/2018 |
| WO | 2019145941 | A1 | 8/2019 |
| WO | 2019145947 | A1 | 8/2019 |
| WO | 2019182645 | A1 | 9/2019 |
| WO | 2019224814 | A1 | 11/2019 |
| WO | 2020240282 | A2 | 12/2020 |
| WO | 2021014440 | A2 | 1/2021 |
| WO | 2021038559 | A1 | 3/2021 |
| WO | 2021038560 | A1 | 3/2021 |
| WO | 2022064401 | A2 | 3/2022 |
| WO | 2022090907 | A1 | 5/2022 |
| WO | 2022101817 | A2 | 5/2022 |
| WO | 2022153131 | A1 | 7/2022 |
| WO | 2022157592 | A1 | 7/2022 |
| WO | 2022172108 | A1 | 8/2022 |
| WO | 2022172149 | A1 | 8/2022 |
| WO | 2022200972 | A1 | 9/2022 |
| WO | 2022224071 | A1 | 10/2022 |
| WO | 2022229815 | A1 | 11/2022 |
| WO | 2022250983 | A1 | 12/2022 |

OTHER PUBLICATIONS

Ahmadi, A., G. Spillner, and Th Johannesson. "Hemodynamic changes following experimental production and correction of acute mitral regurgitation with an adjustable ring prosthesis." The Thoracic and cardiovascular surgeon36.06 (1988): 313-319.

Ahmadi, Ali et al. "Percutaneously adjustable pulmonary artery band." The Annals of thoracic surgery 60 (1995): S520-S522.

Alfieri et al., "An effective technique to correct anterior mitral leaflet prolapse," J Card 14(6):468-470 (1999).

Alfieri et al., "The double orifice technique in mitral valve repair: a simple solution for complex problems," Journal of Thoracic Cardiovascular Surgery 122:674-681 (2001).

Alfieri et al."Novel Suture Device for Beating-Heart Mitral Leaflet Approximation", Ann Thorac Surg. 2002, 74:1488-1493.

Alfieri, "The edge-to-edge repair of the mitral valve," [Abstract] 6th Annual NewEra Cardiac Care: Innovation & Technology, Heart Surgery Forum pp. 103. (2000).

Amplatzer Cardiac Plug brochure (English pages), AGA Medical Corporation (Plymouth, MN) (copyright 2008-2010, downloaded Jan. 11, 2011).

Amplatzer® Cribriform Occluder. A patient guide to Percutaneous, Transcatheter, Atrial Septal Defect Closuer, AGA Medical Corporation, Apr. 2008.

Amplatzer® Septal Occluder. A patient guide to the Non-Surgical Closuer of the Atrial Septal Defect Using the Amplatzer Septal Occluder System, AGA Medical Corporation, Apr. 2008.

Assad, Renato S. "Adjustable Pulmonary Artery Banding." (2014).

Brennan, Jennifer, 510(k) Summary of safety and effectiveness, Jan. 2008.

Daebritz, S. et al. "Experience with an adjustable pulmonary artery banding device in two cases: initial success-midterm failure." The Thoracic and cardiovascular surgeon 47.01 (1999): 51-52.

Dang NC et al. "Simplified Placement of Multiple Artificial Mitral Valve Chords," The Heart Surgery Forum #2005-1005, 8 (3) (2005).

Dictionary.com definition of "lock", Jul. 29, 2013.

Dieter RS, "Percutaneous valve repair: Update on mitral regurgitation and endovascular approaches to the mitral valve," Applications in Imaging, Cardiac Interventions, Supported by an educational grant from Amersham Health pp. 11-14 (2003).

Elliott, Daniel S., Gerald W. Timm, and David M. Barrett. "An implantable mechanical urinary sphincter: a new nonhydraulic design concept." Urology52.6 (1998): 1151-1154.

Langer et al. Ring plus String: Papillary muscle repositioning as an adjunctive repair technique for ischemic mitral regurgitation, The Journal of Thoracic Cardiovascular surgery vol. 133 No. 1, Jan. 2007.

Langer et al. Ring+String, Successful Repair technique for ischemic mitral regurgitation with severe leaflet Tethering, The Department of Thoracic Cardiovascular surgery, Hamburg, Germany, Nov. 2008.

Maisano, The double-orifice technique as a standardized approach to treat mitral . . . , European Journal of Cardio-thoracic Surgery 17 (2000) 201-205.

Odell JA et al., "Early Results 04yf a Simplified Method of Mitral Valve Annuloplasty," Circulation 92:150-154 (1995).

O'Reilly S et al., "Heart valve surgery pushes the envelope," Medtech Insight 8(3): 73, 99-108 (2006).

Park, Sang C. et al. "A percutaneously adjustable device for banding of the pulmonary trunk." International journal of cardiology 9.4 (1985): 477-484.

Swain CP et al., "An endoscopically deliverable tissue-transfixing device for securing biosensors in the gastrointestinal tract," Gastrointestinal Endoscopy 40(6): 730-734 (1994).

Swenson, O. An experimental implantable urinary sphincter. Invest Urol. Sep. 1976;14(2):100-3.

Swenson, O. and Malinin, T.I., 1978. An improved mechanical device for control of urinary incontinence. Investigative urology, 15(5), pp. 389-391.

Swenson, Orvar. "Internal device for control of urinary incontinence." Journal of pediatric surgery 7.5 (1972): 542-545.

Tajik, Abdul, "Two dimensional real-time ultrasonic imaging of the heart and great vessels", Mayo Clin Proc. vol. 53:271-303, 1978.

10
330
333
335
332
343
339
340
226
300
370
341
372
331
360
362,337
226,420
226,422
26
240
222
339,341

1480
923
920
940
226,916
921
953
1490
927
925
A
B
1950
951
1960
962
930
910
26,912
26
226,914
SECTION A–A
SECTION B–B
SECTION C–C
SECTION D–D
226
934
952
932
C
D
942
936

FASTENER AND TECHNIQUES THEREFOR

CROSS-REFERENCES TO RELATED APPLICATIONS

The present application is a Continuation of U.S. patent application Ser. No. 17/478,800 to Brauon et al., titled "Fastener and techniques therefor," filed on Sep. 17, 2021, which published as US 2022/0183842; which is a Continuation of U.S. patent application Ser. No. 16/534,875 to Brauon et al., titled "Annuloplasty system and locking tools therefor," filed on Aug. 7, 2019, which published as US 2020/0015971 (now U.S. Pat. No. 11,123,191); which is a Continuation of PCT Application PCT/IL2019/050777 to Brauon et al., titled: "Annuloplasty system and locking tools therefor," filed on Jul. 11, 2019, which claims priority from:

a) U.S. Provisional Patent Application 62/697,186 to Brauon et al., titled: "Annuloplasty system and locking tool therefor," filed on Jul. 12, 2018; and b) U.S. Provisional Patent Application 62/811,693 to Brauon et al., titled: "Annuloplasty system and locking tool therefor," filed on Feb. 28, 2019.

All of these applications are incorporated herein by reference in their entirety for all purposes.

FIELD OF THE INVENTION

The present invention relates in general to valve repair, for example, to repair of an atrioventricular valve of a patient.

BACKGROUND

Ischemic heart disease can cause valvular regurgitation. For example, mitral regurgitation can be caused by the combination of ischemic dysfunction of the papillary muscles, and the dilatation of the left ventricle that is present in ischemic heart disease, with the subsequent displacement of the papillary muscles and the dilatation of the mitral valve annulus.

Dilation of the annulus of the mitral valve can prevent the valve leaflets from fully coapting when the valve is closed. Mitral regurgitation of blood from the left ventricle into the left atrium results in increased total stroke volume and decreased cardiac output, and ultimate weakening of the left ventricle secondary to a volume overload and a pressure overload of the left atrium.

SUMMARY

This summary is meant to provide some examples and is not intended to be limiting of the scope of the invention in any way. For example, any feature included in an example of this summary is not required by the claims, unless the claims explicitly recite the features. Also, the features, components, steps, concepts, etc. described in examples in this summary and elsewhere in this disclosure can be combined in a variety of ways. The description herein relates to systems, assemblies, methods, devices, apparatuses, combinations, etc. that may be utilized for valve repair. Various features and steps as described elsewhere in this disclosure can be included in the examples summarized here.

In some applications, a multi-component tubular system is provided for accessing a heart of a patient. The system can comprise one or more steerable guiding catheters (e.g., 1, 2, 3, or more) configured for directing the passage of devices therethrough into the heart. The multi-component tubular system can be configured to deliver an implant in a desired orientation to an annulus of a cardiac valve of the patient and to facilitate anchoring of the implant to the annulus. For some applications, the guiding system can be advanced/advanceable transluminally or transthoracically accessing an atrium of the heart. For some applications, the guiding system can be advanced surgically. The system can comprise two or more steerable catheters. A first catheter has a distal portion that is steerable to a first desired spatial orientation. A second catheter is disposed within the first catheter and has a distal portion that is steerable to a second desired spatial orientation. The system provides techniques and relative-spatial-orientation-controlling devices for controlling the orientation of the distal portion of the second catheter with respect to the first catheter without substantially distorting the first spatial orientation of the distal portion of the first catheter. For some applications, the relative-spatial-orientation-controlling device comprises a rotational locking mechanism provided by components of the catheter system.

The distal portion of the first catheter can be steered in a suitable direction following advancement of the first catheter through vasculature of the patient. Following the advancement of the first catheter and steering of the distal portion of the first catheter in any one or more suitable planes, the second catheter is advanced through the first catheter. The first and second catheters can be rotationally locked in order to enable steering of the distal portion of the second catheter in any one or more suitable planes with respect to the distal portion of the first catheter in a manner which substantially maintains the spatial orientation of the first catheter during the steering of the second catheter. Additionally, the first catheter can be further steered without substantially disrupting the spatial orientation of the distal portion of the second catheter.

The distal portions and/or distal ends of the first and second catheters can be configured such that once they have been positioned within an atrium of the heart of the patient, an implantable, adjustable annuloplasty structure (e.g., an annuloplasty ring structure, a closed annuloplasty structure, a closed annuloplasty ring structure, an open annuloplasty structure, a partial annuloplasty ring structure, or other annuloplasty device) can be deployed, e.g., from within the second catheter and anchored to the annulus of the cardiac valve of the patient. The annuloplasty structure can comprise a flexible primary body portion and a contracting member having a first portion extending along a longitudinal length of the primary body portion. A second portion of the contracting member can extend away from the primary body portion of the annuloplasty structure and outside the body of the patient. From a location outside the body of the patient, contracting-member-snare of a contracting-member-uptake tool is used to ensnare a proximal end portion of the contracting member that is disposed outside of the body of the patient. Using the snare, the proximal end portion of the contracting member can then be fed through a distal portion of a primary tube of the tool and subsequently through a lumen of a secondary tube of the tool. The contracting-member-uptake-tool can then be advanced toward the annulus of the patient along the contracting member. During the advancing of the tool toward the annulus, the secondary tube of the tool can move distally along the contracting member as the contracting member passes through the lumen of the secondary tube of the tool by being pulled by the snare.

The contracting-member-uptake-tool can comprise an ejector movable a distal end portion of the tool. The ejector can be removably coupled to a suture fastener which comprises a clamping structure that can be flexed to an open condition through which the contracting member can pass and is biased toward a closed position or closed state which clamps onto the contracting member passed therethrough. The tool can have at least one stop that maintains the suture fastener (e.g., the clamping structure thereof) in its open condition.

The snare portion can be configured or adapted to capture and pull the contracting member proximally through the suture fastener and out of the aligned ports in the tool. The tool can then be advanced toward the annuloplasty structure implanted along the annulus. The tool can then uptake successive portions of the contracting member in order to contract the annuloplasty structure. Subsequently, the ejector of the tool can be moved and converts the suture fastener (e.g., the clamping structure thereof) from its open condition to its closed condition to clamp onto the contracting member passed therethrough.

The tool can comprise a handle portion which can comprise a contracting-member-uptake device which uptakes successive portions of the contracting member. The handle portion can comprise a tension meter configured to measure a degree of tension of the contracting member.

For some applications, an annuloplasty structure (e.g., an annuloplasty ring structure, a closed annuloplasty structure, a closed annuloplasty ring structure, an open annuloplasty structure, a partial annuloplasty ring structure, or other annuloplasty device) comprises a primary body portion comprising a contractible sleeve, a contracting member threaded along the contractible sleeve, and a housing comprising a fastener through which the contracting member passes. Once the annuloplasty structure or annuloplasty ring structure has been contracted, the fastener is deployed within the housing in order to maintain contraction of the annuloplasty structure or annuloplasty ring structure.

A contracting-member-severing tool is provided in which severing of the contracting member running through the tool is possible only once the contracting member has been locked in place by a fastener coupled thereto. The contracting-member-severing tool can be configured in a variety of ways to apply a cutting surface to the contracting member, e.g., with a sharp edge that moves toward the contracting member; multiple edges and/or surfaces that move relative to each other such as in a scissoring motion or like a wire cutter tool; etc.

There is therefore provided, in accordance with some applications, a system and/or an apparatus, including an implantable annuloplasty structure. The annuloplasty structure including a primary body portion and a contracting member. In some implementations, the contracting member can have (1) a first portion extending along a longitudinal length of the primary body portion of the annuloplasty structure, and (2) a second portion extending away from the primary portion of the annuloplasty structure.

The system and/or apparatus can include a contracting-member-uptake tool. The contracting-member-uptake tool can include a primary tube terminating at a distal end portion of the contracting-member-uptake tool, the distal end portion of the contracting-member-uptake tool having a distal tip, and a secondary tube disposed alongside the primary tube, the secondary tube having a secondary-tube lumen being configured for passage therethrough of the contracting member. In some implementations, the contracting-member-uptake tool also includes a contracting-member snare including a distal snare portion and an elongate flexible body portion coupled to the distal snare portion, the distal snare portion being configured to ensnare a portion of the contracting member. The contracting-member snare can be sized to pass through the secondary-tube lumen of the secondary tube in order to pull the second portion of the contracting member through a length of the secondary tube.

For some applications, the distal snare portion is configured to pull the second portion of the contracting member through the distal tip of the contracting-member-uptake tool and subsequently through the length of the secondary tube.

For some applications, the contracting-member-snare includes a wire including stainless steel. For some applications, the contracting-member-snare includes a wire having a diameter of 0.2-0.25 mm.

For some applications, the primary tube and/or the secondary tube is flexible.

For some applications, the annuloplasty structure defines a full annuloplasty ring structure. For some applications, the annuloplasty structure defines a partial annuloplasty ring structure.

For some applications, the secondary tube is shaped to define a longitudinal slit.

For some applications, the contracting-member-uptake tool includes a handle portion and the first and second tubes are connected to the handle portion.

For some applications, the handle portion includes a contracting-member-uptake device configured to uptake successive portions of the contracting member; and a tension meter configured to measure a degree of tension of the contracting member.

For some applications, the contracting-member-uptake device is actuatable to increase tension of the contracting member.

For some applications, the contracting-member-uptake device includes a knob coupled to a proximal portion of the contracting member, the knob being configured to increase tension of the contracting member by pulling the contracting member proximally. For some applications, the knob is fixedly coupled to the proximal portion of the contracting member.

For some applications, the contracting-member-uptake device includes a wheel having a groove configured to couple the contracting member to the wheel. For some applications, the groove is shaped so as to receive a middle portion of the contracting member.

For some applications, the secondary-tube lumen of the secondary tube is sized so as to maintain coupling between the distal snare portion and the contracting member.

For some applications, the snare portion includes a flexible loop, and the secondary-tube-lumen is configured to collapse the loop around the contracting member as the elongate flexible body portion is pulled through the secondary-tube-lumen. For some applications, the secondary-tube lumen of the secondary tube has a diameter of 0.5-1.5 mm.

For some applications, the contracting-member-snare includes a metal wire.

For some applications, at least the distal snare portion of the contracting-member-snare is corrugated to increase friction between the snare portion and the contracting member.

For some applications, the distal snare portion is configured pull the second portion of the contracting member through an entire length of the secondary tube.

For some applications, the contracting member-uptake tool includes:

at least one contracting-member-fastener disposed within the distal end portion of the contracting-member-uptake tool, the contracting-member-fastener including a clamping structure that (a) is biased toward assuming a closed state, in the closed state, the clamping structure is configured to clamp onto the contracting member passed therethrough, and (b) can be flexed to an open state through which the contracting member can move; and a stop removably coupled to the contracting-member-fastener and configured to maintain the contracting-member-fastener in the open state.

For some applications, the at least one contracting-member-fastener includes at least first and second contracting-member-fastener disposed within the distal end portion of the contracting-member-uptake tool.

For some applications, the distal snare portion and the elongate flexible body portion of the contracting-member-snare are sized to pass distally through the contracting-member-fastener in the open state, the snare portion being adapted to capture and pull the contracting member proximally through the contracting-member-fastener and through aligned ports in the distal end portion of the contracting-member-uptake tool.

For some applications, the contracting-member-uptake tool includes a fastener-ejector movable within the distal end portion of the contracting-member-uptake tool, and movement of the fastener-ejector contacts and converts the contracting-member-fastener from the open state to the closed state to clamp onto the contracting member passed therethrough.

For some applications, the fastener-ejector is coupled to the stop and moves the stop that is removably coupled to the fastener.

For some applications, the distal end portion of the contracting-member-uptake tool is shaped so as to define a sharp edge, and the contracting member is disposed in proximity to the sharp edge such that movement of the fastener-ejector against the sharp edge severs the contracting member extending through the fastener.

For some applications, the system and/or apparatus further includes:

at least one contracting-member-fastener configured to surround the contracting member, the contracting-member-fastener including a clamping structure that (a) is biased toward assuming a closed state, in the closed state, the clamping structure is configured to clamp onto the contracting member passed therethrough, and (b) can be flexed to an open state through which the contracting member can move; and a stop removably coupled to the contracting-member-fastener and configured to maintain the contracting-member-fastener in the open state.

For some applications, the contracting-member-uptake tool includes a fastener-ejector movable within the distal end portion of the contracting-member-uptake tool, and movement of the fastener-ejector is configured to convert the contracting-member-fastener from the open state to the closed state to clamp onto the contracting member passed therethrough.

For some applications, the fastener-ejector is removably coupled to the stop and moves the stop that is removably coupled to the fastener.

For some applications, the tool includes a moveable cutting element having a sharp edge, and movement of the stop hammers the stop against the moveable cutting element such that movement of the moveable cutting element severs the contracting member extending through the fastener and through the moveable cutting element.

For some applications, the system and/or apparatus further includes a lock slidable along the contracting member, the lock being fixedly couplable to the contracting member in order to prevent movement of the contracting member. The lock can be shaped so as to define a slit which extends from a proximal surface of the lock toward a distal surface of the lock. The lock can define a lock lumen of the lock extending from a proximal opening in the lock toward a distal opening in the lock. The lock lumen can be configured to surround the contracting member. In some applications, when the lock is compressed, the slit enables the lock to close around the contracting member and thereby lock the lock to the contracting member.

For some applications, the annuloplasty structure is shaped so as to define a recess dimensioned so as to compress the lock when the lock is disposed at least in part within the recess.

For some applications, the recess is dimensioned so as to compress the lock when the lock is disposed at least in part within the recess.

For some applications, the lock lumen is shaped so as to define a distal portion that is wider than a proximal portion of the lock lumen.

For some applications, the recess is shaped so as to define a proximal portion that is narrower than any other portion of the recess distal to the proximal portion.

For some applications, the lock is disposed within the distal end portion of the contracting-member-uptake tool.

For some applications, when the contracting-member-uptake tool is coupled to the annuloplasty structure, the lock is disposed at least in part within the recess.

For some applications, when the contracting-member-uptake tool is coupled to the annuloplasty structure, the lock is disposed entirely proximally to the recess.

For some applications, the lock is disposed within the distal end portion of the contracting-member-uptake tool.

For some applications, the distal snare portion and the elongate flexible body portion of the contracting-member-snare are sized to pass distally through lock, the snare portion adapted to capture and pull the contracting member proximally through the lock and through aligned ports in the distal end portion of the contracting-member-uptake tool.

There is further provided, in accordance with some applications, a system and/or an apparatus, including an implantable annuloplasty structure. The implantable annuloplasty structure including a primary body portion and a contracting member. The contracting member can have (1) a first portion extending along a longitudinal length of the primary body portion of the annuloplasty ring structure, and (2) a second portion extending away from the primary body portion of the annuloplasty ring structure.

The system and/or apparatus can also include a housing configured to be positionable against the primary body portion of the annuloplasty ring structure.

The system and/or apparatus can also include a contracting-member-fastener disposed at least in part within the housing, the contracting-member-fastener including a clamping structure that (a) is biased toward assuming a closed state, in the closed state, the clamping structure is configured to clamp onto the contracting member passed therethrough, and (b) can be flexed to an open state through which the contracting member can move.

The system and/or apparatus can also include a stop removably coupled to the fastener and configured to maintain the contracting-member-fastener in the open state; and a fastener-ejector engageable with the stop such that movement of the fastener-ejector moves the stop removably coupled to the fastener and converts the clamping structure from the open state to the closed state to clamp onto the contracting member passed therethrough.

For some applications, the fastener-ejector is shaped such that movement thereof facilitates severing of the contracting member extending through the fastener.

For some applications, the fastener includes a deformable element having a slanted state and a straight state, the stop is configured to maintain the fastener in the slanted state, and, upon removal of the stop, the fastener is configured to transition to the straight state and claim the contracting member between the fastener and a surface of the housing.

For some applications, the fastener is shaped so as to define a plurality of teeth configured to increase friction between the contracting member and the fastener.

There is further provided, in accordance with some applications, a method, including advancing toward a heart of a patient an implantable annuloplasty structure including a primary body portion and a contracting member. The contracting member be the same as or similar to other contracting members herein and can have (1) a first portion extending along a longitudinal length of the primary body portion of the annuloplasty structure, and (2) a second portion extending away from the primary portion of the annuloplasty ring structure.

The method further includes threading the second portion of the contracting member through a contracting-member-uptake tool. The contracting-member-uptake tool can include a primary tube terminating at a distal end portion of the contracting-member-uptake tool, the distal end portion of the contracting-member-uptake tool having a distal tip and a secondary tube disposed alongside the primary tube, the secondary tube having a secondary-tube lumen being configured for passage therethrough of the contracting member. The contracting-member-uptake tool can also include a contracting-member-snare including a distal snare portion and an elongate flexible body portion coupled to the distal snare portion, the distal snare portion being configured to ensnare a portion of the contracting member and being sized to pass through the secondary-tube lumen of the secondary tube in order to pull the second portion of the contracting member through a length of the secondary tube.

For some applications, the threading includes using the distal snare portion, ensnaring the portion of the contracting member; using the contracting-member-snare, pulling the portion of the contracting member through the secondary tube; and subsequently to the threading, advancing the contracting-member-uptake tool along the contracting member toward the annuloplasty structure.

For some applications, threading the second portion of the contracting member includes threading the second portion of the contracting member subsequently to the advancing.

For some applications, pulling the portion of the contracting member through the secondary tube includes pulling the second portion of the contracting member through the distal tip of the contracting-member-uptake tool and subsequently through the length of the secondary tube.

For some applications, pulling the portion of the contracting member through the secondary tube includes strengthening a coupling between the contracting member and the snare portion.

For some applications, the method further includes, subsequently to the advancing of the contracting-member-uptake tool, contracting the annuloplasty structure using the contracting-member-uptake tool.

For some applications, contracting the annuloplasty structure using the contracting-member-uptake tool includes advancing successive portions of the contracting member with respect to a contracting-member-uptake device.

For some applications, the method further includes, subsequently to the contracting, maintaining the annuloplasty structure in a contracted state by clamping a contracting-member-fastener around a portion of the contracting member.

For some applications, clamping includes deploying the fastener from within the distal end portion of the contracting-member-uptake tool.

For some applications, the method further includes, subsequently to the maintaining the annuloplasty structure in the contracted state, using a sharp edge of the contracting-member-uptake tool, severing the contracting member.

For some applications, advancing the contracting-member-uptake tool includes advancing the contracting-member-uptake tool through vasculature of the patient.

For some applications, contracting-member-uptake tool includes a handle portion including a contracting-member-uptake device configured to uptake successive portions of the contracting member; and a tension meter configured to measure a degree of tension of the contracting member.

For some applications, the method further includes increasing tension of the contracting member using the contracting-member-uptake device.

For some applications, the contracting-member-uptake device includes a wheel and having a groove, and the method further includes coupling the contracting member to the wheel.

For some applications, coupling the contracting member to the wheel includes coupling a middle portion of the contracting member to the wheel.

The method can be performed in a procedure on a living animal or in a simulation/simulated procedure (e.g., on a cadaver, cadaver heart, simulator with a simulated heart, tissue, etc., anthropomorphic ghost, etc.).

There is further provided, in accordance with some applications, a method, including advancing toward a heart of a patient an implantable annuloplasty structure. The implantable annuloplasty structure can be the same as or similar to other annuloplasty structures herein or otherwise known, and can include, for example, a primary body portion, a contracting member, and a housing coupled to the primary body portion of the annuloplasty structure. For some applications the contracting member has (1) a first portion extending along a longitudinal length of the primary body portion of the annuloplasty structure, and (2) a second portion extending away from the primary body portion of the annuloplasty structure.

For some applications, a contracting-member-fastener is disposed within the housing, the contracting-member-fastener including a clamping structure that (a) is biased toward assuming a closed state, in the closed state, the clamping structure is configured to clamp onto the contracting member passed therethrough, and (b) can be flexed to an open state through which the contracting member can move. For some applications, a stop is removably coupled to the fastener and configured to maintain the contracting-member-fastener in the open state.

For some applications, the method further includes converting the contracting-member-fastener from the open state to the closed state in order to clamp onto the contracting member passed therethrough by moving a fastener-ejector engageable with the stop such that movement of the fastener-ejector moves the stop removably coupled to the fastener.

For some applications, the method further includes, subsequently to the advancing, contracting the annuloplasty structure using the contracting member, and converting the contracting-member-fastener from the open state to the closed state including converting subsequently to the contracting.

For some applications, contracting the annuloplasty structure includes contracting the annuloplasty structure using a contracting-member-uptake tool.

For some applications, contracting the annuloplasty structure using the contracting-member-uptake tool includes advancing successive portions of the contracting member with respect to a contracting-member-uptake device.

For some applications, the method further includes, subsequently to the converting of the contracting-member-fastener from the open state to the closed state, using a sharp edge of the contracting-member-uptake tool, severing the contracting member.

The method can be performed in a procedure on a living animal or in a simulation/simulated procedure (e.g., on a cadaver, cadaver heart, simulator with a simulated heart, tissue, etc., anthropomorphic ghost, etc.).

There is further provided, in accordance with some applications, a system, including an implantable annuloplasty structure including a primary body portion and a contracting member extending at least partially along a longitudinal length of the primary body portion of the annuloplasty structure. The system also includes a contracting-member-uptake tool. The contracting-member-uptake tool can include a tube having a lumen configured for passage therethrough of the contracting member and a contracting-member-snare. The contracting-member snare can include a distal snare portion and an elongate flexible body portion coupled to the distal snare portion, the distal snare portion being configured to ensnare a portion of the contracting member and pull it into the lumen.

For some applications, the distal snare portion is configured to pull the portion of the contracting member through an entire length of the lumen.

For some applications, the contracting-member-snare includes a wire including stainless steel. For some applications, the tube is flexible.

For some applications, the contracting-member-uptake tool includes a handle portion and the tube is connected to the handle portion.

For some applications, the handle portion includes a contracting-member-uptake device configured to uptake successive portions of the contracting member; and a tension meter configured to measure a degree of tension of the contracting member.

For some applications, the contracting-member-uptake device is actuatable to increase tension of the contracting member.

For some applications, the contracting-member-uptake device includes a wheel having a groove configured to couple the contracting member to the wheel.

For some applications, the groove is shaped so as to receive a middle portion of the contracting member.

For some applications, the lumen of the tube is sized so as to maintain coupling between the distal snare portion and the contracting member.

For some applications, the distal snare portion includes a flexible loop, and the lumen is configured to collapse the loop around the contracting member as the portion of the contracting member is pulled through the lumen.

For some applications, at least the distal snare portion of the contracting-member-snare is corrugated to increase friction between the snare portion and the contracting member.

For some applications, the distal end portion of the contracting-member-uptake tool is shaped so as to define a sharp edge, and the contracting member-uptake tool is configured to dispose the contracting member in proximity to the sharp edge such that the sharp edge can sever the contracting member.

For some applications, the contracting member-uptake tool includes:

- a contracting-member-fastener disposed within the distal end portion of the contracting-member-uptake tool, the contracting-member-fastener including a clamping structure that (a) is biased toward assuming a closed state, in the closed state, the clamping structure is configured to clamp onto the contracting member passed therethrough, and (b) can be flexed to an open state through which the contracting member can move; and
- a stop removably coupled to the contracting-member-fastener and configured to maintain the contracting-member-fastener in the open state.

For some applications, the distal snare portion and the portion of the contracting-member are sized to pass distally through the contracting-member-fastener in its open state, the distal snare portion being adapted to capture and pull the portion of the contracting member proximally through the contracting-member-fastener and through aligned ports in the distal end portion of the contracting-member-uptake tool.

For some applications, the contracting-member-uptake tool includes a fastener-ejector movable within the distal end portion of the contracting-member-uptake tool, and movement of the fastener-ejector contacts and can convert the contracting-member-fastener from its open state to its closed state to clamp onto the contracting member when passed therethrough.

For some applications, the fastener-ejector is coupled to the stop and moves the stop that is removably coupled to the fastener.

For some applications, the distal end portion of the contracting-member-uptake tool is shaped so as to define a sharp edge, and the contracting-member-uptake tool is configured to dispose the contracting member in proximity to the sharp edge such that movement of the fastener-ejector against the sharp edge severs the contracting member after where it extends through the fastener.

For some applications, the implantable annuloplasty structure is a closed annuloplasty structure.

There is further provided, in accordance with some applications, a system and/or apparatus, including an implantable annuloplasty structure including a primary body portion having a lateral wall and a contracting member. In some applications, the contracting member has (1) a first portion extending along a longitudinal length of the primary body portion of the annuloplasty structure, and (2) a second portion extending away from the primary body portion of the annuloplasty structure, the contracting member being configured to adjust a perimeter of the annuloplasty structure.

The primary body portion of the annuloplasty structure can be shaped to define a recess having a recess axis, the recess extending from an opening in a first surface of the lateral wall of the primary body portion toward an opposite second surface of the lateral wall of the primary body portion, the lateral wall of the primary body portion extending away from the recess along a longitudinal axis that is at a non-zero angle with respect to the recess axis, the contracting member extending through the recess and away from the primary body portion of the annuloplasty structure via the recess.

The system and/or apparatus can include a lock slidable along the contracting member and toward the recess, the lock being fixedly couplable to the contracting member in order to prevent movement of the contracting member, the recess being shaped so as to facilitate fixed coupling of the lock to the contracting member.

For some applications, the lock is disposable at least in part within the recess.

For some applications, the annuloplasty structure includes a full annuloplasty ring structure; in others the annuloplasty structure includes a partial annuloplasty ring structure.

For some applications, the lock is configured to lock the contracting member when the lock is moved at least in part within the recess.

For some applications, the lock is configured to fit entirely within the recess.

For some applications the primary body portion includes a housing, the housing defines at least a portion of the lateral wall, and the housing defines the recess.

For some applications, the lock is shaped so as to define a lock-threaded-portion, and the annuloplasty structure is shaped so as to define an annuloplasty-structure-threaded-portion configured to engage with the lock-threaded-portion.

For some applications, the recess defines a recess lumen extending along the recess axis. For some applications, the recess axis is disposed at the non-zero angle.

For some applications the lock is shaped so as to define a slit which extends from a proximal surface of the lock toward a distal surface of the lock, the lock defines a lock lumen of the lock extending from a proximal opening in the lock toward a distal opening in the lock, the lock lumen is configured to surround the contracting member, and when the lock is disposed within the recess, the slit enables the lock to close around the contracting member and thereby lock the lock to the contracting member.

For some applications, the recess is dimensioned so as to compress the lock when the lock is disposed at least in part within the recess.

For some applications, the slit is shaped so as to define a distal portion that is wider than a proximal portion of the slit.

For some applications, the lock lumen is shaped so as to define a distal portion that is wider than a proximal portion of the lock lumen.

For some applications, the recess is shaped so as to define a proximal-most portion that is narrower than any other portion of the recess distal to the proximal-most portion.

For some applications, the annuloplasty structure includes a housing, and the housing is shaped so as to define the recess, the recess having a recess axis.

For some applications, the lock is shaped so as to define a lock-threaded-portion, and the housing is shaped so as to define an annuloplasty-structure-threaded-portion configured to engage with the lock-threaded-portion.

For some applications, the housing is shaped so as to define a contracting-member lumen that is disposed at a non-zero angle with respect to the recess axis.

For some applications, the housing is shaped so as to provide a contracting-member-lumen wall which is disposed along the contracting-member lumen, and when the lock is disposed within the recess, a distal end of the lock is configured to pinch a first portion of the contracting member against the contracting-member-lumen wall in order to lock the contracting member at least a first pinching point.

For some applications the recess is shaped so as to define a recess-distal-tapered-portion. For some applications, the lock is shaped so as to define a lock lumen of the lock extending from a proximal opening in the lock toward a distal opening in the lock, and a lock-distal-tapered-portion. The lock lumen can be configured to surround the contracting member.

For some applications, when the lock is disposed within the recess, the recess-distal-tapered-portion is configured to compress the lock-distal-tapered-portion which, in turn, is configured to pinch a second portion of the contracting member within the lock lumen at the recess-distal-tapered-portion in order to lock the contracting member at least a second pinching point.

For some applications, the system and/or apparatus further includes a delivery tool, the delivery tool and the contracting member being slidable with respect to each other, the delivery tool being configured to deliver the annuloplasty structure to an annulus of a heart of a patient.

For some applications, the delivery tool includes a knob coupled to a proximal portion of the contracting member, the knob being configured to increase tension of the contracting member by pulling the contracting member proximally.

For some applications, the knob is fixedly coupled to the proximal portion of the contracting member.

For some applications, when the delivery tool is coupled to the annuloplasty structure, a portion of the contracting member is disposed within a lumen of the delivery tool and the lock surrounds a part of the contracting member.

For some applications, when the delivery tool is coupled to the annuloplasty structure, the lock is disposed at least in part within the recess.

For some applications, when the delivery tool is coupled to the annuloplasty structure, the lock is disposed entirely proximally to the recess.

For some applications, the delivery tool includes a lock-ejector movable within a distal end portion of the delivery tool, and movement of the lock-ejector contacts and converts the lock from an open state to a closed state to clamp onto the contracting member passed therethrough.

For some applications, the distal end portion of the delivery tool is shaped so as to define a sharp edge, and the contracting member is disposed in proximity to the sharp edge such that movement of the lock-ejector against the sharp edge severs the contracting member extending through the lock.

There is further provided, in accordance with some applications, a system and/or an apparatus, including an implantable annuloplasty structure including a primary body portion and a contracting member. The contracting member can be the same as or similar to other contracting members herein and can, for example, have a (1) first portion extending along a longitudinal length of the primary body portion of the annuloplasty structure, and a (2) second portion extending away from the primary portion of the annuloplasty structure. The system and/or apparatus can include a lock slidable along the contracting member, the lock being fixedly couplable to the contracting member in order to prevent movement of the contracting member. The lock can be shaped so as to define a slit which extends from a proximal surface of the lock toward a distal surface of the lock.

For some applications, the lock defines a lock lumen of the lock extending from a proximal opening in the lock toward a distal opening in the lock. The lock lumen can be configured to surround the contracting member. When the lock is compressed, the slit can enable the lock to close around the contracting member and thereby lock the lock to the contracting member.

For some applications, the annuloplasty structure includes a full annuloplasty ring structure, in others, the annuloplasty structure includes a partial annuloplasty ring structure.

For some applications, the annuloplasty structure is shaped so as to define a recess dimensioned so as to compress the lock when the lock is disposed at least in part within the recess.

For some applications, the lock is disposable at least in part within the recess.

For some applications, the lock is configured to fit entirely within the recess.

For some applications, the slit is shaped so as to define a distal portion that is wider than a proximal portion of the slit.

For some applications, the lock lumen is shaped so as to define a distal portion that is wider than a proximal portion of the lock lumen.

For some applications, the recess is shaped so as to define a proximal portion that is narrower than any other portion of the recess distal to the proximal portion.

For some applications, the lock is shaped so as to define a lock-threaded-portion, and the annuloplasty structure is shaped so as to define an annuloplasty-structure-threaded-portion configured to engage with the lock-threaded-portion.

For some applications, the annuloplasty structure includes a housing, and the housing is shaped so as to define the recess, the recess having a recess axis.

For some applications, the lock is shaped so as to define a lock-threaded-portion, and the housing is shaped so as to define an annuloplasty-structure-threaded-portion configured to engage with the lock-threaded-portion.

For some applications, the housing is shaped so as to define a contracting-member lumen that is disposed at a non-zero angle with respect to the recess axis.

For some applications, the housing is shaped so as to provide a contracting-member-lumen wall which is disposed along the contracting-member lumen, and when the lock is disposed within the recess, a distal end of the lock is configured to pinch a first portion of the contracting member against the contracting-member-lumen wall in order to lock the contracting member at least a first pinching point.

For some applications the recess is shaped so as to define a recess-distal-tapered-portion, and the lock is shaped so as to define a lock lumen of the lock extending from a proximal opening in the lock toward a distal opening in the lock, and a lock-distal-tapered-portion. The lock lumen can be configured to surround the contracting member. When the lock is disposed within the recess, the recess-distal-tapered-portion can be configured to compress the lock-distal-tapered-portion which, in turn, is configured to pinch a second portion of the contracting member within the lock lumen at the recess-distal-tapered-portion in order to lock the contracting member at least a second pinching point.

For some applications, the system and/or apparatus further includes a delivery tool, the delivery tool and the contracting member being slidable with respect to each other, the delivery tool being configured to deliver the annuloplasty structure to an annulus of a heart of a patient.

For some applications, the delivery tool includes a knob coupled to a proximal portion of the contracting member, the knob being configured to increase tension of the contracting member by pulling the contracting member proximally.

For some applications, the knob is fixedly coupled to the proximal portion of the contracting member.

For some applications, when the delivery tool is coupled to the annuloplasty structure, a portion of the contracting member is disposed within a lumen of the delivery tool and the lock surrounds a part of the contracting member.

For some applications, the annuloplasty structure is shaped so as to define a recess dimensioned so as to compress the lock when the lock is disposed at least in part within the recess, and when the delivery tool is coupled to the annuloplasty structure, the lock is disposed at least in part within the recess.

For some applications, the annuloplasty structure is shaped so as to define a recess dimensioned so as to compress the lock when the lock is disposed at least in part within the recess, and when the delivery tool is coupled to the annuloplasty structure, the lock is disposed entirely proximally to the recess.

For some applications, the delivery tool includes a lock-ejector movable within a distal end portion of the delivery tool, and movement of the lock-ejector contacts and converts the lock from an open state to a closed state to clamp onto the contracting member passed therethrough.

For some applications, the distal end portion of the delivery tool is shaped so as to define a sharp edge, and the contracting member is disposed in proximity to the sharp edge such that movement of the lock-ejector against the sharp edge severs the contracting member extending through the lock.

There is further provided, in accordance with some applications, a method, including advancing toward a heart of a patient an implantable annuloplasty structure. The implantable annuloplasty structure can be the same as or similar to other annuloplasty structures herein or otherwise known, such as for example, having a primary body portion having a lateral wall and a contracting member having (1) a first portion extending along a longitudinal length of the primary body portion of the annuloplasty structure, and (2) a second portion extending away from the primary body portion of the annuloplasty structure, the contracting member being configured to adjust a perimeter of the annuloplasty structure.

The primary body portion of the annuloplasty structure can be shaped to define a recess having a recess axis, the recess extending from an opening in a first surface of the lateral wall of the primary body portion toward an opposite second surface of the lateral wall of the primary body portion, the lateral wall of the primary body portion extending away from the recess along a longitudinal axis that is at a non-zero angle with respect to the recess axis, the contracting member extending through the recess and away from the primary body portion of the annuloplasty structure via the recess; and The method can further include locking the contracting member by sliding a lock along the contracting member to fit within the recess, the lock being fixedly couplable to the contracting member in order to prevent movement of the contracting member, the recess being shaped so as to facilitate fixed coupling of the lock to the contracting member.

For some applications, advancing includes advancing the annuloplasty structure while the lock is disposed at least in part within the recess.

For some applications, advancing includes advancing the annuloplasty structure while the lock is disposed entirely proximally to the recess.

For some applications, locking the contracting member includes sliding the lock fully within the recess.

For some applications, the annuloplasty structure includes a full annuloplasty ring structure or a partial annuloplasty ring structure.

For some applications the lock is shaped so as to define a slit which extends from a proximal surface of the lock toward a distal surface of the lock, the lock defines a lock lumen of the lock extending from a proximal opening in the lock toward a distal opening in the lock, the lock lumen is configured to surround the contracting member, and when the lock is disposed within the recess, the slit enables the lock to close around the contracting member and thereby lock the lock to the contracting member.

For some applications, the recess is dimensioned so as to compress the lock when the lock is disposed at least in part within the recess, and locking includes positioning the lock at least in part within the recess so as to compress the lock.

For some applications, the lock lumen is shaped so as to define a distal portion that is wider than a proximal portion of the lock lumen.

For some applications, the recess is shaped so as to define a proximal portion that is narrower than any other portion of the recess distal to the proximal portion.

For some applications, advancing includes advancing the annuloplasty structure using a delivery tool, and the method further includes sliding the delivery tool and the contracting member with respect to each other.

For some applications, advancing includes advancing the lock within the delivery tool and locking includes sliding the lock using the delivery tool.

For some applications, the delivery tool includes a knob coupled to a proximal portion of the contracting member, and the method further includes using the knob, increasing tension of the contracting member by pulling the contracting member proximally.

For some applications, the knob is fixedly coupled to the proximal portion of the contracting member.

For some applications, the delivery tool includes a lock-ejector movable within a distal end portion of the delivery tool, and the method further includes clamping the lock onto the contracting member passed therethrough by moving the lock-ejector to contact and convert the lock from an open state to a closed state.

For some applications the distal end portion of the delivery tool is shaped so as to define a sharp edge, the contracting member is disposed in proximity to the sharp edge, moving the lock-ejector includes moving the lock-ejector against the sharp edge, and severing the contracting member extending through the lock by the moving of the lock-ejector against the sharp edge.

The method can be performed in a procedure on a living animal or in a simulation/simulated procedure (e.g., on a cadaver, cadaver heart, simulator with a simulated heart, tissue, etc., anthropomorphic ghost, etc.).

There is further provided, in accordance with some applications, a method, including advancing toward a heart of a patient an implantable annuloplasty structure. The annuloplasty structure can be the same as or similar to other annuloplasty structures herein or otherwise known, and can, for example, include a primary body portion having a lateral wall and a contracting member. The contracting member can have (1) a first portion extending along a longitudinal length of the primary body portion of the annuloplasty structure, and (2) a second portion extending away from the primary body portion of the annuloplasty structure, the contracting member being configured to adjust a perimeter of the annuloplasty structure.

The method further includes locking the contracting member by sliding a lock along the contracting member, the lock being fixedly couplable to the contracting member in order to prevent movement of the contracting member. The lock can be shaped so as to define a slit which extends from a proximal surface of the lock toward a distal surface of the lock. The lock can define a lock lumen of the lock extending from a proximal opening in the lock toward a distal opening in the lock. The lock lumen can be configured to surround the contracting member. For some applications, when the lock is compressed, the slit enables the lock to close around the contracting member and thereby lock the lock to the contracting member.

For some applications, the annuloplasty structure includes a full annuloplasty ring structure or a partial annuloplasty ring structure.

For some applications, the annuloplasty structure is shaped so as to define a recess dimensioned so as to compress the lock when the lock is disposed at least in part within the recess, and locking the contracting member includes sliding the lock at least in part within the recess.

For some applications, advancing includes advancing the annuloplasty structure while the lock is disposed at least in part within the recess.

For some applications, advancing includes advancing the annuloplasty structure while the lock is disposed entirely proximally to the recess.

For some applications, locking the contracting member includes sliding the lock fully within the recess.

For some applications, the recess is dimensioned so as to compress the lock when the lock is disposed at least in part within the recess.

For some applications, the lock lumen is shaped so as to define a distal portion that is wider than a proximal portion of the lock lumen.

For some applications, the recess is shaped so as to define a proximal portion that is narrower than any other portion of the recess distal to the proximal portion.

For some applications, advancing includes advancing the annuloplasty structure using a delivery tool, and the method further includes sliding the delivery tool and the contracting member with respect to each other.

For some applications, advancing includes advancing the lock within the delivery tool and locking includes sliding the lock using the delivery tool.

For some applications, the delivery tool includes a knob coupled to a proximal portion of the contracting member, and the method further includes using the knob, increasing tension of the contracting member by pulling the contracting member proximally.

For some applications, the knob is fixedly coupled to the proximal portion of the contracting member.

For some applications, the delivery tool includes a lock-ejector movable within a distal end portion of the delivery tool, and the method further includes clamping the lock onto the contracting member passed therethrough by moving the lock-ejector to contact and convert the lock from an open state to a closed state.

For some applications the distal end portion of the delivery tool is shaped so as to define a sharp edge, the contracting member is disposed in proximity to the sharp edge, moving the lock-ejector includes moving the lock-ejector against the sharp edge, and severing the contracting member extending through the lock by the moving of the lock-ejector against the sharp edge.

The method can be performed in a procedure on a living animal or in a simulation/simulated procedure (e.g., on a cadaver, cadaver heart, simulator with a simulated heart, tissue, etc., anthropomorphic ghost, etc.)

There is further provided, in accordance with some applications, a system and/or an apparatus, including an implantable annuloplasty structure including a primary body portion and a contracting member. The contracting member can be the same as or similar to other contracting members herein or otherwise known, and can, for example, have (1) a first portion extending along a longitudinal length of the primary body portion of the annuloplasty structure, and (2) a second portion extending away from the primary portion of the annuloplasty structure.

The system and/or apparatus further comprising at least one contracting-member-fastener configured to surround the contracting member. the contracting-member-fastener can include a clamping structure that (a) is biased toward assuming a closed state, in the closed state, the clamping structure is configured to clamp onto the contracting member passed therethrough, and (b) can be flexed to an open state through which the contracting member can move.

The system and/or apparatus further comprising a stop removably coupled to the contracting-member-fastener and configured to maintain the contracting-member-fastener in the open state and a contracting-member-severing tool. The contracting-member-severing tool can include a static cutting element having a first cutting surface, a dynamic cutting element having a second cutting surface that opposes the first cutting surface, and one or more graspers configured to pull the stop proximally and remove the stop from the contracting-member-fastener. For some applications, a portion of the contracting member passes through the static cutting element and through the dynamic cutting element, and once pulled proximally, the stop contacts the cutting element and is configured to push against and move the dynamic cutting element with respect to the static cutting element in order to facilitate severing of the contracting member.

For some applications, the first and second cutting surfaces are each concave. For some applications, the first and second cutting surfaces are each diagonal.

For some applications, the tool is arranged such that the tool provides a safety mechanism whereby movement of the dynamic cutting element with respect to the static cutting element is possible only with pushing of the stop against the dynamic cutting element.

For some applications, the system and/or apparatus further includes a housing that houses the fastener and the stop, and the tool is coupled to the housing as the graspers grasp the stop.

For some applications, the tool is configured to deliver the housing, the fastener, and the stop to the implantable annuloplasty structure.

For some applications, the implantable annuloplasty structure includes the housing.

For some applications, the stop is shaped so as to define an overhang, and the graspers are configured to grip the overhang in order to initially couple the tool to the fastener.

For some applications, the system and/or apparatus further includes an outer sleeve portion configured to surround the graspers in order to lock the graspers with respect to the overhang.

There is further provided, in accordance with some applications, a system and/or an apparatus, including a contracting-member fastener configured to fasten to a contracting member. For some applications, at least one contracting-member-fastener is configured to surround the contracting member. The contracting-member-fastener can include a clamping structure that (a) is biased toward assuming a closed state, in the closed state, the clamping structure is configured to clamp onto the contracting member passed therethrough, and (b) can be flexed to an open state through which the contracting member can move.

The system and/or apparatus can include a stop removably coupled to the contracting-member-fastener and configured to maintain the contracting-member-fastener in the open state.

The system and/or apparatus can include a contracting-member-severing tool. The contracting-member-severing tool can include a cutting element configured to cut the contracting member and one or more graspers configured to pull the stop proximally and remove the stop from the contracting-member-fastener. For some applications, once pulled proximally, the stop contacts the cutting element and is configured to push against and move the cutting element in order to facilitate severing of the contracting member by the cutting element.

For some applications, the tool is arranged such that the tool provides a safety mechanism whereby movement of the cutting element is possible only with pushing of the stop against the cutting element.

For some applications, the system and/or apparatus further includes a housing that houses the fastener and the stop, and the tool is coupled to the housing as the graspers grasp the stop.

For some applications, the system and/or apparatus further includes an implantable annuloplasty structure, the tool is configured to deliver the housing, the fastener, and the stop to the implantable annuloplasty structure.

For some applications, the system and/or apparatus further includes an implantable annuloplasty structure, the implantable annuloplasty structure includes the housing.

For some applications, the stop is shaped so as to define an overhang, and the graspers are configured to grip the overhang in order to initially couple the tool to the fastener.

For some applications, the system and/or apparatus further includes an outer sleeve portion configured to surround the graspers in order to lock the graspers with respect to the overhang.

There is further provided, in accordance with some applications, a method, including threading a contracting-member-severing tool along a contracting member, the contracting-member-severing tool including a cutting element in proximity with the contracting member during the threading. The method can also include engaging the tool with a stop that is removably coupled to a contracting-member-fastener surrounding a portion of the contracting member, the stop being configured to maintain the contracting-member-fastener in an open state.

For some applications, the method further includes using the tool, disengaging the stop from the contracting-member-fastener by pulling the stop with the tool, and by the pulling, contacting the stop with the cutting element and facilitating pushing of the stop against the cutting element, and by the pushing, facilitating moving of the cutting element, and thereby facilitating severing of the contracting member by the cutting element.

For some applications, the tool is arranged such that the tool provides a safety mechanism whereby the moving of the cutting element is possible only by the pushing of the stop against the cutting element.

For some applications, the method further includes a housing that houses the fastener and the stop, and the method includes coupling the tool to the housing by gasping the stop with the tool.

For some applications, the method further includes, using the tool, delivering the housing, the fastener, and the stop to an implantable annuloplasty structure.

For some applications, coupling the tool to the housing includes coupling the tool the housing that is coupled to an implantable annuloplasty structure.

For some applications, the stop is shaped so as to define an overhang, and engaging the tool with a stop includes initially coupling the tool to the fastener by gripping the overhang with the tool with graspers.

For some applications, the method further includes locking the graspers with respect to the overhang by passing an outer sleeve portion over the graspers.

The method can be performed in a procedure on a living animal or in a simulation/simulated procedure (e.g., on a cadaver, cadaver heart, simulator with a simulated heart, tissue, etc., anthropomorphic ghost, etc.)

There is further provided, in accordance with some applications, a system and/or an apparatus including an implant including an implantable structure and a flexible elongated contracting member that extends away from the implantable structure; and a contracting-member-uptake tool, which includes a handle portion, which includes an outer housing, a tubular shaft, disposed at least partially within the outer housing, and an inner shaft.

For some application, the inner shaft (a) is partially disposed within a proximal longitudinal portion of the tubular shaft, such that the inner shaft is axially slidable with respect to the tubular shaft, (b) is shaped so as to define an inner-shaft contracting-member-receiving channel, and (c) includes a lock, which is configured (i) when in an unlocked state, to allow sliding of the contracting member with respect to the inner-shaft contracting-member-receiving channel, and (ii) when in a locked state, to axially lock the contracting member with respect to the inner shaft.

For some applications, the system and/or apparatus (e.g., in the handle) further includes a distal force applicator, which (a) is disposed at least partially within a distal longitudinal portion of the tubular shaft, and (b) is shaped so as to define a distal-force-applicator contracting-member-receiving channel, which allows sliding of the contracting member therethrough.

For some applications, the system and/or apparatus (e.g., in the handle) further includes a spring, which is disposed within the tubular shaft, connecting the distal force applicator and a distal portion of the inner shaft; and a contraction-facilitating knob, which is accessible from outside the outer housing, For some applications, the handle portion is shaped so as to define a handle contracting-member-receiving channel from a distal end through to a proximal end of the handle portion, the handle contracting-member-receiving channel includes the inner-shaft contracting-member-receiving channel and the distal-force-applicator contracting-member-receiving channel, For some applications, the handle portion is configured such that actuation of the contraction-facilitating knob, when the contracting member is disposed passing entirely through the handle contracting-member-receiving channel and the lock is in the locked state, causes the handle portion to uptake successive portions of the contracting member by advancing the tubular shaft proximally with respect to the outer housing, which advances the distal force applicator proximally with respect to the outer housing, which applies a proximally-directed force to the spring, which pushes the inner shaft proximally with respect to the outer housing, and which proximally pulls the contracting member.

For some applications, the handle portion is configured such that upon the actuation of the contraction-facilitating knob when the contracting member is disposed passing entirely through the handle contracting-member-receiving channel, the lock is in the locked state, and the contracting member is tensed: the spring pushes the inner shaft proximally with respect to the outer housing to a lesser extent than the tubular shaft proximally advances with respect to the outer housing, and proximal pulling of the contracting member by the inner shaft increases tension in the contracting member.

For some applications, the contraction-facilitating knob is configured to be actuated by rotation thereof.

For some applications, the tubular shaft and the contraction-facilitating knob are in threaded connection with each other, and the handle portion is configured such that actuation of the contraction-facilitating knob rotates the tubular shaft, thereby advancing the tubular shaft proximally with respect to the outer housing.

For some applications, the inner shaft partially protrudes out of a proximal end of the outer housing, and the tubular shaft and the inner shaft together provide a non-electrical mechanical force gauge, in which a relative axial position of the tubular shaft with respect to the inner shaft provides a visual indication of a measure of the tension in the contracting member.

For some applications, the inner shaft is marked with a plurality of fiduciary markers, which are arranged along the inner shaft to indicate the relative axial position of the tubular shaft with respect to the inner shaft.

For some applications, the handle portion further includes a tension-limiting locking assembly, which is configured to axially lock the inner shaft with respect to the outer housing when the handle portion increases the tension in the contracting member to a predetermined threshold level, thereby limiting a maximum tension that the inner shaft can apply to the contracting member.

For some applications, the tension-limiting locking assembly is configured to axially lock the inner shaft with respect to the outer housing when the tubular shaft is disposed at a predetermined relative axial position with respect to the inner shaft, thereby limiting the maximum tension that the inner shaft can apply to the contracting member.

For some applications, the tension-limiting locking assembly includes a detent, which is arranged to axially lock the inner shaft with respect to the outer housing when the tubular shaft is disposed at the predetermined relative axial position with respect to the inner shaft, thereby limiting the maximum tension that the inner shaft can apply to the contracting member.

For some applications, the detent is coupled in axial fixation with the inner shaft and is configured to move radially outward so as to engage the outer housing in order to axially lock the inner shaft with respect to the outer housing.

For some applications, the tension-limiting locking assembly further includes a plurality of indentations that the outer housing is shaped so as to define, the detent is engageable with the indentations to axially lock the inner shaft with respect to the outer housing, and the handle portion is arranged such that the particular one of the indentations with which the detent engages depends upon a relative axial position of the inner shaft with respect to the outer housing when the tubular shaft is disposed at the predetermined relative axial position with respect to the inner shaft.

For some applications, the proximal longitudinal portion of the tubular shaft is shaped so as to define an elongate opening through which the detent passes when the detent axially locks the inner shaft with respect to the outer housing.

For some applications, the tubular shaft includes one or more tracks that run alongside a longitudinal portion of the elongate opening and are arranged to:

(a) prevent the detent from axially locking the inner shaft with respect to the outer housing when the tubular shaft is disposed distally to the predetermined relative axial position with respect to the inner shaft, and (b) allow the detent to axially lock the inner shaft when the tubular shaft is disposed at the predetermined relative axial position with respect to the inner shaft.

For some applications, the one or more tracks are shaped so as to define one or more respective sloping portions, such that after the detent axially locks the inner shaft with respect to the outer housing when the tubular shaft is disposed at the predetermined relative axial position with respect to the inner shaft, subsequent distal motion of the tubular shaft and consequently the one or more tracks with respect to the inner shaft disengages the detent from the outer housing.

For some applications, the inner shaft partially protrudes out of a proximal end of the outer housing, and the tubular shaft and the inner shaft together provide a non-electrical mechanical force gauge, in which a relative axial position of the tubular shaft with respect to the inner shaft provides a visual indication of a measure of the tension in the contracting member.

For some applications, the implantable structure includes an implantable annuloplasty structure.

For some applications, the implantable annuloplasty structure includes a flexible sleeve, and the contracting member extends along and away from the sleeve.

There is further provided, in accordance with some applications, a system and/or an apparatus includes an implant including an implantable structure and a flexible elongated contracting member that extends away from the implantable structure; and a contracting-member-uptake tool. The contracting-member-uptake tool can include a handle portion, which (a) is shaped so as to define a handle contracting-member-receiving channel from a distal end through to a proximal end of the handle portion, and (b) includes: an outer housing; a non-electrical mechanical force gauge; a lock; and a contraction-facilitating knob, which is accessible from outside the outer housing. The lock can be configured (i) when in an unlocked state, to allow sliding of the contracting member with respect to the force gauge, and (ii) when in a locked state, to axially lock the contracting member with respect to an axially-movable portion of the force gauge, the axially-movable portion of the force gauge is axially-movable with respect to the outer housing.

For some applications, the handle portion is configured such that actuation of the contraction-facilitating knob, when the contracting member is disposed passing entirely through the handle contracting-member-receiving channel and the lock is in the locked state, causes the handle portion to uptake successive portions of the contracting member by advancing the force gauge proximally with respect to the outer housing so as to proximally pull the contracting member.

For some applications, the handle portion is configured such that upon the actuation of the contraction-facilitating knob when the contracting member is disposed passing entirely through the handle contracting-member-receiving channel, the lock is in the locked state, and the contracting member is tensed, proximal pulling of the contracting member by the axially-movable portion of the force gauge increases tension in the contracting member, and the force gauge is configured to provide a visual indication of a measure of the tension in the contracting member.

For some applications, the force gauge includes a spring.

For some applications, the force gauge is configured such that the spring applies a proximally-directed force to the axially-movable portion of the force gauge.

For some applications, the handle portion further includes a tension-limiting locking assembly, which is configured to axially lock the axially-movable portion of the force gauge with respect to the outer housing when the handle portion increases the tension in the contracting member to a predetermined threshold level, thereby limiting a maximum tension that the axially-movable portion of the force gauge can apply to the contracting member.

There is further provided, in accordance with some applications, a method including advancing toward a heart of a patient an implantable structure of an implant and a flexible elongated contracting member that extends away from the implantable structure, and threading a portion of the contracting member through a handle contracting-member-receiving channel of a handle portion of a contracting-member-uptake tool. The contracting-member-uptake tool can be the same as or similar to other contracting-member-uptake tools described elsewhere herein, and can, for example, include one, all, or some of an outer housing, a tubular shaft, disposed at least partially within the outer housing, an inner shaft, a distal force applicator, a spring, and a contraction-facilitating knob, which is accessible from outside the outer housing.

The inner shaft can (a) be partially disposed within a proximal longitudinal portion of the tubular shaft, such that the inner shaft is axially slidable with respect to the tubular shaft, (b) be shaped so as to define an inner-shaft contracting-member-receiving channel, and (c) include a lock, which is configured (i) when in an unlocked state, to allow sliding of the contracting member with respect to the inner-shaft contracting-member-receiving channel, and (ii) when in a locked state, to axially lock the contracting member with respect to the inner shaft.

The distal force applicator can (a) be disposed at least partially within a distal longitudinal portion of the tubular shaft, and (b) be shaped so as to define a distal-force-applicator contracting-member-receiving channel, which allows sliding of the contracting member therethrough, the handle contracting-member-receiving channel (a) extends from a distal end through to a proximal end of the handle portion, and (b) includes the inner-shaft contracting-member-receiving channel and the distal-force-applicator contracting-member-receiving channel.

The spring can be disposed within the tubular shaft, connecting the distal force applicator and a distal portion of the inner shaft.

The method further includes transitioning the lock from the unlocked state to the locked state.

For some applications, the method includes, thereafter, actuating the contraction-facilitating knob to cause the handle portion to uptake successive portions of the contracting member until the contracting member is tensed, by: advancing the tubular shaft proximally with respect to the outer housing, which advances the distal force applicator proximally with respect to the outer housing, which applies a proximally-directed force to the spring, which pushes the inner shaft proximally with respect to the outer housing, which proximally pulls the contracting member; and thereafter, once the contracting member is tensed, actuating the contraction-facilitating knob to increase tension in the contracting member by proximal pulling of the contracting member by the inner shaft caused by the spring pushing the inner shaft proximally with respect to the outer housing to a lesser extent than the tubular shaft proximally advances with respect to the outer housing.

For some applications, actuating the contraction-facilitating knob includes rotating the contraction-facilitating knob.

For some applications, the tubular shaft and the contraction-facilitating knob are in threaded connection with each other, and the handle portion is configured such that actuation of the contraction-facilitating knob rotates the tubular shaft, thereby advancing the tubular shaft proximally with respect to the outer housing.

For some applications, the inner shaft partially protrudes out of a proximal end of the outer housing, the tubular shaft and the inner shaft together provide a non-electrical mechanical force gauge, in which a relative axial position of the tubular shaft with respect to the inner shaft provides a visual indication of a measure of the tension in the contracting member, and the method further includes viewing the visual indication.

For some applications, the inner shaft is marked with a plurality of fiduciary markers, which are arranged along the inner shaft to indicate the relative axial position of the tubular shaft with respect to the inner shaft.

For some applications, the handle portion further includes a tension-limiting locking assembly, which is configured to axially lock the inner shaft with respect to the outer housing when the handle portion increases the tension in the contracting member to a predetermined threshold level, thereby limiting a maximum tension that the inner shaft can apply to the contracting member.

For some applications, the tension-limiting locking assembly is configured to axially lock the inner shaft with respect to the outer housing when the tubular shaft is disposed at a predetermined relative axial position with respect to the inner shaft, thereby limiting the maximum tension that the inner shaft can apply to the contracting member.

For some applications, the tension-limiting locking assembly includes a detent, which is arranged to axially lock the inner shaft with respect to the outer housing when the tubular shaft is disposed at the predetermined relative axial position with respect to the inner shaft, thereby limiting the maximum tension that the inner shaft can apply to the contracting member.

For some applications, the detent is coupled in axial fixation with the inner shaft and is configured to move radially outward so as to engage the outer housing in order to axially lock the inner shaft with respect to the outer housing.

For some applications, the tension-limiting locking assembly further includes a plurality of indentations that the outer housing is shaped so as to define, the detent is engageable with the indentations to axially lock the inner shaft with respect to the outer housing, and the handle portion is arranged such that the particular one of the indentations with which the detent engages depends upon a relative axial position of the inner shaft with respect to the outer housing when the tubular shaft is disposed at the predetermined relative axial position with respect to the inner shaft.

For some applications, the proximal longitudinal portion of the tubular shaft is shaped so as to define an elongate opening through which the detent passes when the detent axially locks the inner shaft with respect to the outer housing.

For some applications, the tubular shaft includes one or more tracks that run alongside a longitudinal portion of the elongate opening and are arranged to:

(a) prevent the detent from axially locking the inner shaft with respect to the outer housing when the tubular shaft is disposed distally to the predetermined relative axial position with respect to the inner shaft, and (b) allow the detent to axially lock the inner shaft when the tubular shaft is disposed at the predetermined relative axial position with respect to the inner shaft.

For some applications, the one or more tracks are shaped so as to define one or more respective sloping portions, such that after the detent axially locks the inner shaft with respect to the outer housing when the tubular shaft is disposed at the predetermined relative axial position with respect to the inner shaft, subsequent distal motion of the tubular shaft and consequently the one or more tracks with respect to the inner shaft disengages the detent from the outer housing.

For some applications, the inner shaft partially protrudes out of a proximal end of the outer housing, the tubular shaft and the inner shaft together provide a non-electrical mechanical force gauge, in which a relative axial position of the tubular shaft with respect to the inner shaft provides a visual indication of a measure of the tension in the contracting member, and the method further includes viewing the visual indication.

For some applications, the implantable structure includes an implantable annuloplasty structure, and advancing the implantable structure includes advancing the implantable annuloplasty structure toward the heart.

For some applications, the implantable annuloplasty structure includes a flexible sleeve, and advancing the implantable annuloplasty structure and the contracting member toward the heart such that the contracting member extends along and away from the sleeve.

There is further provided, in accordance with some applications, a method including advancing toward a heart of a patient an implantable structure of an implant and a flexible elongated contracting member that extends away from the implantable structure, and threading a portion of the contracting member through a handle contracting-member-receiving channel of a handle portion of a contracting-member-uptake tool.

The contracting-member-uptake tool can be the same as or similar to other contracting-member-uptake tools described elsewhere herein or otherwise known. For example, in some applications, the contracting-member-uptake tool comprises an outer housing, a non-electrical mechanical force gauge, a lock, and a contraction-facilitating knob. The lock can be configured (i) when in an unlocked state, to allow sliding of the contracting member with respect to the force gauge, and (ii) when in a locked state, to axially lock the contracting member with respect to an axially-movable portion of the force gauge, the axially-movable portion of the force gauge is axially-movable with respect to the outer housing. The contraction-facilitating knob can be accessible from outside the outer housing.

The method further includes transitioning the lock from the unlocked state to the locked state; and thereafter, actuating the contraction-facilitating knob to cause the handle portion to uptake successive portions of the contracting member by advancing the force gauge proximally with respect to the outer housing so as to proximally pull the contracting member.

The method can thereafter include, once the contracting member is tensed, actuating the contraction-facilitating knob to increase tension in the contracting member by proximal pulling of the contracting member by the axially-movable portion of the force gauge, and viewing a visual indication of a measure of the tension in the contracting member, the visual indication provided by the force gauge.

For some applications, the force gauge includes a spring.

For some applications, the force gauge is configured such that the spring applies a proximally-directed force to the axially-movable portion of the force gauge.

For some applications, the handle portion further includes a tension-limiting locking assembly, which is configured to axially lock the axially-movable portion of the force gauge with respect to the outer housing when the handle portion increases the tension in the contracting member to a predetermined threshold level, thereby limiting a maximum tension that the axially-movable portion of the force gauge can apply to the contracting member.

The method can be performed in a procedure on a living animal or in a simulation/simulated procedure (e.g., on a cadaver, cadaver heart, simulator with a simulated heart, tissue, etc., anthropomorphic ghost, etc.)

There is also provided, in accordance with some applications, a system and/or an apparatus, which can include an implantable annuloplasty structure (e.g., an annuloplasty ring structure, a closed annuloplasty structure, a closed annuloplasty ring structure, an open annuloplasty structure, a partial annuloplasty ring structure, or other annuloplasty device). The implantable annuloplasty structure can comprise a primary body portion and a contracting member extending at least partially along a longitudinal length of the primary body portion of the annuloplasty structure. The implantable annuloplasty structure can be the same as or similar to other annuloplasty structures described elsewhere herein.

The system and/or apparatus can also comprise a contracting-member-uptake tool. The contracting-member-uptake tool can be the same as or similar to other contracting-member-uptake tools described elsewhere herein. The contracting-member-uptake tool can comprise one or more tubes (e.g., one tube, a primary tube and a secondary tube, etc.). At least one tube has a lumen configured for passage therethrough of the contracting member. The tube can be flexible, semi-rigid, or rigid. The contracting-member-uptake tool can also comprise a contracting-member-snare. The contracting-member snare can comprise a distal snare portion and an elongate flexible body portion coupled to the distal snare portion. The distal snare portion can be configured to ensnare a portion of the contracting member and pull it into the lumen. The distal snare portion can be configured to pull the portion of the contracting member through some of the lumen or through an entire length of the lumen (e.g., from end to end). The contracting-member-snare can comprise a wire comprising stainless steel. The lumen of the tube can be sized so as to maintain coupling between the distal snare portion and the contracting member.

The contracting-member-uptake tool can comprise a handle portion, and the tube can be connected to the handle portion. The handle portion can comprise a contracting-member-uptake device configured to uptake successive portions of the contracting member. The handle portion can also include a tension meter configured to measure a degree of tension of the contracting member. The contracting-member-uptake device can be actuatable to increase tension of the contracting member. The contracting-member-uptake device can optionally comprise a wheel having a groove configured to couple the contracting member to the wheel. The groove can be shaped so as to receive a middle portion of the contracting member.

The distal snare portion can comprise a flexible loop. The lumen can be configured to collapse the flexible loop around the contracting member as the portion of the contracting member is pulled through the lumen. At least the distal snare portion of the contracting-member-snare can be corrugated to increase friction between the snare portion and the contracting member.

The distal end portion of the contracting-member-uptake tool can be shaped so as to define a sharp edge, and the contracting member-uptake tool can be configured to dispose the contracting member in proximity to the sharp edge such that the sharp edge can sever the contracting member.

The contracting member-uptake tool can comprise a contracting-member-fastener disposed within the distal end portion of the contracting-member-uptake tool. The contracting-member-fastener can comprise a clamping structure. The clamping structure can be biased toward assuming a closed state or closed position, and in the closed state/position, the clamping structure can be configured to clamp onto the contracting member passed therethrough. The clamping structure can also be configured such that it can be flexed to an open state or open position, wherein in the open state/position, the contracting member can move therethrough. The contracting member-uptake tool can also comprise a stop removably coupled to the contracting-member-fastener and configured to maintain the contracting-member-fastener in the open state/position.

The distal snare portion, the portion of the contracting-member, and the clamping structure can be configured and sized to pass distally through the contracting-member-fastener and clamping structure in the open state/position. The distal snare portion can be adapted to capture and pull the portion of the contracting member proximally through the contracting-member-fastener and clamping structure, and through aligned ports in the distal end portion of the contracting-member-uptake tool.

The contracting-member-uptake tool can comprise a fastener-ejector movable within the distal end portion of the contracting-member-uptake tool, which can be configured such that movement of the fastener-ejector contacts and can convert the contracting-member-fastener and clamping structure from the open state/position to the closed state/position to clamp onto the contracting member when passed therethrough. The fastener-ejector can be coupled to the stop and can be configured to move the stop that is removably coupled to the fastener. The distal end portion of the contracting-member-uptake tool can be shaped so as to define a sharp edge, and the contracting-member-uptake tool can be configured to dispose the contracting member in proximity to the sharp edge such that movement of the fastener-ejector against the sharp edge severs the contracting member after or proximate where it extends through the fastener.

The various apparatuses, systems, methods, etc. described above can incorporate and/or substitute various features and components of other embodiments described elsewhere herein.

The present inventions will be more fully understood from the following detailed description of embodiments thereof, taken together with the drawings, in which:

DETAILED DESCRIPTION OF EMBODIMENTS

Figure 1:
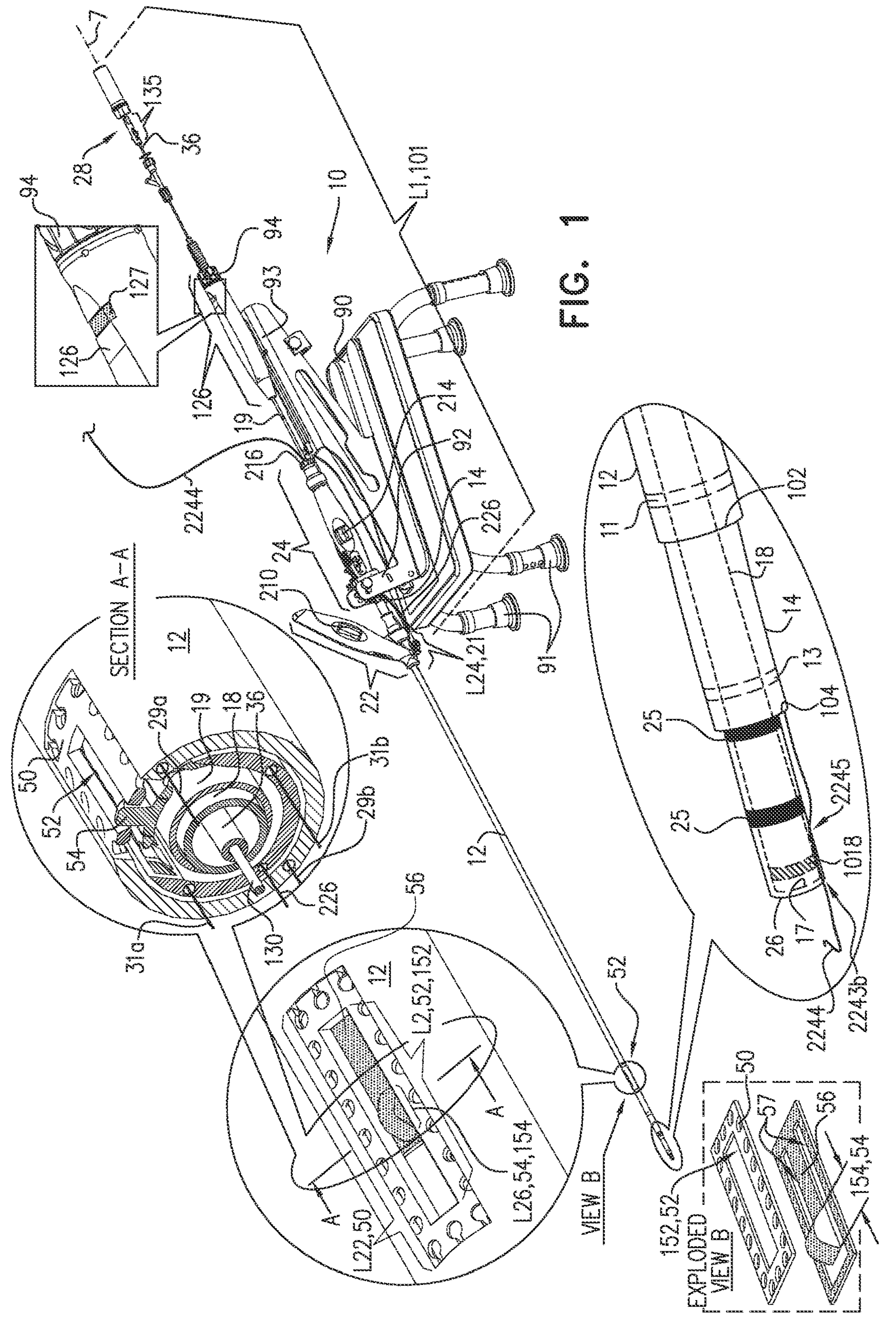
FIGS. 1-2 are schematic illustrations of an example of a multi-component tubular system for delivering and anchoring an implant and for controlling a relative spatial orientation of components of the catheter system.
Figure 2:
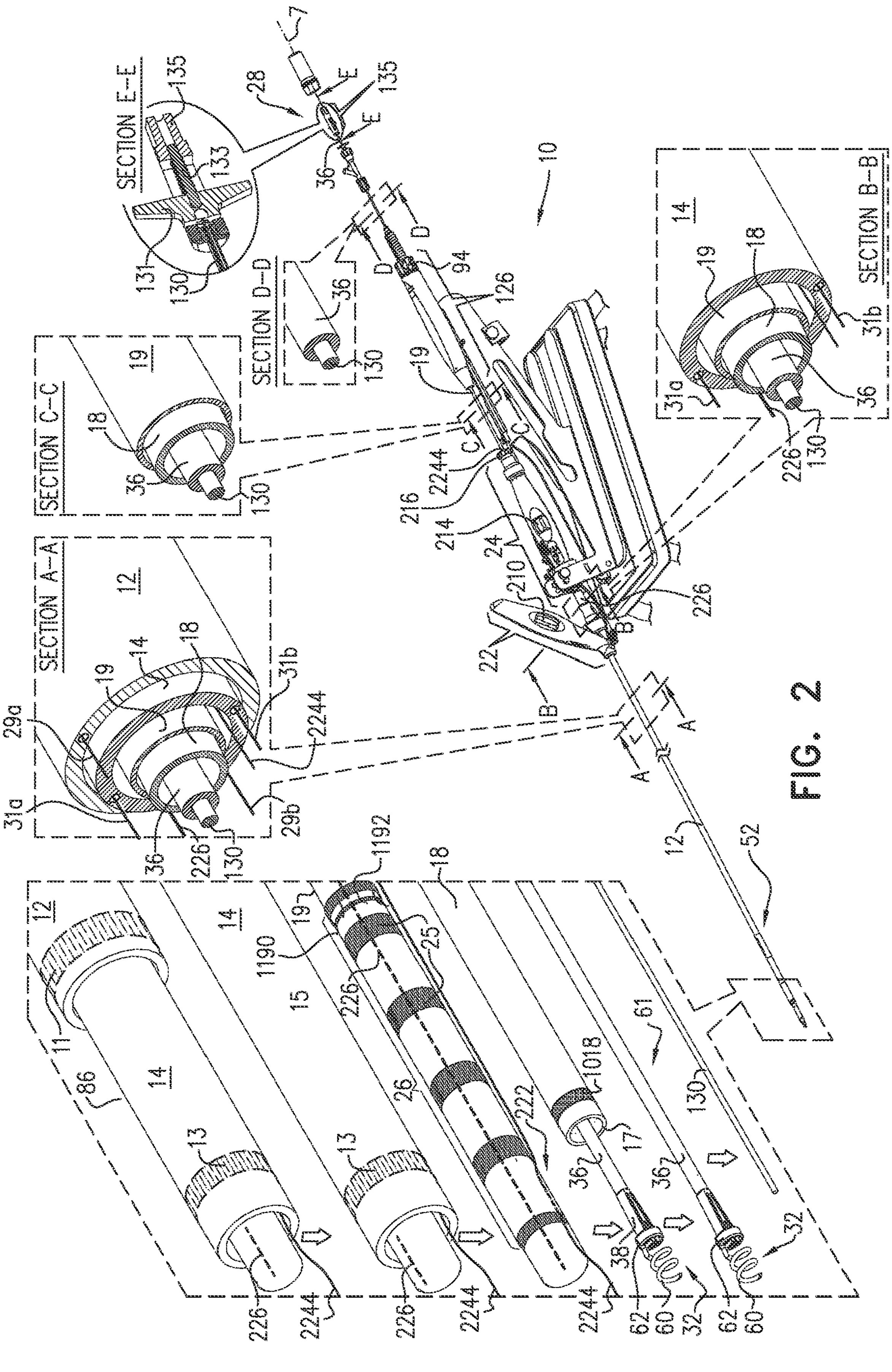

Reference is now made to FIGS. 1-2, which are schematic illustrations of an example of a multi-component tubular system 10 providing one or more rotationally-controlled steering catheters configured for delivering an implant to a heart of a patient. System 10 provides an implant-delivery tool. System 10 can comprise a first, outer catheter 12 comprising a sheath configured for advancement through vasculature of a patient. For some applications, outer catheter 12 comprises a sheath configured for advancement through a femoral artery toward an interatrial septum of a heart of a patient. A distal steerable end portion of outer catheter 12 is configured to pass through the septum and be oriented in a desired spatial orientation. System 10 comprises a second catheter, or guide catheter 14, comprising a steerable distal end portion. Catheter 14 is configured for advancement through a lumen of outer catheter 12. Outer catheter 12 provides a first coupling 152 (e.g., a slit 52) at a distal portion thereof (e.g., a portion of catheter 12 that is proximal to the steerable distal end portion). Guide catheter 14 can comprise a second coupling 154 (e.g., a depressible engager 54) that is coupled to a displaceable tab 56 coupled to a base. As is described herein, depressible engager 54 (or the second coupling 154) is configured so as to protrude within slit 52 (or the first coupling 152). Thus, slit 52 defines a second-coupling-receiving element.

In some embodiments, first coupling 152 of catheter 12 defines a longer coupling, the second coupling 154 of catheter 14 defines a shorter coupling. The first and second couplings 152 and 154 of outer catheter 12 and guide catheter 14, respectively, enable axial advancement and rotational motion of guide catheter 14 through the lumen of outer catheter 12 until engager 54 of catheter 14 is aligned with and engages slit 52 of catheter 12, as will be described hereinbelow. As shown in cross-section A-A of FIG. 1, guide catheter 14 is configured to be concentrically disposed within a lumen of outer catheter 12. In some embodiments, catheter 12 provides the shorter coupling, and catheter 14 provides the longer coupling. For example, catheter 14 can be shaped so as to provide slit 52, and catheter 12 can comprise engager 54, which is configured to engage slit 52 of catheter 14.

As shown in the exploded view of view B, first coupling 152 can be shaped so as to define slit 52. For some applications, slit 52 is provided by a metal frame 50, as shown. Metal frame 50 can have a length L22 of, for example, between 7 and 15 mm, e.g., 13 mm. For such applications, a slit is created in material of catheter 12 (e.g., by creating a slit in the polymer material of catheter 12 during manufacturing of catheter 12), and frame 50 is coupled to catheter 12. Second coupling 154 can comprise an engager 54 which can comprise a protrusion disposed at a distal portion of displaceable tab 56 of a base of engager 54. The base of engager 54 can be shaped so as to define slits 57 which form tab 56. Engager 54 is depressible when a force is applied thereto, and tab 56 facilitates movement of engager 54 in response to and in the absence of force applied to engager 54. For some applications, during manufacture of catheter 14, catheter 14 is manipulated in order to couple thereto engager 54 and tabs 56, e.g., engager 54 and tabs 56 are embedded within the polymer of catheter 14.

Although slit 52 and a depressible engager 54 are shown on outer catheter 12 and guide catheter 14, respectively, at distal portions of catheters 12 and 14, slit 52 and engager 54 can be provided along any suitable portion of catheters 12 and 14, respectively (e.g., respective proximal portions of catheters 12 and 14).

First and second couplings 152 and 154, respectively, can be provided on any standard catheter. That is, coupling 152 comprises frame 50 which can be coupled to an external surface of any standard catheter (in which case, a corresponding slit would be made in the standard catheter). Additionally coupling 154 can be coupled to any standard catheter by coupling the base portion of coupling 154 to any standard catheter. Suitable adjustments to the standard catheter would be made to accommodate the displacing of tab 56 and engager 54 in response to pushing forces applied to engager 54.

FIG. 2 shows an example concentric relationship between components of tubular system 10 (in an exploded view on the left side of FIG. 2). As described hereinabove, a distal end portion of outer catheter 12 is steerable. The distal end portion of outer catheter 12 can comprise a pull ring 11 that is coupled to two or more steering or pull wires 29*a* and 29*b*, that are disposed within respective secondary lumens within a wall of catheter 12 (as shown in section A-A). As shown in the exploded view, guide catheter 14 can be configured to be concentrically disposed within the lumen of catheter 12. As described hereinabove, the distal end portion of guide catheter 14 is steerable. The distal end portion of catheter 14 can comprise a pull ring 13 that is coupled to two or more pull wires 31*a* and 31*b*, that are disposed within respective secondary lumens within a wall of catheter 14 (as shown in sections A-A and B-B).

Guide catheter 14 is steerable to a desired spatial orientation in order to facilitate advancing and implantation of an implant in a body cavity of the patient. As shown, the implant comprises an annuloplasty structure 222 (e.g., an annuloplasty ring structure, a closed annuloplasty structure, a closed annuloplasty ring structure, an open annuloplasty structure, a partial annuloplasty ring structure, etc.) comprising a flexible sleeve 26 (shown in the exploded view of FIG. 2). Sleeve 26 can comprise a braided fabric mesh, e.g., comprising DACRON™. Sleeve 26 can be configured to be placed only partially around a cardiac valve annulus (i.e., to assume a C-shape), and, once anchored in place, to be contracted so as to circumferentially tighten the valve annulus. Although, the ring structure can also be configured to be placed entirely around the valve annulus. In order to tighten the annulus, annuloplasty structure or annuloplasty ring structure 222 comprises a flexible elongate contracting member 226 that extends along sleeve 26. Elongate contracting member 226 can comprise a wire, a ribbon, a rope, or a band, which can comprise one or more of a variety of materials, for example, a flexible and/or superelastic material, e.g., nitinol, polyester, stainless steel, or cobalt chrome. For some applications, the wire comprises a radiopaque material. For some applications, contracting member 226 comprises a braided polyester suture (e.g., Ticron). For some applications, contracting member 226 is coated with polytetrafluoroethylene (PTFE). For some applications, contracting member 226 comprises a plurality of wires that are intertwined to form a rope structure.

For applications in which system 10 is used to deliver an implant to the mitral valve of the patient, outer catheter 12 can be configured for initial advancement through vasculature of the patient until a distal end 102 (which can be a distal-most end or tip) of catheter 12 is positioned in the left atrium. The distal steerable end portion of catheter 12 is then steered such that distal end 102 of catheter 12 is positioned in a desired spatial orientation within the left atrium. The steering procedure can be performed with the aid of imaging, such as fluoroscopy, transesophageal echo, and/or echocardiography. Following the steering of the distal end portion of catheter 12, guide catheter 14 (which houses annuloplasty structure 222) is advanced through catheter 12 in order to facilitate delivery and implantation of structure 222 along the annulus of the mitral valve. During the delivery, at least a portion of the steerable distal end portion of catheter 14 can be exposed from distal end 102 of catheter 12 and is thus free for steering toward the annulus of the mitral valve, as is described hereinbelow.

In addition, system 10 comprises an attachment mechanism (e.g., anchor(s), adhesive, clamp(s), clip(s), fastener(s), etc.), such as a plurality of anchors 32, which can be, for example, between about 5 and about 20 anchors, such as about 10 or about 16 anchors. Each anchor 32 can comprise a tissue-engaging element 60 (e.g., a helical tissue-engaging element), and a tool-coupling head 62, fixed to one end of the tissue-engaging element. One anchor 32 is shown in FIG. 2 as being reversibly coupled to a deployment element 38 of a rotating anchor driver 36 of an anchor deployment manipulator 61. When sleeve 26 is disposed along the annulus of the cardiac valve, deployment manipulator 61 is configured to advance within a lumen of sleeve 26 and deploy each anchor 32 from within sleeve 26 through a wall of sleeve 26 and into cardiac tissue, thereby anchoring sleeve 26 around a portion of the valve annulus. The insertion of the anchors into the sleeve and deployment of the anchors into cardiac tissue is described in detail hereinbelow.

Anchors 32 can comprise a biocompatible material, such as stainless steel 316 LVM. For some applications, anchors 32 comprise nitinol. For some applications, anchors 32 are coated fully or partially with a non-conductive material.

Deployment manipulator 61, as shown in FIG. 2, comprises anchor driver 36 and deployment element 38.

As shown in the exploded view of FIG. 2, sleeve 26 is disposed within a lumen of guide catheter 14. A force is applied to a proximal end of sleeve 26 by a distal end of a reference-force tube 19. As shown, an implant-decoupling channel 18 is advanceable within a lumen of reference-force tube 19 and through a lumen of sleeve 26 such that a portion of channel 18 that is disposed within the sleeve is coaxial with the sleeve. As shown in the enlarged image of FIG. 1, a distal end 17 of implant-decoupling channel 18 is disposed in contact with an inner wall of sleeve 26 at a distal end thereof. Additionally, a distal end portion of channel 18 comprises a radiopaque marker 1018. As shown, tube 19 and sleeve 26 are longitudinally and coaxially disposed with respect to each other.

Anchor driver 36 can be advanced within channel 18. For some applications, system 10 comprises a plurality of anchor drivers 36, each driver being coupled to a respective anchor 32. Each driver 36 can be advanced within channel 18 in order to advance and implant anchor 32 in tissue. Following implantation of anchor 32, anchor 32 is decoupled from driver 36, as described herein, and driver 36 is removed from within channel 18. Subsequently, a new driver 36 coupled to another anchor 32 is then advanced within channel 18.

As will be described hereinbelow, a first anchor 32 is configured to be deployed through the wall of the sleeve into cardiac tissue, when sleeve 26 is positioned along the annulus of the valve. Following the deployment of the first anchor, a distal portion of sleeve 26 is slid distally off a portion of implant-decoupling channel 18. In order to decouple sleeve 26 distally from a portion of outer surface of channel 18, (1) a proximal force is applied to channel 18, while (2) reference-force tube 19 is maintained in place in a manner in which a distal end of tube 19 provides a reference force to sleeve 26 in order to facilitate freeing of a successive portion of sleeve 26 from around channel 18. Channel 18 is then positioned at a successive location within the lumen of sleeve 26 while either tube 19 and/or catheter 14 is steered toward a successive location along the annulus of the valve (as will be described hereinbelow). Consequently, the successive portion of sleeve 26 provides a free lumen for advancement of a successive anchor 32 and deployment of the anchor through the wall of the sleeve at the successive portion thereof. Such freeing of the successive portion of sleeve 26 creates a distance between successive anchors deployed from within the lumen of sleeve 26.

For some applications, sleeve 26 comprises a plurality of radiopaque markers 25, which are positioned along the sleeve at respective longitudinal sites. The markers can provide an indication in a radiographic image (such as a fluoroscopy image) of how much of the sleeve has been deployed at any given point during an implantation procedure, in order to enable setting a desired distance between anchors 32 along the sleeve. For some applications, the markers comprise a radiopaque ink.

Often, at least a portion (e.g., three, at least three, some, all, etc.) of the longitudinal sites of the radiopaque markers are longitudinally spaced at a constant interval. The longitudinal distance between the distal edges of adjacent markers, and/or the distance between the proximal edges of adjacent markers, can be set equal to the desired distance between adjacent anchors. For example, the markers can comprise first, second, and third markers, which first and second markers are adjacent, and which second and third markers are adjacent, and the distance between the proximal and/or distal edges of the first and second markers equal the corresponding distance between the proximal and/or distal edges of the second and third markers. For example, the distance can be between 3 and 15 mm, such as 6 mm, and the longitudinal length of each marker can be between 0.1 and 14 mm, such as 2 mm (If, for example, the distance were 6 mm and the length were 2 mm, the longitudinal gaps between adjacent markers would have lengths of 4 mm.)

Each anchor 32 can be coupled to deployment element 38 of anchor driver 36. Anchor driver 36 comprises an elongate tube having at least a flexible distal end portion. The elongate tube of driver 36 extends within a lumen of channel 18, through system 10 toward a proximal end of a proximal handle portion 101 of system 10. The tube of anchor driver 36 provides a lumen for slidable advancement therethrough of an elongate rod 130. Rod 130 facilitates the locking and unlocking of anchor 32 to deployment element 38, as is described hereinbelow. As shown in Section E-E of FIG. 2, a proximal end of rod 130 is coupled to a component of an anchor-release mechanism 28 at a proximal end of system 10. Mechanism 28 comprises a housing 135 and a finger-engager 131 that is coupled to the proximal end of rod 130. Finger-engager 131 is coupled to a housing 135 via a spring 133 (section E-E of FIG. 2). A proximal end of the tube of anchor driver 36 is coupled to housing 135. As is described hereinbelow, the user (e.g., a physician, health care professional, etc.) releases anchor 32 from deployment element 38 when finger-engager 131 is pulled proximally, thereby pulling rod 130 proximally.

For some applications, anchor driver 36 (e.g., rotation and/or proximal-distal movement thereof, and/or release of anchor 32) is electronically controllable, such as by using an extracorporeal controller and/or electric motor coupled to a proximal end of the anchor driver and/or housing 135.

Proximal handle portion 101 can be supported by a stand having support legs 91 and a handle-sliding track 90. Handle portion 101 comprises an outer-catheter handle 22, a guide-catheter handle 24, an implant-manipulating handle 126, and anchor-release mechanism 28. Handle 22 is coupled to a proximal end of outer catheter 12. Handle 24 is coupled to a proximal portion of guide catheter 14. Handle 126 is coupled to a proximal portion of reference-force tube 19, and linear movement of handle 126 with respect to handle 24 moves reference-force tube 19 (and thereby typically structure 222) through catheter 14. As described hereinabove, housing 135 of anchor-release mechanism 28 is coupled to a proximal portion of the tube of anchor driver 36. The relative positioning of each of the concentrically-disposed components of system 10 is shown in the exploded view and sections A-A, B-B, C-C, and D-D of FIG. 2.

The stand supporting proximal handle portion 101 can be moved distally and proximally to control a position of the entire multi-component system 10, particularly so as to adjust a distance of distal end 102 of catheter 12 from the interatrial septum. Handle 22 comprises a steering knob 210 that is coupled to pull wires 29*a* and 29*b* disposed within respective secondary lumens in the wall of outer catheter 12. Rotation of knob 210 adjusts a degree of tension of wires 29*a* and 29*b* which, in turn, apply a force to pull ring 11 at the distal end portion of outer catheter 12. Such force steers the distal end portion of catheter 12 within the atrium of the heart of the patient in a manner in which the distal end portion of catheter 12 is steered in a first plane that is parallel with the plane of the annulus of the valve (e.g., in a direction from the interatrial septum toward surrounding walls of the atrium). For some applications, the distal end portion of catheter 12 can be pre-shaped so as to point downward toward the valve. For other applications, the distal end portion of catheter 12 can be pulled to assume an orientation in which the distal end portion points downward toward the valve. For some applications, the distal end portion of catheter 12 is not made to point downward toward the valve.

Handle 24 can be coupled to track 90 via a first mount 92. Mount 92 can be slidable proximally and distally along track 90 in order to control an axial position of guide catheter 14 with respect to outer catheter 12. Mount 92 can be slidable via a control knob 216. For example, control knob 216 of mount 92 can control the proximal and distal axial movement of the distal steerable portion of guide catheter 14 with respect to distal end 102 of outer catheter 12. Handle 24 can comprise a steering knob 214 that is coupled to pull wires 31*a* and 31*b* disposed within respective secondary lumens in the wall of guide catheter 14. Rotation of knob 214 adjusts a degree of tension of wires 31*a* and 31*b* which, in turn, apply a force to pull ring 13 at the distal end portion of guide catheter 14. Such force steers the distal end portion of catheter 14 in a second plane within the atrium of the heart of the patient downward and toward the annulus of the cardiac valve. As described hereinbelow, the distal end portion of guide catheter 14 can be steered in the second plane that is substantially perpendicular with respect to the first plane in which the distal end portion of outer catheter 12 is steered.

The combined steering of the respective distal end portions of catheters 12 and 14 directs sleeve 26 down toward the annulus (e.g., via the steering of the distal end portion of catheter 14) and along the perimeter of annulus (e.g., from the posterior section of the valve to the anterior section of the valve, and vice versa), via the steering of the distal end portion of catheter 12.

For some applications, handle 22 can be tilted by the user (e.g., an operating physician, etc.), in order to further adjust a position of the distal end of catheter 12.

For some applications, handle 22 comprises an indicator that indicates a degree of steering (e.g., bending) of the distal end portion of catheter 12 that has been produced using knob 210. For some applications, handle 24 comprises an indicator that indicates a degree of steering (e.g., bending) of the distal end portion of catheter 12 that has been produced using knob 214.

As described herein, first and second couplings 152 and 154 of outer catheter 12 and guide catheter 14, respectively (e.g., slit 52 and engager 54, respectively), provide a controlled steerable system in which, during the steering and bending of the distal end portion of guide catheter 14, the distal end portion of outer catheter 12 is maintained in its steered configuration, or in its spatial orientation, without substantially affecting the steering or the bending of the distal end portion of guide catheter 14. Thus, first and second couplings 152 and 154, respectively, minimize the effect of the distal end portion of outer catheter 12 on the steering and bending of catheter 14. That is, first and second couplings 152 and 154 of outer catheter 12 and guide catheter 14, respectively, collectively define a relative-spatial-orientation-controlling device which rotationally locks the relative spatial orientation of the steerable distal end portion and the bending section of outer catheter 12 with respect to the steerable distal end portion and the bending section of guide catheter 14.

Contracting member 226 exits from the lumen in the wall of guide catheter 14 at a portion of handle portion 101 that is between handles 22 and 24.

Handle 126 can be coupled to track 90 via a second mount 93. Mount 93 can be slidable proximally and distally along a track, in order to control an axial position of reference-force tube 19 and at least a proximal portion of sleeve 26 with respect to guide catheter 14. Mount 93 can be slidable via a control knob. For example, the control knob of mount 93 can control the proximal and distal axial movement of the tube 19 and at least the proximal portion of sleeve 26 with respect to distal end 104 of guide catheter 14. Taken together with the steering of the distal end portion of guide catheter 14, such movement of tube 19 and at least the proximal portion sleeve 26 moves the proximal portion of sleeve 26 toward a desired portion of tissue of the annulus of the valve during deployment of anchors 32 from within the lumen of sleeve 26, as is described hereinbelow.

As is described hereinabove, in order to decouple sleeve 26 from a portion of an outer surface of channel 18, (1) channel 18 can be pulled proximally, while (2) reference-force tube 19 is maintained in place. A proximal end of channel 18 can be coupled to a knob 94 which adjusts an axial position of channel 18 proximally and distally with respect to reference-force tube 19 and sleeve 26.

Handle portion 101 can comprise a release-decision-facilitation member 127, such as a latch or button, that automatically engages when a given length of sleeve 26 has advanced off channel 18 (e.g., when channel 18 is at a given position with respect to tube 19); often just before sleeve 26 becomes completely decoupled from channel 18. Engagement of member 127 inhibits proximal movement of channel 18 with respect to tube 19, thereby reducing a likelihood of (e.g., preventing) inadvertent release of sleeve 26. In order to release sleeve 26 (e.g., to decouple channel 18 from the sleeve), the user (e.g., an operating physician) must disengage member 127, such as by pushing the button, before continuing to withdraw channel 18 proximally. When engaged, member 127 can also inhibit distal movement of channel 18 with respect to tube 19.

Handle portion 101 (comprising handles 22, 24, and 126 and anchor-release mechanism 28) can have a length L1 of between 65 and 85 cm, e.g., 76 cm. As shown, a majority of the body portion of outer-catheter handle 22 can be disposed at a non-zero angle with respect to a longitudinal axis 7 of the multiple components of system 10. The steering mechanism provided by handle 22 in order to steer the distal end portion of catheter 12 is disposed within the portion of handle 22 that is disposed at the non-zero angle with respect to axis 7. Handle 22 comprises an in-line tubular portion 21 which is longitudinally disposed in-line along axis 7 and coaxially with respect to handles 24 and 126 and release mechanism 28. Tubular portion 21 is shaped so as to define a lumen for inserting guide catheter 14 therethrough and subsequently into the lumen of outer catheter 12. Tubular portion 21 has a length L24 of between 7 and 11 cm, e.g., 7 cm. Such spatial orientation of the majority of handle 22 at an angle with respect to axis 7 reduces an overall functional length of handle portion 101.

Reference is now made to FIGS. 3A-I, which are schematic illustrations of an example of a procedure for implanting an annuloplasty structure 222 (e.g., an annuloplasty ring structure, a closed annuloplasty structure, a closed annuloplasty ring structure, an open annuloplasty structure, a partial annuloplasty ring structure, etc.) to repair a mitral valve 230. This procedure is one example of a procedure that can be performed using system 10.

Annuloplasty structure or annuloplasty ring structure 222 can be used to repair a dilated valve annulus of an atrioventricular valve, such as mitral valve 230. For some applications, the annuloplasty structure is configured to be placed only partially around the valve annulus (e.g., to assume a C-shape), and, once anchored or otherwise secured in place, to be contracted so as to circumferentially tighten the valve annulus. For some applications, the annuloplasty structure is configured to be placed fully around the valve annulus (e.g., to assume a closed shape, such as a circle, oval, D-shape, etc.), and, once secured in place, to be contracted so as to circumferentially tighten the valve annulus. The annuloplasty structure can comprise a flexible sleeve 26. The annuloplasty structure can also comprise and/or be used with an attachment means (e.g., anchor(s), fastener(s), clamp(s), suture(s), clip(s), etc.), such as a plurality of anchors 32. Anchor deployment manipulator 61 is advanced into a lumen of sleeve 26, and, from within the lumen, deploys the anchors through a wall of the sleeve and into cardiac tissue, thereby anchoring the sleeve around a portion of the valve annulus. For some applications, annuloplasty structure or annuloplasty ring structure 222 is implemented using techniques described in U.S. application Ser. No. 12/437,103, filed May 7, 2009 which issued as U.S. Pat. No. 8,715,342, and/or U.S. application Ser. No. 12/689,635, filed Jan. 19, 2010 which issued as U.S. Pat. No. 8,545,553, both of which are assigned to the assignee of the present application and are incorporated herein by reference.

Figure 3A:
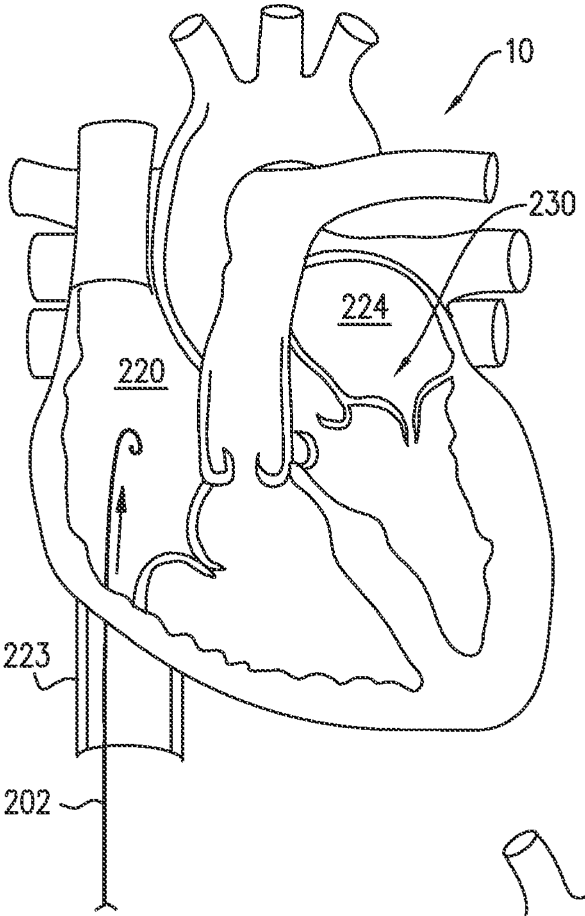
FIGS. 3A-I are schematic illustrations of an example procedure for implanting an annuloplasty structure to repair a mitral valve.

As shown in FIG. 3A, the procedure can begin by advancing a semi-rigid guidewire 202 into a right atrium 220 of the patient. The procedure can be performed with the aid of imaging, such as fluoroscopy, transesophageal echo, and/or echocardiography.

Figure 3B:
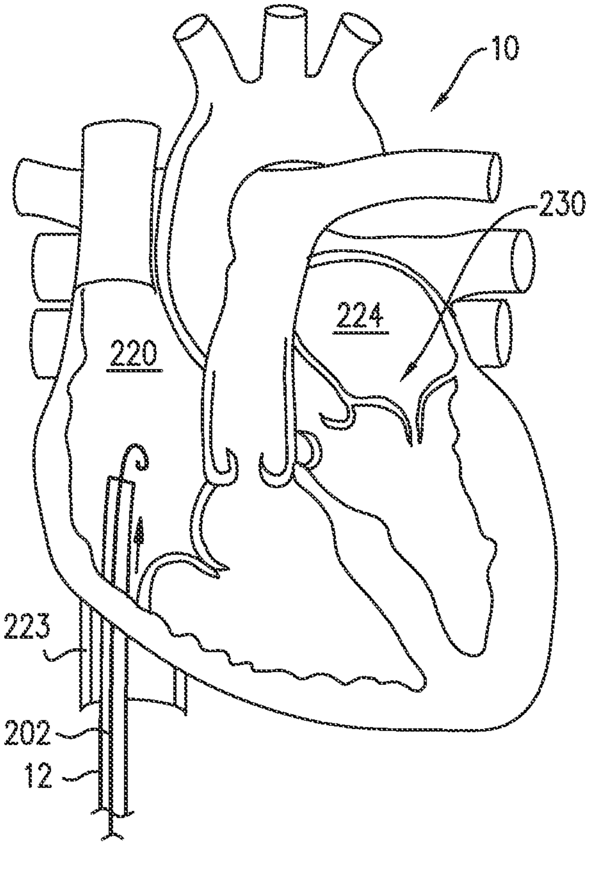

As show in FIG. 3B, guidewire 202 provides a guide for the subsequent advancement of outer catheter 12 therealong and into the right atrium. Once a distal portion of catheter 12 has entered the right atrium, guidewire 202 is retracted from the patient's body. Catheter 12 can comprise a 14-24 F sheath, although any size may be selected as appropriate for a given patient. Catheter 12 is advanced through vasculature into the right atrium using a suitable point of origin determined for a given patient. For example:

- catheter 12 can be introduced into the femoral vein of the patient, through an inferior vena cava 223, into right atrium 220, and into a left atrium 224 transseptally, for example, through the fossa ovalis;
- catheter 12 can be introduced into the basilic vein, through the subclavian vein to the superior vena cava, into right atrium 220, and into left atrium 224 transseptally, for example, through the fossa ovalis; or
- catheter 12 can be introduced into the external jugular vein, through the subclavian vein to the superior vena cava, into right atrium 220, and into left atrium 224 transseptally, for example, through the fossa ovalis.

For some applications, catheter 12 is advanced through inferior vena cava 223 of the patient (as shown) and into right atrium 220 using a suitable point of origin for a given patient.

Figure 3C:
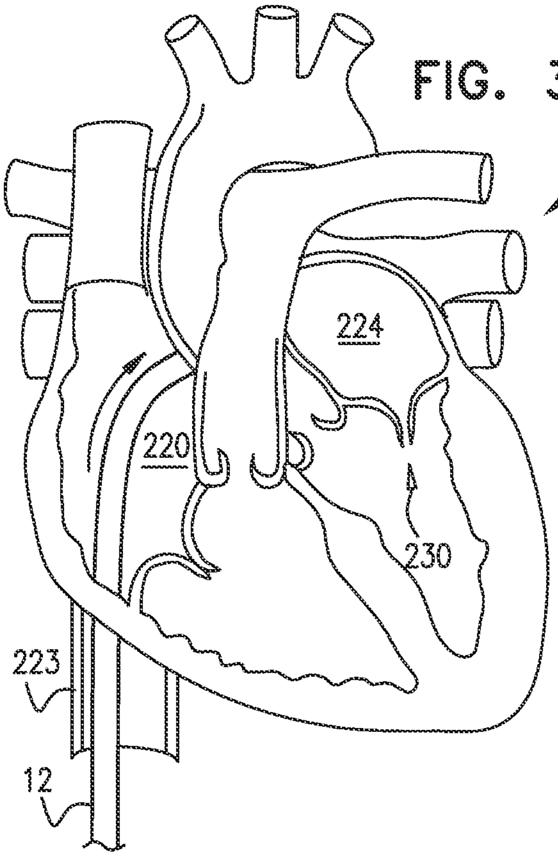

Catheter 12 can be advanced distally until the sheath reaches the interatrial septum, and guidewire 202 is withdrawn, as shown in FIG. 3C.

Figure 3D:
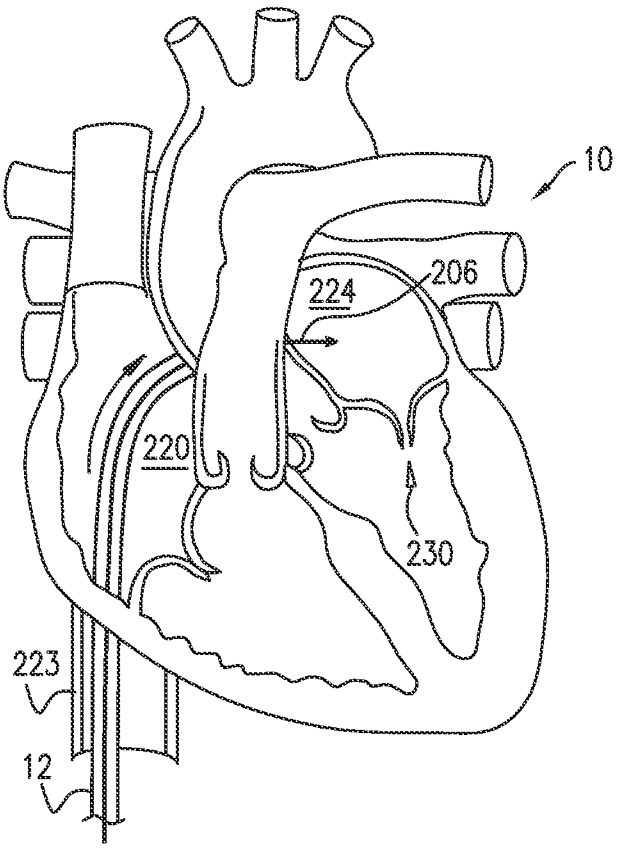

As shown in FIG. 3D, a resilient needle 206 and a dilator (not shown) are advanced through catheter 12 and into the heart. In order to advance catheter 12 transseptally into left atrium 224, the dilator is advanced to the septum, and needle 206 is pushed from within the dilator and is allowed to puncture the septum to create an opening that facilitates passage of the dilator and subsequently catheter 12 therethrough and into left atrium 224. The dilator is passed through the hole in the septum created by the needle. The dilator can be shaped to define a hollow shaft for passage along needle 206, and the hollow shaft is shaped to define a tapered distal end. This tapered distal end is first advanced through the hole created by needle 206. The hole is enlarged when the gradually increasing diameter of the distal end of the dilator is pushed through the hole in the septum. For some applications, a distal end 102 of catheter 12 is tapered so as to facilitate passage of the distal portion of catheter 12 through the opening in the septum.

Figure 3E:
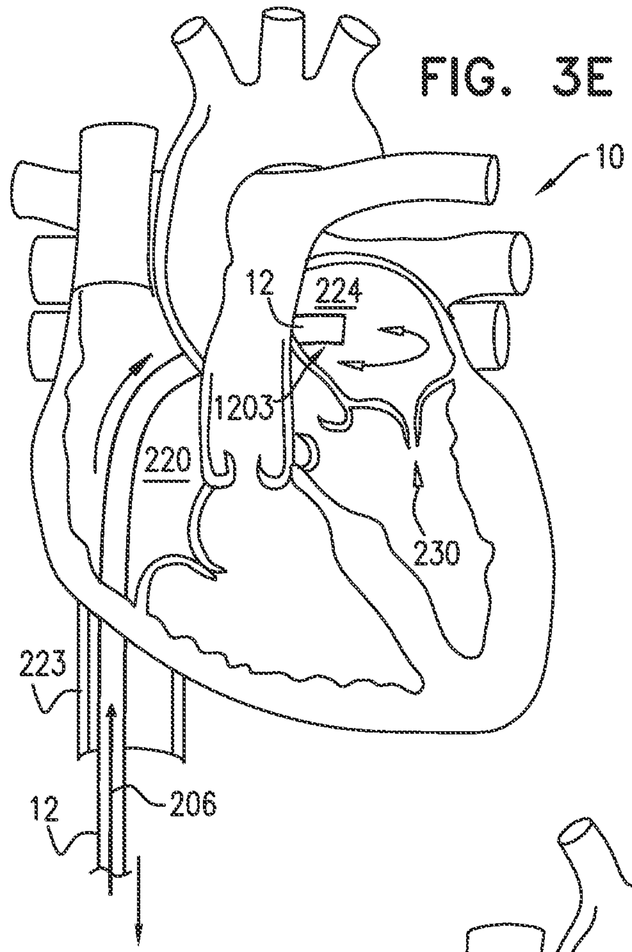

The advancement of catheter 12 through the septum and into the left atrium can be followed by the extraction of the dilator and needle 206 from within catheter 12, as shown in FIG. 3E. Once the distal portion of catheter 12 is disposed within atrium 224, the steerable distal end portion of catheter 12 (e.g., a bending section 1203 of catheter 12) can be steered in a first plane that is parallel to a plane of the annulus of mitral valve 230. Such steering moves the distal end portion of catheter 12 in a direction from the interatrial septum toward surrounding walls of the atrium, as indicated by the arrow in atrium 224. As described hereinabove, steering of the distal portion of catheter 12 can be performed via steering knob 210 of handle 22 in handle portion 101 (in FIGS. 1 and 2).

Figure 3F:
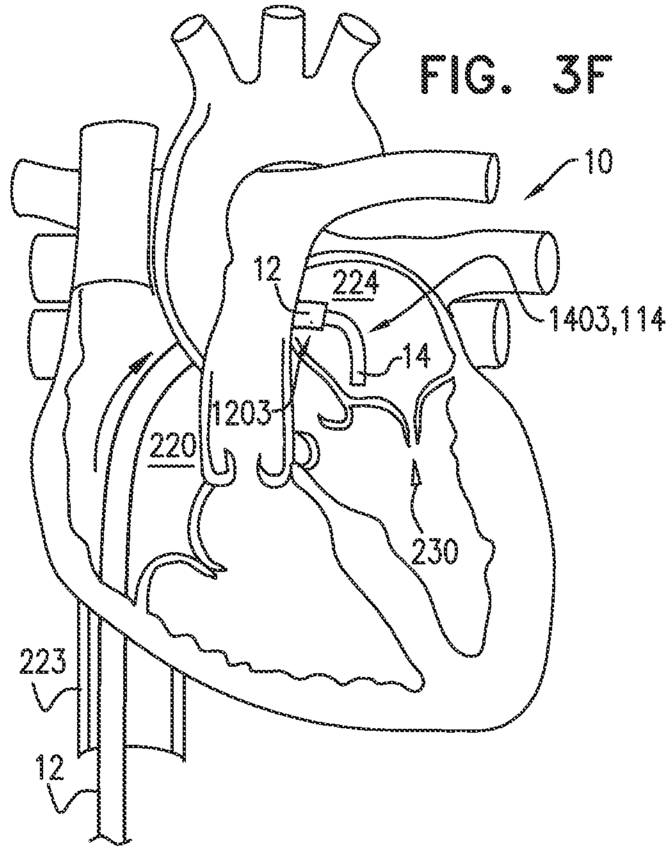

As shown in FIG. 3F, annuloplasty structure or annuloplasty ring structure 222 (not shown for clarity of illustration, with anchor deployment manipulator 61 therein) is advanced through guide catheter 14, which is in turn, advanced through catheter 12 into left atrium 224. As shown in FIG. 3F, an exposed distal end portion 114 (e.g., a bending section 1403) of catheter 14 extends beyond distal end 102 of catheter 12. Exposed distal end portion 114 is then (1) steered toward the annulus of valve 230 along a plane that is perpendicular with respect to the steering plane of catheter 12 and that is perpendicular with respect to valve 230, and is (2) bent, via bending section 1403 toward valve 230. As described hereinabove, steering of the distal portion of catheter 14 is performed via steering knob 214 of handle 24 in handle portion 101 (in FIGS. 1 and 2).

Figure 3G:
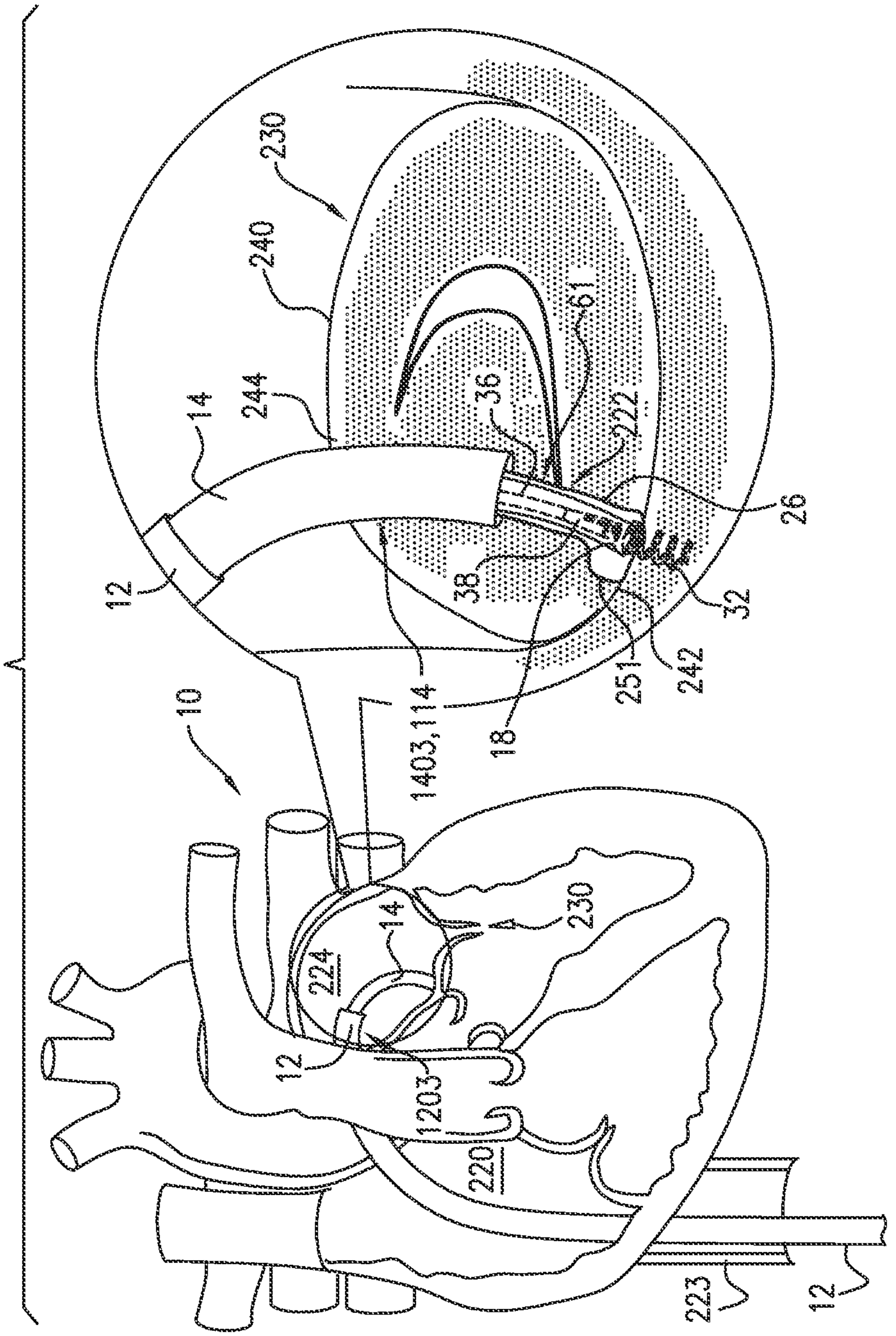

As shown in FIG. 3G, a distal end 251 of sleeve 26 is positioned in a vicinity of a left fibrous trigone 242 of an annulus 240 of mitral valve 230. (It is noted that for clarity of illustration, distal end 251 of sleeve 26 is shown schematically in the cross-sectional view of the heart, although left trigone 242 is in reality not located in the shown cross-sectional plane, but rather out of the page closer to the viewer.) Alternatively, the distal end of sleeve 26 is positioned in a vicinity of a right fibrous trigone 244 of the mitral valve (configuration not shown). Further alternatively, the distal end of the sleeve is not positioned in the vicinity of either of the trigones, but is instead positioned elsewhere in a vicinity of the mitral valve, such as in a vicinity of the anterior or posterior commissure. Once positioned at the desired site near the selected trigone, deployment manipulator 61 deploys a first anchor 32 through the wall of sleeve 26 (by penetrating the wall of the sleeve in a direction in a direction parallel to a central longitudinal axis of deployment manipulator 61, or anchor driver 36, through the distal end of channel 18, and/or parallel to central longitudinal axis of tissue-engaging element 60 of anchor 32) into cardiac tissue near the trigone. Following the deployment of anchor 32 in the cardiac tissue, deployment element 38 is decoupled from anchor 32 by moving rod 130 proximally.

Anchors 32 can be deployed from a distal end of manipulator 61 while the distal end is positioned such that a central longitudinal axis through the distal end of manipulator 61 forms an angle with a surface of the cardiac tissue of between about 20 and 90 degrees, e.g., between 45 and 90 degrees, such as between about 75 and 90 degrees, such as about 90 degrees. Anchors 32 can be deployed from the distal end of manipulator 61 into the cardiac tissue in a direction parallel to the central longitudinal axis through the distal end of manipulator 61. Such an angle can be provided and/or maintained by channel 18 being more rigid than sleeve 26. Distal end 17 (shown in FIG. 2) of channel 18 can be brought close to the surface of the cardiac tissue (and the wall of sleeve 26 that is disposed against the surface of the cardiac tissue), such that little of each anchor 32 is exposed from channel 18 before penetrating the sleeve and the tissue. For example, distal end 17 of channel 18 can be placed (e.g., pushed) against the wall of the sleeve, sandwiching the sleeve against the cardiac tissue.

For some applications, this placement of distal end 17 of channel 18 against the cardiac tissue (via the wall of the sleeve), stabilizes the distal end during deployment and anchoring of each anchor 32, and thereby facilitates anchoring. For some applications, pushing of distal end 17 against the cardiac tissue (via the wall of the sleeve) temporarily deforms the cardiac tissue at the site of contact. This deformation can facilitate identification of the site of contact using imaging techniques (e.g., by identifying a deformation in the border between cardiac tissue and blood), and thereby can facilitate correct positioning of the anchor.

For some applications, anchors 32 can be deployed from a lateral portion of manipulator 61.

Figure 3H:
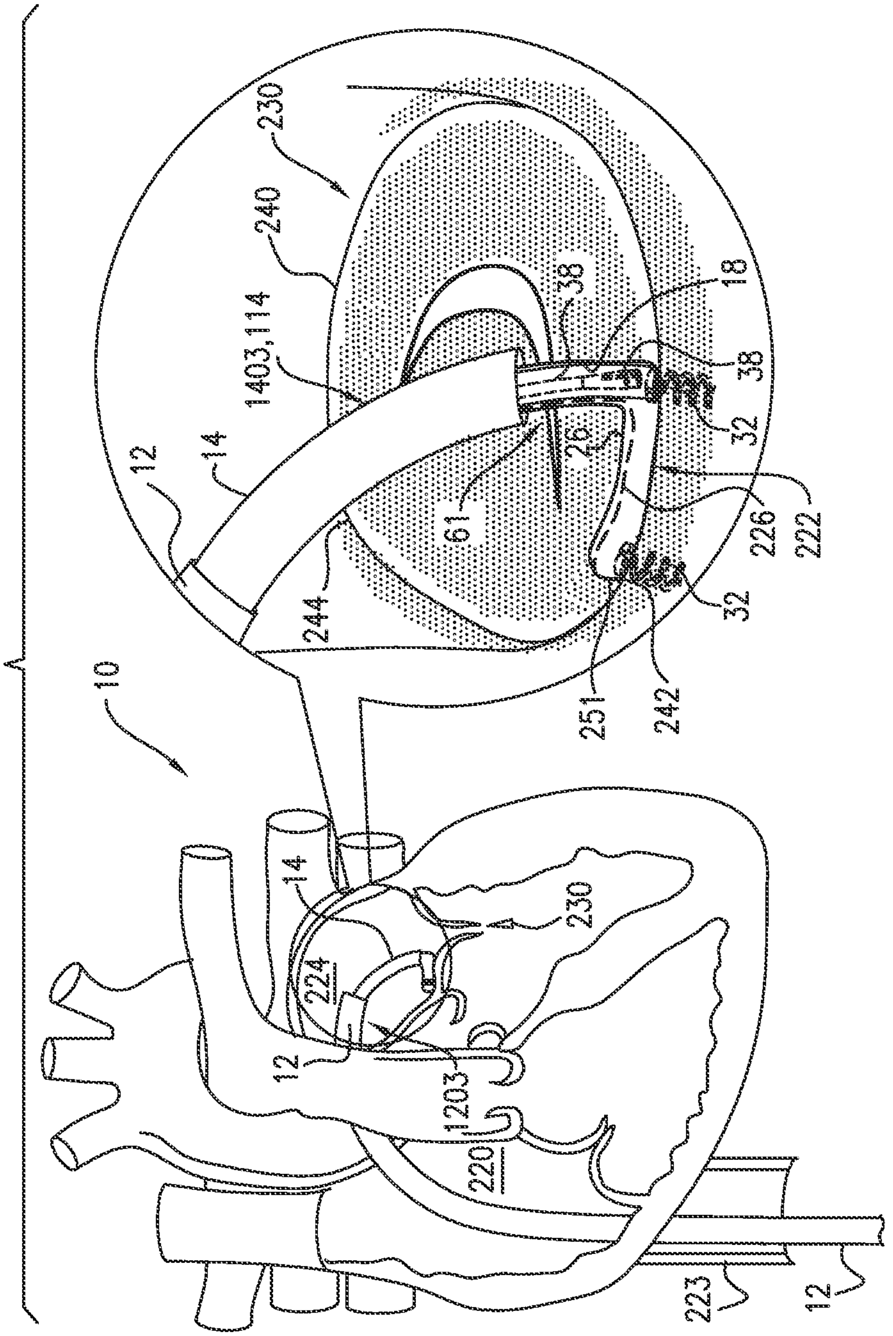

Reference is now made to FIGS. 3G and 2. Following the deployment of the first anchor, a distal portion of sleeve 26 can be decoupled from a portion of implant-decoupling channel 18. In order to decouple the portion of sleeve 26 from outer surface of channel 18, (1) channel 18 can be pulled proximally, while (2) reference-force tube 19 is maintained in place in a manner in which a distal end of tube 19 provides a reference force to sleeve 26 in order to facilitate retraction freeing of a successive portion of sleeve 26 from around channel 18. In order to decouple sleeve 26 from the outer surface of channel 18, (1) channel 18 can be pulled proximally, while (2) reference-force tube 19 is maintained in place. An indicator (such as indicator 2120 described in PCT patent application PCT/IL2012/050451 to Sheps et al., which published as WO/2013/069019, which is incorporated herein by reference) on handle 126 provides an indication of how much channel 18 is withdrawn from within sleeve 26 (i.e., how much the delivery tool is decoupled from sleeve 26, and how much the sleeve has advanced off channel 18 and against tissue). A proximal end of channel 18 is coupled to a knob 94 (FIG. 2) which adjusts an axial position of channel 18 proximally and distally with respect to reference-force tube 19 and sleeve 26. As shown in FIG. 3H, deployment manipulator 61 is repositioned along annulus 240 to another site selected for deployment of a second anchor 32. Reference is now made to FIGS. 1 and 3H. Such repositioning of manipulator 61 is accomplished by:

(1) the steering of the distal end portion of catheter 12 (e.g., by steering knob 210 of handle 22) in the first plane that is parallel with respect to annulus 240 of valve 230 to a desired spatial orientation and in a manner which bends a bending section 1203 of catheter 12, (2) the steering of the distal end portion of portion of catheter 14 (e.g., by steering knob 214 of handle 24) in the second plane that is perpendicular with respect to annulus 240 of valve 230 to a desired spatial orientation, and in a manner which bends bending section 1405 of catheter 14 (specifically bending section 1403), (3) by axially moving catheter 14 with respect to catheter 12 via knob 216, (4) by axially moving the stand supporting handles 22 and 24 to move both catheters 12 and 14, (5) by moving tube 19 and sleeve 26 axially by sliding mount 93 along track 90 via knob 95, and/or (6) by moving channel 18 relative to tube 19 by actuating knob 94.

Often, the first anchor is deployed most distally in the sleeve (generally at or within a few millimeters of the distal tip of the sleeve), and each subsequent anchor is deployed more proximally, such that the sleeve is gradually decoupled from channel 18 of deployment manipulator 61 in a distal direction during the anchoring procedure (i.e., channel 18 is withdrawn from within sleeve 26, and handle 126 is moved distally so as to retract the tool to make the successive proximal portion sleeve 26 ready for implantation of a subsequent anchor). The already-deployed first anchor 32 holds the anchored end of sleeve 26 in place, so that the sleeve is drawn from the site of the first anchor towards the site of the second anchor. As sleeve 26 is decoupled from channel 18, deployment manipulator 61 can be moved generally laterally along the cardiac tissue, as shown in FIG. 3H. Deployment manipulator 61 deploys the second anchor through the wall of sleeve 26 into cardiac tissue at the second site. Depending on the tension applied between the first and second anchor sites, the portion of sleeve 26 therebetween can remain tubular in shape, or can become flattened, which may help reduce any interference of the ring with blood flow.

Figure 3I:
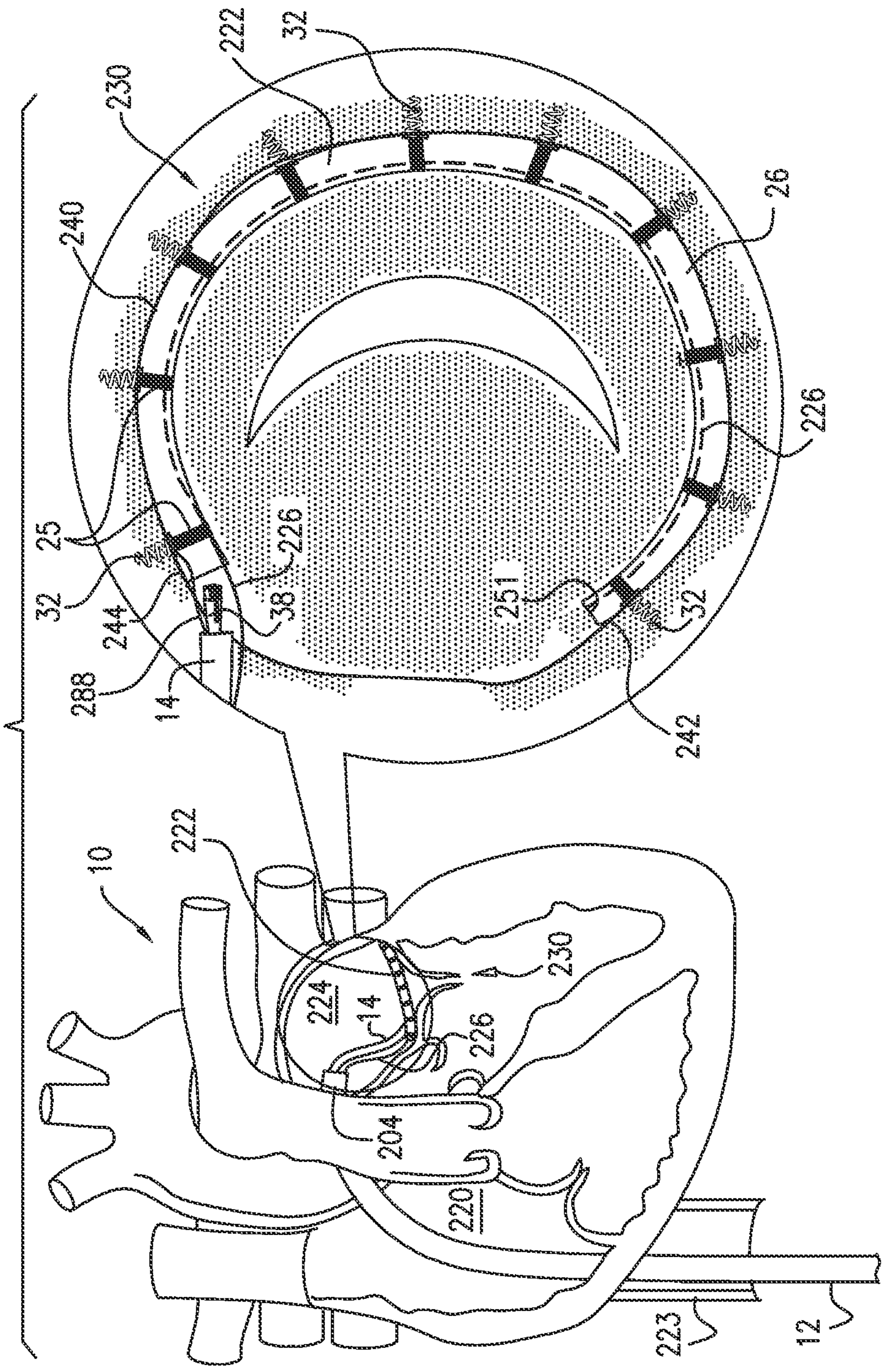

As shown in FIG. 3I, deployment manipulator 61 can be repositioned along the annulus to additional sites, at which respective anchors are deployed, until the last anchor is deployed in a vicinity of right fibrous trigone 244 (or left fibrous trigone 242 if the anchoring began at the right trigone). Optionally, the last anchor is not deployed in the vicinity of a trigone, but is instead deployed elsewhere in a vicinity of the mitral valve, such as in a vicinity of the anterior or posterior commissure. Then, system 10 is removed, leaving behind implant structure 222 and contracting member 226. As is described hereinbelow, a contracting-member-uptake tool is then threaded over and advanced along contracting member 226 and toward structure 222, and is used to contract structure 222 by adjusting a degree of tension of contracting member 226 (not shown in FIG. 3I, but (i) advancing of contracting-member-uptake tool over contracting member 226 is described with reference to FIGS. 4A-5D, mutatis mutandis, and (ii) applying tension to member 226 is described hereinbelow with reference to FIGS. 6A-B).

Once the desired level of adjustment of structure 222 is achieved (e.g., by monitoring the extent of regurgitation of the valve under echocardiographic and/or fluoroscopic guidance), the contracting-member-uptake tool (1) locks contracting member 226 so as to maintain a degree of tension of member 226 in order to maintain structure 222 in a contracted state, and (2) severs any excess portion of contracting member 226 which is then removed from the heart. For some applications, a distal portion of guide member 86 may be left within the heart of the patient and the proximal end can be accessible outside the body, e.g., using a port. For such applications, adjusting mechanism 40 can be accessed at a later stage following initial implantation and adjustment of ring structure 222.

For some applications, a re-access wire 288 can be provided, coupled to a proximal portion of the implant (e.g., a portion of the implant that is deployed last), such as to a last anchor 32 (as shown in FIG. 3I) or sleeve 26, such that, upon anchoring, the wire extends proximally, e.g., out of the body of the subject, such as via catheter 14 and/or catheter 12. Should it be determined, after implantation (e.g., and after adjustment) of annuloplasty structure 222, that one or more anchors 32 require adjustment or retrieval, re-access wire 288 facilitates guidance of an anchor-manipulation tool to annuloplasty structure 222 and/or into the lumen thereof. For example, such an anchor-manipulation tool can comprise an anchor-manipulation tool described in a PCT patent application PCT/IL2013/050861 to Herman et al, titled “Percutaneous tissue anchor techniques”, filed on Oct. 23, 2013, and incorporated herein by reference. Systems, apparatuses, and techniques described in the present patent application can be used in combination with systems, apparatuses, and techniques described in said PCT patent application PCT/IL2013/050861.

As shown, sleeve 26 of ring structure 222 comprises a plurality of radiopaque markers 25, which are positioned along the sleeve at respective longitudinal sites to indicate anchor-designated target areas. The markers can provide an indication in a radiographic image (such as a fluoroscopy image) of how much of sleeve 26 has been deployed at any given point during an implantation procedure, in order to enable setting a desired distance between anchors 32 along the sleeve 26.

For some applications, and as shown in FIG. 3I, anchors 32 are deployed at longitudinal sites of sleeve 26 at which radiopaque markers 25 are disposed (e.g., the anchors are driven through a radiopaque ink of the radiopaque markers). Alternatively, anchors 32 can be deployed at longitudinal sites of sleeve 26 between markers 25. For example, when dispensing sleeve 26 from channel 18 (i.e., when advancing sleeve 26 with respect to channel 18 and/or withdrawing channel 18 from sleeve 26), the appearance of a marker 25 at the distal end of channel 18 (e.g., the marker 25 becoming aligned with marker 1018 of channel 18) can indicate that a correct length of sleeve 26 has been dispensed. Subsequent limited movement of the channel with respect to the sleeve may occur. For example, when channel 18 is placed against the annulus, the channel may tension the portion of sleeve 26 between the previously-deployed anchor and the distal end of the channel, such that when the anchor is deployed, it passes through the sleeve slightly proximally to the marker 25 (e.g., 1-2 mm proximally to the marker).

Alternatively, annuloplasty structure 222 is implanted by right or left thoracotomy, mutatis mutandis.

For some applications, following implantation of sleeve 26 along the annulus, an excess portion of sleeve 26 may be present at the proximal portion of sleeve. In such applications, following removal of manipulator 61, a cutting tool (not shown) can be advanced within channel 18 and into the lumen of the excess portions of sleeve 26 (e.g., from within sleeve 26) in order to cut the sleeve proximal to the proximal-most-deployed anchor 32.

Figure 4A:
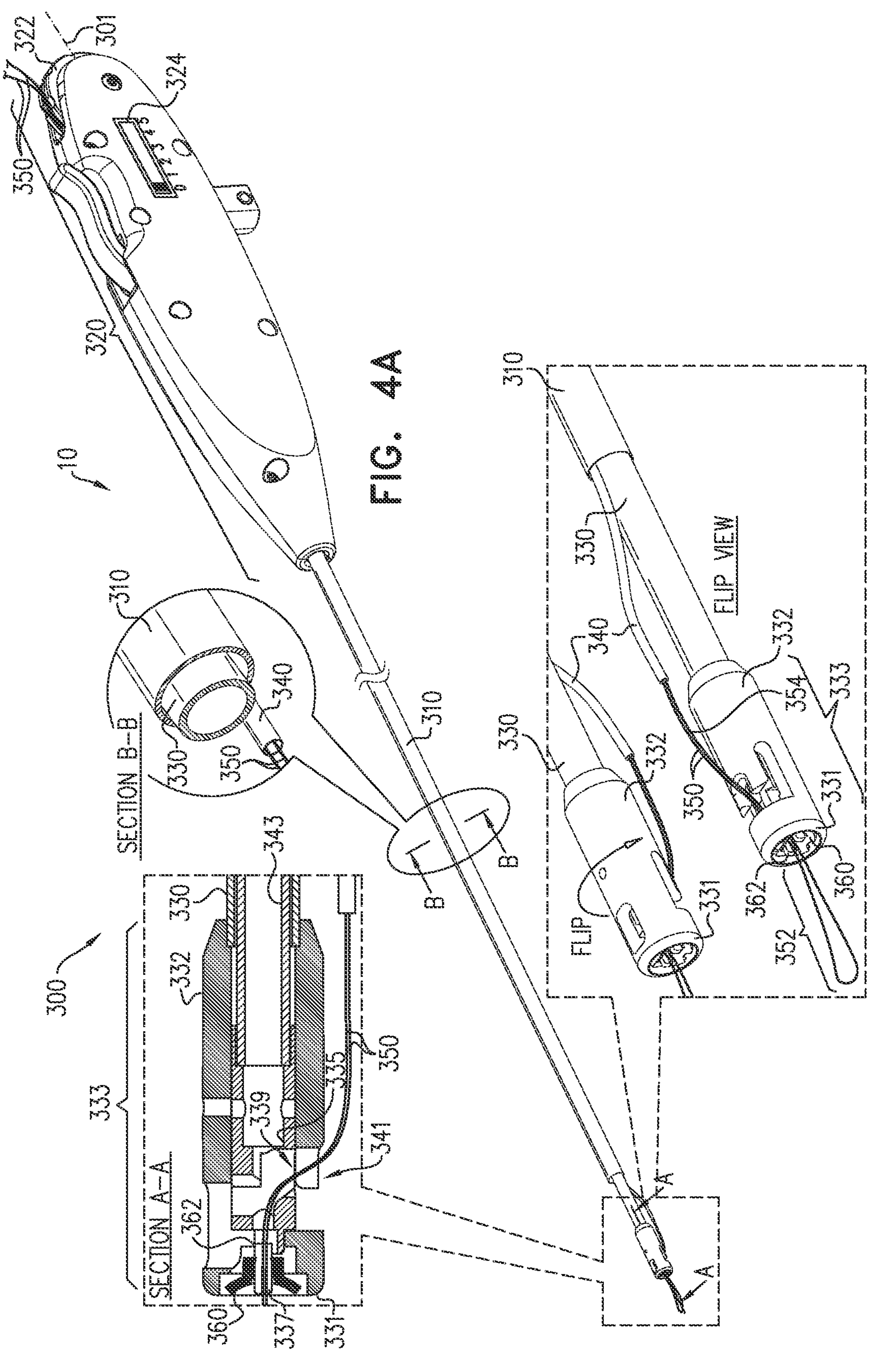
FIGS. 4A-B are schematic illustrations of an example contracting-member-uptake tool which is configured to contract a contracting member of the annuloplasty structure of FIGS. 3A-I and sever any excess portions of the contracting member.
Figure 4B:
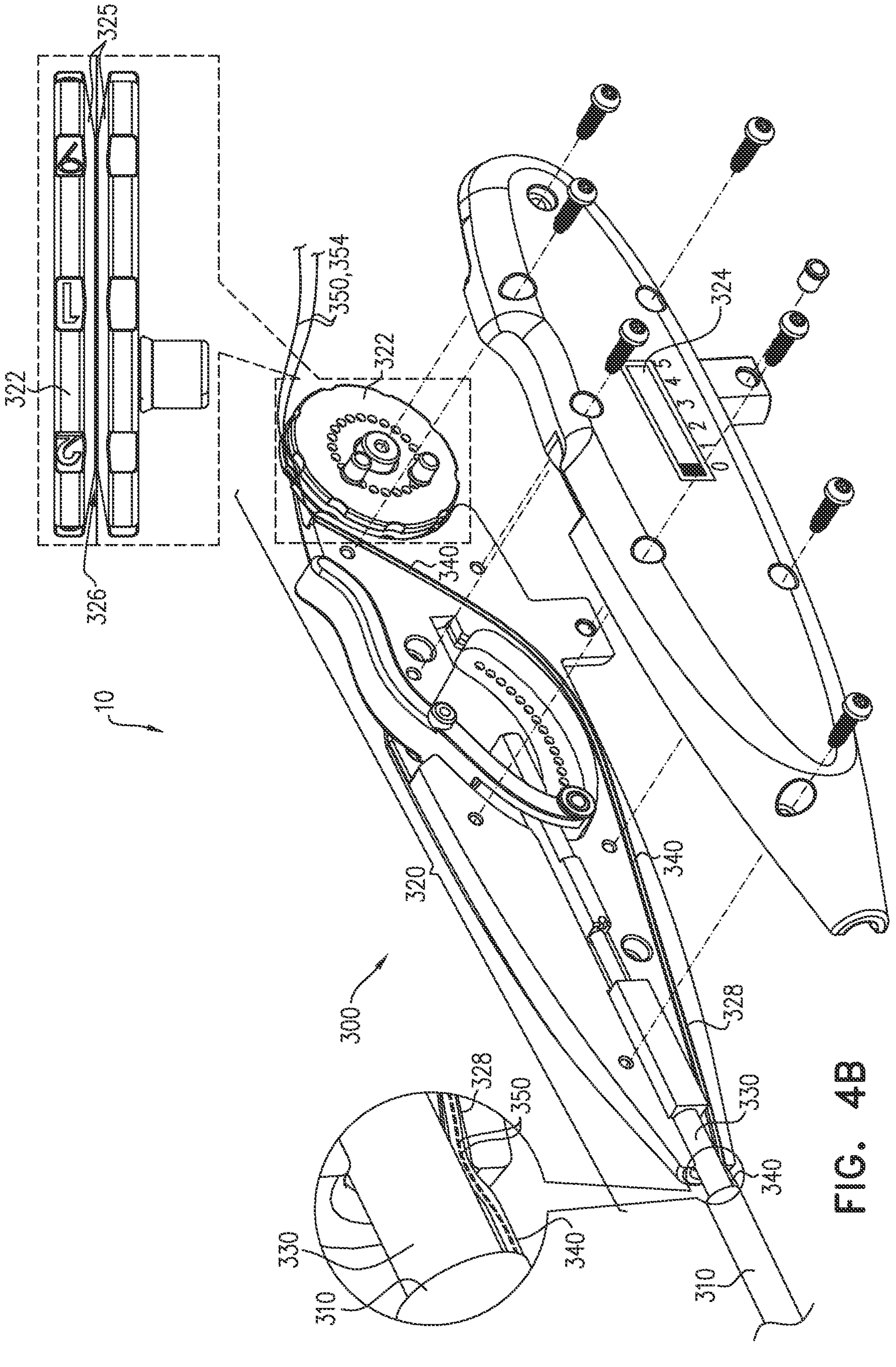

Reference is now made to FIGS. 4A-B, which are schematic illustrations of an example system 10 comprising an example contracting-member-uptake tool 300 which is configured to contract contracting member 226 and sever any excess portions of contracting member 226. Tool 300 comprises a handle portion 320 and an elongate sheath 310 coupled thereto. Sheath 310 encases a primary tube 330 and a secondary tube 340 disposed alongside primary tube 330. Both primary tube 330 and secondary tube 340 are coupled to handle portion 320 at respective proximal ends of tubes 330 and 340. Secondary tube 340 has a secondary-tube-lumen configured for passage therethrough of contracting member 226. Tool 300 defines a longitudinal axis 301.

For some applications, sheath 310 is shaped so as to define a lumen in a wall of sheath 310. For such applications, tool 300 does not comprise secondary tube 340, but rather, the lumen in the wall of sheath 310 functions as secondary tube 340 and the primary lumen defined by the wall of sheath 310 functions as primary tube 330.

Sheath 310, primary tube 330, and secondary tube 340 can be flexible such that sheath 310, primary tube 330, and secondary tube 340 are configured for passage through vasculature of the patient during a transvascular, transcatheter procedure. However, similar features can be used for surgical procedures. For some applications, sheath 310, primary tube 330, and secondary tube 340 comprise silicone. For some applications, sheath 310, primary tube 330, and secondary tube 340 comprise polyurethane.

Tool 300 can comprise a contracting-member-snare 350 comprising a distal snare portion 352 and an elongate flexible body portion 354 coupled to distal snare portion 352. Distal snare portion 352 is configured to ensnare a portion of contracting member 226 as will be described hereinbelow and is sized to pass through the secondary-tube lumen of secondary tube 340 in order to pull contracting member 226 through a length of secondary tube 340.

Distal snare portion 352 can define a looped portion, as shown. For some applications, distal snare portion 352 is shaped so as to define a hook.

Tool 300 can comprise a distal end portion 333 having a distal tip 331 which defines a distal end of tool 300. Primary tube 330 terminates at distal end portion 333. Distal end portion 333 comprises a housing 332 which is shaped so as to hold and be removably coupled to a contracting-member-fastener 360. Contracting-member-fastener 360 comprises a clamping structure that can be biased toward assuming a closed state or closed position, and in the closed state/position, the clamping structure can be configured to clamp onto the contracting member 226 passed therethrough (not shown). The clamping structure can also be configured such that it can be flexed to an open state through which contracting member 226 (not shown) can move.

Tool 300 can comprise a fastener-ejector 335 movable within distal end portion 333 of contracting-member-uptake tool 300. Movement of fastener-ejector 335 converts contracting-member-fastener 360 (or clamping structure thereof) from its open state to its closed state to clamp onto contracting member 226 passed therethrough, as will be described hereinbelow. Tool 300 comprises a stop 362 removably coupled to contracting-member-fastener 360 and configured to maintain contracting-member-fastener 360 in the open state, as shown in Section A-A of FIG. 4A. Stop 362 comprises one or more, e.g., two, prongs 337 which maintain fastener 360 in the open state. Ejector 335 is coupled to stop 362 and moves stop 362 that is removably coupled to fastener 360 in order to convert fastener 360 from the open state to a closed state, as is described hereinbelow.

FIG. 4B shows handle portion 320 of tool 300 with a casing removed in order to view the inside of handle portion 320. Handle portion 320 comprises a contracting-member-uptake device 322 configured to uptake successive portions of contracting member 226 (not shown), as is described hereinbelow. Contracting-member-uptake device 322 is actuatable to increase tension of the contracting member, as is described hereinbelow. Tension of contracting member 226 is measured by a tension meter 324 of handle portion 320.

Contracting-member-uptake device 322 can optionally comprise a wheel, which can have two opposing wedged portions 325 which together define a groove 326 configured to couple contracting member 226 to the wheel of device 322. Wedged portions 325 can be shaped so as to receive any portion of contracting member 226, e.g., a proximal end of member 226 and/or a middle portion of member 226. For some applications, opposing wedged portions 325 are configured to grip contracting member 226. As shown, the wheel of device 322 can have a numerical indicator to indicate the number of turns of the wheel.

As shown, handle portion 320 is coupled to respective proximal portions of primary tube 330 and secondary tube 340.

Handle portion 320 can be shaped so as to define a lumen 328 for passage therethrough of snare 350 from within the lumen of secondary tube 340. Snare 350 passes through lumen 328 and beyond groove 326 of contracting-member-uptake device 322. Often, but not necessarily, device 322 does not uptake snare 350 but rather, snare 350 passes through groove 326. As is described hereinbelow, pulling on snare 350 pulls on contracting member 226 coupled thereto such that contracting member 226 is pulled through secondary tube 340, through lumen 328 and ultimately toward contracting-member-uptake device 322. Once the proximal end of contracting member 226 (or a portion in a vicinity of the proximal end of member 226) is pulled through tube 340 and through lumen 328, contracting member 226 is coupled to contracting-member-uptake device 322 by being fed into groove 326. Contracting-member-uptake device 322 is then actuated in order to apply tension to contracting member 226, and thereby to annuloplasty structure 222 implanted along the annulus. With each rotation of the wheel of device 322, successive portions of contracting member 226 are wound within groove 326 of device 322.

FIGS. 5A-D are schematic illustrations of an example contracting-member-uptake tool 300 useable to uptake contracting member 226. At this stage, annuloplasty structure or annuloplasty ring structure 222 has been implanted along annulus 240, as described hereinabove with reference to FIGS. 3A-I. Once structure 222 has been implanted along the annulus, contracting member 226 extends away from structure 222 and through vasculature of the patient such that a proximal end portion of member 226 is disposed outside the body of the patient.

Contracting member 226 can exit sleeve 26 of structure 222 at any suitable location along structure 222. For example, contracting member 226 can exit sleeve 26 of structure 222 at a portion of structure 222 in a vicinity of a left fibrous trigone of the valve, as shown. For some applications, contracting member 226 exits sleeve 26 of structure 222 at a portion of structure 222 in a vicinity of a right fibrous trigone of the valve. For some applications, contracting member 226 exits sleeve 26 of structure 222 at a middle portion of structure 222.

Figure 5A:
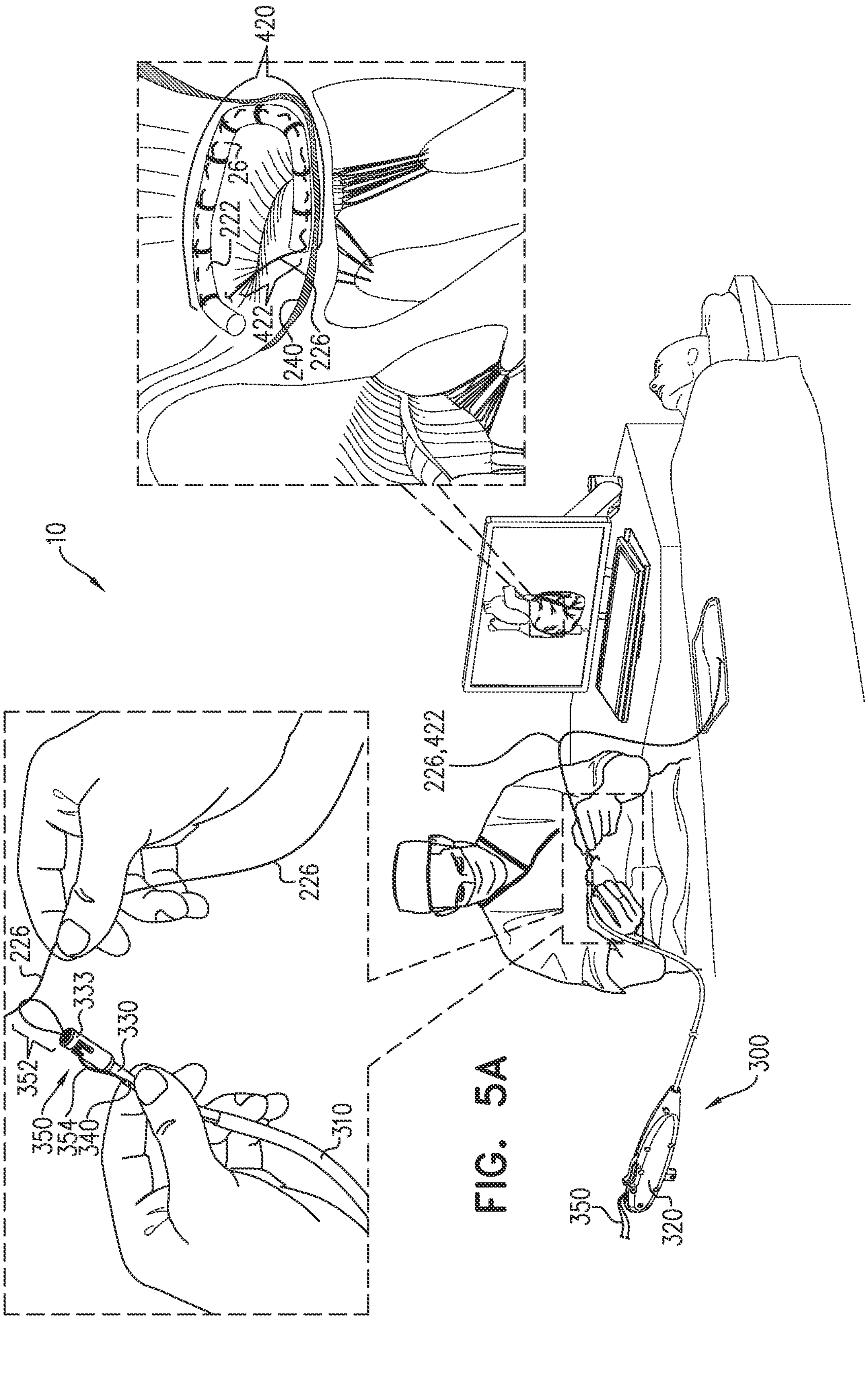
FIGS. 5A-D are schematic illustrations of the example contracting-member-uptake tool of FIGS. 4A-B used to uptake the contracting member.

As shown, structure 222 comprises sleeve 26 which defines the primary body portion of structure 222. Contracting member 226 has a first portion 420 extending along a longitudinal length of the primary body portion of annuloplasty structure 222. The first portion 420 can extend along the longitudinal length of structure 222 when structure 222 is in a linear state as well as in a curved state, as shown in FIG. 5A. Contracting member 226 also defines a second portion 422 extending away from the primary body portion of annuloplasty structure 222.

In FIG. 5A, the user (e.g., an operating physician, etc.) can hold a distal end of tool 300 in one hand and a proximal end portion of contracting member 226 in another hand. The user or physician threads the proximal end portion of contracting member 226 through distal snare portion 352 of contracting-member-snare 350.

Figures 5B, 5C, 5D:
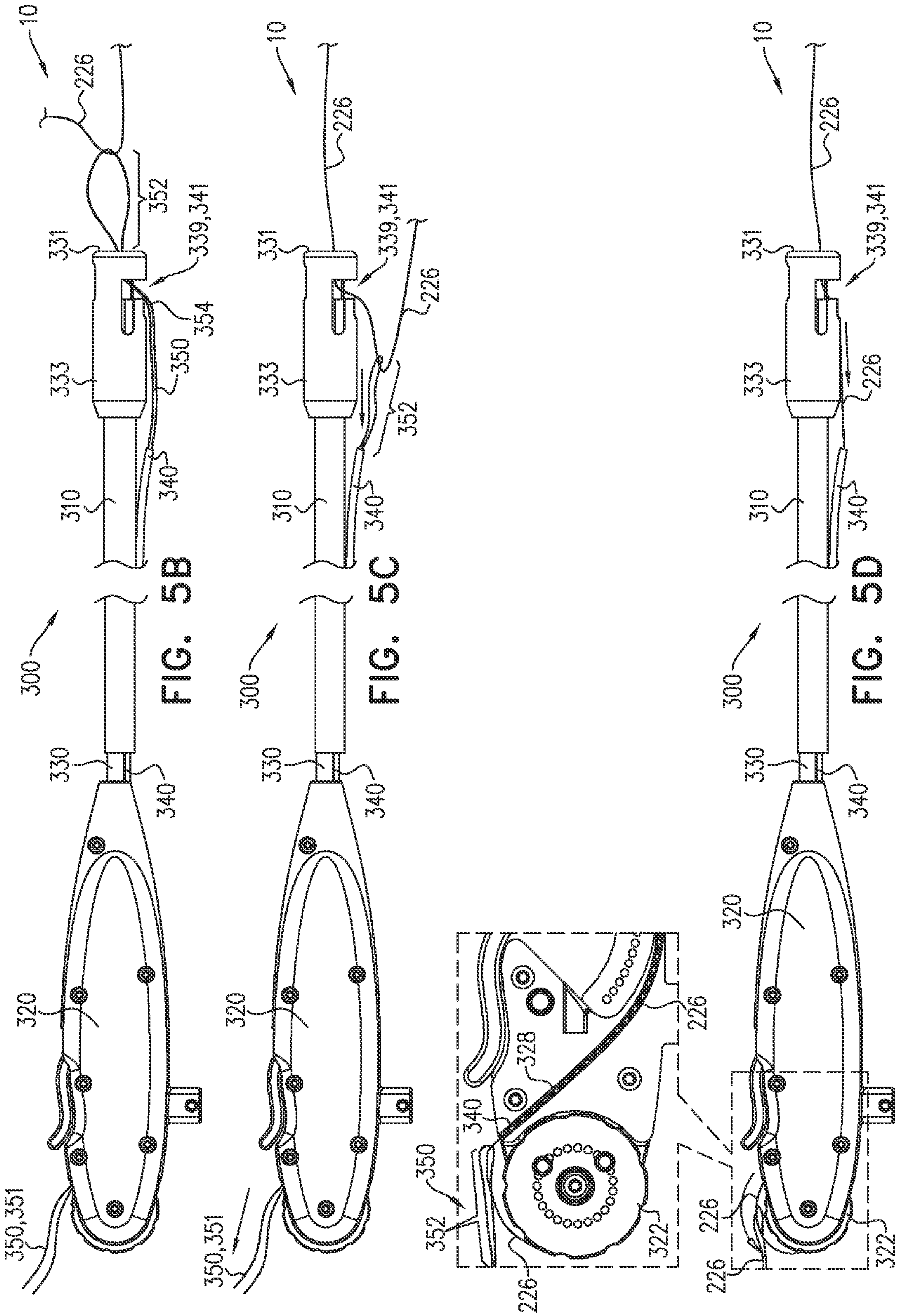

FIG. 5B shows tool 300 in a state in which distal snare portion 352 ensnares contracting member 226. For some applications, distal snare portion 352 is shaped so as to increase the coupling between snare 350 and contracting member 226. For example, for some applications, distal snare portion 352 is corrugated to increase friction between snare portion 352 and contracting member 226. For some applications, distal snare portion 352 can comprise a coiled section to increase friction between snare portion 352 and contracting member 226. For some applications, snare 350 comprises a metal wire. For some applications, snare 350 comprises a metal wire comprising stainless steel. Snare 350 (including distal snare portion 352) can have a variety of sizes, for example, a diameter of 0.15-0.5 mm or 0.15-0.35 mm.

Reference is now made to FIGS. 4A and 5B. As shown in Section A-A of FIG. 4A, contracting-member-snare 350 passes through aligned ports 339 and 341 in distal end portion 333 of tool 300.

Snare 350 can be pulled proximally, e.g., by the user or physician holding the proximal exposed end portions 351 of snare 350 proximally away from tool 300. Pulling on snare 350 proximally, as shown in FIG. 5C, pulls distal snare portion 352 and contracting member 226 looped therethrough through distal tip 331 of tool 300, through the fastener disposed within distal end portion 333 of tool 300, through aligned ports 339 and 341 in distal end portion 333 of tool 300, and subsequently, through the lumen of secondary tube 340.

Snare 350 is pulled until distal snare portion 352 enters the lumen of secondary tube 340. As a result, the looped portion of distal snare portion 352 is compressed and collapses around contracting member 226 looped therethrough, in order to maintain coupling between snare portion 352 and contracting member 226 as elongate flexible body portion 354 (shown in FIG. 5B) is pulled through the lumen of secondary tube 340. As the looped portion of snare portion 352 collapses within the lumen of secondary tube 340, the portion of contracting member 226 ensnared by snare portion 352 bends, and coupling between contracting member 226 and snare portion 352 is strengthened. This strengthening is also brought about as a result of the relatively small diameter of secondary tube 340 of 0.5-1.0 mm.

In FIG. 5D, snare 350 is pulled entirely through secondary tube 340, through lumen 328 of handle portion 320 and beyond groove 326 of contracting-member-uptake device 322 in order to pull contracting member 226 along this path. All the while, sheath 310 of tool 300 is advanced through vasculature and toward annuloplasty structure 222 implanted along annulus 240 of the valve. Once distal snare portion 352 and the portion of contracting member 226 coupled thereto exit lumen 328 of handle portion 320, the portion of contracting member 226 is coupled to contracting-member-uptake device 322 by being positioned within groove 326. For some applications, the proximal end portion of contracting member 226 is fed within groove 326. For some applications, a middle portion of contracting member 226 (e.g., a portion in a vicinity of the proximal end of contracting member 226) is fed within groove 326. Contracting member 226 is then tightened by actuating, e.g., rotating, contracting-member-uptake device 322 such that successive portions of contracting member 226 are wound within contracting-member-uptake device 322 and contracting-member-uptake device 322 uptakes the successive portions.

Once snare 350 has been pulled through tool 300, snare 350 can be discarded.

Figure 6A:
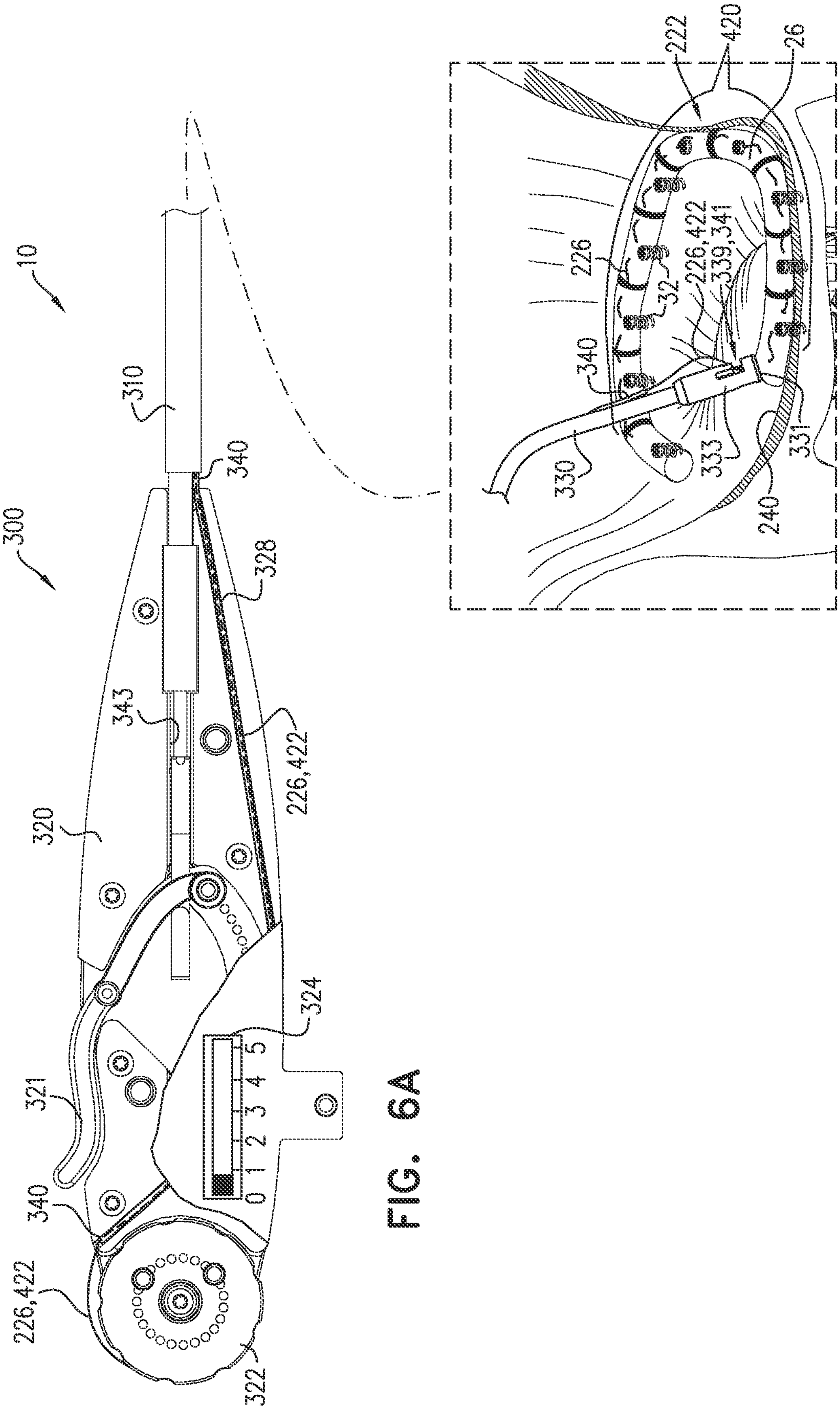
FIGS. 6A-B are schematic illustrations of the example contracting-member-uptake tool of FIGS. 4A-B used to uptake the contracting member in order to contract the annuloplasty structure coupled to the contracting member.
Figure 6B:
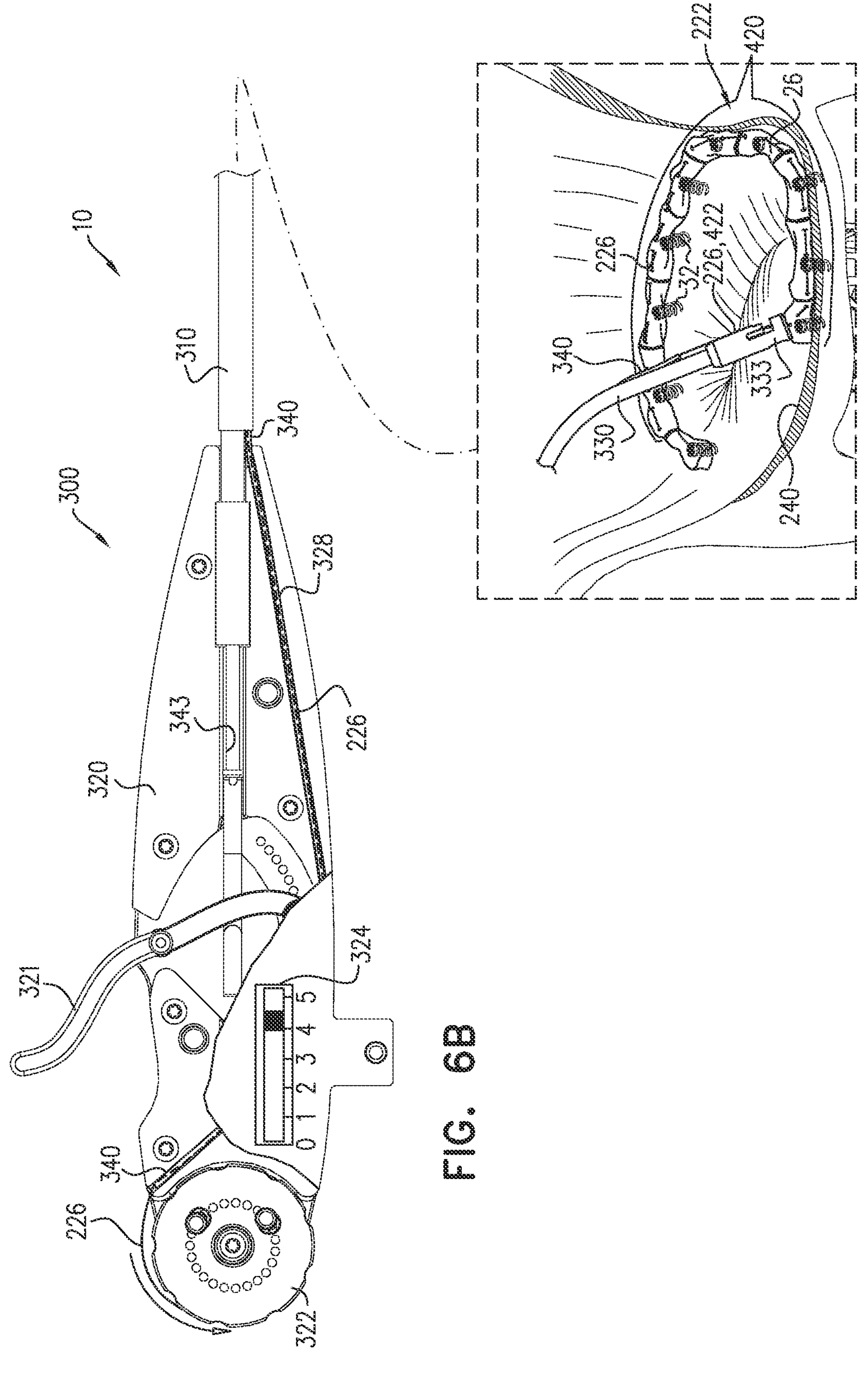

Reference is now made to FIGS. 6A-B, which are schematic illustrations of an example tool 300 used to pull on contracting member 226 in order to contract contracting member 226 and thereby annuloplasty structure or annuloplasty ring structure 222 coupled thereto. Contracting-member-uptake device 322 is rotated in order to facilitate the uptake of successive portions of contracting member 226.

As shown in FIG. 6A, prior to rotating contracting-member-uptake device 322, tension meter 324 of handle portion 320 reads a tension of contracting member 226 at zero or close to zero. Similarly, sleeve 26 of annuloplasty structure 222 coupled to annulus 240 is in a relaxed, non-tense state. At this point, tool 300 has been sufficiently advanced through vasculature of the patient such that distal tip 331 is in proximity to structure 222 disposed along the annulus, while a proximal portion of contracting member 226 is disposed outside the body of the patient.

In FIG. 6B, contracting-member-uptake device 322, is rotated to contract and apply tension to contracting member 226. Tension meter 324 of handle portion 320 reads a tension of contracting member 226 between 4 and 5. Similarly, sleeve 26 of annuloplasty structure 222 coupled to annulus 240 is in a tense, contracted state. As shown in FIG. 6B, contracting member 226 is in a tense state with respect to tool 300.

Reference is now made to FIGS. 7A-E, which are schematic illustrations of an example tool 300 used to lock and secure annuloplasty structure 222 in its contracted state and subsequently, sever excess portions of contracting member 226.

Figures 7A, 7B, 7C:
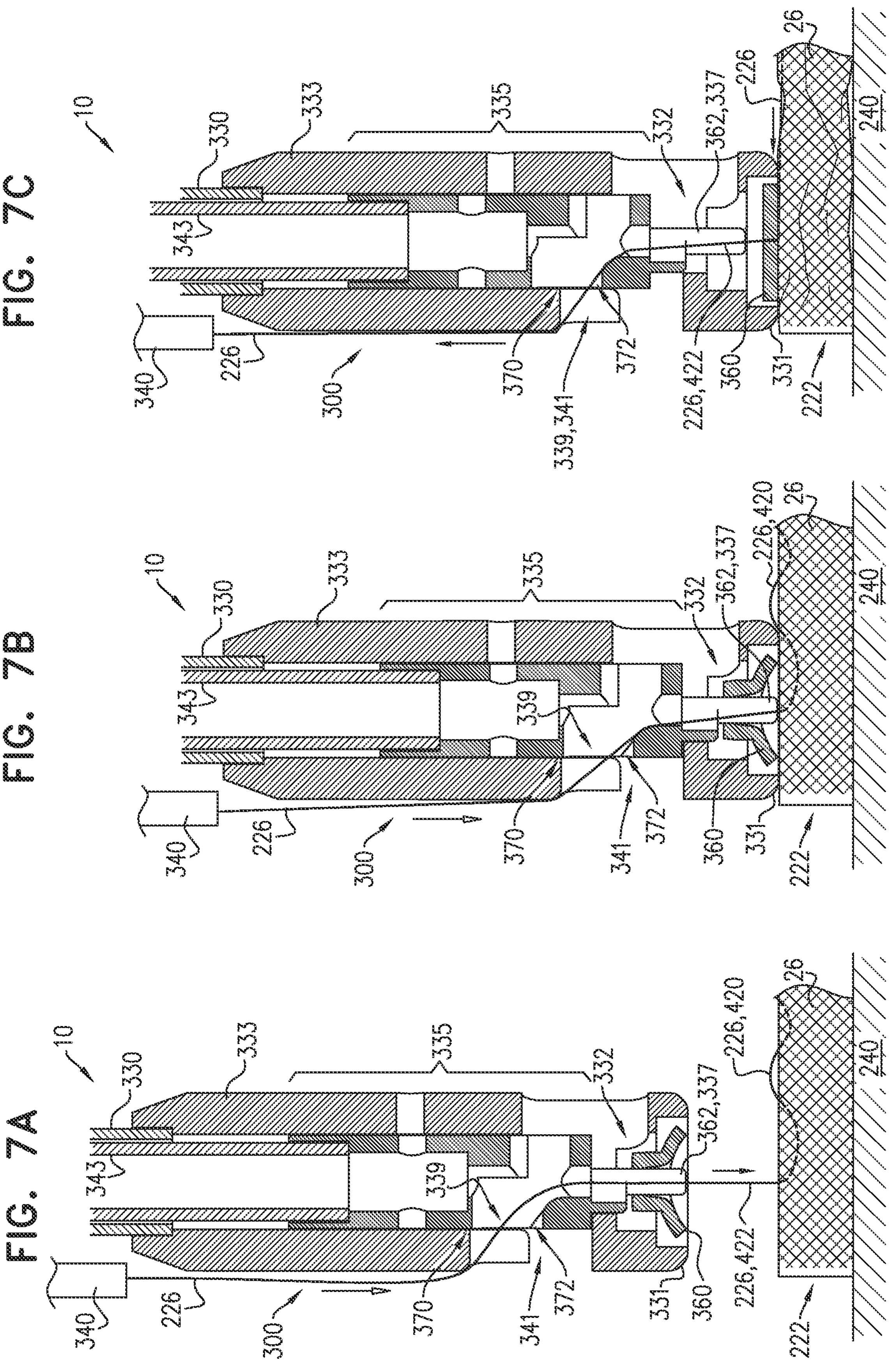
FIGS. 7A-E are schematic illustrations of the example contracting-member-uptake tool of FIGS. 4A-B used to lock and secure the annuloplasty structure in its contracted state and subsequently, sever excess portions of the contracting member.

FIG. 7A shows annuloplasty structure or annuloplasty ring structure 222 in a non-contracted state. Distal tip 331 of tool 300 can be brought close to structure 222. Contracting member 226 can be threaded along sleeve 26 and out of a portion of sleeve 26 of structure 222. As described hereinabove, contracting member 226 can be threaded through tool 300 in a manner in which member 226 passes through distal tip 331, through contracting-member-fastener 360 that can be held in the open state, such as by prongs 337 of stop 362, through aligned ports 339 and 341 in distal end portion 333 of tool 300, and through secondary tube 340.

As shown in FIG. 7B, once distal tip 331 of tool 300 contacts sleeve 26 of structure 222, tool 300 can be used to contract structure 222 by tool 300 pulling on contracting member 226. During contraction of structure 222, fastener 360 is not deployed.

In FIG. 7C, contracting member 226 has been pulled tight, and annuloplasty structure 222 has been contracted and in a tense, contracted state. Distal end portion 333 of tool 300 is then used to eject and deploy fastener 360 from within tool 300 in order to lock structure 222 in the contracted state.

Reference is now made to FIGS. 6B and 7C. Once distal tip 331 contacts sleeve 26, a trigger 321 (shown in FIG. 6B) at handle portion 320 of tool 300 is pulled partially, in order to facilitate ejecting and deploying of contracting-member-fastener 360 from within housing 332 of distal end portion 333. As described hereinabove, fastener-ejector 335 is movable within distal end portion 333 of contracting-member-uptake tool 300. Movement of fastener-ejector 335 converts contracting-member-fastener 360 from its open state to its closed state to clamp onto contracting member 226 passed therethrough. Fastener-ejector 335 is coupled to prongs 337 of stop 362 in a manner in which when ejector 335 is moved proximally within portion 333, stop 362 is decoupled from contracting-member-fastener 360 as prongs 337 move proximally away from contracting-member-fastener 360. Once contracting-member-fastener 360 is no longer held in the open state by stop 362, fastener 360 closes, as it tends to do, and clamps around contracting member 226 passing therethrough.

A proximal portion of fastener-ejector 335 can be coupled to a distal end of a movement tube 343 which can be coupled at a proximal end thereof to trigger 321. Movement tube 343 is movable proximally in response movement of trigger 321, and consequently, fastener-ejector 335 is moved proximally with respect to distal tip 331 of tool 300 and with respect to fastener 360. As shown in FIG. 7B, fastener 360 has been ejected and deployed from within housing 332 of ejector 335.

Figure 7D:
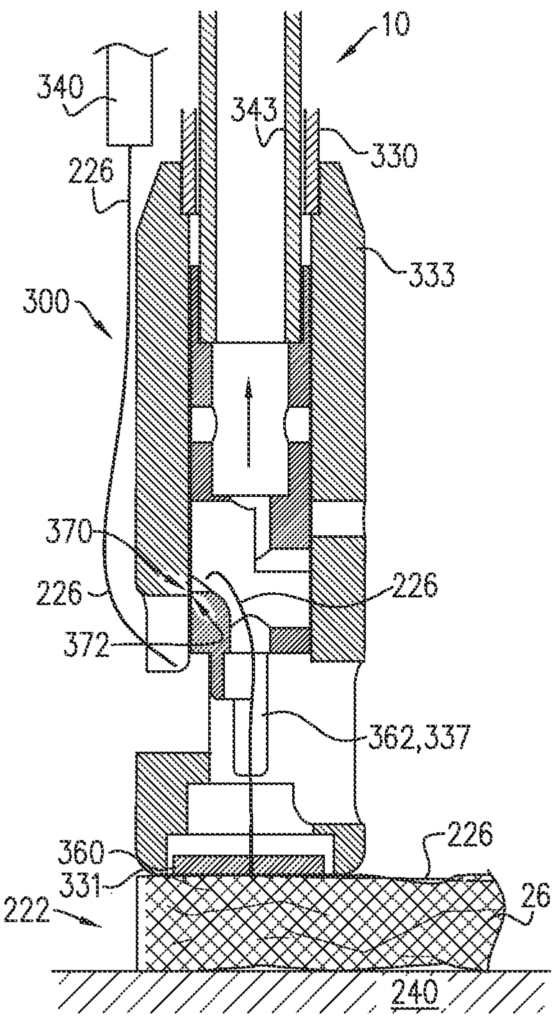

In FIG. 7D, fastener-ejector 335 can be moved further proximally in response to the further pulling of trigger 321, in order to sever excess portions of contracting member 226. Tool 300 can be shaped so as to define a cutting-facilitating edge 370 in distal end portion 333 of tool 300. For some applications, cutting-facilitating edge 370 defines a sharp edge. While contracting member 226 passes through aligned ports 339 and 341 in distal end portion 333 of tool 300, as shown in FIGS. 7A-C, contracting member 226 is in proximity with cutting-facilitating edge 370. Movement of fastener-ejector 335 proximally brings a cutting-facilitating edge 372 of ejector 335 against cutting-facilitating edge 370 of tool 300, thus sandwiching a portion of contracting member 226 between edges 370 and 372, in order to sever and cut contracting member 226 extending through ports 339 and 341. For some applications, cutting-facilitating edge 372 defines a sharp edge. FIG. 7D shows contracting member 226 severed once cutting-facilitating edge 372 of ejector 335 has been brought against cutting-facilitating edge 370 of tool 300.

Figure 7E:
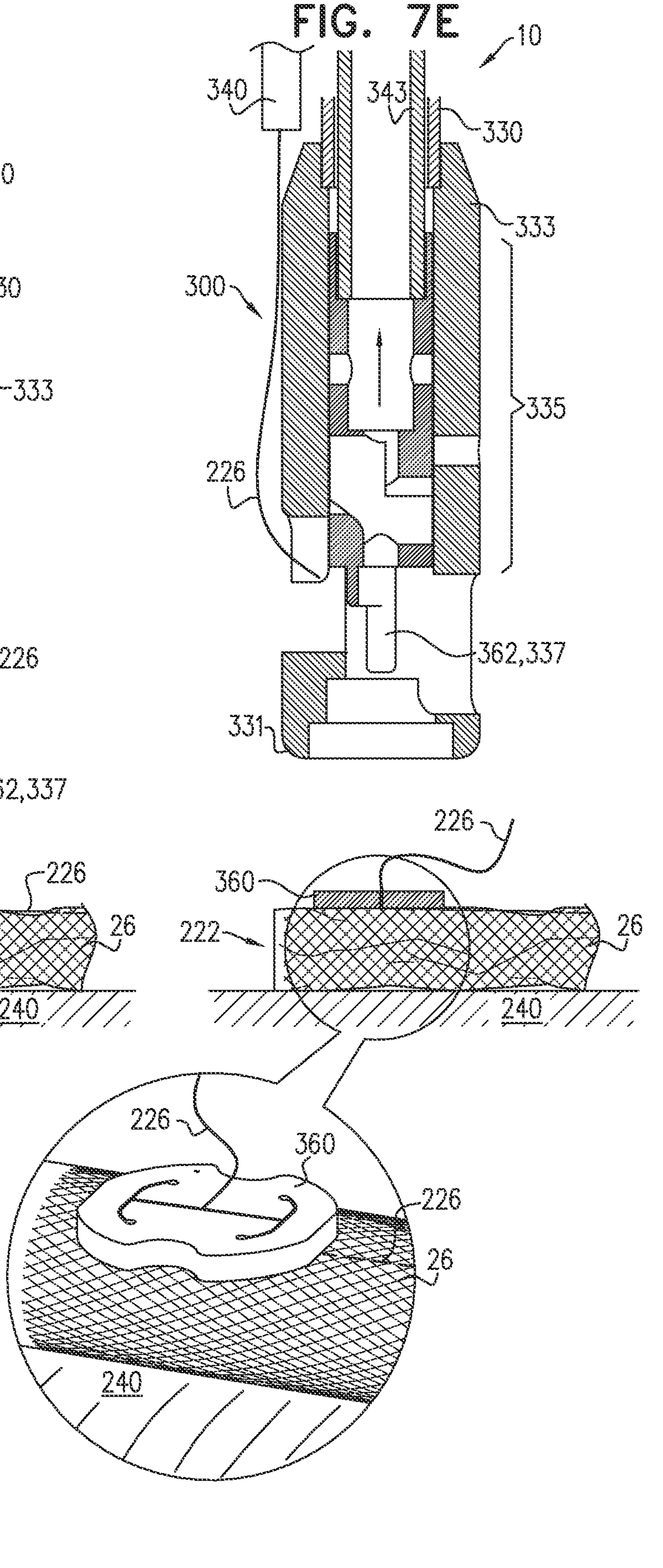

As shown in FIG. 7E, once contracting member 226 has been severed, tool 300 is withdrawn proximally, bringing together with it the excess portion of contracting member 226.

Reference is now made to FIGS. 8A-D, which are schematic illustrations of an example of a system 510 for contracting annulus 240 of the patient using an annuloplasty structure 522 (e.g., an annuloplasty ring structure, a closed annuloplasty structure, a closed annuloplasty ring structure, an open annuloplasty structure, a partial annuloplasty ring structure, etc.), which can comprise a housing 530. Housing 530 can house a contracting-member-fastener 360. Except for the differences described hereinbelow, annuloplasty structure 522 can be the same as or generally similar to annuloplasty structure 222, described hereinabove with reference to FIGS. 1-7E and like reference numerals refer to like parts.

Figure 8A:
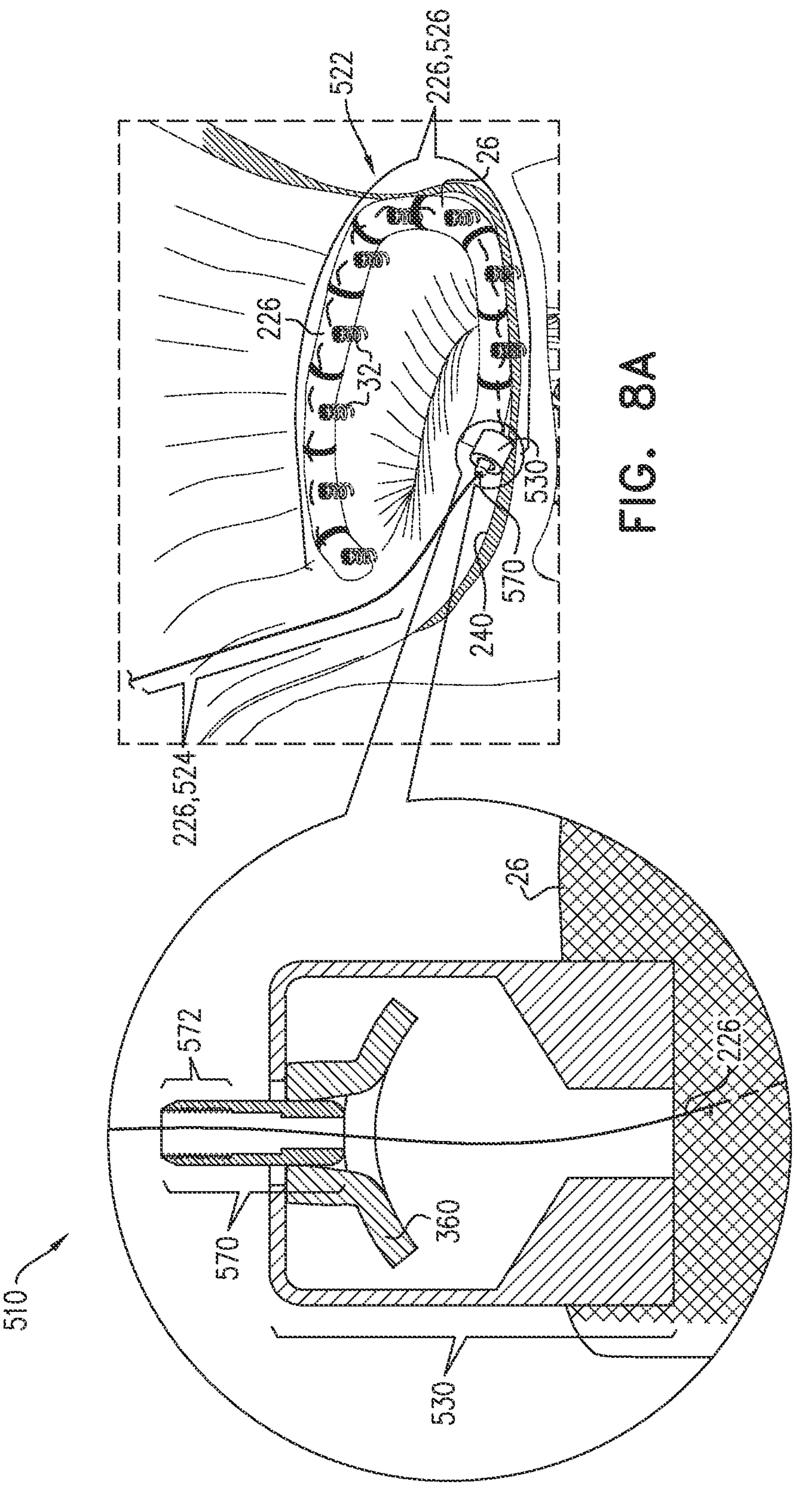
FIGS. 8A-D are schematic illustrations of an example of a system for contracting the annulus of the patient using an annuloplasty structure comprising a housing which houses a contracting-member-fastener.

Annuloplasty structure or annuloplasty ring structure 522 can comprise sleeve 26 which can define a primary body portion of structure 522. Structure 522 comprises contracting member 226 having a first portion 526 extending along a longitudinal length of the primary body portion of annuloplasty structure 522. The first portion 526 can extend along the longitudinal length of structure 522 when structure 522 is in a linear state as well as in a curved state, as shown in FIG. 8A. Contracting member 226 also defines a second portion 524 extending away from the primary body portion of annuloplasty structure 522.

Contracting member 226 can extend through housing 530 and through a stop 570 (e.g., a holder) that is disposed within an opening of contracting-member-fastener 360. Stop 570 is shown as being cylindrical by way of illustration and not limitation. The outer surface of stop 570 maintains fastener 360 in the open state. Stop 570 is shaped so as to define a threaded portion 572 which enables coupling thereto of a contracting-member-uptake tool, as is described hereinbelow.

Annuloplasty structure or annuloplasty ring structure 522 is implanted as described hereinabove with reference to FIGS. 3A-I using the system described hereinabove with reference to FIGS. 1-3I.

Housing 530 can be coupled to sleeve 26 of structure 522 at any suitable location along structure 522. For example, housing 530 can be coupled to sleeve 26 of structure 522 at a portion of structure 522 in a vicinity of a left fibrous trigone of the valve, as shown. For some applications, housing 530 can be coupled to sleeve 26 of structure 522 at a portion of structure 522 in a vicinity of a right fibrous trigone of the valve. For some applications, housing 530 can be coupled to sleeve 26 of structure 522 at a middle portion of structure 522. As shown, housing 530 can be coupled to a lateral surface of sleeve 26. In such applications, housing 530 does not block them lumen of sleeve 26 of structure 522.

Figure 8B:
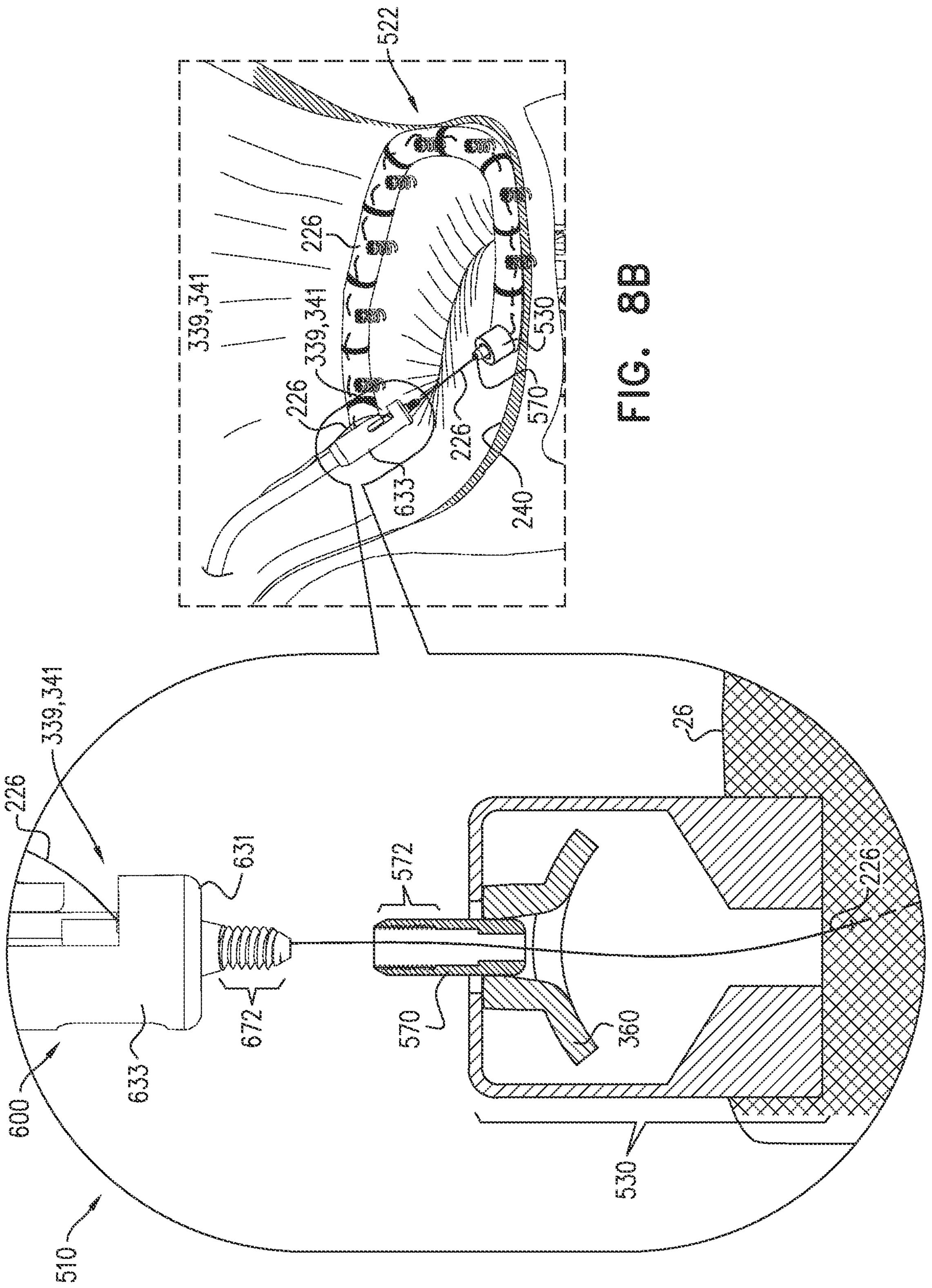

FIG. 8B shows a contracting-member-uptake tool 600 through which contracting member 226 has been threaded. Contracting member 226 can be ensnared by tool 600 using a snare as described herein above with regard to snare 350 with reference to FIGS. 4A-5D. Tool 600 can be advanced along contracting member 226 toward housing 530 of structure 522, in a manner similar to tool 300 advancing along contracting member 226, as described hereinabove with reference to FIGS. 4A-5D.

Tool 600 can comprise a distal tip 631 and a distal end portion 633 which is generally similar to distal end portion 533 of tool 300, described hereinabove with reference to FIGS. 4A-7E and like reference numerals refer to like parts. Since annuloplasty structure 522 comprises contracting-member-fastener 360 and stop 570 removably coupled to fastener 360, distal end portion 633 of tool 600 is unlike distal end portion 533 of tool 300 of FIGS. 4A-7E, remaining parts of tool 600 correspond to the remaining parts of tool 300.

Once tool 600 is threaded along contracting member 226, contracting member 226 extends from sleeve 26, through stop 570, through a stop-coupler 672 of tool 600, through distal tip 631, and then through aligned ports 339 and 341 of distal end portion 633 of tool 600.

Stop-coupler 672 of tool 600 screws into and engages threaded portion 572 of stop 570 coupled to contracting-member-fastener 360 disposed within housing 530 of structure 522.

Figure 8C:
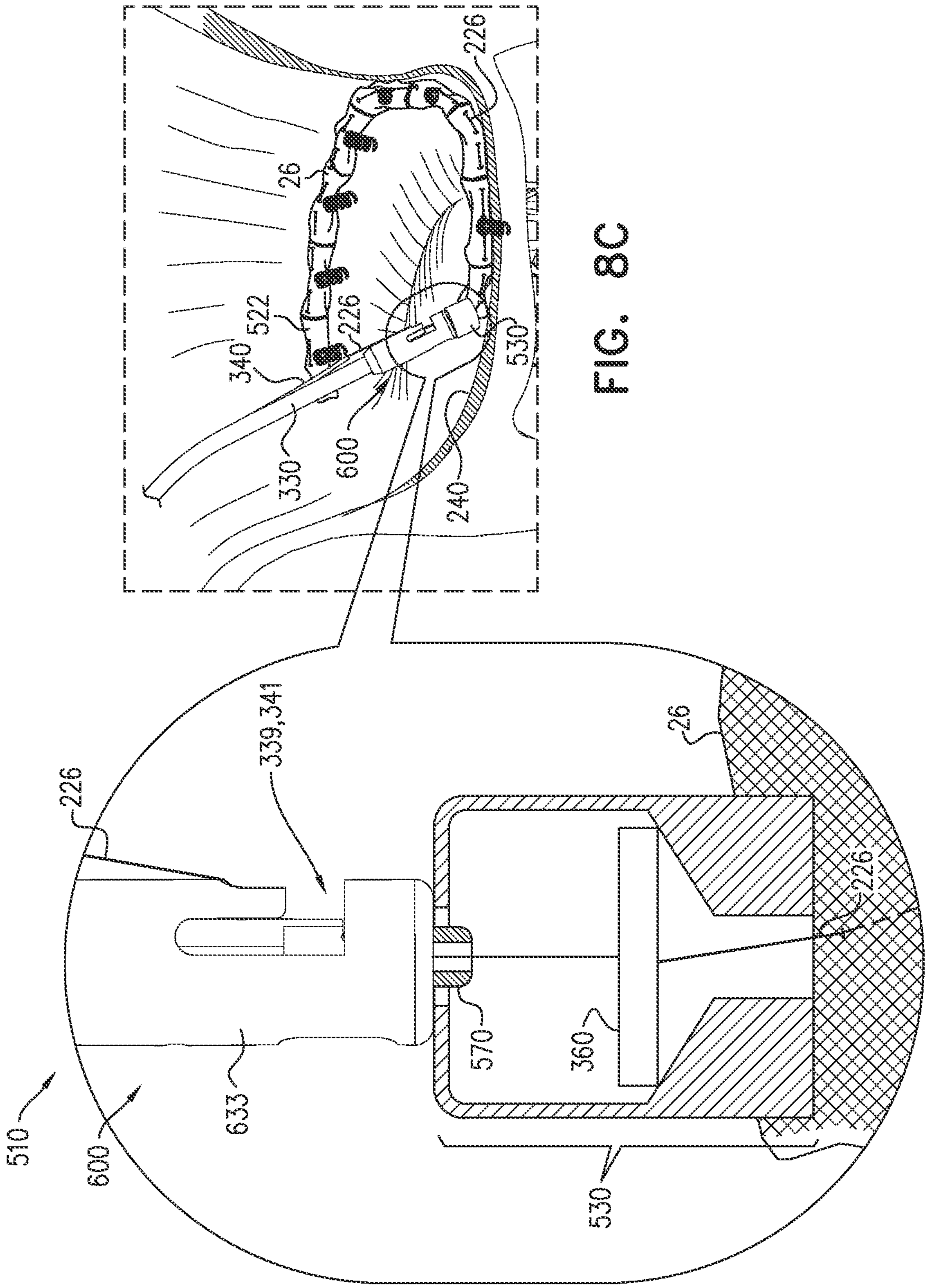

As described hereinabove with reference to FIGS. 6A-B, a contracting-member-uptake device of tool 600 (not shown, but similar to contracting-member-uptake device 322 of tool 300) can be used to contract contracting member 226. Once contracting member 226 is contracted and structure 522 is contracted, as shown in FIG. 8C, tool 600 removes stop 570 by pulling stop 570 proximally away from fastener 360. Since fastener 360 tends to close, in the absence of stop 570, fastener 360 closes and clamps around contracting member 226 passing through fastener 360. In such a manner, structure 522 is locked by fastener 360 and the contracted state of structure 522 is maintained.

Figure 8D:
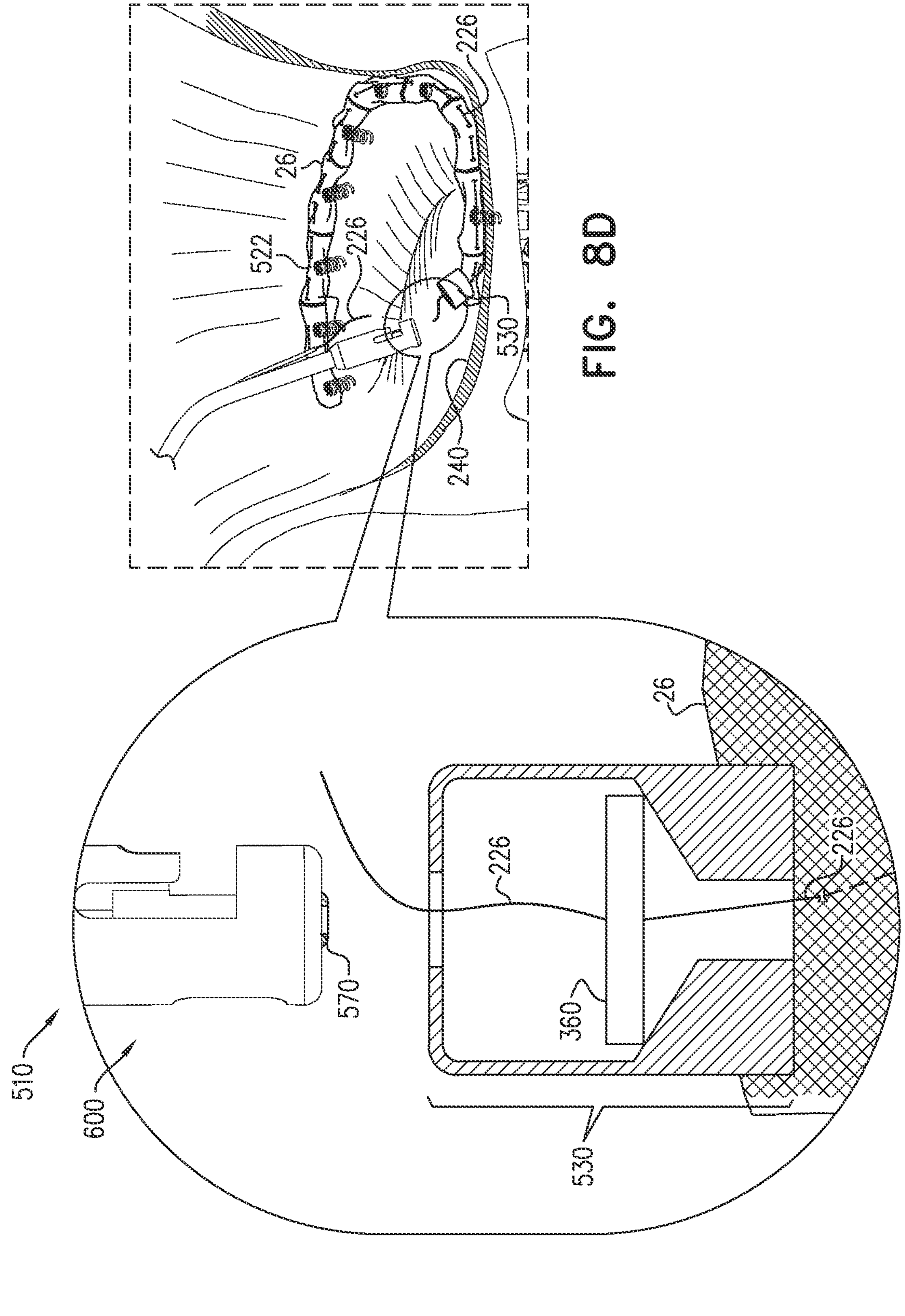

FIG. 8D shows contracting member 226 being severed proximal to fastener 360 and excess portions of contracting member 226 being removed from the body of the patient using tool 600. Severing of contracting member 226 is performed in a manner as described hereinabove with reference to FIGS. 7A-E, mutatis mutandis.

Reference is now made to FIGS. 9A-D, which are schematic illustrations of an example contracting-member-uptake tool 600 used to lock and secure annuloplasty structure 522 of FIGS. 8A-D in its contracted state and subsequently, sever excess portions of contracting member 226.

Figure 9A:
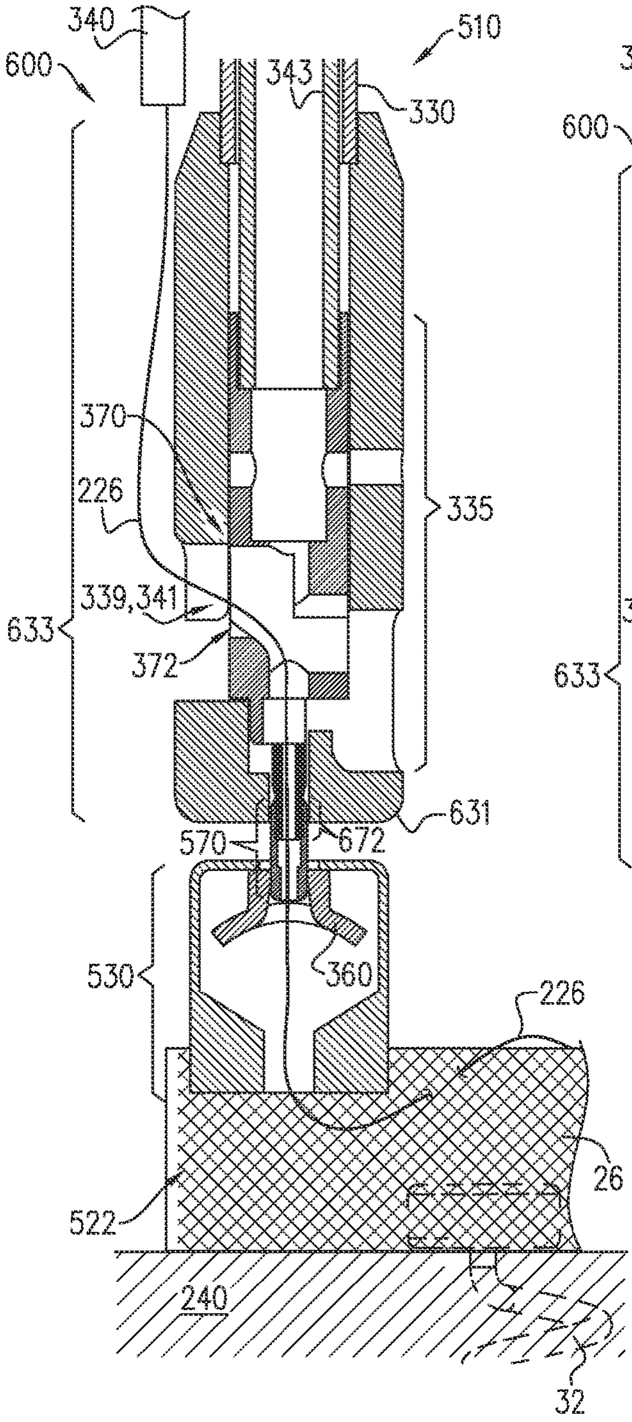
FIGS. 9A-D are schematic illustrations of an example contracting-member-uptake tool used to lock and secure the annuloplasty structure of FIGS. 8A-D in its contracted state and subsequently, sever excess portions of the contracting member.

FIG. 9A shows annuloplasty structure 522 in a partially, contracted state. Contracting member 226 can be threaded along sleeve 26 and out of a portion of sleeve 26 of structure 222. As described hereinabove, contracting member 226 can be threaded through tool 600 in a manner in which member 226 passes through a stop-coupler 672 of tool 600, through distal tip 631, through aligned ports 339 and 341 in distal end portion 633 of tool 600, and through secondary tube 340.

Figure 9B:
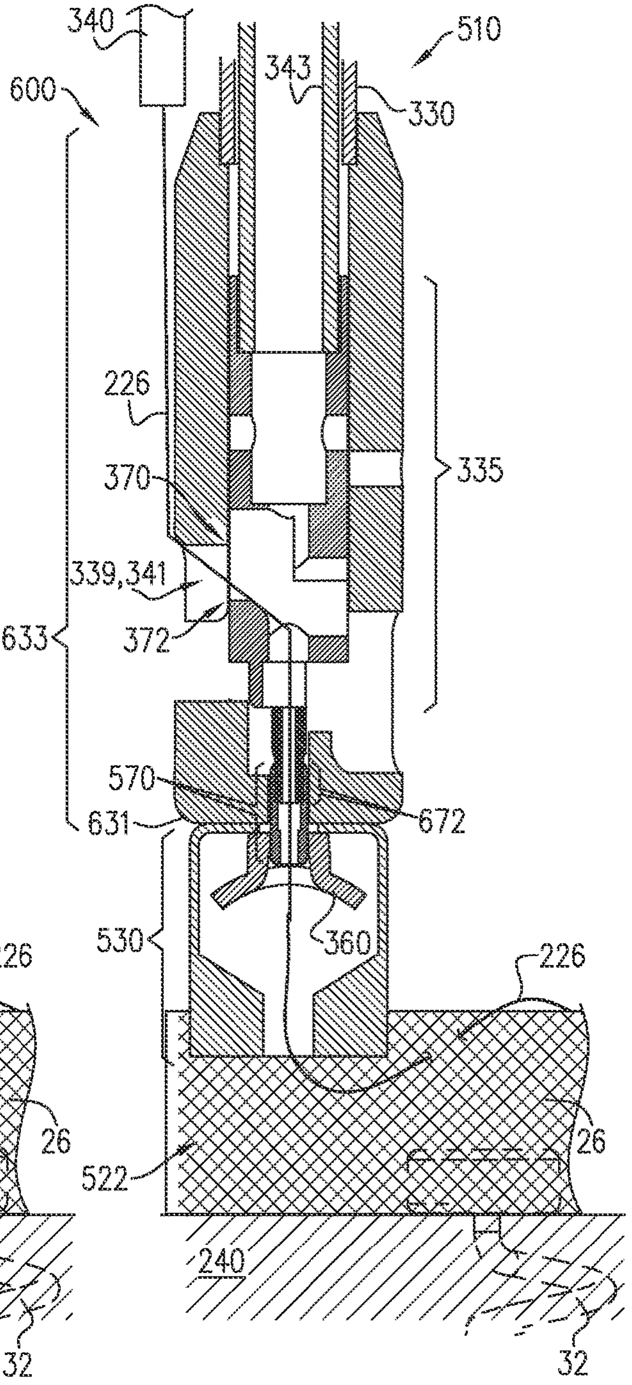

In FIG. 9B, contracting member 226 has been pulled tight, and annuloplasty structure 522 has been contracted and in a tense, contracted state. Distal end portion 633 of tool 300 is brought closely to annuloplasty structure 522 (e.g., tip 631 contacts housing 530 or is brought close, as shown) in order to eject and deploy fastener 360 within housing 530 in order to lock structure 522 in the contracted state.

Once distal end portion 633 is brought into proximity with sleeve 26, trigger on the handle portion of tool 600 (similar to trigger 321 of tool 300 as shown in FIG. 6B) can be pulled partially, in order to facilitate ejecting and deploying of contracting-member-fastener 360 distally within housing 530 of annuloplasty structure 522. Fastener-ejector 335 is movable within distal end portion 633 of contracting-member-uptake tool 600. Movement of fastener-ejector 335 converts contracting-member-fastener 360 (e.g., a clamping structure thereof) from its open state to its closed state to clamp onto contracting member 226 passed therethrough. Fastener-ejector 335 is coupled to stop-coupler 672 of tool 600 which screws into and engages threaded portion 572 of stop 570 in a manner in which when ejector 335 is moved proximally within portion 633 of tool 600, stop 570 is pulled away from fastener 630 and decoupled therefrom. Once contracting-member-fastener 360 is no longer held in the open state by stop 570, fastener 360 closes, as it tends to do, and clamps around contracting member 226 passing therethrough.

Figure 9C:
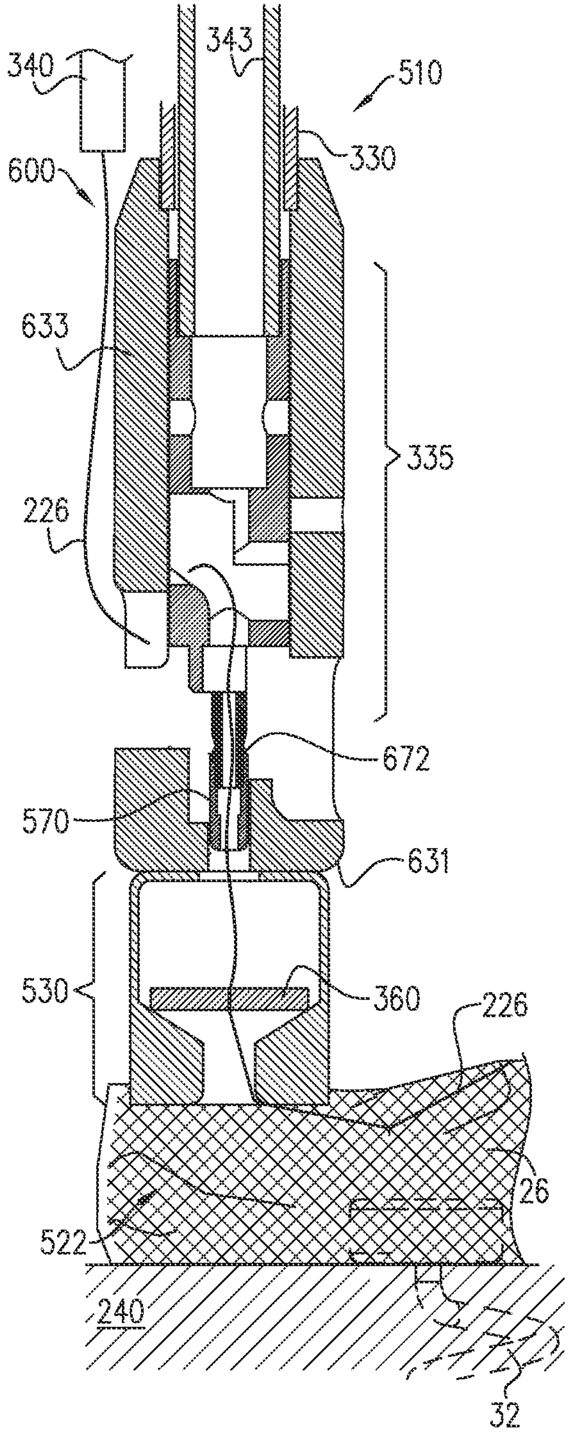

In FIG. 9C, fastener-ejector 335 can be moved further proximally (in response to the further pulling of the trigger of the handle portion of tool 600), in order to sever excess portions of contracting member 226. Tool 600 can be shaped so as to define a cutting-facilitating edge 370 in distal end portion 633 of tool 600. For some applications, cutting-facilitating edge 370 defines a sharp edge. While contracting member 226 passes through aligned ports 339 and 341 in distal end portion 633 of tool 600, as shown in FIG. 9B, contracting member 226 is in proximity with cutting-facilitating edge 370. Movement of fastener-ejector 335 proximally brings a cutting-facilitating edge 372 of ejector 335 against cutting-facilitating edge 370 of tool 300, thus sandwiching a portion of contracting member 226 between edges 370 and 372, in order to sever and cut contracting member 226 extending through ports 339 and 341. For some applications, cutting-facilitating edge 372 defines a sharp edge. FIG. 9C shows contracting member 226 severed once cutting-facilitating edge 372 of ejector 335 has been brought against cutting-facilitating edge 370 of tool 600.

Figure 9D:
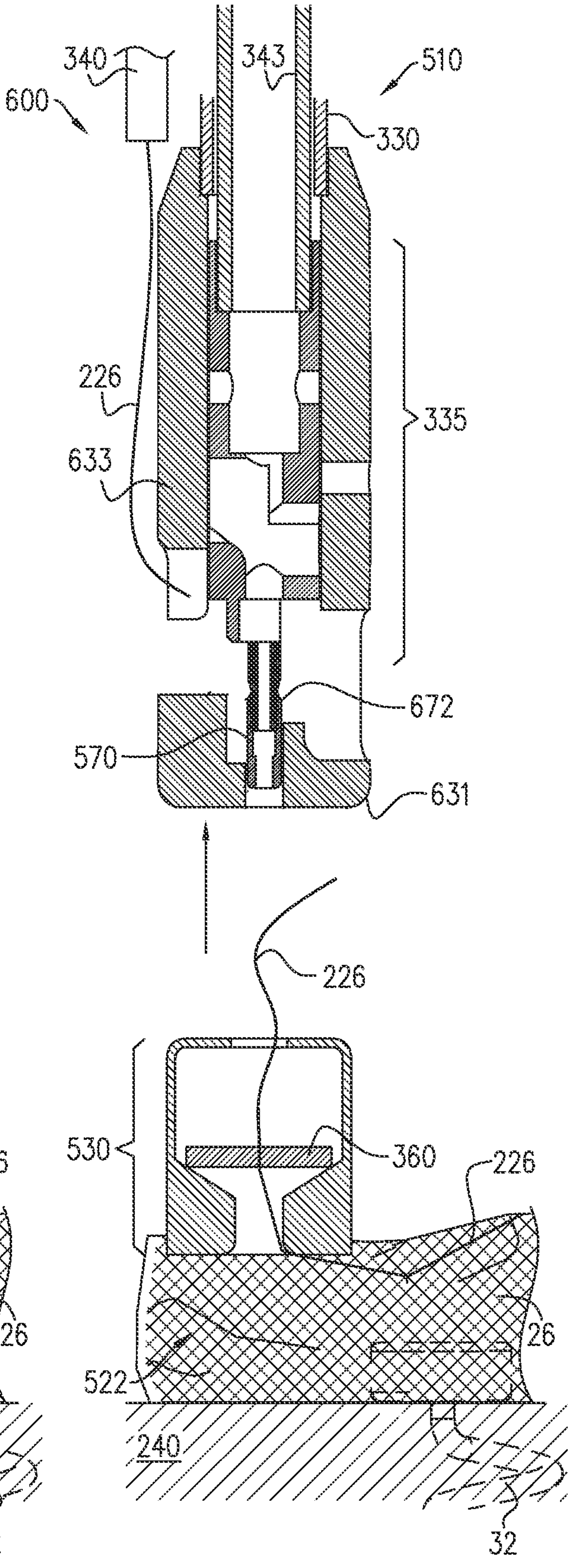

As shown in FIG. 9D, once contracting member 226 has been severed, tool 600 is withdrawn proximally, bringing together with it the excess portion of contracting member 226.

Reference is now made to FIGS. 8A-9D. System 510 provides an annuloplasty structure 522 (e.g., an annuloplasty ring structure, a closed annuloplasty structure, a closed annuloplasty ring structure, an open annuloplasty structure, a partial annuloplasty ring structure, etc.) in which housing 530 houses contracting-member-fastener 360, rather than fastener 360 being disposed outside sleeve 26. In such a manner, system 510 reduces the possibility of embolism and/or clotting.

Reference is now made to FIGS. 4A-9D. Contracting-member-uptake tools 300 and 600 can be used to (1) apply tension to the contracting member, (2) deploy a lock in order to secure tension of the contracting member, and (3) subsequently cut and sever the contracting member of any annuloplasty structure, e.g., a full annuloplasty ring structure, a partial annuloplasty ring structure, etc.

Reference is again made to FIGS. 8A-D and 9A-D. It is to be noted that although tool 600 is described as being advanceable toward housing 530 that is already coupled to annuloplasty structure 522, the scope herein includes tool 600 being coupled to housing 530 from a site outside the body of the patient and being configured to deliver housing 530 along contracting member 226 to sleeve 26 of structure 522 that is already implanted at the annulus. For such applications, housing 530 is configured to be positionable against the primary body portion of structure 522.

Figure 10A:
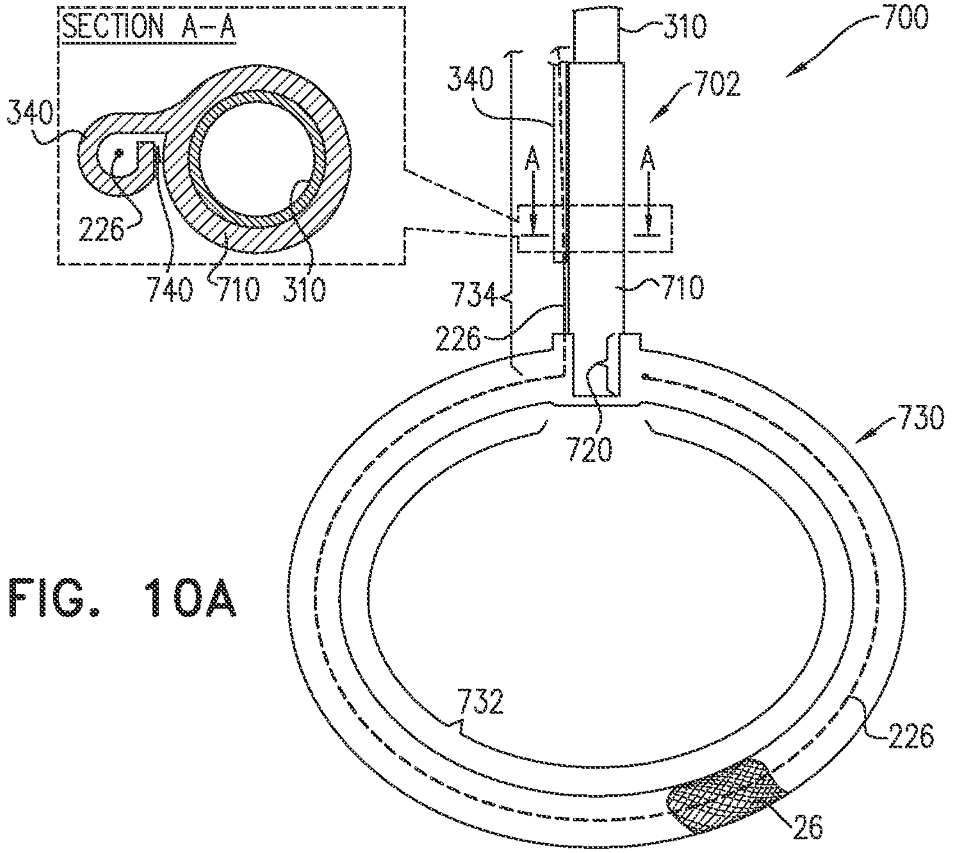
FIGS. 10A-B are schematic illustrations of an example of a contracting-member-uptake tool useable to engage a contracting member and sever any excess portions of the contracting member.
Figure 10B:
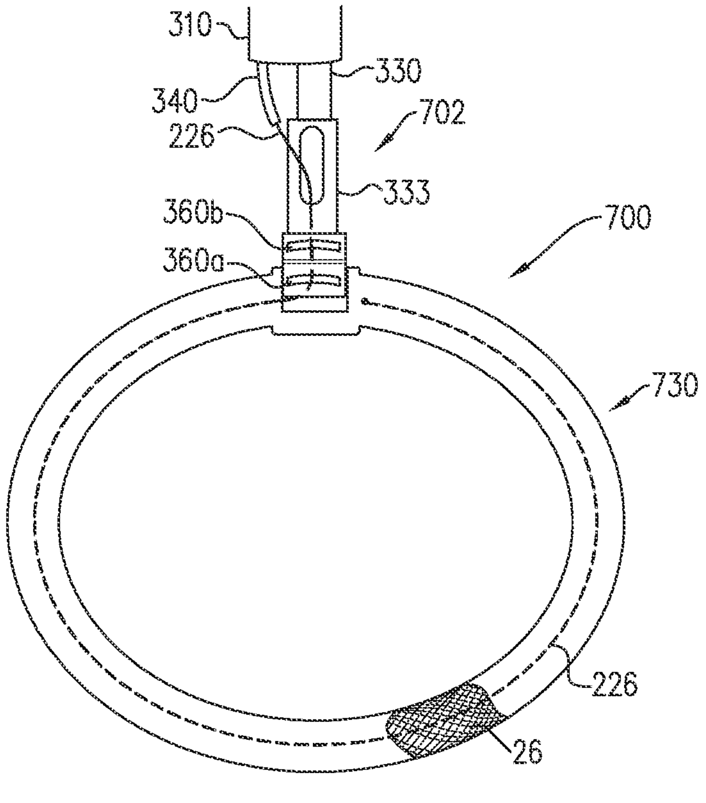

Reference is now made to FIGS. 10A-B, which are schematic illustrations of an example system 700 comprising an example contracting-member-uptake tool 702 which is configured to contract contracting member 226 and sever any excess portions of contracting member 226.

Except for the differences described hereinbelow, contracting-member-uptake tool 702 can be the same as or generally similar to contracting-member-uptake tools 300 and 600, described hereinabove with reference to FIGS. 4A-9D, used to (1) apply tension to the contracting member, (2) deploy a lock in order to secure tension of the contracting member, and (3) subsequently cut and sever the contracting member of any annuloplasty structure, e.g., a full (or closed) annuloplasty ring structure or a partial (or open) annuloplasty ring structure.

Example contracting-member-uptake tool 702 is useable to uptake contracting member 226 of an annuloplasty structure 730. Annuloplasty structure 730 can be the same as or generally similar to annuloplasty structures 222 or 522, described hereinabove with reference to FIGS. 1-9D and like reference numerals refer to like parts. At this stage, annuloplasty structure 730 (e.g., an annuloplasty ring structure, a closed annuloplasty structure, a closed annuloplasty ring structure, an open annuloplasty structure, a partial annuloplasty ring structure, etc.) has been implanted along the annulus, as described hereinabove with reference to FIGS. 3A-I. Once structure 730 has been implanted along the annulus, contracting member 226 extends away from structure 730 and through vasculature of the patient such that a proximal end portion of member 226 is disposed outside the body of the patient.

Except for the differences described hereinbelow, annuloplasty structure 730 can be the same as or generally similar to annuloplasty structures 222 and 522, described hereinabove with reference to FIGS. 1-9D and like reference numerals refer to like parts. Annuloplasty structure 730 can be a full (or closed) or partial (or opened) annuloplasty structure.

As shown, structure 730 comprises sleeve 26 which defines the primary body portion of structure 730. Contracting member 226 has a first portion 732 extending along a longitudinal length of the primary body portion of annuloplasty structure 730. Contracting member 226 also defines a second portion 734 extending away from the primary body portion of annuloplasty structure 730.

Although tool 702 is used to implant a full (or closed) annuloplasty structure 730, as shown, the annuloplasty structure can be an annuloplasty ring structure and can comprise a partial (or open) annuloplasty structure.

For some applications, annuloplasty structure 730 is implemented using techniques described in U.S. application Ser. No. 12/341,960, filed Dec. 22, 2008, which issued as U.S. Pat. No. 8,241,351, U.S. application Ser. No. 12/437,103, filed May 7, 2009 which issued as U.S. Pat. No. 8,715,342, and/or U.S. application Ser. No. 12/689,635, filed Jan. 19, 2010 which published as U.S. Pat. No. 8,545,553, both of which are assigned to the assignee of the present application and are incorporated herein by reference.

Tool 702 can be configured in various ways. In some applications, tool 702 comprises an elongate sheath 310. In some applications, sheath 310 encases a primary tube 330 and a secondary tube 340 disposed alongside primary tube 330. For such applications, sheath 310 is shaped to as to define secondary tube 340. Secondary tube 340 is shaped so as to define a longitudinal slit 740. Slit 740 facilitates ease of coupling and engagement of contracting member 226 within the lumen of tube 340. Slit 740 also enables ease of release of contracting member 226 from within the lumen of tube 340. For some applications, slit 740 facilitates ease of coupling and/or release of the contracting-member-snare as described hereinabove with reference to FIGS. 4A-B. For some applications, a distal-most section of slit 740 is at a longitudinal position along tube 340 that is proximal to a distal-most end of tube 340, e.g., a part of tube 340 that is configured to be disposed proximally to a ventricle of the heart of the patient, such that leaking of blood from within the heart through slit 740 is prevented.

Tool 702 is used to deploy one or more (e.g., two as shown) contracting-member-fasteners 360*a* and 360*b*. Fasteners 360*a* and 360*b* are similar to or the same as fasteners 360 described hereinabove with reference to FIGS. 4A-9D. The use of two fasteners 360*a* and 360*b* can provide redundant and more secure fastening of a perimeter of structure 730 following contraction thereof. Fasteners 360*a* and 360*b* can be disposed coaxially around a portion of contracting member 226

For some applications, a pushing tube (not shown) is used to deploy contracting-member-fasteners 360*a* and 360*b*. The pushing tube comprises a semi-rigid material used to deploy by pushing fasteners 360*a* and 360*b*. Fasteners 360*a* and 360*b* can be disposed coaxially around a portion of contracting member 226 and distally to a distal end of the pushing tube. For some applications, fasteners 360*a* and 360*b* are removably disposed around a portion of the pushing tube.

Following the deployment of fasteners 360*a* and 360*b*, tool 702 is used to sever any excess portions of contracting member 226, as described hereinbelow with reference to tools 300 and 600 as described hereinabove with reference to FIGS. 4A-9D.

For some applications, oversheath 710 is not used and tool 702 is coupled to the annuloplasty structure using male and female couplings, as shown hereinbelow with reference to FIGS. 12, 13, and 15.

Figure 11A:
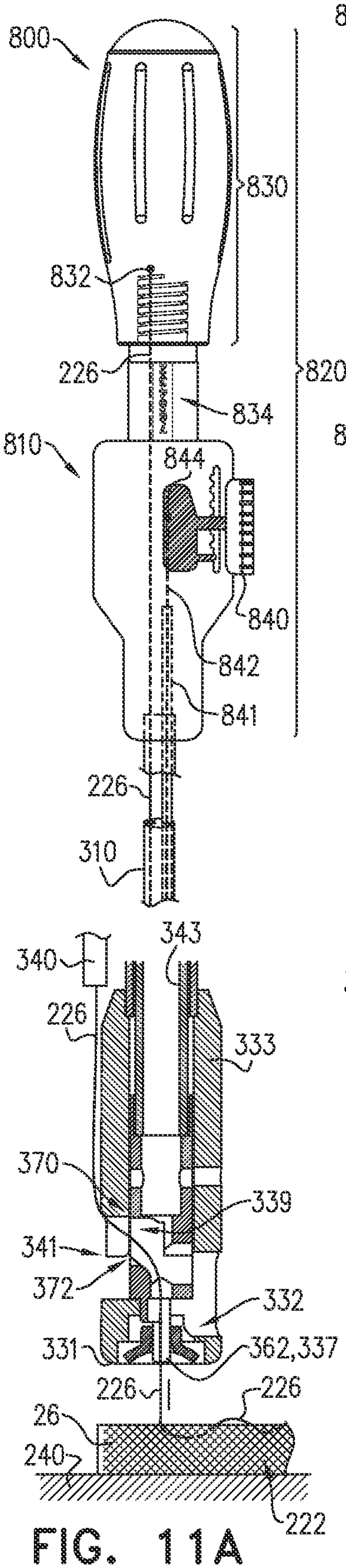
FIGS. 11A-C are schematic illustrations of an example of a contracting-member-uptake tool used to lock and secure the annuloplasty structure in its contracted state and subsequently, sever excess portions of the contracting member.
Figure 11B:
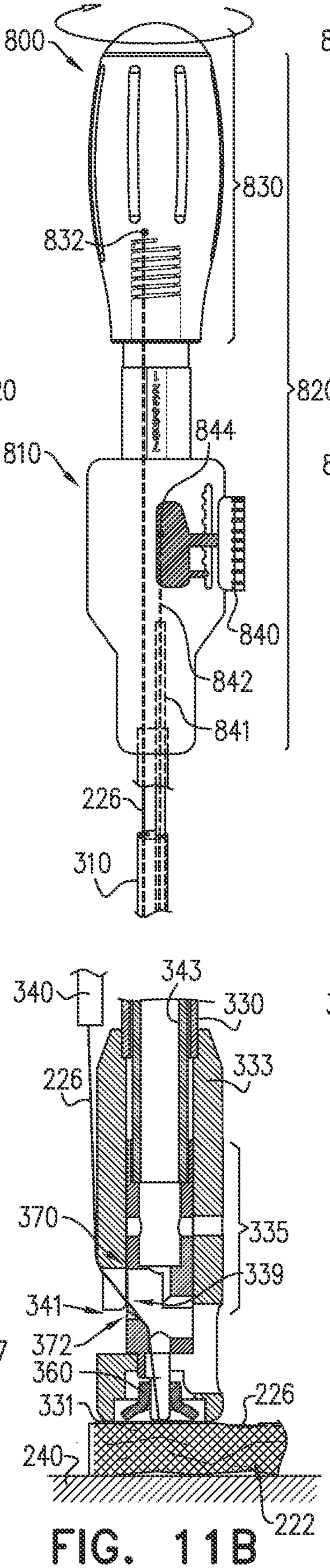
Figure 11C:
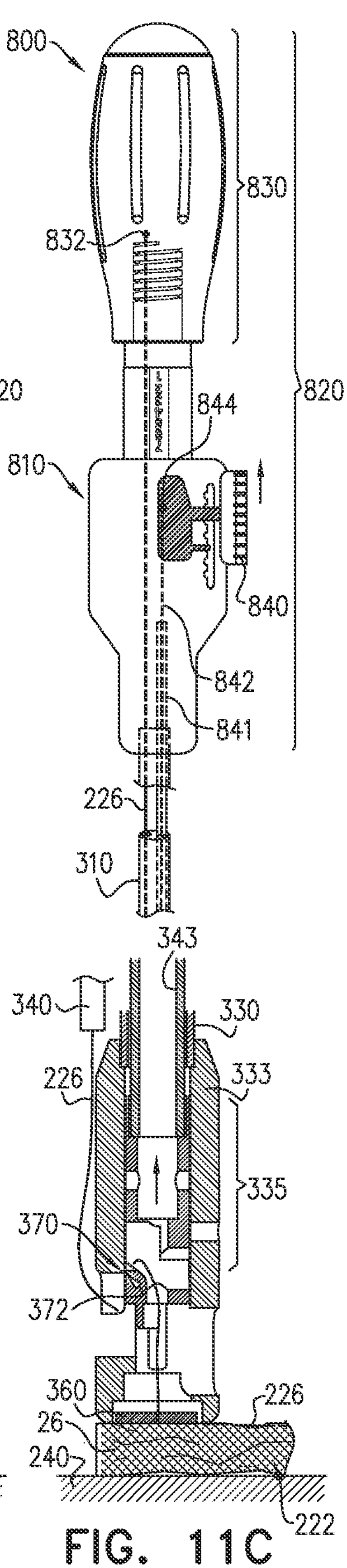

Reference is now made to FIGS. 11A-C, which are schematic illustrations of an example system 800 comprising an example contracting-member-uptake tool 810 used to lock and secure annuloplasty structure 222 in its contracted state and subsequently, sever excess portions of contracting member 226, in accordance with some applications.

Except for the differences described hereinbelow, contracting-member-uptake tool 810 can be the same as or generally similar to contracting-member-uptake tools 300 and 600, described hereinabove with reference to FIGS. 4A-9D, used to (1) apply tension to the contracting member, (2) deploy a lock in order to secure tension of the contracting member, and (3) subsequently cut and sever the contracting member of any annuloplasty structure, e.g., a full (or closed) annuloplasty ring structure, a partial (or open) annuloplasty structure, etc.

FIG. 11A shows annuloplasty structure or annuloplasty ring structure 222 in a non-contracted state. Distal tip 331 of tool 810 can be brought close to structure 222. Contracting member 226 can be threaded along sleeve 26 and out of a portion of sleeve 26 of structure 222. As described hereinabove, contracting member 226 can be threaded through tool 810 in a manner in which member 226 passes through distal tip 331, through contracting-member-fastener 360 that can be held in the open state, such as by prongs 337 of stop 362, through aligned ports 339 and 341 in distal end portion 333 of tool 810, and through secondary tube 340. For some applications, the distal end portion of tool 810 is similar to the distal end portion of tool 702 as described hereinabove with reference to FIGS. 10A-B. For some applications, the distal end portion of tool 810 is similar to the distal end portion of tool 920 as shown hereinbelow with reference to FIGS. 12, 13, and 15. For such applications, tool 920 comprises male coupling 925 and annuloplasty structure 222 comprises housing 930 shaped so as to define female coupling 927.

Tool 810 comprises a proximal handle portion 820. Handle portion 820 comprises a proximal contraction-facilitating knob 830. Knob 830 is fixedly coupled to a proximal end 832 of contracting member 226. Rotation of contraction-facilitating knob 830 as shown in FIG. 11A moves knob 830 proximally. As knob 830 is pulled proximally, contracting member 226 is pulled proximally. Responsively, annuloplasty structure 222 is contracted. Tool 810 comprise a gauge 834 indicating a level of contraction of the ring responsively to the number of rotations of knob 830.

As shown in FIG. 11B, once distal tip 331 of tool 810 contacts sleeve 26 of structure 222 (or for some applications a housing of annuloplasty structure, as described hereinabove with reference to FIGS. 12, 13, and 15), tool 810 can be used to contract structure 222 by tool 810 pulling on contracting member 226 responsively to rotation of the knob 830 as described hereinabove with reference to FIG. 11A. During contraction of structure 222, fastener 360 is not deployed.

In FIG. 11C, contracting member 226 has been pulled tight, and annuloplasty structure 222 has been contracted and in a tense, contracted state. Distal end portion 333 of tool 810 is then used to eject and deploy fastener 360 from within tool 810 in order to lock structure 222 in the contracted state.

In some applications, once distal tip 331 contacts sleeve 26, a trigger knob 840 at handle portion 820 of tool 810 is pulled partially, in order to facilitate ejecting and deploying of contracting-member-fastener 360 from within a housing 332 of distal end portion 333. Fastener-ejector 335 is movable within distal end portion 333 of contracting-member-uptake tool 810. A proximal portion of ejector 335 is coupled to a distal portion of an actuating wire 842. A proximal end 844 of actuating wire 842 is coupled to trigger knob 840. Proximal movement of trigger knob 840 pulls proximally on actuating wire 842, which, in turn, pulls maximally fastener-ejector 335. Movement of fastener-ejector 335 proximally converts contracting-member-fastener 360 from its open state to its closed state to clamp onto contracting member 226 passed therethrough. Fastener-ejector 335 is coupled to prongs 337 of stop 362 in a manner in which when ejector 335 is moved proximally within portion 333, stop 362 is decoupled from contracting-member-fastener 360 as prongs 337 move proximally away from contracting-member-fastener 360. Once contracting-member-fastener 360 is no longer held in the open state by stop 362, fastener 360 closes, as it tends to do, and clamps around contracting member 226 passing therethrough.

Actuating wire 842 is disposed within an inner sheath 841 which runs the length of elongate sheath 310. For such applications, as shown in FIGS. 11A-C, elongate sheath 310 comprises a multi-lumen sheath defining (1) a first lumen for passage therethrough of inner sheath 841 housing within it actuating wire 842, and (2) a second lumen for passage therethrough of contracting member 226.

As shown in FIG. 11C, fastener 360 has been ejected and deployed from within housing 332 of ejector 335. Subsequently, fastener-ejector 335 is moved further proximally in response to the further pulling proximally of trigger knob 840, in order to sever excess portions of contracting member 226. Similar to tool 300 and 600 described hereinabove, tool 810 is shaped so as to define a cutting-facilitating edge 370 in distal end portion 333 of tool 810. For some applications, cutting-facilitating edge 370 defines a sharp edge. While contracting member 226 passes through aligned ports 339 and 341 in distal end portion 333 of tool 810, as shown in FIGS. 11A-C, contracting member 226 is in proximity with cutting-facilitating edge 370. Movement of fastener-ejector 335 proximally brings a cutting-facilitating edge 372 of ejector 335 against cutting-facilitating edge 370 of tool 810, thus sandwiching a portion of contracting member 226 between edges 370 and 372, in order to sever and cut contracting member 226 extending through ports 339 and 341. For some applications, cutting-facilitating edge 372 defines a sharp edge. FIG. 11C shows contracting member 226 severed once cutting-facilitating edge 372 of ejector 335 has been brought against cutting-facilitating edge 370 of tool 300.

Following the severing of contracting member 226, tool 810 is removed from the body of the patient by being withdrawn proximally, bringing together with it the excess portion of contracting member 226.

Reference is now made to FIGS. 11A-C. For some applications, trigger knob 840 is coupled to a safety mechanism in order to prevent unintentional deployment of fastener 360.

Figures 12A, 12B, 12C:
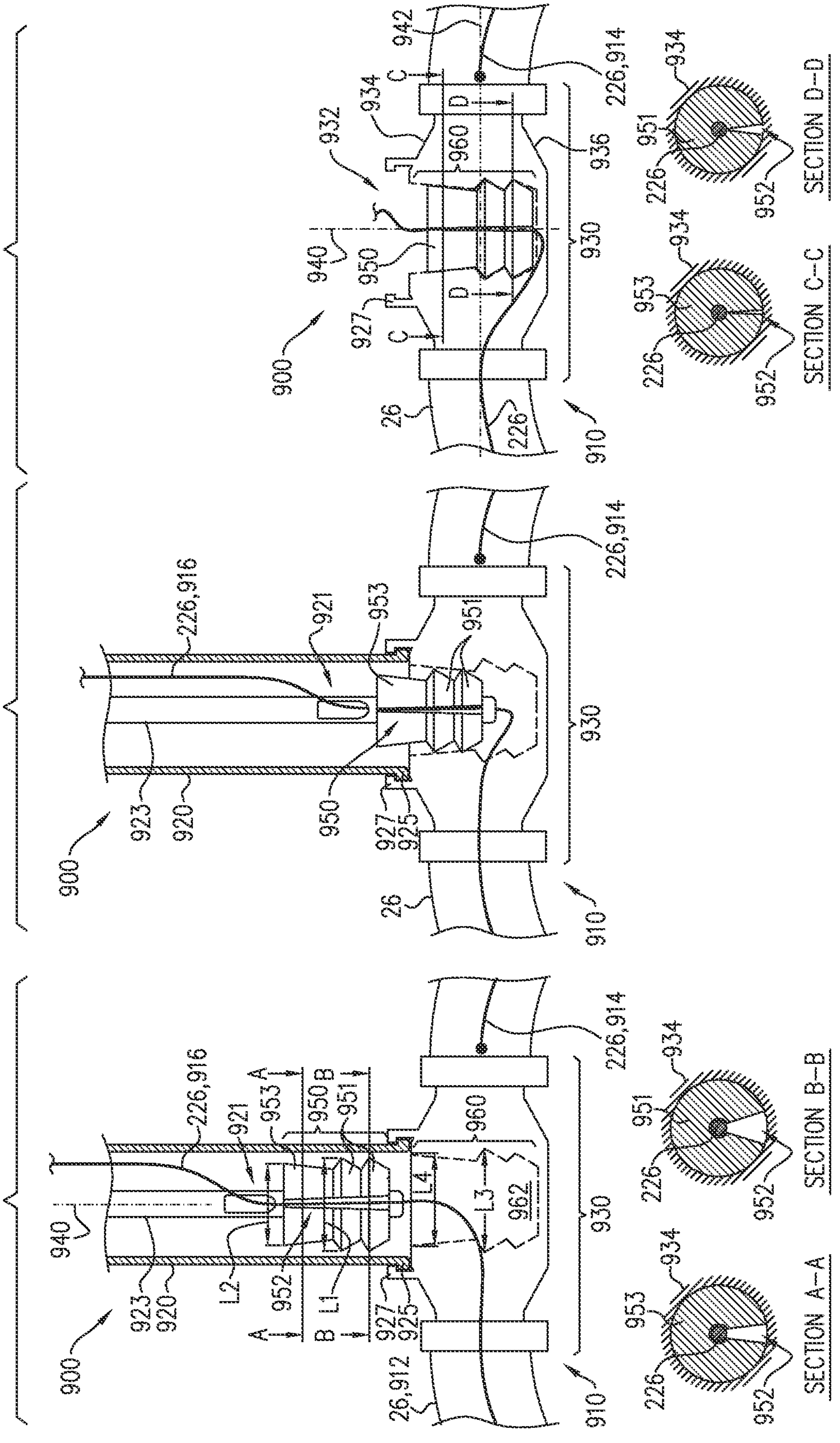
FIGS. 12A-C are schematic illustrations of an example of a system comprising an example annuloplasty structure comprising a sleeve, a contracting member, and a lock.

Reference is now made to FIGS. 12A-C, which are schematic illustrations of an example of a system 900 comprising an example annuloplasty structure 910 (e.g., an annuloplasty ring structure, a closed annuloplasty structure, a closed annuloplasty ring structure, an open annuloplasty structure, a partial annuloplasty ring structure, etc.) comprising a sleeve 26, a contracting member 226, and a lock 950. Implantable annuloplasty structure 910 comprises a primary body portion 912. Contracting member 226 has a first portion 914 extending along a longitudinal length of primary body portion 912 of annuloplasty structure 910, and a second portion 916 extending away from primary body portion 912 of annuloplasty structure 910. Contracting member 226 is configured to adjust a perimeter of annuloplasty structure 910.

Except for the differences described hereinbelow, annuloplasty structure 910 can be the same as or generally similar to annuloplasty structures 222, 522, and 730 described hereinabove with reference to FIGS. 1-11C and like reference numerals refer to like parts. Annuloplasty structure 910 can be a full (or closed) or partial (or opened) annuloplasty structure.

Primary body portion 912 of structure 910 has a lateral wall and is shaped so as to define a recess 960 having a recess axis 940. Recess 960 extends from an opening 932 in a first surface 934 of the lateral wall of primary body portion 912 toward an opposite second surface 936 of the lateral wall of the primary body portion 912 (illustrated in FIG. 12C). The lateral wall of primary body portion 912 extends away from recess 960 along a longitudinal axis 942 that is at a non-zero angle with respect to recess axis 940. Contracting member 226 extends through recess 960 and away from primary body portion 912 of annuloplasty structure 910 via recess 960.

Recess 960 is shaped so as to define a recess lumen 962. Recess lumen 962 is disposed along recess axis 940.

For some applications, primary body portion 912 comprises a housing 930 coupled to sleeve 26. For such applications, housing 930 defines at least a portion of the lateral wall and housing 930 defines recess 960. Sleeve 26 defines the remaining portion of the lateral wall.

For some applications, structure 910 does not comprise a housing 930, and sleeve 26 defines the lateral wall.

Recess 960 is shaped so as to receive lock 950. Recess 960 is dimensioned so as to compress lock 950 when lock 950 is disposed at least in part within recess 960. Lock 950 is shaped to as to define a series of tapered segments 951. Each segment 951 having a longest length L1 of 0.2-1.5 mm A proximal-most section of lock 950 has a length L2 of 0.2-2 mm Correspondingly, recess 960 corresponds to the shape of lock 950 and is slightly smaller than the shape of lock 950 such that the walls that define recess 960 compress lock 950 as it slides into recess 960. That is, the section of recess 960 that receives longest length L1 of segment 951 has a longest length L3 of 0.2-1.5 mm A proximal-most section of recess 960 has a length L4 of 0.2-2 mm.

Lock 950 is shaped so as to define a lock lumen configured to surround contracting member 226. Lock 950 is shaped so as to define a longitudinal slit 952 which extends from a proximal surface of lock 950 toward a distal surface of lock 950. For some applications, slit 952 defines the lock lumen of lock 950. Slit 952 enables lock 950 to squeeze into the smaller recess 960 and thereby be compressed. When lock 950 is compressed, slit 952 enables lock 950 to close around contracting member 226 and thereby lock 950 to contracting member 226.

For some applications (not shown), the lock lumen has a dimension (e.g., a diameter) that is consistent along a length of the lock lumen from the proximal surface of lock 950 to a distal surface of lock 950.

As shown, for some applications, the lock lumen is shaped so as to define a distal portion that is wider than a proximal portion of the lock lumen. For such applications, the proximal-most section of recess 960 is narrower than any other portion of recess 960 distal to the proximal-most portion.

A delivery tool 920 is used to deliver lock 950 to recess 960. Except for the differences described hereinbelow, delivery tool 920 can be the same as or generally similar to tools 300, 600, 702, and 810 described hereinabove with reference to FIGS. 4A-11C and like reference numerals refer to like parts. Tool 920 comprises a contracting-member severing section 921 which can comprise elements of tools 300, 600, 702, and 810 described hereinabove with respect to the cutting elements.

As shown in FIG. 12A, delivery tool 920 delivers annuloplasty structure or annuloplasty structure 910 and lock 950 together toward the annulus. Delivery tool 920 and contracting member 226 are slidable with respect to each other. When delivery tool 920 is coupled to annuloplasty structure 910, a portion of contracting member 226 (e.g., second portion 916) is disposed within a lumen of delivery tool 920 and lock 950 surrounds a part of the contracting member. When delivery tool 920 is coupled to annuloplasty structure 910, lock 950 is disposed entirely proximally to recess 960.

FIG. 12B shows partial position of lock 950 within a proximal portion of recess 960. During the partial positioning of lock 950, the distal portion of lock 950 is compressed (e.g., a distal-most tapered segment 951). Since the distal portion of the lock lumen of lock 950 is wider than the proximal portion of the lock lumen, as the distal portion of lock 950 is compressed within the proximal portion of recess 960, the distal portion of lock 950 doesn't fully close around contracting member 226 such that at this stage, lock 950 is not locked with respect to contracting member 226 which would pull contracting member distally as lock 950 is pushed further distally within recess 960. Only once lock 950 has been pushed entirely within recess 960, since the proximal-most section of recess 960 is narrower than any other portion of recess 960 distal to the proximal-most portion, and since the lock lumen of lock 950 is narrower at a proximal portion 953 of lock 950, at least proximal portion 953 of lock 950 closes around contracting member 226 in order to lock 950 to contracting member and, thereby, maintain the perimeter of annuloplasty structure 910. That is, tool 920 pushes lock 950, often using a lock-ejector 923 which is similar to fastener-ejector 335 described hereinabove. Lock-ejector 923 is movable within a distal end portion of tool 920. Movement of lock-ejector 923 contacts and converts lock 950 from an open state (shown in FIG. 12A) to a closed state (shown in FIG. 12C) in order to clamp lock 950 onto contracting member 226 passed therethrough.

As shown in FIG. 12C, lock 950 is shaped so as to fit entirely within recess 960. As described hereinabove with reference to tools 300, 600, 702, and 810 described hereinabove with reference to FIGS. 4A-11C, tool 920 is configured to sever excess portions of contracting member 226 following the locking of lock 950 to contracting member 226 by being positioned within recess 960. That is, the distal end portion of tool 920 is shaped so as to define a sharp edge, similar to edge 370 of tool 300 as described hereinabove. Additionally, as described hereinabove, contracting member 226 is disposed in proximity to the sharp edge such that movement of lock-ejector 923 against the sharp edge severs contracting member 226 extending through lock 950.

Figures 13A, 13B, 13C:
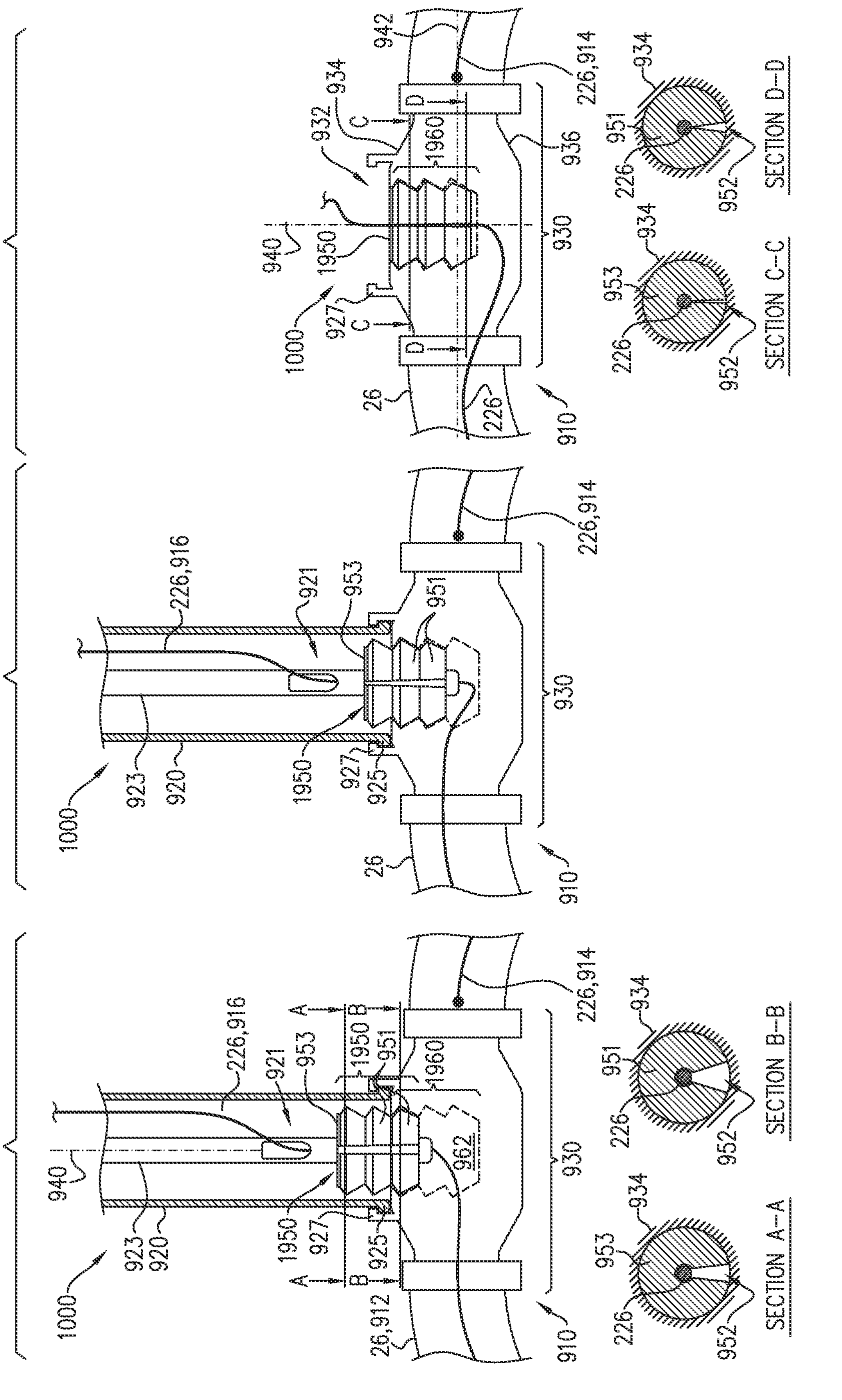
FIGS. 13A-C are schematic illustrations of an example of a system comprising an example annuloplasty structure comprising a sleeve, a contracting member, and a lock.

Reference is now made to FIGS. 13A-C, which are schematic illustrations of an example of a system 1000 comprising an example annuloplasty structure or annuloplasty structure 910 (e.g., an annuloplasty ring structure, a closed annuloplasty structure, a closed annuloplasty ring structure, an open annuloplasty structure, a partial annuloplasty ring structure, etc.) comprising a sleeve 26, a contracting member 226, and a lock 1950. Except for the differences described herein below, system 1000 is the same or generally similar to system 900 as described hereinabove with reference to FIGS. 12A-C with the exception that when delivery tool 920 is coupled to annuloplasty structure 910, lock 1950 is disposed at least in part and retained within recess a 1960. As shown, a distal-most tapered segment 951 is disposed within a proximal section of recess 1960. In such a manner, system 1000 reduces the possibility of embolism and/or clotting.

Reference is now made to FIGS. 10A-13C. In FIG. 10A, tool 702 comprises an oversheath 710 at least a distal portion of tool 702. Oversheath 710 comprises grippers 720 which are configured to surround at least a portion of annuloplasty structure coupled to tool 702. For some applications, any of tools 300, 600, and 810 described herein comprise oversheath 710 comprising grippers 720. Grippers 720 and oversheath 710 are configured to provide a counterforce to the annuloplasty structure during deployment of the fasteners 360 and/or lock 950 described herein, because in order to deploy the fasteners 360 and/or lock 950, the fasteners

360 and/or lock 950 are pushed by the tool. For some applications, tools described herein do not comprise grippers 720.

Figure 14:
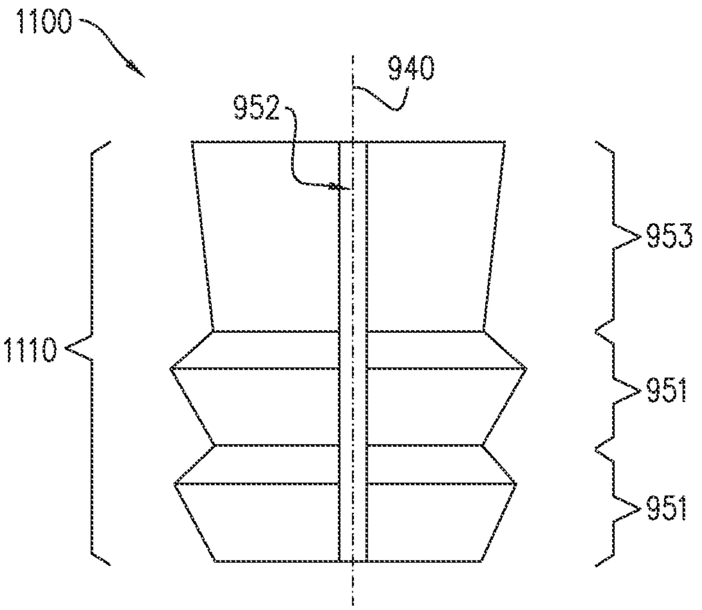
FIG. 14 is a schematic illustration of an example lock useable to lock a perimeter of an annuloplasty structure.

Reference is now made to FIG. 14, which is a schematic illustration of an example system 1100 comprising a lock 1110 configured to lock a perimeter of an annuloplasty structure (e.g., an annuloplasty ring structure, a closed annuloplasty structure, a closed annuloplasty ring structure, an open annuloplasty structure, a partial annuloplasty ring structure, etc.), in accordance with some applications. Except for the differences described hereinbelow, lock 1110 can be generally similar to lock 950, described hereinabove with reference to FIGS. 12A-13C and like reference numerals refer to like parts. Slit 952 of lock 1110 is uniform along a longitudinal axis of lock 1110 from a proximal end of lock 1110 to a distal end of lock 1110. For some applications, as shown in FIGS. 12A-13C, the lock lumen is uniform. For some applications, as shown in FIGS. 15A-C, the lock lumen is narrower at the proximal end portion and wider at the distal end portion of the lock.

Lock 1110 can be used to lock any annuloplasty structure described herein, for example, lock 1110 can be used to lock any of annuloplasty structures 222, 522, 730, and 910 described hereinabove with reference to FIGS. 1-13C.

A delivery tool can be used to deliver lock 1110 toward the annuloplasty structure or annuloplasty ring structure. The delivery tool can be the same as or generally similar to tools 300, 600, 702, 810, and 920 described hereinabove with reference to FIGS. 4A-13C and like reference numerals refer to like parts. The delivery tool comprises a contracting-member severing section which can comprise elements of tools 300, 600, 702, 810, and 920 described hereinabove with respect to the cutting elements.

Figures 15A, 15B, 15C:
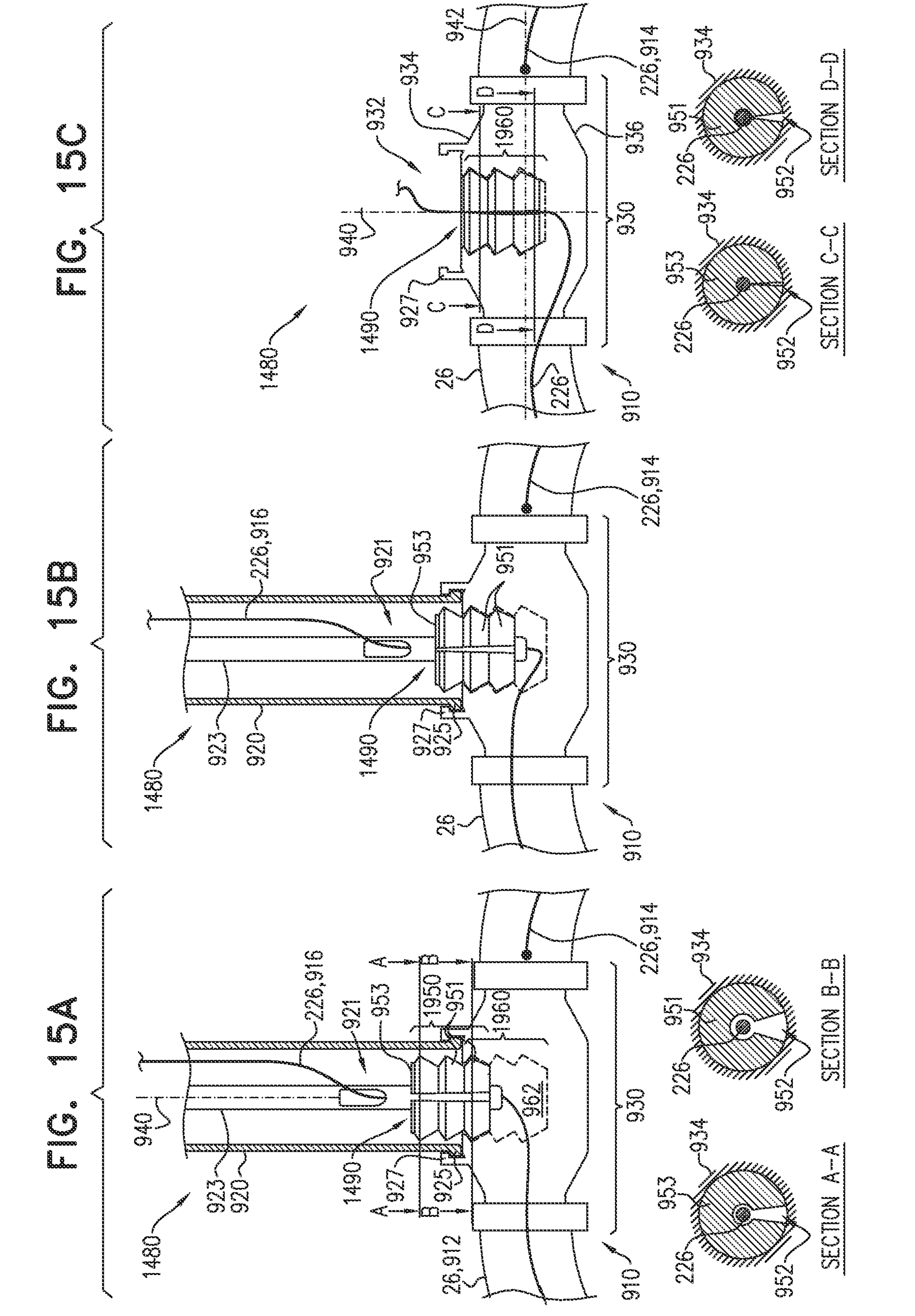
FIGS. 15A-C are schematic illustrations of an example of a system comprising an example annuloplasty structure comprising a sleeve, a contracting member, and a lock.

Reference is now made to FIGS. 15A-C, which are schematic illustrations of an example system 1480 comprising an example annuloplasty structure 910 (e.g., an annuloplasty ring structure, a closed annuloplasty structure, a closed annuloplasty ring structure, an open annuloplasty structure, a partial annuloplasty ring structure, etc.) comprising a sleeve 26, a contracting member 226, and a lock 1490, in accordance with some applications. Except for the differences described herein below, system 1480 is the same or generally similar to system 1000 as described hereinabove with reference to FIGS. 13A-C with the exception that lock 1490 has a lumen that is narrower at the proximal end portion of lock 1490 and wider at the distal end portion of lock 1490. Section A-A of FIG. 15A shows the lock lumen being wider around contracting member 226 at the proximal end portion of lock 1490 than a width of the lock lumen around contracting member 226 at the distal end portion of lock 1490 shown in Section B-B. As shown in FIG. 15C, once lock 1490 is disposed entirely within recess 960, the proximal end portion closes tightly around contracting member 226, as shown in Section C-C, while the distal end portion closes around contracting member 226, which may not close as tightly as the proximal end portion closes around contracting member 226, as shown in Section D-D.

As shown, lock 1490 is shaped so as to define slit 952 that is narrower at the proximal end portion of lock 1490 and wider at the distal end portion of lock 1490.

For some applications, lock 1490 is shaped so as to define slit 952 that is uniform along the length of lock 1490 as shown in FIG. 14.

For some applications, when delivery tool 920 is coupled to annuloplasty structure 910, lock 1490 is disposed entirely proximally to recess 1960, as shown in FIGS. 12A-C.

Figure 16:
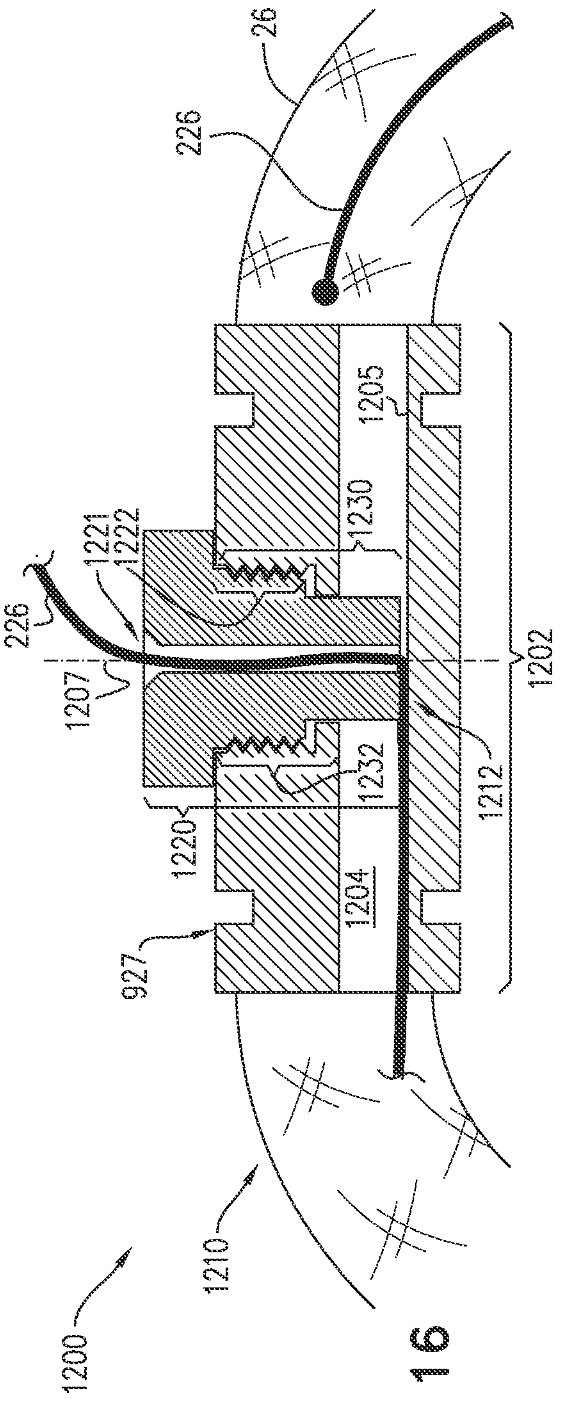
FIG. 16 is a schematic illustration of an example of a system comprising an example annuloplasty structure comprising a sleeve, a contracting member, and a lock.

Reference is now made to FIG. 16, which is a schematic illustration of an example system 1200 comprising an example annuloplasty structure 1210 (e.g., an annuloplasty ring structure, a closed annuloplasty structure, a closed annuloplasty ring structure, an open annuloplasty structure, a partial annuloplasty ring structure, etc.) comprising a sleeve 26, a contracting member 226, and a lock 1220. Implantable annuloplasty structure 1210 comprises a primary body portion. Contracting member 226 has a first portion extending along a longitudinal length of the primary body portion of annuloplasty structure 1210, and a second portion extending away from the primary portion of annuloplasty structure 1210. Contracting member 226 is configured to adjust a perimeter of annuloplasty structure 1210.

Except for the differences described hereinbelow, annuloplasty structure 1210 can be the same as or generally similar to annuloplasty structures 222, 522, 730, and 910 described hereinabove with reference to FIGS. 1-15C and like reference numerals refer to like parts. Annuloplasty structure 1210 can be a full (or closed) or partial (or opened) annuloplasty structure.

Structure 1210 comprises a housing 1202 shaped so as to define a lateral wall and is shaped so as to define a recess 1230 having a recess axis. Recess 1230 extends from an opening in a first surface of the housing toward an opposite second surface of housing 1202. Housing 1202 is shaped so as to provide a contracting-member-lumen wall 1205 which is disposed along a contracting-member lumen 1204. Contracting-member lumen 1204 is disposed at a non-zero angle with respect to a recess axis 1207 of recess 1230. Recess 1230 is shaped so as to define a recess lumen that is disposed along recess axis 1207.

Lock 1220 is shaped so as to define a lock-threaded-portion 1222. Housing 1202 of annuloplasty structure 1210 is shaped so as to define annuloplasty-structure-threaded-portion 1232 configured to engage with lock-threaded-portion 1222. In order to advance lock 1220 within recess 1230 of housing 1202, the physician uses a delivery tool in order to screw lock 1220 within housing 1202. The delivery tool can be the same as or generally similar to tools 300, 600, 702, 810, and 920 described hereinabove with reference to FIGS. 4A-13C and like reference numerals refer to like parts. The delivery tool comprises a contracting-member severing section which can comprise elements of tools 300, 600, 702, 810, and 920 described hereinabove with respect to the cutting elements.

When lock 1220 is disposed within the recess, a distal surface of a distal end of lock 1220 is configured to pinch a first portion of contracting member 226 against contracting-member-lumen wall 1205 in order to lock contracting member 226 at least a first pinching point 1212.

For some applications, housing 1202 defines at least a portion of a lateral wall of the annuloplasty structure 1210, and housing 1202 defines recess 1230.

Lock 1220 is shaped so as to define a lock lumen 1221 configured to surround contracting member 226. Lock 1220 is shaped so as to define a longitudinal slit which extends from a proximal surface of lock 1220 toward a distal surface of lock 1220. For some applications, the slit defines lock lumen 1221 of lock 1220. The slit enables lock 1220 to squeeze into the smaller recess 1230 and thereby be compressed. When lock 1220 is compressed, the slit enables lock 1220 to close around contracting member 226 and thereby lock 1220 to contracting member 226.

For some applications, lock lumen 1221 has a dimension (e.g., a diameter) that is consistent along a length of lock lumen 1221 from the proximal surface of lock 1220 to a distal surface of lock 1220.

Reference is now made to FIGS. 15A-C, and 16. For some applications, lock lumen 1221 of lock 1220 is shaped so as to define a distal portion that is wider than a proximal portion of lock lumen 1221. For such applications, the proximal-most section of recess 1230 can be narrower than any other portion of recess 1230 distal to the proximal-most portion.

Reference is now made to FIGS. 12A-C, 13A-C, 15A-C, and 16. For some applications, the slit of lock 1220 is wider at the distal end portion of lock 1220 and narrower at the proximal end portion of lock 1220.

Reference is now made to FIGS. 14 and 16. For some applications, the slit of lock 1220 is uniform along the length of the slit. For some applications, lock lumen 1221 is uniform along the length of lock 1220.

Figure 17:
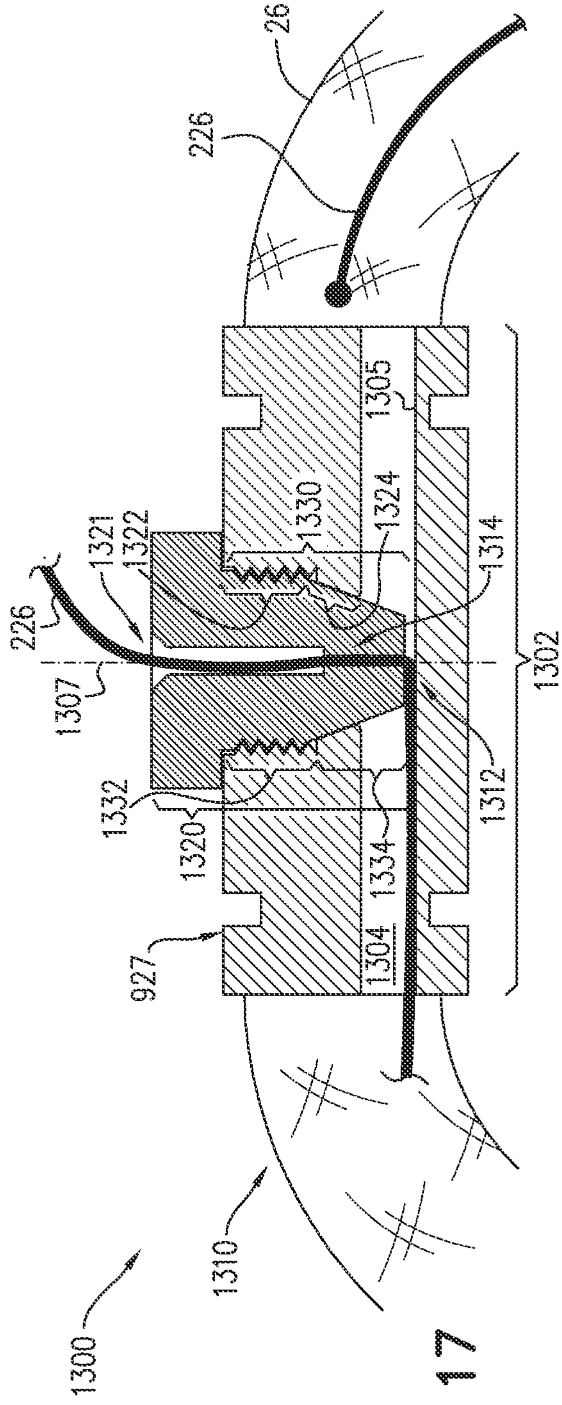
FIG. 17 is a schematic illustration of an example of a system comprising an example annuloplasty structure comprising a sleeve, a contracting member, and a lock.

Reference is now made to FIG. 17, which is a schematic illustration of an example system 1300 comprising an example annuloplasty structure 1310 (e.g., an annuloplasty ring structure, a closed annuloplasty structure, a closed annuloplasty ring structure, an open annuloplasty structure, a partial annuloplasty ring structure, etc.) comprising a sleeve 26, a contracting member 226, and a lock 1320. Implantable annuloplasty structure 1310 comprises a primary body portion. Contracting member 226 has a first portion extending along a longitudinal length of the primary body portion of annuloplasty structure 1310, and a second portion extending away from the primary portion of annuloplasty structure 1310. Contracting member 226 is configured to adjust a perimeter of annuloplasty structure 1310.

Except for the differences described hereinbelow, annuloplasty structure 1310 can be the same as or generally similar to annuloplasty structures 222, 522, 730, and 910 described hereinabove with reference to FIGS. 1-15C and like reference numerals refer to like parts. Annuloplasty structure 1310 can be a full (or closed) or partial (or opened) annuloplasty structure.

Structure 1310 comprises a housing 1302 shaped so as to define a lateral wall and is shaped so as to define a recess 1330 having a recess axis. Recess 1330 extends from an opening in a first surface of the housing toward an opposite second surface of housing 1302. Housing 1302 is shaped so as to provide a contracting-member-lumen wall 1305 which is disposed along a contracting-member lumen 1304. Contracting-member lumen 1304 is disposed at a non-zero angle with respect to a recess axis 1307 of recess 1330. Recess 1330 is shaped so as to define a recess lumen that is disposed along recess axis 1307.

Lock 1320 is shaped so as to define a lock-threaded-portion 1222. Housing 1302 of annuloplasty structure 1310 is shaped so as to define annuloplasty-structure-threaded-portion 1332 configured to engage with lock-threaded-portion 1322. In order to advance lock 1320 within recess 1330 of housing 1302, the physician uses a delivery tool in order to screw lock 1320 within housing 1302. The delivery tool can be the same as or generally similar to tools 300, 600, 702, 810, and 920 described hereinabove with reference to FIGS. 4A-13C and like reference numerals refer to like parts. The delivery tool comprises a contracting-member severing section which can comprise elements of tools 300, 600, 702, 810, and 920 described hereinabove with respect to the cutting elements.

When lock 1320 is disposed within the recess, a distal surface of a distal end of lock 1320 is configured to pinch a first portion of contracting member 226 against contracting-member-lumen wall 1305 in order to lock contracting member 226 at least a first pinching point 1312. Lock 1320 is shaped so as to define a lock lumen 1321 along a longitudinal length and a lock-distal-tapered-portion 1334. Housing 1302 and recess 1330 are shaped so as to define a recess-distal-tapered-portion 1324. When lock 1320 is disposed within recess 1330, and lock-distal-tapered-portion 1334 is within recess-distal-tapered-portion 1324, recess-distal-tapered-portion 1324 is configured to compress lock-distal-tapered-portion 1334 which, in turn, is configured to pinch a second portion of contracting member 226 within lock lumen 1321 at recess-distal-tapered-portion 1324 in order to lock contracting member 226 at least a second pinching point 1314.

For some applications, housing 1302 defines at least a portion of a lateral wall of the annuloplasty structure 1310, and housing 1302 defines recess 1330.

Lock lumen 1321 configured to surround contracting member 226. Lock 1320 is shaped so as to define a longitudinal slit which extends from a proximal surface of lock 1320 toward a distal surface of lock 1320. For some applications, the slit defines lock lumen 1321 of lock 1320. The slit enables lock 1320 to squeeze into the smaller recess 1330 and thereby be compressed. When lock 1320 is compressed, the slit enables lock 1320 to close around contracting member 226 and thereby lock 1320 to contracting member 226.

For some applications, lock lumen 1321 has a dimension (e.g., a diameter) that is consistent along a length of lock lumen 1321 from the proximal surface of lock 1320 to a distal surface of lock 1320.

Reference is now made to FIGS. 15A-C, and 17. For some applications, lock lumen 1321 of lock 1320 is shaped so as to define a distal portion that is wider than a proximal portion of lock lumen 1321. For such applications, the proximal-most section of recess 1330 can be narrower than any other portion of recess 1330 distal to the proximal-most portion.

Reference is now made to FIGS. 12A-C, 13A-C, 15A-C, and 17. For some applications, the slit of lock 1320 is wider at the distal end portion of lock 1320 and narrower at the proximal end portion of lock 1320.

Reference is now made to FIGS. 14 and 17. For some applications, the slit of lock 1320 is uniform along the length of the slit. For some applications, lock lumen 1321 is uniform along the length of lock 1320.

Reference is now made to FIGS. 16-17. Systems 1200 and 1300 provide a locking assembly which allows for the operating physician to readjust the perimeter of the annuloplasty structure post-locking. For example, if the physician would like to readjust once locks 1220 and 1320 are in place, the physician is able to unscrew locks 1220 and 1230 respectively in order to readjust the perimeter of the annuloplasty structure by giving slack to or tightening contracting member 226 without disengaging locks 1220 and 1300 from the respective recess 1230 and 1330. Subsequently to the readjusting of contracting member 226, locks 1220 and 1320 are repositioned within the respective recess 1230 and 1330.

Figure 18:
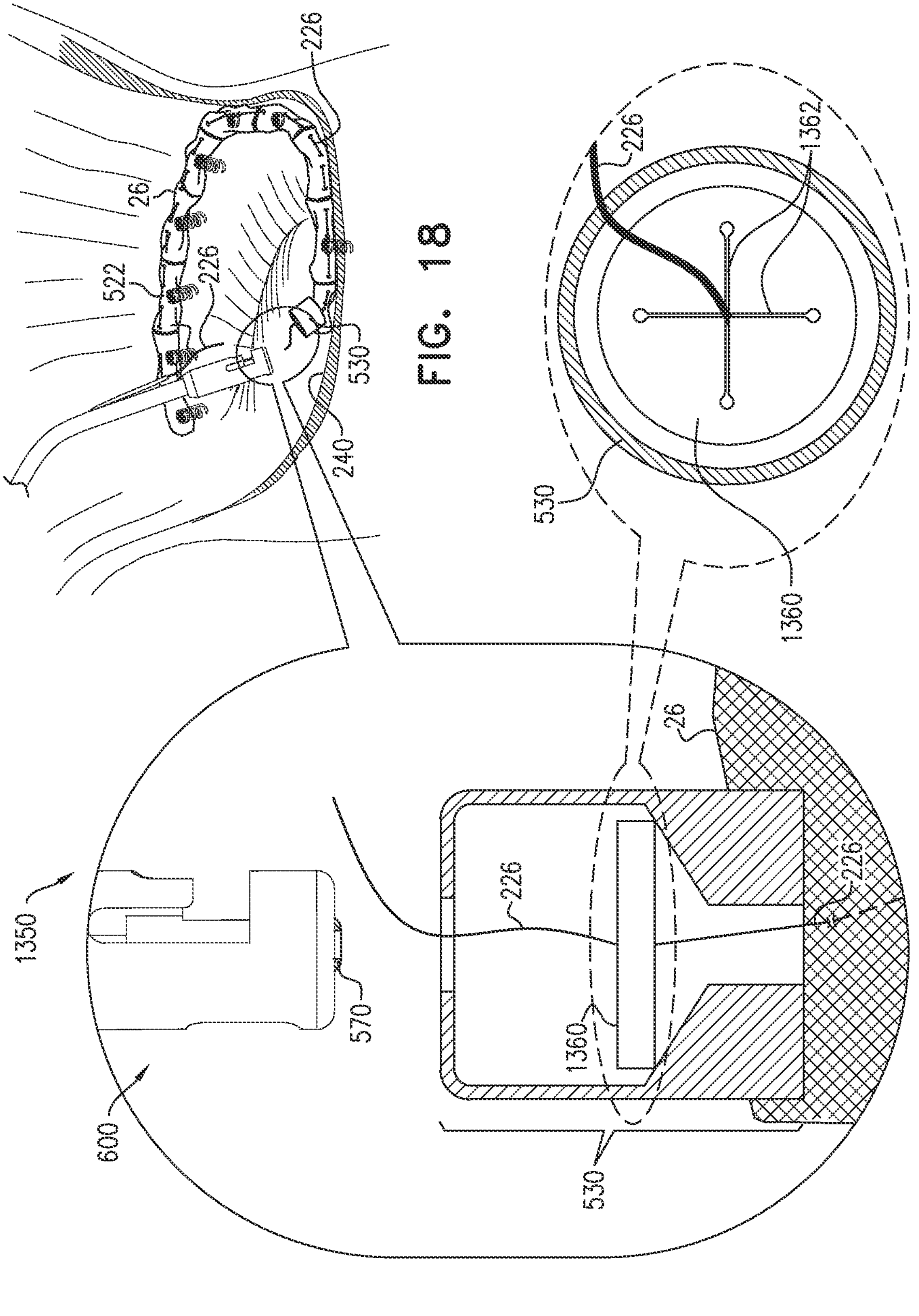
FIG. 18 is a schematic illustration of an example of a system for contracting the annulus of the patient using an annuloplasty structure comprising a housing which houses a contracting-member-fastener.

Reference is now made to FIG. 18, which is a schematic illustration of an example of a system 1350 for contracting annulus 240 of the patient using an annuloplasty structure 522 (e.g., an annuloplasty ring structure, a closed annuloplasty structure, a closed annuloplasty ring structure, an open annuloplasty structure, a partial annuloplasty ring structure, etc.), which can comprise a housing 530. Housing 530 can house a contracting-member-fastener 1360. Except for the differences described hereinbelow, annuloplasty structure 522 can be the same as or generally similar to annuloplasty structure 222, described hereinabove with reference to FIGS. 1-7E and like reference numerals refer to like parts.

Annuloplasty structure or annuloplasty ring structure 522 can comprise sleeve 26 which can define a primary body portion of structure 522. Structure 522 comprises contracting member 226 having a first portion extending along a longitudinal length of the primary body portion of annuloplasty structure 522. Contracting member 226 also defines a second portion extending away from the primary body portion of annuloplasty structure 522.

Contracting member 226 can extend through housing 530 and through a stop 570 (e.g., a holder) that is disposed within an opening of contracting-member-fastener 1360. Stop 570 is shown as being cylindrical by way of illustration and not limitation. The outer surface of stop 570 maintains fastener 1360 in the open state. Stop 570 is shaped so as to define a threaded portion which enables coupling thereto of contracting-member-uptake tool 600, as is described hereinabove.

Annuloplasty structure or annuloplasty ring structure 522 is implanted as described hereinabove with reference to FIGS. 3A-I using the system described hereinabove with reference to FIGS. 1-3I.

Housing 530 can be coupled to sleeve 26 of structure 522 at any suitable location along structure 522. For example, housing 530 can be coupled to sleeve 26 of structure 522 at a portion of structure 522 in a vicinity of a left fibrous trigone of the valve, as shown. For some applications, housing 530 can be coupled to sleeve 26 of structure 522 at a portion of structure 522 in a vicinity of a right fibrous trigone of the valve. For some applications, housing 530 can be coupled to sleeve 26 of structure 522 at a middle portion of structure 522. As shown, housing 530 can be coupled to a lateral surface of sleeve 26. In such applications, housing 530 does not block them lumen of sleeve 26 of structure 522.

Fastener 1360 is generally similar to fastener 360 of FIGS. 8A-D, with the exception that fastener 1360 is shaped so as to define intersecting slits 1362 which form the opening of fastener 1360 through which contracting member 226 passes into a generally "X" or generally "+" (plus) shape.

FIG. 18 shows contracting member 226 being severed proximal to fastener 1360 and excess portions of contracting member 226 being removed from the body of the patient using tool 600. Severing of contracting member 226 can be performed in a manner as described hereinabove with reference to FIGS. 7A-E, mutatis mutandis.

Figure 19A:
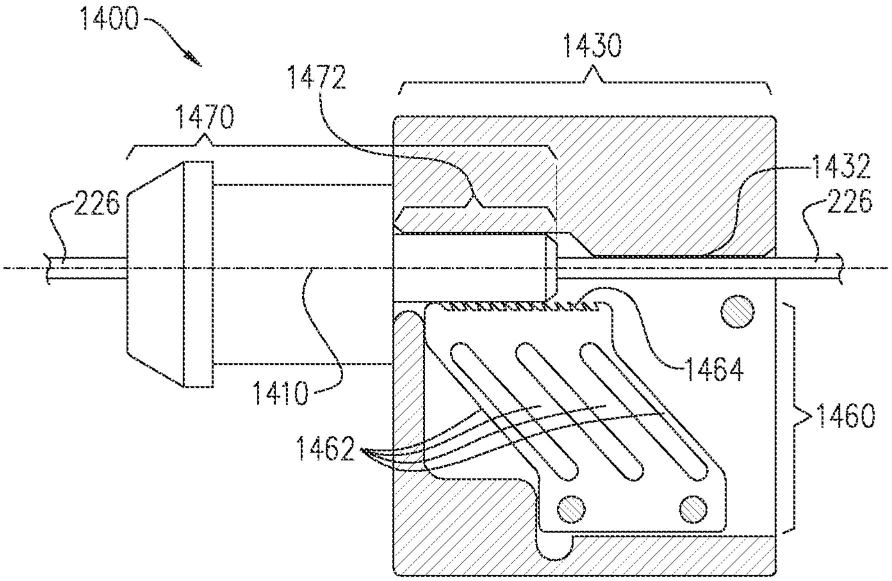
FIGS. 19A-B are schematic illustrations of an example of a system for contracting the annulus of the patient using an annuloplasty structure comprising a housing which houses a contracting-member-fastener.
Figure 19B:
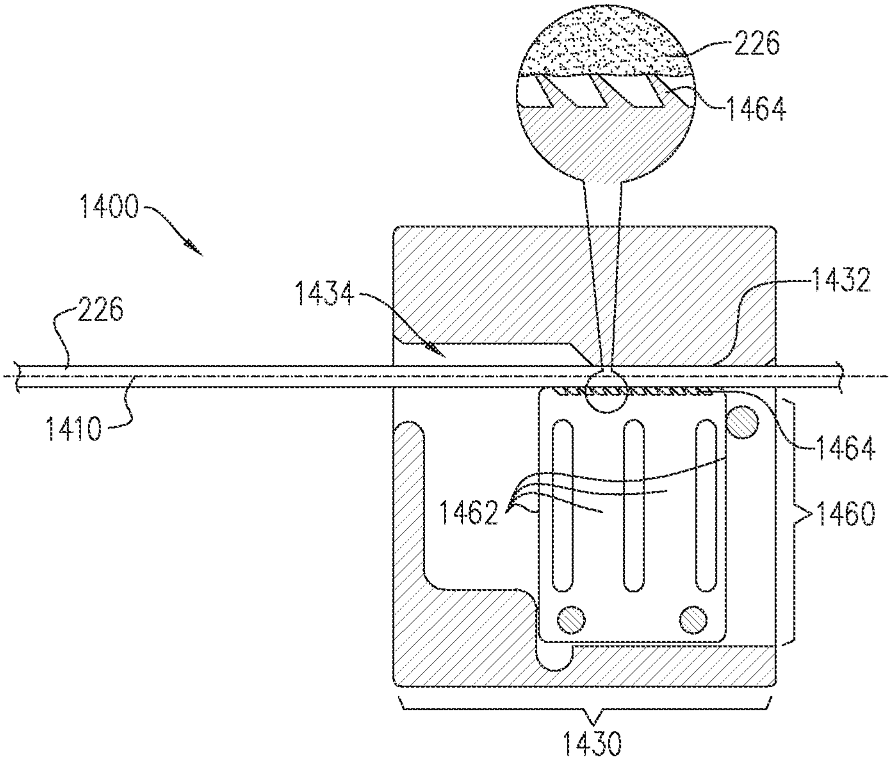

Reference is now made to FIGS. 19A-B, which are schematic illustrations of an example of a system 1400 for contracting the annulus of the patient using an annuloplasty structure (e.g., an annuloplasty ring structure, a closed annuloplasty structure, a closed annuloplasty ring structure, an open annuloplasty structure, a partial annuloplasty ring structure, etc.), which can be coupled to a housing 1430. Housing 1430 can house a contracting-member-fastener 1460. For some applications, the annuloplasty structure can be the same as or generally similar to annuloplasty structure 222, described hereinabove with reference to FIGS. 1-7E and like reference numerals refer to like parts. For some applications, the annuloplasty structure comprises housing 1430. For some applications, housing 1430 is discrete from the annuloplasty structure and deliverable and couplable to the annuloplasty structure only once the annuloplasty structure has been anchored to the annulus.

Housing 1430 can be coupled to the sleeve 26 of the annuloplasty structure at any suitable location along the annuloplasty structure. For example, housing 1430 can be coupled to the sleeve 26 of the annuloplasty structure at a portion of the annuloplasty structure in a vicinity of a left fibrous trigone of the valve, as shown. For some applications, housing 1430 can be coupled to the sleeve of the annuloplasty structure at a portion of the annuloplasty structure in a vicinity of a right fibrous trigone of the valve. For some applications, housing 1430 can be coupled to the sleeve of the annuloplasty structure at a middle portion of the annuloplasty structure. As shown, housing 1430 can be coupled to a lateral surface of the sleeve. In such applications, housing 1430 does not block them lumen of the sleeve of the annuloplasty structure.

The annuloplasty structure or annuloplasty ring structure can comprise the sleeve which can define a primary body portion of the structure. The structure comprises contracting member 226 having a first portion extending along a longitudinal length of the primary body portion of annuloplasty structure. The contracting member also defines a second portion extending away from the primary body portion of the annuloplasty structure.

Fastener 1460 is shaped so as to define a generally-rectangular, planar clip comprising a super-elastic material, e.g., nitinol. Fastener 1460 comprises a deformable element shaped so as to define a plurality of slits which are surrounded by a plurality of flexible legs 1462 which enable the clip to transition between slanted (FIG. 19A) and straight (FIG. 19B) states. The contracting-wire-engaging surface of the clip is shaped to define a plurality of teeth 1464. For some applications, teeth 1464 are jagged. For some applications, the upper surface of the clip does not comprise teeth 1464 and is flat. Teeth 1464 are configured to increase friction between contracting member 226 and fastener 1460.

Fastener 1460 comprises a clamping structure that is (a) biased toward assuming a closed state (FIG. 19B). In the closed state, the clamping structure is configured to clamp onto contracting member 226 passed therethrough, and (b) can be flexed to an open state (FIG. 19A) through which contracting member 226 can move.

Contracting member 226 can extend through a channel 1434 of housing 1430 and through a stop 1470 (e.g., a holder) that is disposed within an opening of contracting-member-fastener 1460. Channel 1434 extends along a longitudinal axis 1410 of housing 1430. Stop 1470 can be shaped so as to define a lumen therethrough for surrounding contracting member 226 and is shown as being shaped to as to define a larger cylindrical section that is engageable by a tool, and a narrower cylindrical engager 1472. Engager 1472 can be shaped so as to fit snugly within channel 1434 such that it pushes against the contracting-wire-engaging surface of the clip and maintains fastener 1460 in a slanted state, i.e., an unlocked state of fastener 1460. In the slanted state as shown in FIG. 19A, the clip is deformed and does not push against contracting member 226. In the slanted state, contracting member 226 is free to move with respect to fastener 1460, housing 1430, and stop 1470. Contracting member 226 is pulled until it sufficiently contracts the annuloplasty structure.

In FIG. 19B, stop 1470 has been decoupled and removed from housing 1430. In the absence of force applied to the contracting-wire-engaging surface of the clip by engager 1472, the clip returns to its resting, straight state and traps contracting member 226 between the contracting-wire-engaging surface of the clip and a surface 1432 of housing 1430, e.g., an inner wall. As such, fastener 1460 is now in a locked state in which the clip locks and crimps contracting member 226.

Reference is now made to FIGS. 20A-F, which are schematic illustrations of an example of a portion of a multi-component tubular system 1500 comprising a contracting-member-severing tool 1502 and a contracting-member-uptake tool 1600, described hereinbelow with reference to FIGS. 21A-26B. Contracting member 226 is threaded through and passes through contracting-member severing tool 1502 and through contracting-member-uptake tool 1600. Contracting member 226 can be ensnared by tool 1502 using a snare as described herein above with regard to snare 350 with reference to FIGS. 4A-5D. Tool 1502 can be advanced along contracting member 226 toward an annuloplasty structure 1522 (e.g., an annuloplasty ring structure, a closed annuloplasty structure, a closed annuloplasty ring structure, an open annuloplasty structure, a partial annuloplasty ring structure, etc.). For some applications, tool 1502 is advanced toward a housing 1530 that is already coupled to structure 1522, in a manner similar to tool 300 advancing along contracting member 226, as described hereinabove with reference to FIGS. 4A-5D. Annuloplasty structure 1522 can comprise a flexible primary body portion. Contracting member 226 has a first portion extending along a longitudinal length of the primary body portion. A second portion of contracting member 226 can extend away from the primary body portion of annuloplasty structure 1522 and outside the body of the patient.

System 1500 is used to contract the annulus of the patient using annuloplasty structure 1522 (e.g., an annuloplasty ring structure, a closed annuloplasty structure, a closed annuloplasty ring structure, an open annuloplasty structure, a partial annuloplasty ring structure, etc.), which can comprise a housing 1530. Housing 1530 can house a contracting-member-fastener 1560. Except for the differences described hereinbelow, annuloplasty structure 1522 can be the same as or generally similar to annuloplasty structure 222, described hereinabove with reference to FIGS. 1-7E and like reference numerals refer to like parts.

It is to be noted that fastener 1560 can comprise fasteners 360 described hereinabove with reference to FIGS. 4A-B, 7A-E, 8A-D, 9A-D, 10A-B, and 11A-C, lock 950 described hereinabove with reference to FIGS. 12A-C, lock 1950 described hereinabove with reference to FIGS. 12A-C, lock 1110 described hereinabove with reference to FIG. 14, lock 1490 described hereinabove with reference to FIGS. 15A-C, lock 1220 described hereinabove with reference to FIG. 16, lock 1320 described hereinabove with reference to FIG. 17, or any other fastener, lock, and/or crimp known in the art.

Annuloplasty structure or annuloplasty ring structure 1522 can comprise sleeve 26 which can define a primary body portion of structure 1522. Structure 1522 comprises contracting member 226 having a first portion extending along a longitudinal length of the primary body portion of annuloplasty structure 1522. Contracting member 226 also defines a second portion extending away from the primary body portion of annuloplasty structure 1522.

Contracting member 226 can extend through housing 1530 and through a stop 1570 (e.g., a holder) that is disposed within an opening of contracting-member-fastener 1560. Stop 1570 is shaped so as to define a lumen therethrough for surrounding contracting member 226 and is shown as being shaped to as to define a larger cylindrical section that is engageable by a tool, and a narrower cylindrical engager 1574. The outer surface of engager 1574 maintains fastener 1560 in the open state, as shown in FIGS. 20A-D. Stop 1570 is shaped so as to define an overhang 1572, which enables coupling thereto of contracting-member-severing tool 1502, as is described hereinbelow.

Annuloplasty structure or annuloplasty ring structure 1522 is implanted as described hereinabove with reference to FIGS. 3A-I using the system described hereinabove with reference to FIGS. 1-3I.

Housing 1530 can be coupled to sleeve 26 of structure 1522 at any suitable location along structure 1522. For example, housing 1530 can be coupled to sleeve 26 of structure 1522 at a portion of structure 1522 in a vicinity of a left fibrous trigone of the valve, as shown. For some applications, housing 1530 can be coupled to sleeve 26 of structure 1522 at a portion of structure 1522 in a vicinity of a right fibrous trigone of the valve. For some applications, housing 1530 can be coupled to sleeve 26 of structure 1522 at a middle portion of structure 1522. As shown, housing 1530 can be coupled to a lateral surface of sleeve 26. In such applications, housing 1530 does not block them lumen of sleeve 26 of structure 1522.

Figure 20A:
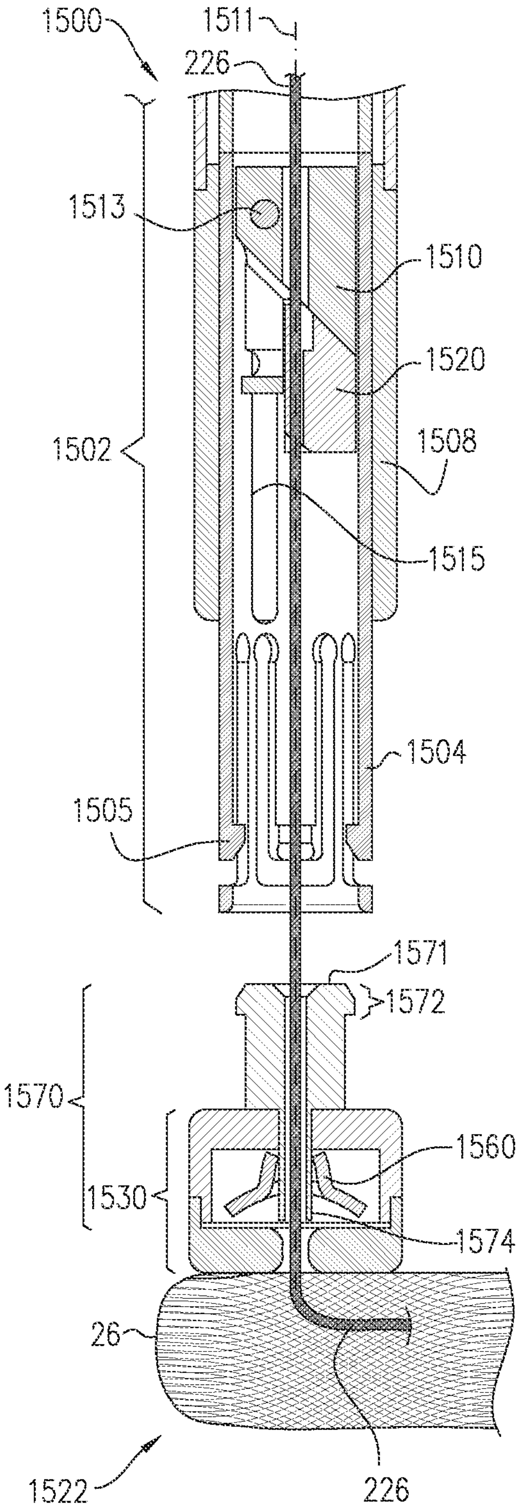
FIGS. 20A-F are schematic illustrations of an example of a contracting-member-uptake and contracting-member severing tool for use with an annuloplasty structure comprising a housing which houses a contracting-member-fastener.

FIG. 20A shows contracting-member-severing tool 1502 through which contracting member 226 has been threaded. Contracting member 226 can be ensnared by tool 1502 using a snare as described herein above with regard to snare 350 with reference to FIGS. 4A-5D. Tool 1502 can be advanced along contracting member 226 toward housing 1530 of structure 1522, in a manner similar to tool 300 advancing along contracting member 226, as described hereinabove with reference to FIGS. 4A-5D.

Once tool 1502 is threaded along contracting member 226, contracting member 226 extends from sleeve 26, through engager 1574, through the proximal portion of stop 1570, through cutting elements 1510 and 1520 of tool 1502, and through the remaining proximal portion of tool 1502. As such, contracting member 226 is disposed in a vicinity of the cutting elements. Contracting member 226 is disposed along a longitudinal axis 1511 of tool 1502 along the entire length of tool 1502. The relative spatial orientation of the components of tool 1502 enable contracting member 226 to pass straightly and directly though the lumen of tool 1502 and along axis 1511 without taking a winding path through tool 1502. This direct and unwinding path of member 226 through tool 1502 reduces friction of member 226 as it moves within tool 1502. This direct path for contracting member 226 is enabled due to the orientation of components of tool 1502, as opposed to the winding path member 226 through tools 300, 600, 810, and 920 described hereinabove. The reduces friction on contracting member 226 reduces noise during the measurement of tension of the contracting member 226, as described hereinbelow with reference to FIGS. 21A-26B.

Figure 20B:
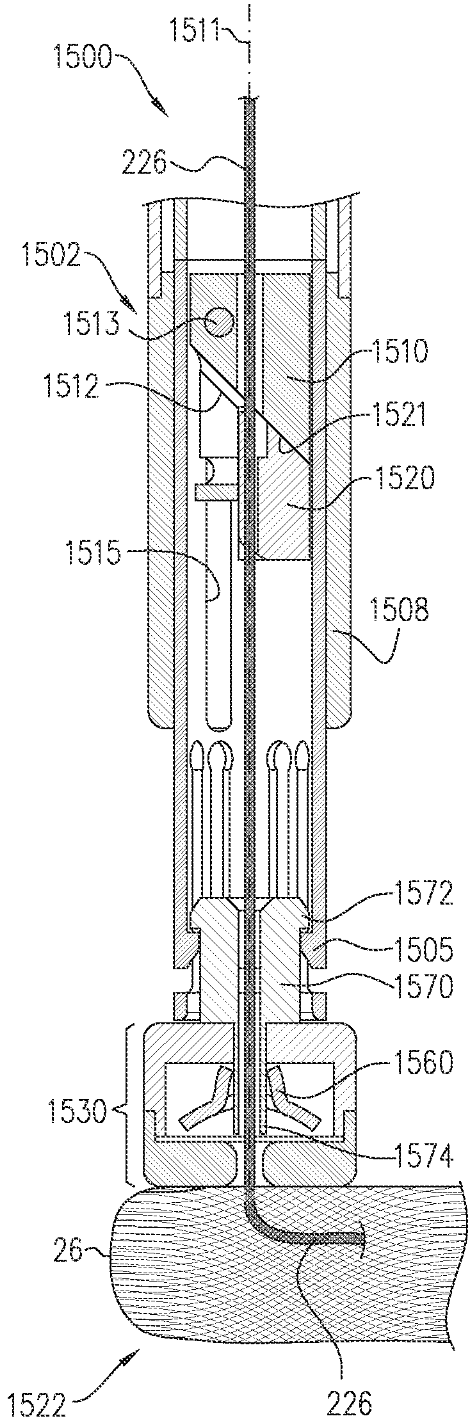

Tool 1502 comprises an inner tube 1504 that is slidable with respect to an outer sleeve portion 1508. The distal end of inner tube 1504 is shaped so as to define graspers 1505, or fastener-ejectors. Since the distal end portion of tube 1504 is slotted, and since graspers 1505 are sloped, graspers 1505 have a tendency to be pushed radially outwardly in the presence of a force applied thereto by overhang 1572. Once tube 1504 is pushed sufficiently distally, graspers 1505 pass distally around overhang 1572 and close around stop 1570 at a site distal to overhang 1572, as shown in FIG. 20B. Graspers 1505 provide the primary and initial coupling and locking of tool 1502 to housing 1530 by gripping overhang 1572.

Tool 1502 comprises a static cutting element 1510 and a moveable, dynamic cutting element 1520. Static cutting element 1510 is shaped so as to define a concave cutting surface 1512 (i.e., a sharp edge), and dynamic cutting element 1520 is shaped so as to define a concave cutting surface 1521 (i.e., a sharp edge) which opposes concave cutting surface 1512 of static cutting element 1510. As is described hereinbelow, dynamic cutting element 1520 slides proximally and diagonally with respect to static cutting element 1510, along concave cutting surface 1512 of static cutting element 1510.

Figures 20C, 20D:
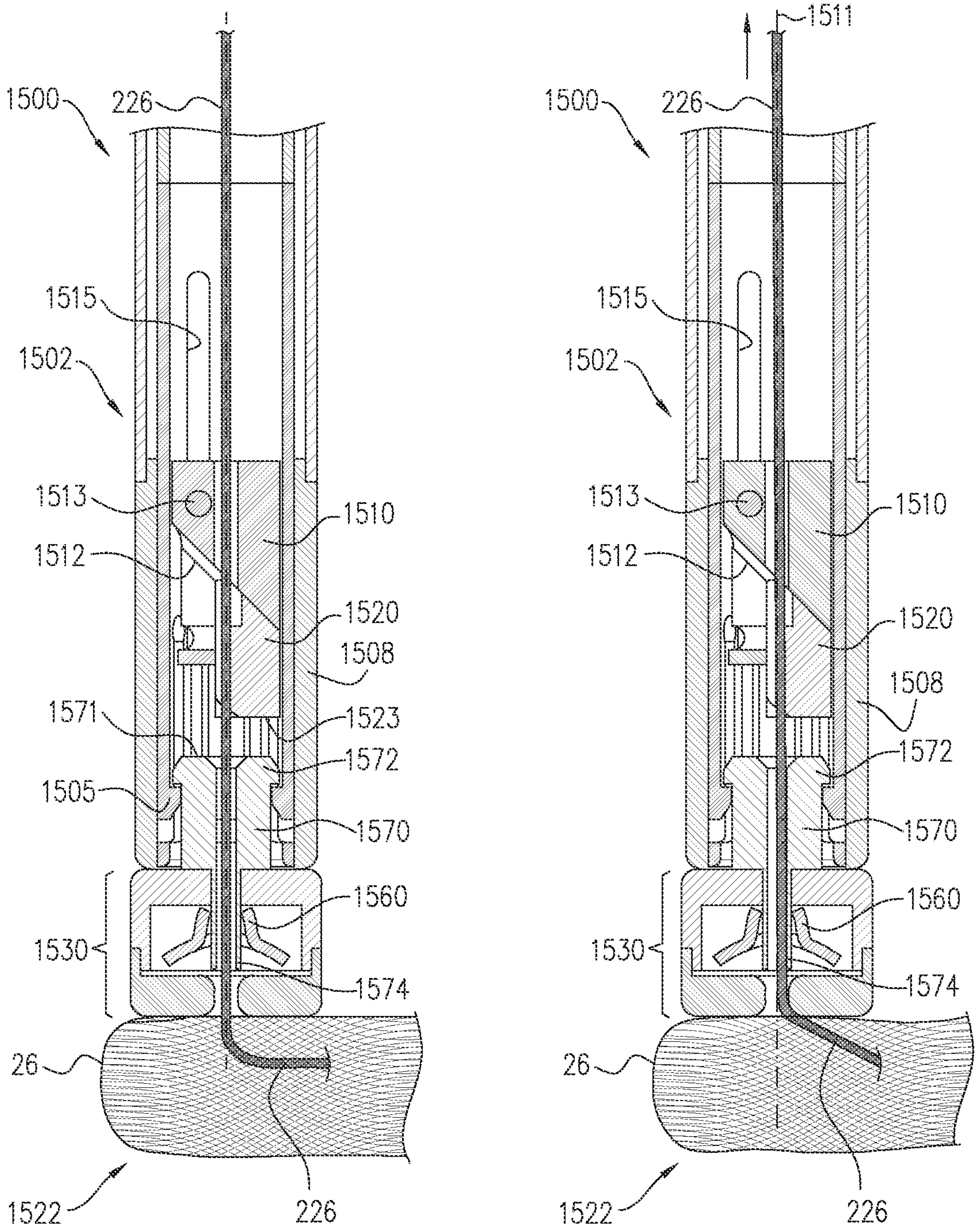

Once stop 1570 is engaged by inner tube 1504, outer sleeve portion 1508 is moved distally along inner tube 1504 and toward housing 1530 until a distal end of outer sleeve portion 1508 contacts a proximal end of housing 1530, as shown in FIG. 20C. Such distal movement of portion 1508 locks in place tube 1504 with respect to stop 1570 and thereby locks in place tool 1502 with respect to housing 1530. Since graspers 1505 are slanted, they are able to slide proximally around overhang 1572 in response to proximal pulling of tool 1502. Thus, surrounding the slotted distal end portion of tube 1504 and surrounding graspers 1505 of tube 1504 by outer sleeve portion 1508 prevents radial movement of graspers 1505 responsively to application of a proximal pulling force to stop 1570 by tool 1502 during the release of fastener 1560 in order to lock contracting member 226 in place and retain annuloplasty structure 1522 in a tensed state, as will be described hereinbelow. Outer sleeve portion 1508 thus locks graspers 1505 with respect to overhang 1572 and provides a secondary coupling and locking of tool 1502 to housing 1530.

Static cutting element 1510 comprises a pin 1513 which slides proximally and distally within a slit 1515 of tube 1404. As such, static cutting element 1510 is coupled to tube 1404, and to the tube surrounding tube 1404. That is, pin 1513 is coupled to outer sleeve portion 1508. As outer sleeve portion 1508 is moved distally, as shown in FIG. 20C, pin 1513 moves distally within slit 151 and static cutting element 1510 and dynamic cutting element 1520 are pushed distally within tube 1404. In this state, a distal surface 1523 of dynamic cutting element 1520 is still disposed at a distance from a proximal surface 1571 of stop 1570.

FIG. 20D shows contracting of annuloplasty structure 1522 responsively to proximal pulling of contracting member 226 by tool 1502. During the pulling of contracting member 226, tool 1502 remains coupled to housing 1530 due to graspers 1505 grasping overhang 1572 while outer sleeve portion 1508 surrounds the distal portion of inner tube 1504 and surrounds graspers 1505.

Figure 20E:
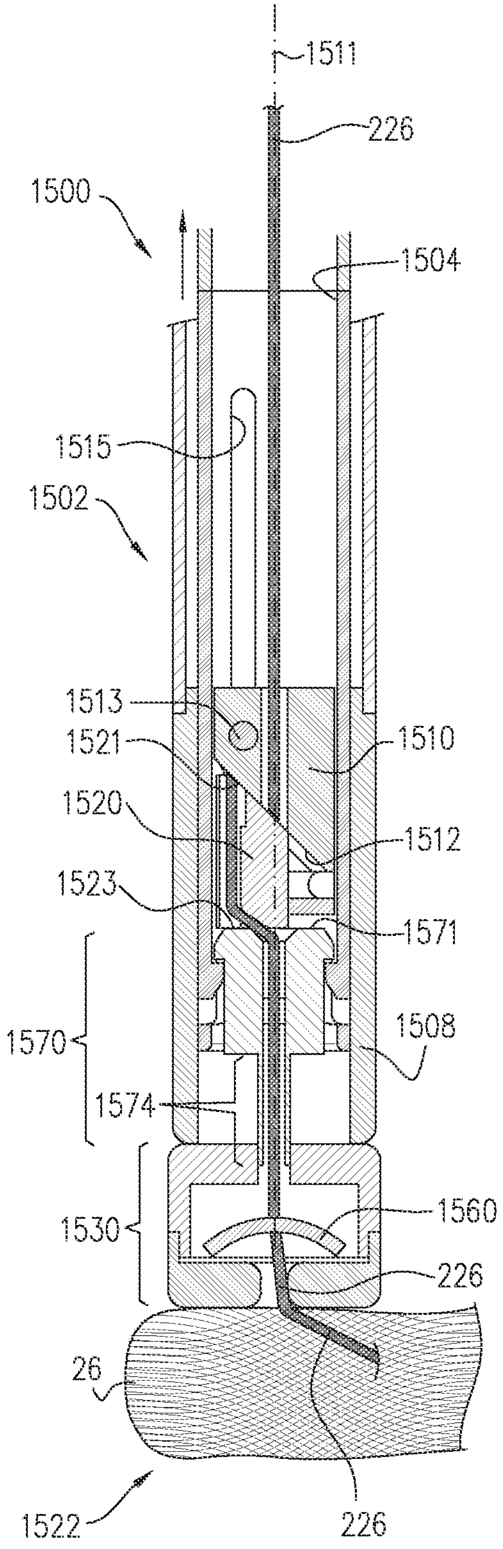

Tool 1502 can comprise a contracting-member-uptake device 322 of tool 300 as described hereinabove with reference to FIGS. 4A-B. The contracting-member-uptake device can be used to contract contracting member 226. Once contracting member 226 is contracted and structure 1522 is contracted, as shown in FIG. 20D, tool 1502 removes stop 1570 by pulling stop 1570 proximally away from fastener 1560, as is described in FIG. 20E. While maintaining distal force to outer sleeve portion 1508, tube 1404 is pulled proximally with respect to portion 1508. Pulling of tube 1504 proximally pulls on stop 1570 since graspers 1505 maintain grasp on overhang 1572 of stop 1570 due to the presence of outer sleeve portion 1508. During the pulling of tube 1504 proximally, outer sleeve portion 1508 prevents radial outward movement of graspers 1505 as proximal force is being applied to tube 1504. Tube 1504 is pulled proximally until stop 1570 is disengaged from housing 1530, i.e., until engager 1574 of stop 1570 is decoupled and disengaged from fastener 1560, as shown in FIG. 20E. Since fastener 1560 tends to close, in the absence of stop 1570, fastener 1560 closes and clamps around contracting member 226 passing through fastener 1560. In such a manner, structure 1522 is locked by fastener 1560, and the contracted state of structure 1522 is maintained.

As stop 1570 is pulled proximally, proximal surface of stop 1570 hammers into distal surface 1523 of dynamic cutting element 1520. Responsively to the pushing of stop 1570 against dynamic cutting element 1520, dynamic cutting element 1520 is pushed proximally such that dynamic cutting element 1520 moves diagonally proximally. Cutting surface 1521 of dynamic cutting element 1520 and cutting element 1520 slide diagonally proximally along cutting surface 1512 of static cutting element 1510. The portion of contracting member 226 disposed between cutting surfaces 1512 and 1521 is severed. Since cutting surfaces 1512 and 1521 are concave and face each other, surfaces 1512 and 1521 compress contracting member 226 during the cutting, and thereby, contracting member 226 is severed cleanly and without fraying.

Thus, tool 1502 is arranged such that tool 1502 advantageously provides a safety mechanism by which contracting member 226 can only be severed by proximal force applied thereto by stop 1570 after fastener 1560 has been transitioned into the fastened, or locked, state and locks in place contracting member 226. That is, tool 1502 cannot inadvertently sever contracting member 226 all the while tool 1502 is not coupled to stop 1570 and all the while stop 1570 does not push against cutting element 1520. In one swift motion, tool 1502 (1) locks in place contracting member 226 by transitioning fastener 1560 into the locked state, and (2) severs contracting member 226.

Figure 20F:
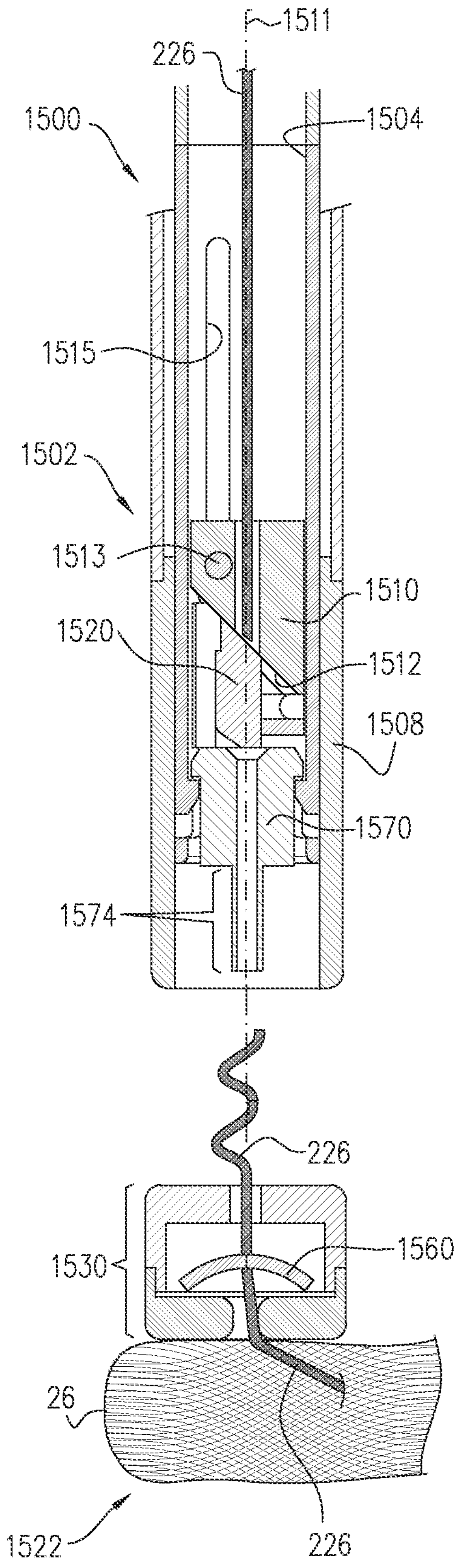

FIG. 20F shows contracting member 226 after having been severed proximal to fastener 1560, and excess portions of contracting member 226 being removed from the body of the patient using tool 1502. The entire tool 1502 is pulled proximally in order to decouple tool 1502 from housing 1530 and from structure 1522 carrying stop 1570 within the lumen of tool 1502. Since stop 1570 is no longer coupled to housing 1530, a simple proximal pull on tool 1502 is enough to decouple tool 1502 from annuloplasty structure 1522.

Reference is again made to FIGS. 20A-F. It is to be noted that although tool 1502 is described as being advanceable toward housing 1530 that is already coupled to annuloplasty structure 1522, the scope herein includes tool 1502 being coupled to housing 1530 from a site outside the body of the patient and being configured to deliver housing 1530 along contracting member 226 to sleeve 26 of structure 1522 that is already implanted at the annulus. For such applications, housing 1530 is configured to be positionable against the primary body portion of structure 1522.

Figures 21A, 21B:
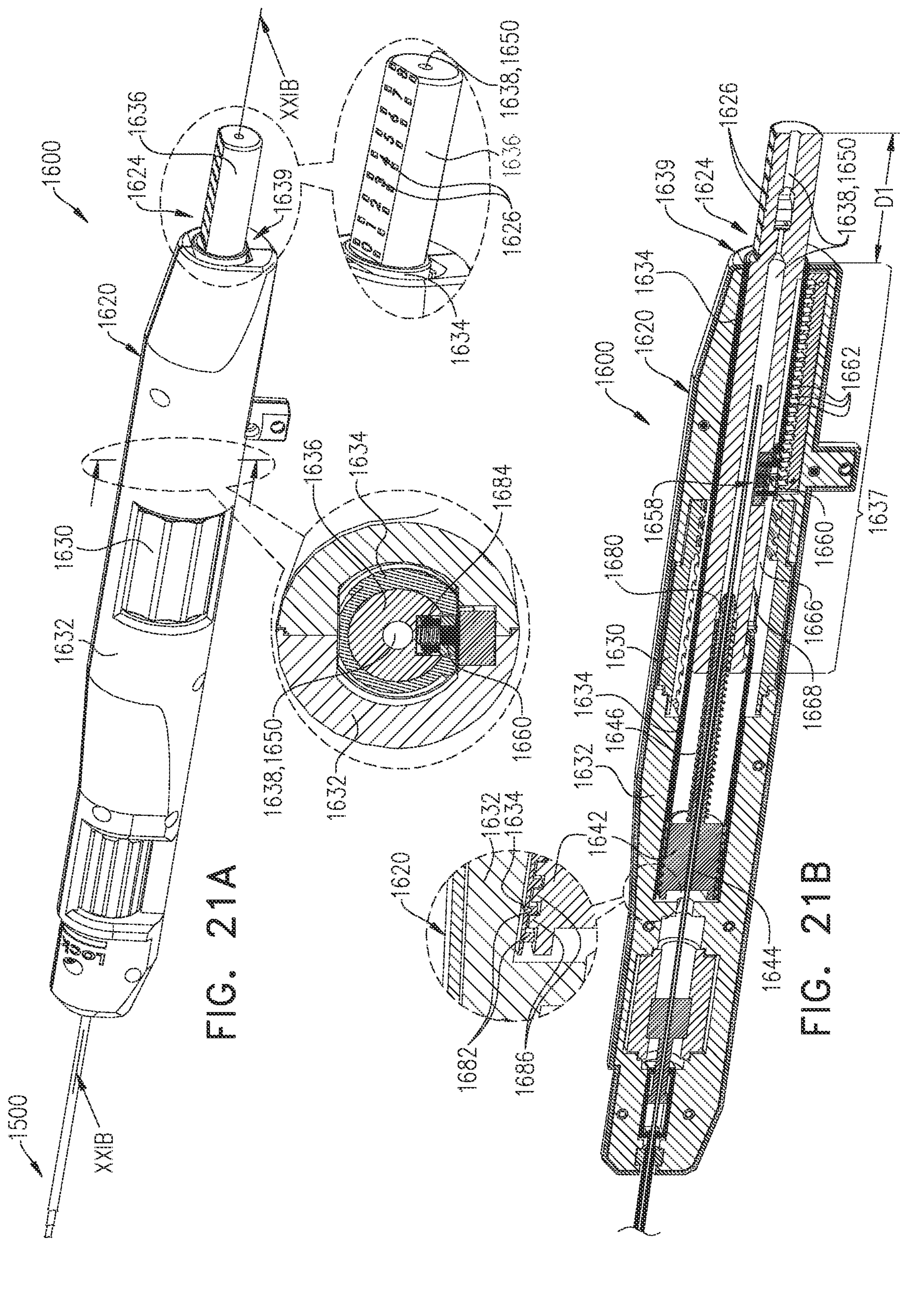
FIGS. 21A-B are schematic illustrations of an example of a contracting-member-uptake tool of the multi-component tubular system of FIGS. 20A-F, before insertion of a flexible elongated contracting member, in accordance with some applications.

Reference is now made to FIGS. 21A-26B, which are schematic illustrations of another portion of multi-component tubular system 1500, described hereinabove with reference to FIGS. 20A-F, comprising contracting-member-uptake tool 1600, which is configured to contract flexible elongated contracting member 226, in accordance with some applications. FIGS. 21A-B show contracting-member-uptake tool 1600 before insertion of flexible elongated contracting member 226, and FIGS. 22A-26B show contracting-member-uptake tool 1600 after insertion of flexible elongated contracting member 226.

Multi-component tubular system 1500 is used with an implant comprising an implantable structure and flexible elongated contracting member 226 that extends away from the implantable structure. The implant may comprise any of the implants described herein, such as implantable annuloplasty structure 222, which may, for example, comprise flexible sleeve 26. Alternatively, the implant may comprise another implant known in the art (including those described in the patents and patent application publications incorporated hereinbelow by reference), which may or may not comprise a sleeve.

Contracting-member-uptake tool 1600 comprises a handle portion 1620, which optionally may be supported by a stand, such as described hereinabove with reference to FIGS. 1-2. Handle portion 1620 can comprise one, some, or all of:

- an outer housing 1632, which can be shaped ergonomically for holding by a user (e.g., a physician, healthcare professional, etc.);
- a tubular shaft 1634, disposed at least partially within outer housing 1632;
- an inner shaft 1636, which (a) is partially disposed within a proximal longitudinal portion 1637 of tubular shaft 1634, such that inner shaft 1636 is axially slidable with respect to tubular shaft 1634, and (b) is shaped so as to define an inner-shaft contracting-member-receiving channel 1638;
- a distal force applicator 1642, which (a) is disposed at least partially within a distal longitudinal portion of tubular shaft 1634, and (b) is shaped so as to define a distal-force-applicator contracting-member-receiving channel 1644, which allows sliding of contracting member 226 therethrough;
- a spring 1646, which is disposed within tubular shaft 1634, connecting distal force applicator 1642 and a distal portion 1647 of inner shaft 1636; and
- a contraction-facilitating knob 1630, which is accessible from outside outer housing 1632.

Handle portion 1620 is shaped so as to define a handle contracting-member-receiving channel 1650 from a distal end through to a proximal end of handle portion 1620 (as used in the present application, including in the claims, "proximal" means toward the user, i.e., away from the implant; with reference to FIGS. 21A-26B, "proximal" means to the right in the drawings). Handle contracting-member-receiving channel 1650 includes inner-shaft contracting-member-receiving channel 1638, distal-force-applicator contracting-member-receiving channel 1644, and optionally additional contracting-member-receiving channels of handle portion 1620. A portion of contracting member 226 is threaded through handle contracting-member-receiving channel 1650 either after or before the implantable structure and contracting member 226 are advanced toward the heart of the patient.

Inner shaft 1636 can comprise a lock 1640, which is configured (i) when in an unlocked state, to allow sliding of contracting member 226 with respect to inner-shaft contracting-member-receiving channel 1638, and (ii) when in a locked state, to axially lock contracting member 226 with respect to inner shaft 1636. Optionally, lock 1640 applies friction to axially lock contracting member 226 with respect to inner shaft 1636, such as using a set screw or a lever, as is known in the art.

Figures 22A, 22B:
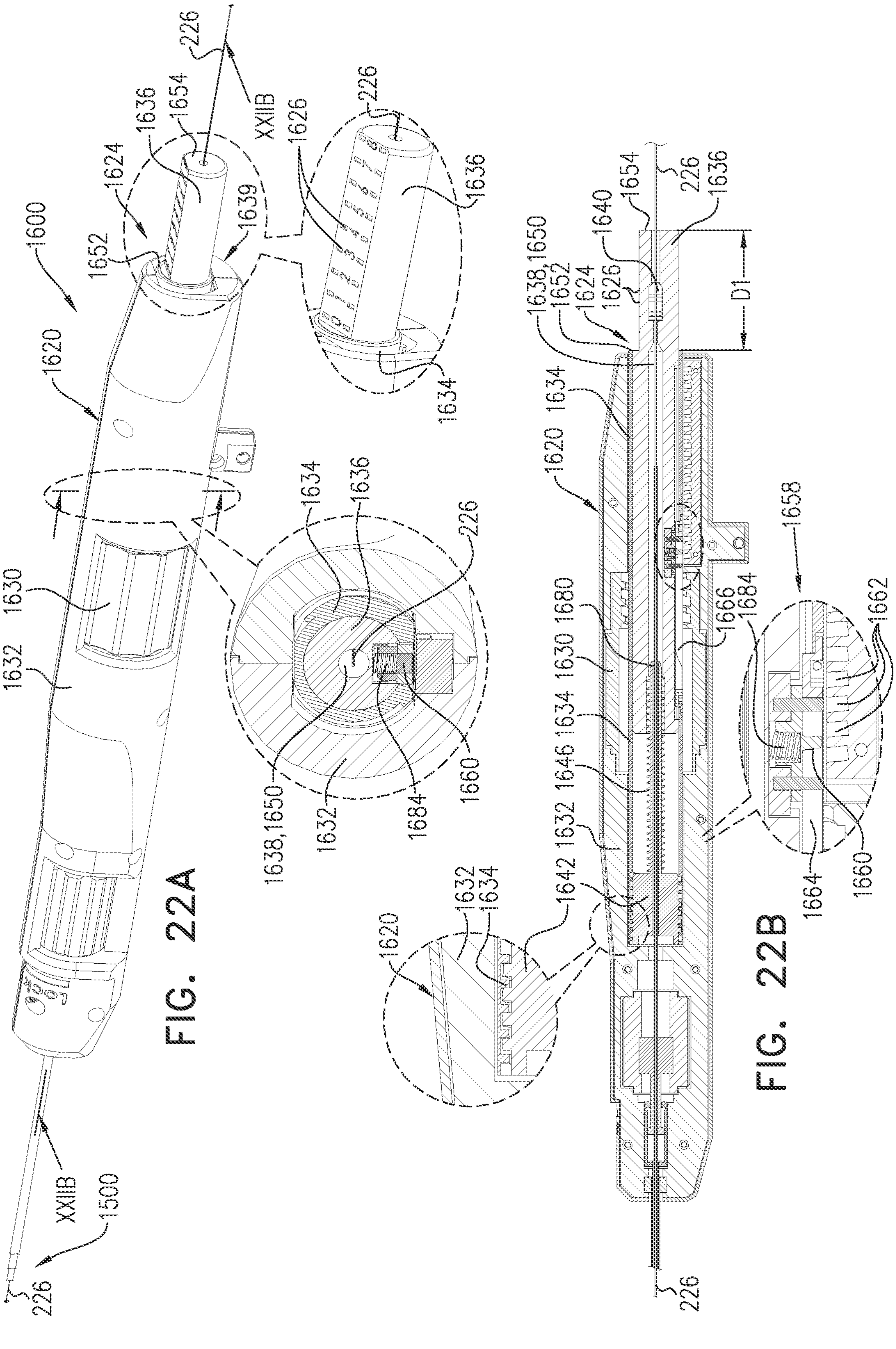
FIGS. 22A-B are schematic illustrations of the contracting-member-uptake tool of FIGS. 21A-B after insertion of the flexible elongated contracting member, in accordance with some applications.
Figure 23A:
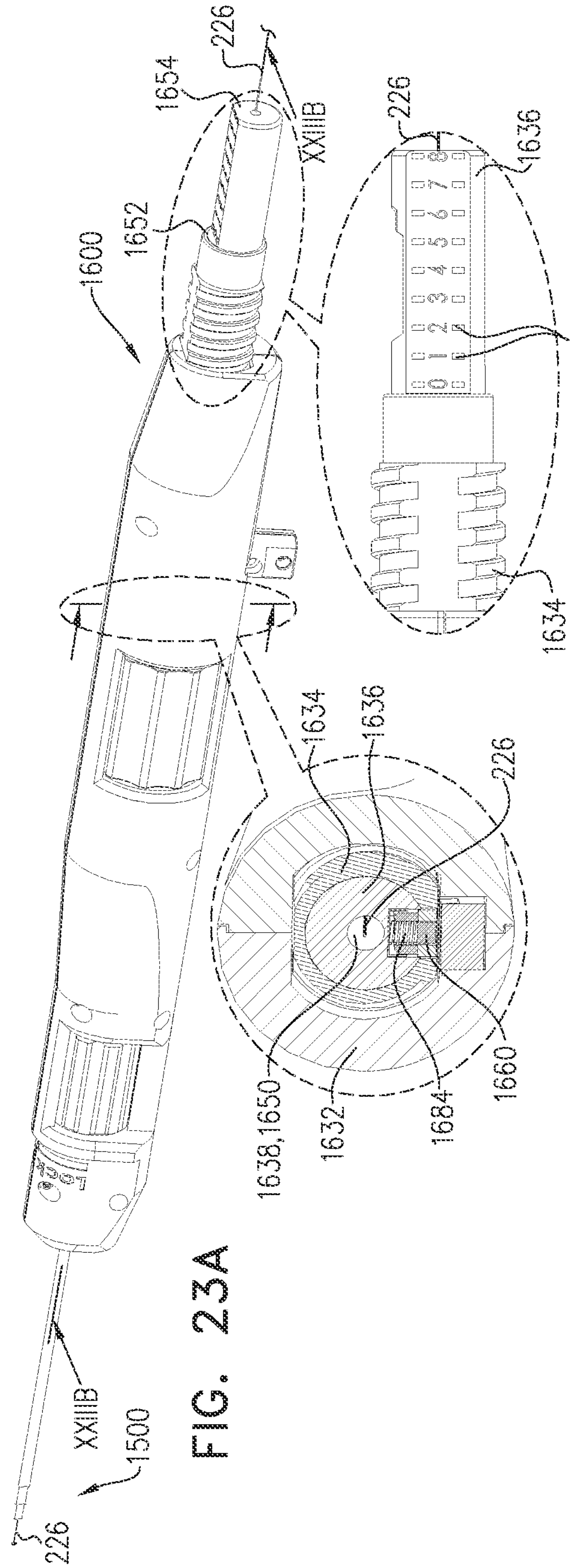
FIGS. 23A-B, 24A-B, and 25A-B are schematic illustrations of the contracting-member-uptake tool of FIGS. 21A-B after successive levels of actuation of a contraction-facilitating knob of the tool, in accordance with some applications.
Figure 23B:
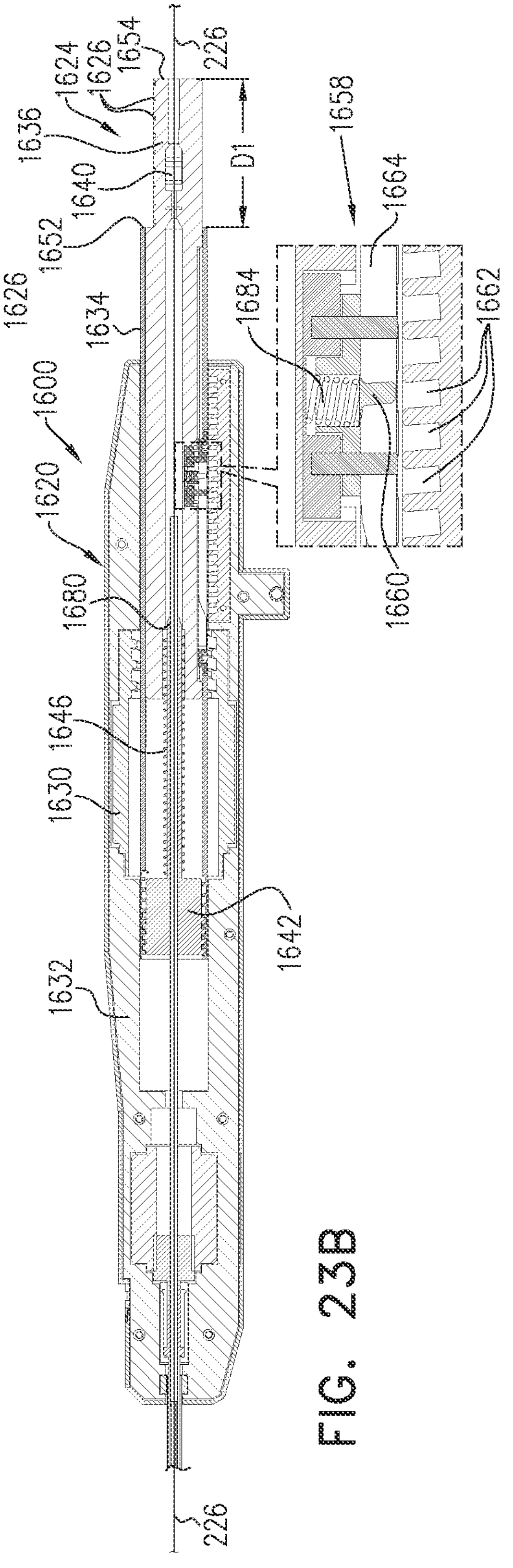

Handle portion 1620 is configured such that actuation of contraction-facilitating knob 1630, when contracting member 226 is disposed passing entirely through handle contracting-member-receiving channel 1650 and lock 1640 is in the locked state, causes handle portion 1620 to uptake successive portions of contracting member 226. FIGS. 22A-B show handle portion 1620 before actuation of contraction-facilitating knob 1630, when contracting member 226 is disposed passing entirely through handle contracting-member-receiving channel 1650 and lock 1640 is in the locked state. FIGS. 23A-B, 24A-B, and 25A-B show handle portion 1620 after successive levels of actuation of contraction-facilitating knob 1630, as described below.

As shown in FIGS. 21A-B and 22A-B, before initial actuation of contraction-facilitating knob 1630, the portion of contracting member 226 between handle portion 1620 and the implant may be somewhat slack or at most minimally tensed. A proximal end 1652 of tubular shaft 1634 and a proximal end 1654 of inner shaft 1636 are disposed at an initial offset distance D1 therebetween, indicative of essentially no tension in contracting member 226, i.e., that contracting member 226 is not tensed. For applications in which the implant comprises implantable annuloplasty structure 222, which comprises flexible sleeve 26, sleeve 26 (coupled to annulus 240) is in a relaxed, non-tense state. At this point, the tool has been sufficiently advanced through vasculature of the patient such that the distal tip of the tool is in proximity to structure 222 disposed along the annulus.

As shown, for example, in the transition between FIGS. 22A-B and FIGS. 23A-B, the actuation of contraction-facilitating knob 1630 can cause handle portion 1620 to uptake successive portions of contracting member 226 by:

- advancing tubular shaft 1634 proximally with respect to outer housing 1632, which advances distal force applicator 1642 proximally with respect to outer housing 1632 (distal force applicator 1642 can be axially fixed to tubular shaft 1634 during ordinary use of handle portion 1620),
- which applies a proximally-directed force to spring 1646,
- which pushes inner shaft 1636 proximally with respect to outer housing 1632 (by spring 1646 applying a proximally-directed force to inner shaft 1636,
- which proximally pulls contracting member 226 (which is axially locked to inner shaft 1636 by lock 1640, as described above).

Sometimes, during the initial proximal movement of distal force applicator 1642 with respect to outer housing 1632 illustrated in the transition between FIGS. 22A-B and 23A-B, contracting member 226 is relatively slack, as mentioned above, such that inner shaft 1636 offers no or relatively little resistance to the proximally-directed force applied to inner shaft 1636 by spring 1646, and spring 1646 is not, or is only minimally, axially compressed. As a result, inner shaft 1636 advances proximally with respect to the outer housing 1632 to the same, or approximately the same, extent as the tubular shaft 1634 advances proximally with respect to the outer housing 1632, and the offset distance remains at its initial value (D1), indicating that there is still essentially no tension in contracting member 226. This initial proximal advancement of tubular shaft 1634 and inner shaft 1636 with respect to outer housing 1632 serves to accommodate differing initial levels of slack in contracting member 226.

At a certain distance of proximal advancement of distal force applicator 1642 with respect to outer housing 1632, contracting member 226 becomes tensed (at an initial low level of tension), such that inner shaft 1636 gradually offers increasing resistance to the proximally-directed force applied to inner shaft 1636 by spring 1646, and spring 1646 becomes gradually more compressed. As used in the present application, including in the claims, contracting member 226 is considered to be "tensed" even when tensed at a low level of tension.

Figure 24A:
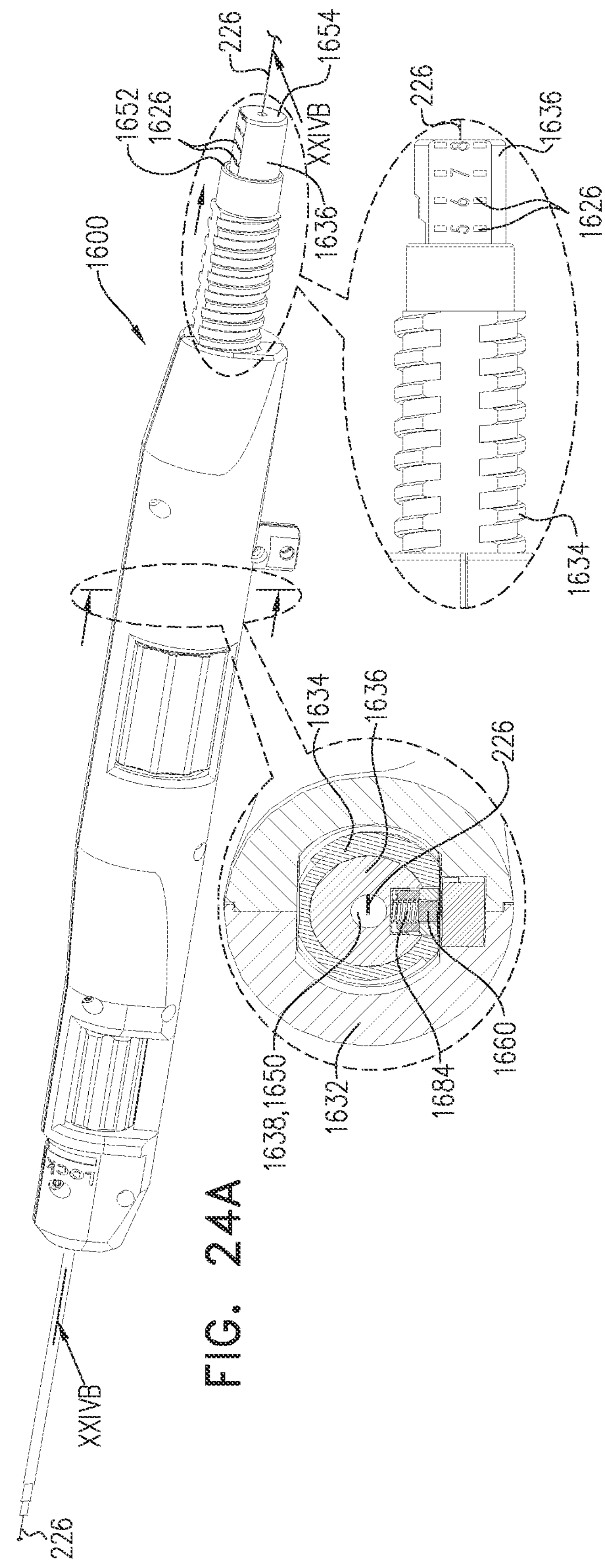
Figure 24B:
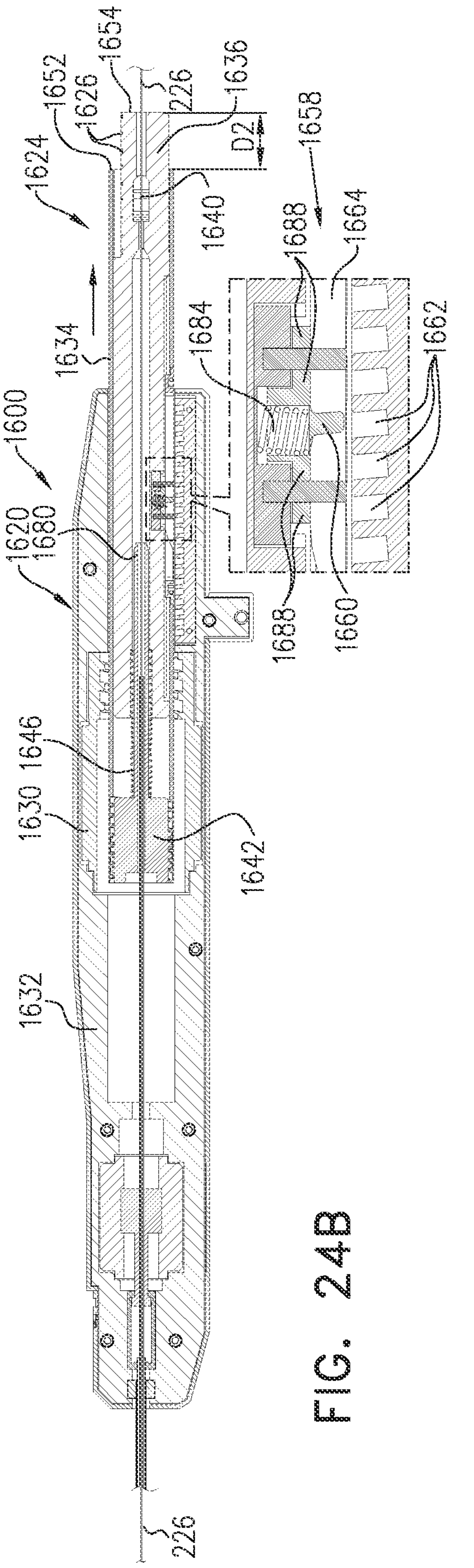

As shown in the transition between FIGS. 23A-B and 24A-B, as spring 1646 becomes more compressed, distal force applicator 1642 moves axially closer to inner shaft 1636, such that tubular shaft 1634 moves proximally with respect to inner shaft 1636. As a result, spring 1646 pushes inner shaft 1636 proximally with respect to outer housing 1632 to a lesser extent than tubular shaft 1634 proximally advances with respect to outer housing 1632, and proximal pulling of the contracting member 226 by the inner shaft 1636 increases tension in the contracting member 226. Therefore, the offset distance between proximal end 1652 of tubular shaft 1634 and proximal end 1654 of inner shaft 1636 decreases to a tensed offset distance D2, as shown in FIGS. 24A-B. (In actual use of the handle, many tensed offset distances D2 occur; a single offset is shown for the sake of illustration.) The tensed offset distance D2 is less than the initial offset distance D1, reflecting the fact that the portion of inner shaft 1636 that protrudes from proximal end 1652 of tubular shaft 1634 has decreased.

Contraction-facilitating knob 1630 can have any shape that enables actuation thereof, and is not necessarily round, tubular, or generally cylindrical. For example, for some applications, contraction-facilitating knob 1630 is configured to be actuated by rotation thereof, e.g., about a central longitudinal axis of tubular shaft 1634, such as shown in the drawings. Optionally, for some applications, contraction-facilitating knob 1630 is configured to be actuated by axially sliding thereof with respect to outer housing 1632 (configuration not shown). Contraction-facilitating knob 1630 can be non-electrical, i.e., entirely mechanical, or may optionally comprise electrical components, including, for example, circuitry.

For some applications, tubular shaft 1634 and contraction-facilitating knob 1630 are in threaded connection with each other, and handle portion 1620 is configured such that actuation of contraction-facilitating knob 1630 rotates tubular shaft 1634, thereby advancing tubular shaft 1634 proximally with respect to outer housing 1632. For some of these applications, contraction-facilitating knob 1630 is configured to be actuated by rotation thereof, e.g., about the central longitudinal axis of tubular shaft 1634, such as shown in the drawings.

For some applications, handle portion 1620 further comprises an inner stabilization tube 1680, which (a) extends proximally from and is axially fixed to distal force applicator 1642 and (b) defines therethrough a portion of handle contracting-member-receiving channel 1650. A portion of inner stabilization tube 1680 is disposed within inner-shaft contracting-member-receiving channel 1638; the length of the portion varies with the distance between distal force applicator 1642 and inner shaft 1636. Spring 1646 can be configured to surround a portion of inner stabilization tube 1680 and be free to move axially with respect to the outer surface of inner stabilization tube 1680.

For some applications, inner shaft 1636 partially protrudes out of a proximal end 1639 of outer housing 1632, such that a portion of inner shaft 1636 is visible to the user. For these applications, tubular shaft 1634 and inner shaft 1636 together provide a non-electrical mechanical force gauge 1624, in which a relative axial position of tubular shaft 1634 with respect to inner shaft 1636 (i.e., the offset distance D between proximal end 1652 of tubular shaft 1634 and proximal end 1654 of inner shaft 1636) provides a visual indication of a measure of the tension in contracting member 226. Tubular shaft 1634, at least after it begins advancing proximally, can also protrude out of proximal end 1639 of outer housing 1632. For these applications, inner shaft 1636 can be marked with a plurality of fiduciary markers 1626, which are arranged along inner shaft 1636 to indicate the relative axial position of the tubular shaft 1634 with respect to the inner shaft 1636. For example, fiduciary markers 1626 may provide a reading of zero or close to zero when proximal end 1652 of tubular shaft 1634 and proximal end 1654 of inner shaft 1636 are disposed as the initial offset distance D1 therebetween, as shown in FIGS. 22A-B. (The force applied to spring 1646 at any given level of compression of the spring equals the tension in contracting member 226.)

It is noted that force gauge 1624 does not measure the length of contracting member 226 that handle portion 1620 uptakes. (This uptake length is equal to the distance that inner shaft 1636 moves proximally.) As discussed above, an initial portion of the uptake length is sometimes due to proximal movement of inner shaft 1636 while tubular shaft 1634 proximally moves approximately in tandem with inner shaft 1636 before contracting member 226 is tensed. During this optional initial motion, tension in contracting member 226 does not materially increase, even though handle portion 1620 uptakes contracting member 226.

More generally, inner shaft 1636 can be considered an axially-movable portion of force gauge 1624. The axially-movable portion of force gauge 1624 is axially-movable with respect to the outer housing 1632 (and, often, with respect to one or more other portions of force gauge 1624, which themselves may or may not be axially movable with respect to outer housing 1632).

For some applications, inner shaft 1636 does not protrude out of proximal end 1639 of the outer housing 1632, in which case handle portion 1620 does not provide non-electrical mechanical force gauge 1624. Handle portion 1620 may nevertheless still be entirely useful for regulating the tension in contracting member 226, such as is configurations in which handle portion 1620 further comprises tension-limiting locking assembly 1658 for limiting the maximum tension that inner shaft 1636 can apply to contracting member 226, as described hereinbelow.

Reference is again made to FIGS. 24A-B and 25A-B. Reference is also made to FIGS. 26A-B, which are schematic illustrations of a portion of outer housing 1632 and tubular shaft 1634, in accordance with some applications. For clarity of illustration, inner shaft 1636 is not shown. For some applications, handle portion 1620 further comprises a tension-limiting locking assembly 1658, which is configured to axially lock inner shaft 1636 with respect to outer housing 1632 when handle portion 1620 increases the tension in contracting member 226 to a predetermined threshold level, thereby limiting a maximum tension that inner shaft 1636 can apply to contracting member 226. Tension-limiting locking assembly 1658 can be configured to axially lock inner shaft 1636 with respect to outer housing 1632 when tubular shaft 1634 is disposed at a predetermined relative axial position with respect to inner shaft 1636, thereby limiting the maximum tension that inner shaft 1636 can apply to contracting member 226. Tension-limiting locking assembly 1658 can also be configured to axially lock tubular shaft 1634 with respect to outer housing 1632 when tubular shaft 1634 is disposed at a predetermined relative axial position with respect to inner shaft 1636.

Figure 25A:
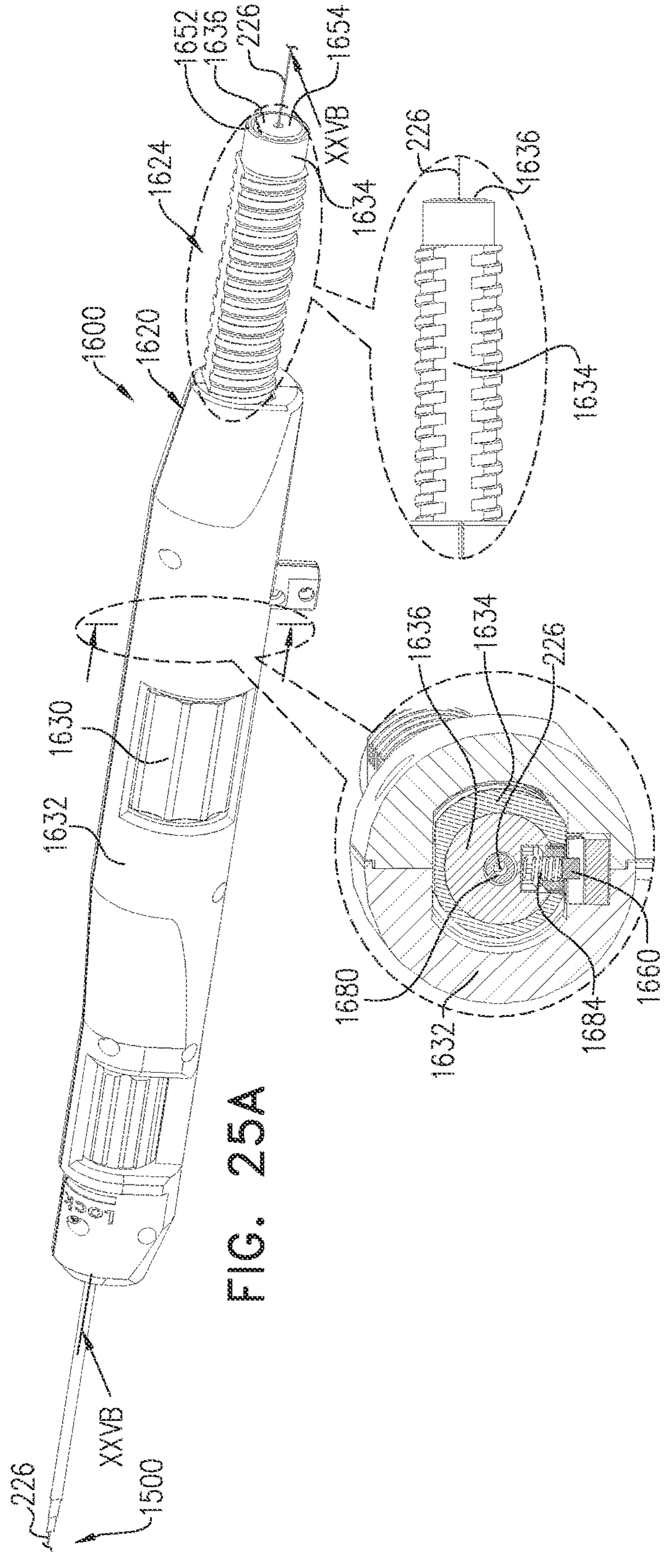
Figure 25B:
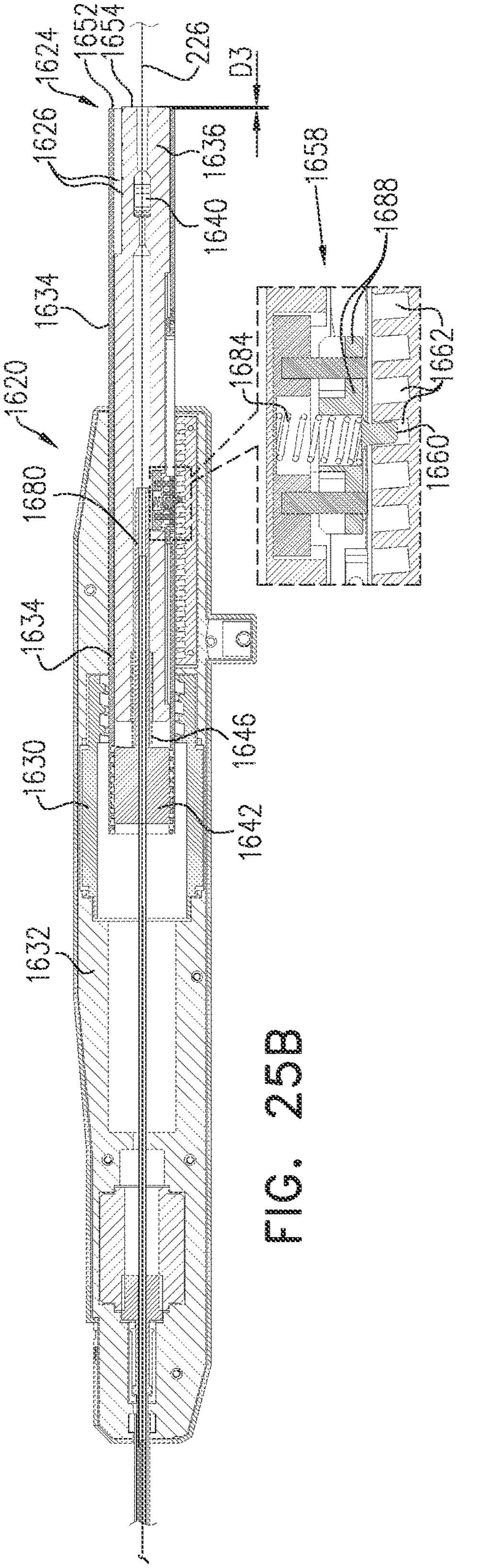
Figure 26A:
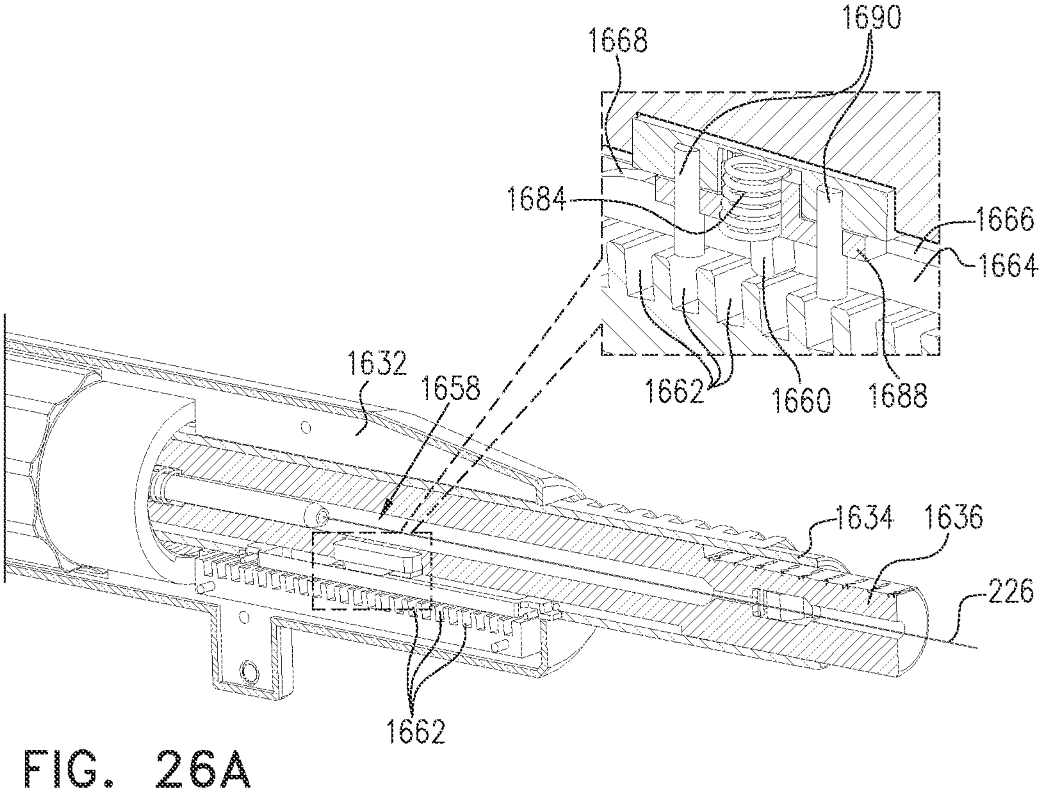
FIGS. 26A-B are schematic illustrations of a portion of an outer housing and a tubular shaft of the contracting-member-uptake tool of FIGS. 21A-B, in accordance with some applications.
Figure 26B:
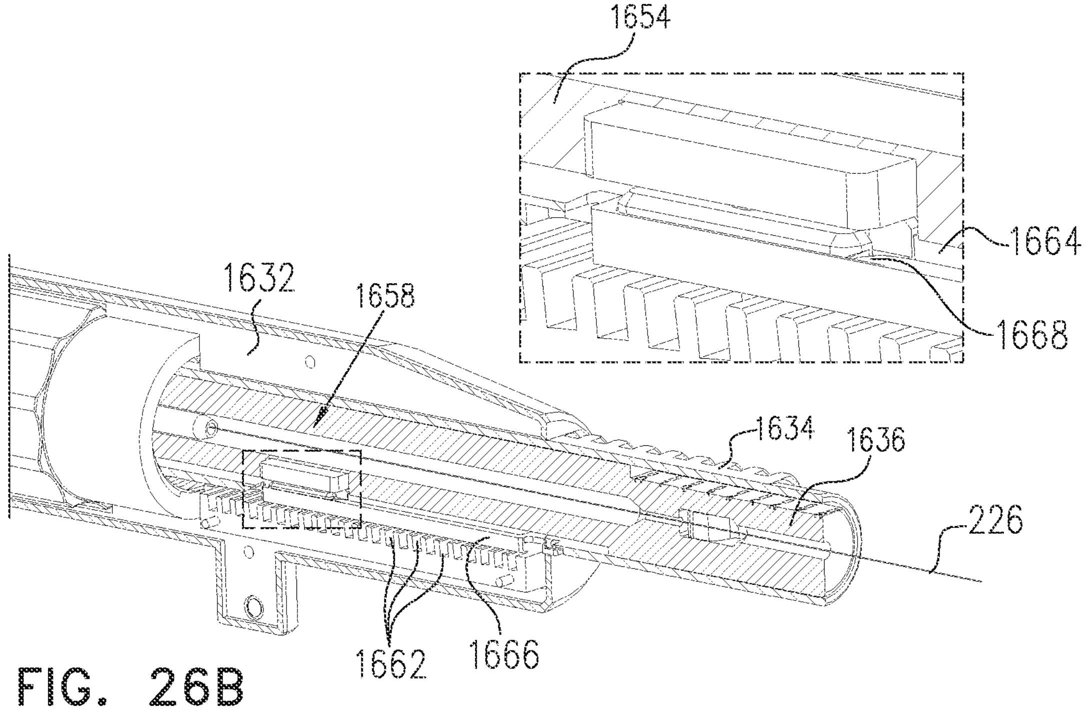

For some applications, tension-limiting locking assembly 1658 comprises a detent 1660, which is arranged to axially lock inner shaft 1636 with respect to outer housing 1632 when tubular shaft 1634 is disposed at the predetermined relative axial position with respect to inner shaft 1636, such as shown in FIGS. 25A-B, thereby limiting the maximum tension that inner shaft 1636 can apply to contracting member 226.

As shown in the transition between FIGS. 24A-B and 25A-B, as spring 1646 becomes more compressed, distal force applicator 1642 moves axially closer to inner shaft 1636, such that tubular shaft 1634 moves proximally with respect to inner shaft 1636. As a result, the offset distance between proximal end 1652 of tubular shaft 1634 and proximal end 1654 of inner shaft 1636 decreases to a maximum-tensed offset distance D3 (which may optionally be zero or close to zero, as illustrated), which is less than the tensed offset distance D2, and equal to the above-mentioned predetermined relative axial position of tubular shaft 1634 with respect to inner shaft 1636. Often, but not necessarily, a relatively small portion of inner shaft 1636 still protrudes from proximal end 1652 of tubular shaft 1634, particularly in configurations in which handle portion 1620 provides non-electrical mechanical force gauge 1624, as described above.

For applications in which the implant comprises implantable annuloplasty structure 222, which comprises flexible sleeve 26, sleeve 26 of annuloplasty structure 222 coupled to annulus 240 can be in a tense, contracted state.

Tension-limiting locking assembly 1658 optionally obviates the need for non-electrical mechanical force gauge 1624, described hereinabove. In addition, for applications in which force gauge 1624 is provided, tension-limiting locking assembly 1658 obviates the need for the user to repeatedly check the reading of force gauge 1624, thereby allowing the user to focus attention on other aspects of the procedure, such as fluoroscopy images. Often, the predetermined relative axial position of tubular shaft 1634 with respect to inner shaft 1636 has the effect of setting a predetermined maximum tension that can be applied to contracting member 226 using contracting-member-uptake tool 1600.

It is noted that tension-limiting locking assembly 1658 often does not axially lock inner shaft 1636 directly in response to the length of contracting member 226 that handle portion 1620 uptakes. (This uptake length is equal to the distance that inner shaft 1636 moves proximally.) In addition, tension-limiting locking assembly 1658 often does not axially lock inner shaft 1636 directly in response to relative axial movement between inner shaft 1636 and outer housing 1632, or directly in response to relative axial movement between tubular shaft 1634 and outer housing 1632. As discussed above, an initial portion of the uptake length is sometimes due to proximal movement of inner shaft 1636 while tubular shaft 1634 proximally moves approximately in tandem with inner shaft 1636 before contracting member 226 is tensed. Since tension-limiting locking assembly 1658 is often configured to axially lock inner shaft 1636 with respect to outer housing 1632 when tubular shaft 1634 is disposed at a predetermined relative axial position with respect to inner shaft 1636, tension-limiting locking assembly 1658 is not affected or triggered by any movement of inner shaft 1636 and tubular shaft 1634 in tandem with each other.

For some applications, detent 1660 is coupled in axial fixation with inner shaft 1636, and is configured to move radially outward so as to engage outer housing 1632 in order to axially lock inner shaft 1636 with respect to outer housing 1632, such as shown in FIGS. 24A-B. For example, a detent-spring 1684 can be provided that applies a radially-outwardly-directed force to detent 1660. Handle portion 1620 is configured such that when tubular shaft 1634 is not disposed at the predetermined relative axial position with respect to inner shaft 1636, such as shown in FIGS. 22A-23B, an element of handle portion 1620 prevents the radially-outward motion of detent 1660, for example as described below. As used in the present application, including in the claims, “radially outward” means in a direction farther from a central longitudinal axis of outer housing 1632, and “radially inward” means in the opposite direction closer to the central longitudinal axis.

For some applications, tension-limiting locking assembly 1658 further comprises a plurality of indentations 1662 that outer housing 1632 is shaped so as to define. Detent 1660 is engageable with indentations 1662 to axially lock inner shaft 1636 with respect to outer housing 1632. Handle portion 1620 is arranged such that the particular one of indentations 1662 with which detent 1660 engages depends upon a relative axial position of inner shaft 1636 with respect to outer housing 1632 when tubular shaft 1634 is disposed at the predetermined relative axial position with respect to inner shaft 1636. In this arrangement, even though the relative axial position of tubular shaft 1634 with respect to inner shaft 1636 at which detent 1660 axially locks inner shaft 1636 with respect to outer housing 1632 is predetermined, the relative positions of tubular shaft 1634 and inner shaft 1636 with respect outer housing 1632 can vary to accommodate differing initial levels of slack in contracting member 226.

For some applications, wherein proximal longitudinal portion 1637 of tubular shaft 1634 is shaped so as to define an elongate opening 1664 through which detent 1660 passes when detent 1660 axially locks inner shaft 1636 with respect to outer housing 1632. For some of these applications, tubular shaft 1634 comprises one or more tracks 1666 that run alongside a longitudinal portion of elongate opening 1664 and are arranged to:

- prevent detent 1660 from axially locking inner shaft 1636 with respect to outer housing 1632 when tubular shaft 1634 is disposed distally to the predetermined relative axial position with respect to inner shaft 1636 (by blocking the radially-outward motion of detent 1660), and
- allow detent 1660 to axially lock inner shaft 1636 when tubular shaft 1634 is disposed at the predetermined relative axial position with respect to inner shaft 1636 (by allowing the radially-outward motion of detent 1660).

A portion of the one or more tracks 1666 that prevents detent 1660 from axially locking inner shaft 1636 with respect to outer housing 1632 can be disposed radially inward of a portion of the one or more tracks 1666 that allows detent 1660 to axially lock inner shaft 1636.

For some of these applications, proximal longitudinal portion 1637 of tubular shaft 1634 comprises one or more detent supports 1688, which are fixed to detent 1660 and are configured to axially slide along the one or more tracks 1666. When tubular shaft 1634 is disposed distally to the predetermined relative axial position, the one or more tracks 1666 prevent radially-outward motion of the one or more detent supports 1688, thereby preventing the radially-outward motion of detent 1660. For some applications, proximal longitudinal portion 1637 of tubular shaft 1634 comprises one or more detent support posts 1690, which stabilize the one or more detent supports 1688 during radial motion thereof; the one or more detent supports 1688 can slide radially with respect to the one or more detent support posts 1690.

For some of these applications, the one or more tracks 1666 are shaped so as to define one or more respective sloping portions 1668. After detent 1660 axially locks inner shaft 1636 with respect to outer housing 1632 when tubular shaft 1634 is disposed at the predetermined relative axial position with respect to inner shaft 1636, subsequent distally-directed motion of tubular shaft 1634 and corresponding distally-directed motion of the one or more tracks 1666 with respect to inner shaft 1636 disengages detent 1660 from outer housing 1632. For example, this disengagement can be caused by the one or more sloping portions 1668 sliding the one or more detent supports 1688 radially inward and onto the portion of the one or more tracks 1665 that are disposed radially inward. The distally-directed motion of tubular shaft 1634 can be caused by actuation of contraction-facilitating knob 1630 in the opposite direction of actuation for the proximally-directed motion described hereinabove. This allows the user to reduce the tension in contracting member 226 if necessary during the procedure, even if the level of tension was high enough to trigger the tension-limiting locking of detent 1660. Of course, if necessary the user can also reduce the tension in contracting member 226 even before the tension-limiting locking of detent 1660.

For some applications, once the desired level of tension in contracting member 226 is achieved (by monitoring force gauge 1624, by detent 1660 limiting the maximum tension, and/or, for example, by monitoring the extent of regurgitation of the valve under echocardiographic and/or fluoroscopic guidance), contracting-member-uptake tool 1600 locks contracting member 226 so as to maintain a degree of tension in contracting member 226 in order to maintain contracting member 226 (and, optionally, structure 222, if provided) in a contracted state.

For some applications, as perhaps can best be seen in the blow-up in FIG. 25B, detent 1660 and/or indentations 1662 are slightly angled (e.g., between 1 and 45 degrees, such as between 1 and 30 degrees, e.g., between 1 and 15 degrees, such as about 5 degrees) with respect to a direction perpendicular to the central longitudinal axis of handle portion 1620, such that detent 1660 faces slightly in a proximal direction and/or the openings of indentations 1662 face slightly in a distal direction. Because detent 1660 moves proximally immediately before engaging one of indentations 1662, this angling eases the catching and engagement of the detent with indentation 1662, and can also ease disengagement if necessary, as discussed above. Alternatively, detent 1660 and/or indentations 1662 are not angled and are perpendicular to the central longitudinal axis of handle portion 1620.

Reference is again made to FIGS. 21A-B. For some applications, spring 1646 is preloaded when proximal end 1652 of tubular shaft 1634 and proximal end 1654 of inner shaft 1636 are disposed at the initial offset distance D1 therebetween. Often, handle portion 1620 is configured to maintain this preload before use of handle portion 1620, by preventing proximal advancement of inner shaft 1636 with respect to tubular shaft 1634 beyond a predetermined maximum distance. For example, a proximal end of elongate opening 1664 (shown, for example, in FIG. 22B) may block proximal advancement of an element of tension-limiting locking assembly 1658 (e.g., one or more of the detent support posts 1690 or a proximal portion of the one or more detent supports 1688, labeled in FIG. 26A). Setting of the preload is described immediately hereinbelow.

Reference is again made to FIG. 21B. For some applications, a radially-inward surface of tubular shaft 1634 near a distal end thereof is shaped so as to define a thread 1682, and a radially-outward surface of distal force applicator 1642 is shaped so as to define a corresponding thread 1686. The threads allow the adjustment of the precise axial location of distal force applicator 1642 with respect to tubular shaft 1634 during a calibration procedure during manufacture of handle portion 1620, by rotation of distal force applicator 1642 with respect to tubular shaft 1634. For example, this rotation can be readily performed before insertion into outer housing 1632 of tubular shaft 1634, inner shaft 1636, distal force applicator 1642, spring 1646, and the other elements fixed to inner shaft 1636. During use of handle portion 1620 during a medical procedure, as described hereinabove, distal force applicator 1642 is rotationally fixed, and thus axially fixed, with respect to tubular shaft 1634.

For some applications, the adjustment of the axial location of distal force applicator 1642 with respect to tubular shaft 1634 during the calibration procedure adjusts the preload in spring 1646 (by compression of the spring) to set a desired level of maximum tension that inner shaft 1636 can apply to contracting member 226. For example, a distally-directed force can be applied to proximal end 1654 of inner shaft 1636 until the offset distance between proximal end 1652 of tubular shaft 1634 and proximal end 1654 of inner shaft 1636 decreases to the maximum-tensed offset distance D3 (at which tension-limiting locking assembly 1658 is triggered during subsequent use). This applied distally-directed force can be measured with a force gauge, and the axial location of distal force applicator 1642 with respect to tubular shaft 1634 may be adjusted until the applied distally-directed force equals the desired level of maximum tension that inner shaft 1636 can apply to contracting member 226 before tension-limiting locking assembly 1658 is triggered during subsequent use. Upon removal of this calibration distally-directed force, spring 1646 will elongate until further advancement of inner shaft 1636 is blocked, as described above, and spring 1646 will have a desired level of preload.

Reference is again made to FIGS. 1-26B. Systems 10, 510, 700, 800, 900, 1000, 1100, 1200, 1300, 1350, 1400, 1480, and 1500 and methods for repairing a dilated annulus of the patient can be used to treat any cardiac valve of the patient, e.g., the aortic valve, the pulmonary valve, the mitral valve, and the tricuspid valve. Further, systems described herein for treatment of valves can be used to treat other annular muscles within the body of the patient. For example, the systems described herein can be used in order to treat a sphincter muscle within a stomach of the patient.

Reference is again made to FIGS. 1-26B. Systems 10, 510, 700, 800, 900, 1000, 1100, 1200, 1300, 1350, 1400, 1480, and 1500 can be anchored to tissue of the annulus using any of the anchoring devices described in US Patent Application Publication 2015/0272734 to Sheps et al., including the anchor driver and the deployment manipulator.

Reference is again made to FIGS. 1-26B. Systems 10, 510, 700, 800, 900, 1000, 1100, 1200, 1300, 1350, 1400, 1480, and 1500 and methods described hereinabove can be used on any suitable tissue of the patient (e.g., stomach tissue, urinary tract, and prostate tissue).

Reference is now made to FIGS. 1-26B. Tools described herein can be used to deploy, anchor, and adjust a perimeter of any annuloplasty structure, e.g., a full (or closed) annuloplasty structure or a partial (or open) annuloplasty structure. Any tool described herein can be coupled to the annuloplasty structure using any coupling described herein with reference to FIGS. 7A-26B. For example, any annuloplasty structure described herein can comprise housing 930 having female coupling 927 and the tools described herein can comprise male coupling 925 tools as described hereinabove with reference to FIGS. 12, 13, and 15. The annuloplasty structures described herein can comprise elements and structures as described in PCT Publication WO 10/073246 to Cabiri et al. which is incorporated herein by reference.

Additionally, applications described in one or more of the following can be used with the various embodiments in this disclosure:

U.S. patent application Ser. No. 12/435,291 to Maisano et al., entitled, "Adjustable repair chords and spool mechanism therefor," filed on May 4, 2009, which issued as U.S. Pat. No. 8,147,542;

U.S. patent application Ser. No. 12/437,103 to Zipory et al., entitled, "Annuloplasty ring with intra-ring anchoring," filed on May 7, 2009, which issued as U.S. Pat. No. 8,715,342;

U.S. patent application Ser. No. 12/548,991 to Maisano et al., entitled, "Implantation of repair chords in the heart," filed on Aug. 27, 2009, which issued as U.S. Pat. No. 8,808,368;

PCT Patent Application PCT/IL2009/001209 to Cabiri et al., entitled, "Adjustable annuloplasty devices and mechanisms therefor," filed on Dec. 22, 2009, which published as PCT Publication WO 10/073246;

PCT Patent Application PCT/IL2010/000357 to Maisano et al., entitled, "Implantation of repair chords in the heart," filed on May 4, 2010, which published as WO 10/128502;

PCT Patent Application PCT/IL2010/000358 to Zipory et al., entitled, "Deployment techniques for annuloplasty ring and over-wire rotation tool," filed on May 4, 2010, which published as WO 10/128503;

US Patent Application Publication 2014/0309661 to Sheps et al.; and/or

US Patent Application Publication 2015/0272734 to Sheps et al.

All of these applications are incorporated herein by reference. Techniques described herein can be practiced in combination with techniques described in one or more of these applications. Additionally, any and all of the methods, techniques, steps, etc. described herein can be performed on a living animal or in a simulation/simulated method (e.g., on a cadaver, cadaver heart, simulator with a simulated heart, tissue, etc., anthropomorphic ghost, etc.)

The present invention is not limited to what has been particularly shown and described hereinabove. Rather, the scope of the present invention includes both combinations and subcombinations of the various features described hereinabove, as well as variations and modifications thereof that are not in the prior art, which would occur to persons skilled in the art upon reading the foregoing description.

What is claimed:

1. An apparatus, comprising:

an annuloplasty structure, comprising a flexible and elongate contracting member;

a fastener configured to receive the contracting member therethrough such that the fastener surrounds at least a portion of the contracting member, the fastener comprising:

a housing, and a clamping structure disposed within the housing, wherein the clamping structure:

(a) has an open state in which the contracting member can pass through the fastener, and (b) is biased toward assuming a closed state in which the clamping structure clamps onto the contracting member disposed through the fastener;

a stop removably coupled to the fastener in a manner that maintains the fastener in the open state; and a tool, comprising a static cutting element and a dynamic cutting element, and configured to:

apply tension to the contracting member by pulling the contracting member proximally through the fastener, lock the tension in the contracting member by pulling the stop proximally out from the fastener such that the fastener responsively transitions toward the closed state, and sever the contracting member proximally from the fastener by moving the dynamic cutting element with respect to the static cutting element.

2. The apparatus according to claim 1, wherein the stop comprises a narrow cylindrical engager that has an outer surface and that, when the stop is coupled to the fastener, maintains the fastener in the open state by extending through the fastener such that the outer surface constrains the fastener.

3. The apparatus according to claim 2, wherein the tool is configured to apply the tension to the contracting member by pulling the contracting member through the narrow cylindrical engager.

4. The apparatus according to claim 2, wherein the narrow cylindrical engager defines a lumen for the contracting member to extend therethrough.

5. The apparatus according to claim 1, wherein the tool is configured to apply the tension to the contracting member by pulling the contracting member through the static cutting element.

6. The apparatus according to claim 5, wherein the tool is configured to apply the tension to the contracting member by pulling the contracting member through the dynamic cutting element.

7. The apparatus according to claim 1, wherein the static cutting element defines a static-cutting-element lumen for the contracting member to extend therethrough.

8. The apparatus according to claim 7, wherein the dynamic cutting element defines a dynamic-cutting-element lumen for the contracting member to extend therethrough.

9. The apparatus according to claim 1, further comprising a grasper that provides coupling between the tool and the housing, the apparatus having a state in which the coupling between the tool and the housing is locked.

10. The apparatus according to claim 9, wherein, in the state, the tool is decouplable from the housing by pulling the stop proximally out from the fastener and the tool proximally away from the housing.

11. The apparatus according to claim 1, wherein the tool is configured to:

lock the tension in the contracting member by pulling the stop proximally out from the fastener along an axis of the tool, and sever the contracting member proximally from the fastener by moving the dynamic cutting element proximally obliquely with respect to the axis.

12. The apparatus according to claim 1, wherein the tool is configured to sever the contracting member proximally from the fastener by sliding the dynamic cutting element against the static cutting element.

13. The apparatus according to claim 1, wherein the static cutting element defines a first cutting surface, the dynamic cutting element defines a second cutting surface, and each of the first and second cutting surfaces is oblique with respect to an axis along which the tool is configured to pull the stop.

14. The apparatus according to claim 1, wherein the tool comprises a tube within which the stop, the static cutting element, and the dynamic cutting element are disposed.

15. The apparatus according to claim 14, wherein, within the tube, the dynamic cutting element is disposed distally from the static cutting element.

16. The apparatus according to claim 14, wherein the tube is couplable to the housing.

17. The apparatus according to claim 14, wherein the static cutting element comprises a pin that extends laterally in a manner that engages the tube.

18. The apparatus according to claim 1, wherein the annuloplasty structure further comprises an anchor coupled to the contracting member.

19. The apparatus according to claim 18, wherein:

the anchor is a first anchor, and the apparatus further comprises a second anchor, slidably coupled to the contracting member, and wherein the fastener is configured to, in the closed state, maintain a distance between the first anchor and the second anchor by locking the tension in the contracting member.

20. The apparatus according to claim 1, wherein the static cutting element defines a first cutting surface, the dynamic cutting element defines a second cutting surface, and each of the first and second cutting surfaces is concave.

* * * * *